US012628858B2

(12) United States Patent
Goncalves et al.

(10) Patent No.: US 12,628,858 B2
(45) Date of Patent: May 19, 2026

(54) THERAPY FOR COLORECTAL AND SMALL INTESTINE CANCERS

(71) Applicant: Cornell University, Ithaca, NY (US)

(72) Inventors: Marcus Goncalves, Garden City, NY (US); Lewis C. Cantley, Cambridge, MA (US); Jihye Yun, Houston, TX (US)

(73) Assignee: Cornell University, Ithaca, NY (US)

( * ) Notice: Subject to any disclaimer, the term of this patent is extended or adjusted under 35 U.S.C. 154(b) by 656 days.

(21) Appl. No.: 17/441,416

(22) PCT Filed: Mar. 20, 2020

(86) PCT No.: PCT/US2020/024012
§ 371 (c)(1),
(2) Date: Sep. 21, 2021

(87) PCT Pub. No.: WO2020/191356
PCT Pub. Date: Sep. 24, 2020

(65) Prior Publication Data

US 2022/0400732 A1 Dec. 22, 2022

Related U.S. Application Data

(60) Provisional application No. 62/821,546, filed on Mar. 21, 2019.

(51) Int. Cl.

*A61P 35/04* (2006.01)
*A23L 33/20* (2016.01)
*A61K 45/06* (2006.01)

(52) U.S. Cl.
CPC .............. *A23L 33/20* (2016.08); *A61K 45/06* (2013.01); *A61P 35/04* (2018.01)

(58) Field of Classification Search
CPC .......... A23L 33/20; A61K 45/06; A61P 35/04
See application file for complete search history.

(56) References Cited

U.S. PATENT DOCUMENTS 10,118,913 B2 * 11/2018 Oslob .................... A61P 31/12
10,227,350 B2 * 3/2019 Chandrasekhar ....... A61P 13/12
2009/0325877 A1 12/2009 Grunt et al.
2014/0011749 A1 1/2014 Lynch
2015/0031742 A1 * 1/2015 Morton ................ C12Q 1/6827 514/44 A
2015/0291576 A1 10/2015 Lemieux et al.
2016/0303056 A1 10/2016 Longo et al.
2017/0273964 A1 9/2017 Heuer
2018/0050997 A1 2/2018 Bair et al.
2019/0231761 A1 * 8/2019 Shen .................. C12N 15/1137
2019/0247399 A1 8/2019 Weiss et al.

FOREIGN PATENT DOCUMENTS

WO WO-2005119261 A2 12/2005
WO WO-8241607 8/2012
WO WO-2017144877 A1 8/2017
WO WO-2017161205 A1 9/2017
WO 2018170517 9/2018
WO WO-2018170485 A1 9/2018
WO WO-2020191356 A1 9/2020

OTHER PUBLICATIONS

Zhang et al., Multiple Roles of APC and its Therapeutic Implications in Colorectal Cancer. JNCI J Natl Cancer Inst (2017) 109(8) (Year: 2017).*
"International Application Serial No. PCT/US2020/024012, International Search Report mailed Jun. 18, 2020", 3 pgs.
"International Application Serial No. PCT/US2020/024012, Written Opinion mailed Jun. 18, 2020", 8 pgs.
"International Application Serial No. PCT US2020 024012, International Preliminary Report on Patentability mailed Sep. 30, 2021", 10 pgs.

* cited by examiner

*Primary Examiner* — Robert A Wax
*Assistant Examiner* — Ngoc-Anh Thi Nguyen
(74) *Attorney, Agent, or Firm* — Schwegman Lundberg & Woessner, P.A.

(57) ABSTRACT

As described herein ingestion of high amounts of sugar, especially fructose, can increase the growth of intestinal tumors. Such cancer growth can be inhibited or prevented by limiting the amounts of sugar and amino acids ingested, by inhibiting ketohexokinase (KHK), fructose transport (via GLUT5), fatty acid synthesis (via FASN), phosphoinositide 3-kinases (PI3K), or by limiting amounts of sugar and amino acids ingested while also receiving KHK inhibitors, GLUT5 inhibitors, FASN inhibitors, PI3K inhibitors, or a combination of such inhibitors.

9 Claims, 33 Drawing Sheets

Specification includes a Sequence Listing.

THERAPY FOR COLORECTAL AND SMALL INTESTINE CANCERS

This application is a U.S. national stage filing under 35 U.S.C. § 371 from International Application No. PCT/US2020/024012, filed on Mar. 20,2020, and published as WO2020/191356 A1 on Sep. 24, 2020, which claims benefit of priority to the filing date of U.S. Provisional Application Ser. No. 62/821,546, filed Mar. 21, 2019, the contents of which are specifically incorporated by reference herein in their entirety.

GOVERNMENT SUPPORT

This invention was made with government support under R35 CA197588, HD067244, and R01 NS093872 awarded by the National Institutes of Health and under 1K22CA216036 and K08 CA230318 awarded by the National Cancer institute. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 4, 2022, is named 2259548.txt and is 131,072 bytes in size.

BACKGROUND

Colorectal cancer (CRC) is the third-leading cancer type in the world and contributes to 7.9% of the world cancer-related deaths in 2000. In Japan, CRC is the leading cause of death and the number of the patients has been increasing every year. In the United States, there is a rising incidence of CRC in young adults. The development of an agent and therapeutic method which are highly effective and safe is strongly desired.

The five-year survival rate of colorectal cancer is relatively high with stage I and stage II because the cancer lesions can be removed almost completely by surgical operation. However, this rate is significantly reduced with advanced cancer (stage III and stage IV).

SUMMARY

Methods are described herein that include (a) reducing or eliminating sucrose, fructose, glycine, serine, or a combination thereof from a subject's diet; (b) administering a GLUT5 inhibitor; (c) administering a ketohexokinase (KHK) inhibitor; (d) administering a fatty acid synthase (FASN) inhibitor; (e) administering a phosphoinositide 3 (PI3) kinase inhibitor, or (4) a combination two or more thereof to inhibit the onset of colorectal or small intestine cancer or to reduce colorectal or small intestine tumor growth in the subject.

As shown herein, high-fructose corn syrup enhances intestinal tumor growth and the incidence of high-grade tumors. Such cancer/tumor growth can be inhibited or prevented by genetic deletion of ketohexokinase (KHK), the major enzyme that initiates fructose metabolism, or fatty acid synthase (FASN). Methods and compositions are described herein for dietary changes and therapeutic inhibition of (1) fructose transport (via GLUT5), (2) metabolism (KHK), (3) fatty acid synthesis (FASN), (4) phosphoinositide 3-kinases, or (5) a combination thereof to inhibit and/or prevent tumor growth. Such methods can also include modifications of diet including to reduce or eliminate consumption of certain types of amino acids, sugars and/or carbohydrates. Also, as illustrated herein, the KHK-derived metabolite, fructose 1-phosphate (HP), allosterically inhibits pyruvate kinase M2 (PKM2). This inactivation can accelerate tumor growth. Hence, small molecules that activate PKM2 (e.g. TEPP-46) may also inhibit and/or prevent intestinal tumor growth.

DESCRIPTION OF THE FIGURES

FIG. 1A graphically illustrates the mean weight of untreated control $APC^{-/-}$ mice (Con), $APC^{-/-}$ mice treated with a daily oral gavage of HFCS, and $APC^{-/-}$ mice fed with unlimited HFCS in drinking water bottle (WB) following the induction of intestinal tumors. n=12. FIG. 1B graphically illustrates the body composition (weight) as detected by magnetic resonance after 8 weeks of treatment of untreated control $APC^{-/-}$ mice (Con) (n=8), $APC^{-/-}$ mice treated with a daily oral gavage of HFCS (n=6), and $APC^{-/-}$ mice fed with unlimited HFCS in drinking water bottle (WB) (n=9) groups. BM, body mass; FM, fat mass; FFM, fat-free mass. The data in FIGS. 1A and 1B was analyzed by Two-way analysis of variance (ANOVA) followed by Holm-Sidak post-test for multiple comparisons. FIG. 1C shows sections of H&E (hematoxylin and eosin) stained distal small intestines from control untreated $APC^{-/-}$ mice (Con) or $APC^{-/-}$ mice treated with HFCS via daily oral gavage for 8 weeks. Black bar indicates 2 mm. FIG. 1D graphically illustrates the number of tumors with a diameter over 3 mm in the intestine as determined using a dissecting microscope of whole-mount tissues after methylene blue staining. Data represent the number of tumors over 3 mm in diameter in control (Con) and HFCS-treated $APC^{-/-}$ mice. n=12. FIG. 1E illustrates representative pathologic grading of intestinal sections from Con and HFCS-treated $APC^{-/-}$ mice. Black bar indicates 2 mm. White bar indicates 200 mm. FIG. 1F graphically illustrates the percentage of high-grade lesions from Con (n=7) and HFCS-treated (n=8) $APC^{-/-}$ mice. The data in FIGS. 1D and 1F was analyzed by Student's t test; NS: not significant. P<0.01. All data represent means±SEM. FIG. 1G-1L illustrate changes in body composition and food intake following treatment with high-fructose corn syrup. FIG. 1I graphically illustrates final body weight in WT and APC$^{-/-}$ mice following 8 weeks of treatment with Con, HFCS, and WB. Although there were no differences in cumulative food intake in the WB versus Con groups, the high intake of HFCS (approximately 48% of total daily calorie intake) significantly increased body weight. WT Con (n=22), HFCS (n=12), and WB (n=21). APC$^{-/-}$ Con (n=17), HFCS (n=13), and WB (n=17). Two-way ANOVA with Holm-Sid-A post-test comparing HFCS and WB to Con 0, and APC$^{-/-}$ Con to WT Con (#) *P<0.05, *P<0.001, **P<0.0001. FIG. 1J graphically illustrates gonadal white adipose tissue weight (WAT) in WT and APC$^{-/-}$ mice following 8 weeks of treatment with Con, HFCS, and WB. WT Con (n=22), HFCS (n=12), and WB (n=10). APC$^{-/-}$ Con (n=9), HFCS (n=6), and WB (n=9). Two-way ANOVA with Holm-Sidak post-test comparing HFCS and WB to Con (*), and APC$^{-/-}$ Con to WT Con (no significant changes) *P<0.05, ****P<0,0001, FIG. 1K graphically illustrates body mass (BM), fat mass (FM), and fat-free mass (FFM) in WT and APC$^{-/-}$ mice following 8 weeks of treatment with Con, HFCS, and WB. WT Con (n=22), HFCS (n=12), and WB (n=22), APC$^{-/-}$ Con (n=8), HFCS (n=9), and WB (n=9). Two-way ANOVA with Holm-Sidak post-test comparing HFCS and WB to Con (*), and APC$^{-/-}$ Con to WT Con (no significant changes) P<0.01, *P<0.001 **P<0.0001. FIG. 1L graphically illustrates gastrocnemius weight in WT and APC mice following 8 weeks of treatment with Con, HFCS, and WB, WT Con (n=17), HFCS (n=12), and WB (n=16), APC$^{-/-}$ Con (n=17), HFCS (n=14), and WB (n=17). Two-way ANOVA with Holm-Sidak post-test comparing HFCS and WB to Con showed no differences, comparisons between APC$^{-/-}$ Con to WT Con **P<0,0001. All data represent means±S.E.M.

FIG. 2A-1 graphically illustrates the amounts of radioactivity in the serum 20 min after an oral bolus of HFCS that contained U-[$^{14}$C]-fructose tracer in wild-type (WT) (n=4) and tumor-bearing APC$^{-/-}$ mice (n=6). Radioactivity amount is presented as disintegrations per minute (DPM) per microliter (serum) or per microgram of protein input (liver). WT and APC$^{-/-}$ compared by Student's t test, P<0.01. FIG. 2A-2 graphically illustrates the amounts of radioactivity in the liver 20 min after an oral bolus of HFCS that contained U-[$^{14}$C]-fructose tracer in wild-type (WT) (n=4) and tumor-bearing APC$^{-/-}$ mice (n=6). Radioactivity amount is presented as disintegrations per minute (DPM) per microliter (serum) or per microgram of protein input (liver). WT and APC$^{-/-}$ compared by Student's t test, P<0.01. FIG. 2B shows a schematic depicting key enzymes and metabolites in glycolysis, fructolysis, and purine salvage pathways. Key fructose metabolites are F1P, GA, and G3P. The enzymes shown include HK, KHK, PFK, AMPD2, ALDOB, and PK. Abbreviations: Glu, glucose; Fruc, fructose; G6P, glucose 6-phosphate; FBP, fructose 1,6-bisphosphate; G3P, glyceraldehyde 3-phosphate; Pyr, pyruvate; F1P, fructose 1-phosphate; GA, glyceraldehyde; DHAP, dihydroxyacetone phosphate; ATP, adenosine triphosphate; ADP, adenosine diphosphate; AMP, adenosine monophosphate; IMP, inosine monophosphate; HK, hexokinase; PFK, phosphofructokinase; PK, pyruvate kinase; ALDOB, aldolase B; KHK, ketohexokinase; AMPD2, AMP deaminase 2. FIG. 2C graphically illustrates the percent labeling of fructose 1-phosphate following a 10-min ex vivo incubation with 10 mM U-[$^{13}$C]-glucose, 10 mM U-[$^{13}$C]-glucose with 10 mM fructose, 10 mM U-[$^{13}$C]-fructose, and 10 mM U-[$^{13}$C]-fructose with 10 mM glucose. FIG. 2D graphically illustrates the percent labeling of lactate following a 10-min ex vivo incubation with 10 mM U-[$^{13}$C]-glucose, 10 mM U-[$^{13}$C]-glucose with 10 mM fructose, 10 mM U-[$^{13}$C]-fructose, and 10 mM U-[$^{13}$C]-fructose with 10 mM glucose. The isotopic labeling of each metabolite in FIG. 2C-2D is indicated by the M+# designation indicated in the legend where the # represents how many [$^{12}$C] were replaced with [$^{13}$C]. For example, the M+3 species for fructose 1-phosphate has the chemical formula $^{13}C_3{}^{12}C_3H_{13}O_9P$. n=3 to 4 per group. Two-way ANOVA with Holm-Sidak post-test compared to the U-[$^{13}$C]-glucose condition. *P<0.05, $^{13}$C Fru, U-[$^{13}$C]-0.001, **P<0.0001. Abbreviations: $^{13}$C Glu, U-[$^{13}$C]-glucose; $^{13}$C Fru, U-[$^{13}$C]-fructose. FIG. 2E graphically illustrates the relative abundance of key metabolites in the adenine purine salvage pathway. Control (Con, n=14), HFCS (n=9). Two-way ANOVA with Holm-Sidak post-test *P<0.05, P<0.01, *P<0.001, ****P<0.0001. All data represent means±SEM. FIG. 2F-2K illustrate changes in systemic glucose metabolism following treatment with high-fructose corn syrup in WT and tumor-bearing APC$^{-/-}$ mice. FIG. 2F graphically illustrates liver triglyceride (TG) in wild-type (WT) and tumor-bearing mice (APC$^{-/-}$) following 8 weeks of treatment with water (Con), a daily oral gavage of high-fructose corn syrup (HFCS), and mice supplied with unlimited high-fructose corn syrup via the water bottle (WB). n=8 per group. Two-way ANOVA with Holm-Sidak post-test comparing HFCS and WB to Con (*), and APC$^{-/-}$ Con to WT Con (no significant changes) ****P<0.0001 FIG. 2G graphically illustrates liver weight in WT and APC$^{-/-}$ mice following 8 weeks of treatment with Con, HFCS, and WB. WT Con (n=22), HFCS (n=12), and WB (n=21). APC$^{-/-}$ Con (n=17), HFCS (n=14), and WB (n=17). Two-way ANOVA with Holm-Sidak post-test with no significant changes. FIG. 2H graphically illustrates fasting serum glucose in WT and APC$^{-/-}$ mice following 8 weeks of treatment with Con, HFCS, and WB. WT n=12 per group. APC$^{-/-}$ Con (n=7), HFCS (n=7), and WB (n=8). Two-way ANOVA with Holm-Sidak post-test comparing HFCS and WB to Con (*), and APC$^{-/-}$ Con to WT Con (no significant changes) *P<0.001, **P<0.0001 FIG. 2I graphically illustrates fasting serum insulin in WT and APC.$^{-/-}$ mice following 8 weeks of treatment with Con, HFCS, and WB. WT n=8 per group. APC$^{-/-}$ Con (n=7), HFCS (n=7), and WB (n=8). Two-way ANOVA with Holm-Sidak post-test comparing HFCS and WB to Con (*), and APC$^{-/-}$ Con to WT Con (no significant changes) ****P<0.0001. FIG. 2J graphically illustrates serum glucose following intraperitoneal injection of 2 mg/kg glucose in WT and APC$^{-/-}$ mice following 8 weeks of treatment with Con, HFCS, and W B. FIG. 2K graphically illustrates mean area under the curve (AUC) of serum glucose. WT n=12 per group. APC$^{-/-}$ Con (n=9), HFCS (n=6), and WB (n=9). Two-way ANOVA with Holm-Sidak post-test comparing HFCS and WB to Con, *P<0.05, ****p<0.0001. Interestingly, APC$^{-/-}$ mice were protected from HFCS-induced metabolic dysfunction. All data represent means±S.E.M.

FIG. 3A shows a Heatmap depicting the relative expression of the indicated genes involved in fatty acid synthesis from APC$^{-/-}$ tumors (n=19) and intestinal epithelial cells (IECs, n=16) using RNA-seq data. FIG. 3B graphically illustrates the relative abundance of saturated and unsaturated 16-carbon and 18-carbon fatty acid species in APC$^{-/-}$ tumors treated daily with water (Con, n=14) or HFCS (n=9). Groups were compared by Student's t test with correction for multiple comparisons using the Holm-Sidak method. **P<0.0001. FIG. 3C shows a schematic diagram depicting key enzymes, genes, and metabolites in the de novo lipogenesis pathway. Enzyme names included ACL (ALLY gene); ACC (ACACA gene); FAS (FASN gene): SCD1/2; and ELOVL6. FIG. 3D graphically illustrates the numbers of tumors greater than 3 mm in diameter in $APC^{-/-}$ $FASN^{-/-}$ mice treated with a daily oral gavage containing water (Con, n=9) or HFCS (n=10) starting the day after tamoxifen injection. Animals were killed at eight weeks. The size of each tumor (diameter) in the intestine was determined in whole-mount tissue after methylene blue staining, using a dissecting microscope. Data represent the number of tumors >3 mm in diameter in Con and HFCS-treated mice. Groups compared by Student's t test. NS, not significant. FIG. 3E graphically illustrates the percentage of high-grade tumors (n=11 per group) from Con and HFCS-treated $APC^{-/-}$; $FASN^{-/-}$ mice. Student's t test. NS, not significant. All data represent means±SEM. FIGS. 3F-3M illustrate increased tumor size but not total number following high-fructose corn syrup treatment for 8 weeks. FIG. 3F-1 shows a representative image of the distal small intestine in $APC^{-/-}$ mice following daily oral gavage with water (Con) for 8 weeks. Tissue is shown as a whole mount after methylene blue staining. Black bar indicates 1 cm, FIG. 3F-2 shows a representative image of the distal small intestine in $APC^{-/-}$ mice following daily oral gavage with high-fructose corn syrup (HFCS) for 8 weeks. Tissue is shown as a whole mount after methylene blue staining. Black bar indicates 1 cm. FIG. 3G graphically illustrates the total number of tumors in Con and HFCS treated $APC^{-/-}$ mice, n=12 per group. Student's t-test. NS: not significant. Ha 3H graphically illustrates the numbers of different sized tumors (diameter) in the intestine as determined in whole-mount tissue after methylene blue staining, using a dissecting microscope. Data presented is the tumor size distribution in Con and HFCS treated $APC^{-/-}$ mice. n=12 per group. Con vs HFCS compared by t-test with correction for multiple comparisons using Holm-Sidak method P<0.01. FIG. 3I-1 shows a representative image of the colon in CDX2P-$CreER^{T2}$; $APC^{flox/flox}$ (CDX2-$APC^{-/-}$) mice following daily oral gavage with water (Con) or HFCS for 8 weeks. Tissue is shown as a whole mount after methylene blue staining. Black bar indicates 1 cm. FIG. 3I-2 shows a representative image of the colon in CDX2P-$CreER^{T2}$; $APC^{flox/flox}$ (CDX2-$APC^{-/-}$) mice following daily oral gavage with high-fructose corn syrup (HFCS) for 8 weeks. Tissue is shown in whole mount after methylene blue staining. Black bar indicates 1 cm. FIG. 3J graphically illustrates the numbers of tumors in the intestine as determined in whole-mount tissue after methylene blue staining, using a dissecting microscope. Data presented is the total number of tumor in Con and HFCS created CDX2-$APC^{-/-}$ mice. Con (n=15), HFCS (n=18). Student's t-test. *P<0.05. FIG. 3K graphically illustrates the numbers of differently sized tumors (diameter) in the intestine as determined in whole-mount tissue after methylene blue staining, using a dissecting microscope. Data presented is the tumor size distribution in Con and HFCS treated CDX2-$APC^{-/-}$ mice. Con (n=15), HFCS (n=18), Con vs HFCS compared by t-test with correction for multiple comparisons using Holm-Sid-A method *P<0.05, *P<0.001. FIG. 3L graphically illustrates the number of tumors over 3 mm in diameter in Con and HFCS created CDX2-$APC^{-/-}$ mice. Con (n=15), HFCS (n=18), Student's t-test. *P<0.001. FIG. 3M graphically illustrates the percent of high-grade lesions from the intestine of Con and HFCS treated CDX2-$APC^{-/-}$ mice. Con (n=17), HFCS (n=18), Student's t-test. ****P<0.0001. All data represent means±S.E.M.

FIG. 4A graphically illustrates the numbers of tumors with a diameter greater than 3 mm in the intestine as determined in whole-mount tissue after methylene blue staining, using a dissecting microscope. Data represent the number of tumors >3 mm in diameter in Con (n=19) and IIFCS-treated (n=18) $APC^{-/-}$ and $APC^{-/-}$; $KHK^{-/-}$ mice (n=10 per group). Groups compared by two-way ANOVA with Holm-Sidak post-test. P<0.01. FIG. 4B graphically illustrates the percentage of high-grade tumors from Con (n=11) and HIVS-treated (n=10) $APC^{-/-}$ and $APC^{-/-}$; $KHK^{-/-}$ mice (Con n=12, HFCS n=11). Groups were compared by two-way ANOVA with Holm-Sidak post-test. P<0.0001. FIG. 4**C graphically illustrates the normalized abundance of ATP in tumors from $APC^{-/-}$ (n=5 per group) and $APC^{-/-}$; $KHK^{-/-}$ (n=8 per group) mice treated ex vivo with and without 10 mM HFCS for 10 min. Two-way ANOVA with Holm-Sidak post-test. *P<0.05. FIG. 4D graphically illustrates the normalized phosphofructokinase (PFK) activity (mU/mg) in tumors from $APC^{-/-}$ (Con n=6, HFCS n=8) and $APC^{-/-}$; $KHK^{-/-}$ (Con n=9, HFCS n=8) mice treated for 8 weeks. Two-way ANOVA with Holm-Sidak post-test. P<0.01, FIG. 4**E graphically illustrates the normalized abundance of lactate in tumors from $APC^{-/-}$ (Con n=7, HFCS n=8) and $APC^{-/-}$; $KHK^{-/-}$ (Con n=6, HFCS n=7) mice treated ex vivo with and without 10 mM HFCS for 10 min. Two-way ANOVA with Holm-Sidak post-test. *P<0.05. All data represent means±SEM. FIG. 4F-4I illustrate that tumors directly take up fructose and glucose in the intestinal lumen and serum, respectively, following a bolus of HFCS via oral gavage. FIG. 4F graphically illustrates that glucose and fructose concentration in the colonic lumen over time in wild-type (WT) mice (C57BL/6.1) following a single oral gavage bolus of HFCS. n=5 per group. Two-way ANOVA with Holm-Sidak post-test comparing time 0 to subsequent times. *P<0.05, P<0.01, *P<0.001, **P<0.0001. FIG. 4**G graphically illustrates that glucose and fructose concentration in the serum ever time in wild-type (WT) mice (C57BL/6J) following a single oral gavage bolus of HFCS. n=5 per group. Two-way ANOVA with Holm-Sidak post-test comparing time 0 to subsequent times. *P<0.05, P<0.01, *P<0.001, **P<0.0001. FIG. 4**H graphically illustrates the amount of radioactivity in hexoses present in $APC^{-/-}$ tumors and intestinal epithelial cells (IEC) 30 min after an oral gavage bolus with U-[$^{14}$C]-labeled glucose ($^{14}$C-Glu) or U-[$^{14}$C]-labeled fructose ($^{14}$C-Fru) in the presence of glucose (Glu) or fructose (Fru) as indicated. Radioactivity amount is presented as disintegrations per minute (DPM) per microgram of protein. n=5 per group. Two-way ANOVA with Holm-Sidak post-test comparing tumor to intestinal epithelial cells (IECs), *P<0.05. FIG. 4I graphically illustrates the fructose concentration in the ileum and colonic lumen 90 min following an oral gavage bolus of equimolar HFCS (100 mg glucose 100 mg fructose) or sucrose (200 mg). Both HFCS and sucrose treatment via oral gavage give similar levels of fructose in the lumen of the ileum and the colon. n=3 per group. Comparisons were made using t-test with correction for multiple comparisons using Holm-Sidak method. NS, not significant. All data represent means±S.E.M.

FIG. 5A illustrates the relative abundance of various proteins (including GLUT5) in the liver from a WT $KHK^{-/-}$ mouse and in the liver and tumor tissue from $APC^{-/-}$ mice treated with a daily oral gavage of water (Con) or high-fructose corn syrup (HFCS) for 8 weeks at which time the tissues were removed, homogenized, and subjected to immunoblot. Abbreviations: GLUT1, Glucose transporter 1; GLUT2, Glucose transporter 2; GLUT5. Glucose transporter 5; SGLT1. Sodium/glucose cotransporter 1; HK1, Hexokinase 1; HK2, Hexokinase 2; KHK, Ketohexokinase; ALDOA, Adolase A; ALDOB, Adolase B; ALDOC, Aldolase C; PKL, Pyruvate Kinase Liver Isozyme; PKM1, Pyruvate Kinase Muscle Isozyme isoform 1; PKM2, Pyruvate Kinase Muscle Isozyme isoform 2; and ENOI, enolase 1, as a control between tissues. FIG. 5B-1 graphically illustrates the relative abundance of fructose 1-phosphate (F1P) in $APC^{-/-}$ tumors treated with HFCS ex vivo for 10 minutes. Con (n=3), HFCS (n=5). Student t-test, $^{*}P<0.05$. FIG. 5B-2 graphically illustrates the relative abundance of fructose 1,6-bisphosphate (FBP) in $APC^{-/-}$ tumors treated with HFCS ex vivo for 10 minutes. Con (n=3), HFCS (n=5). Student t-test, $^{*}P<0.05$. FIG. 5C graphically illustrates expression of aldolases (ALDOA, Adolase A; ALDOB, Adolase B; ALDOC, Aldolase C) in $APC^{-/-}$ tumors treated with a daily oral gavage of water (Con) or HFCS (HFCS) for 8 weeks. Expression is reported as Fragments Per Kilobase of transcript per Million mapped reads (FPKM). n=4 per group. Comparison was made using t-tests with correction for multiple comparisons using Holm-Sidak method (no significant changes). FIG. 5D graphically illustrates the percent of fully labeled ($M^{+3}$) lactate isolated from tumors of $APC^{-/-}$ mice 2 hours following an oral bolus of 400 μL containing no sugar (None), 25% $^{13}$C-Glu, or 12.5% $^{13}$C-Glu+12.5% Fru. None (n=4), $^{13}$C Glu (n=7), $^{13}$C Glu+Fru (n=14) tumors taken from n=2, 4, and 7 mice, respectively. Student's t-test. $^{**}P<0.01$. All data represent means S.E.M.

FIG. 6A graphically illustrates the normalized abundance of saturated and unsaturated fatty acids from $APC^{-/-}$ tumors compared to intestinal epithelial cells (IEC), where IEC (n=7), and tumor (n=12) Comparisons were made using t-tests with correction for multiple comparisons using Holm-Sidak method. An asterisk indicates P<0.01. Bolded fatty acids are increased in tumor vs IEC. FIG. 6B illustrates the amount of radioactivity in lipid (non-polar) extracts of $APC^{-/-}$ tumors and LECs 4 hours after a bolus of HFCS containing 5 μCi U-[$^{14}$C]-glucose. Radioactivity amount is presented as disintegrations per minute (DPM) per milligram of protein input. n=5 per group. Tumor and IEC compared by student's t-test $^{}P<0.01$. Glu. Glucose, Fru, Fructose. FIG. 6**C illustrates the percent of labeled $W^2$) citrate following a 10 min ex vivo incubation with no sugar (None), 10 mM U-[$^{13}$C]-Glucose (13C Glu), or 13C Glu with 10 mM fructose (Fru). n=3 per group. One-way ANOVA with Holm-Sidak post-test. $^{*}P<0.05$. FIG. 61) illustrates pathway enrichment analysis of LC/MS-derived metabolites from $APC^{-/-}$ tumors created with a daily oral gavage of HFCS as compared to water-treated $APC^{-/-}$ tumors performed using Ingenuity Pathway Analysis (IPA) software. The top six significantly enriched pathways in HFCS tumors are shown. FIG. 6E illustrates principle component analysis (PCA) using untargeted LC/MS metabolomics data from $APC^{-/-}$ tumors vested with a daily oral gavage of water (Con) or HFCS over 8 weeks. Con (n=14), HFCS (n=9). FIG. 6F graphically illustrates the normalized abundance of lipid species from $APC^{-/-}$ tumors treated with a daily oral gavage of water (Con) or high-fructose corn syrup (HFCS). Con (n=14), HFCS (n=9). Comparisons were made using t-tests with correction for multiple comparisons using Holm-Sidak method, Asterisk indicates P<0.01.

FIG. 7A graphically illustrate the number of tumors of various sizes in the intestine as determined in whole-mount tissues after methylene blue staining, using a dissecting microscope. Shown is the tumor size distribution from $APC^{-/-}$ $FASN^{-/-}$ mice following daily oral gavage of water (Con) or high-fructose corn syrup (HFCS) for 8 weeks. Con (n=9), HFCS (n=10). Con vs HFCS compared by t-test with correction for multiple comparisons using Holm-Sidak method. No significant differences. FIG. 7B graphically illustrates tumor size distribution from Con and HFCS-treated $APC^{-/-}$, $KHK^{-/-}$ nice. n=7 per group. Con vs HFCS compared by t-test with correction for multiple comparisons using Holm-Sidak method. No significant differences. FIG. 7C graphically illustrates the total number of tumors from $APC^{-/-}$ and $APC^{-/-}$; $KHK^{-/-}$ mice treated with a daily oral gavage of water (Con) or HFCS for 8 weeks. $APC^{-/-}$ Con (n=19) and HFCS (n=18); $APC^{-/-}$; $KHK^{-/-}$ mice. n=10 per group. Two-way ANOVA showing no significant changes between groups. FIG. 7D graphically illustrate the relative abundance of saturated and unsaturated fatty acids from $APC^{-/-}$ tumors compared to $APC^{-/-}$; $KHK^{-/-}$ tumors. n=3 per group. Student's t-test $^{*}P<0.05$. All data represent means±S.E.M.

DETAILED DESCRIPTION

Figure 1A:
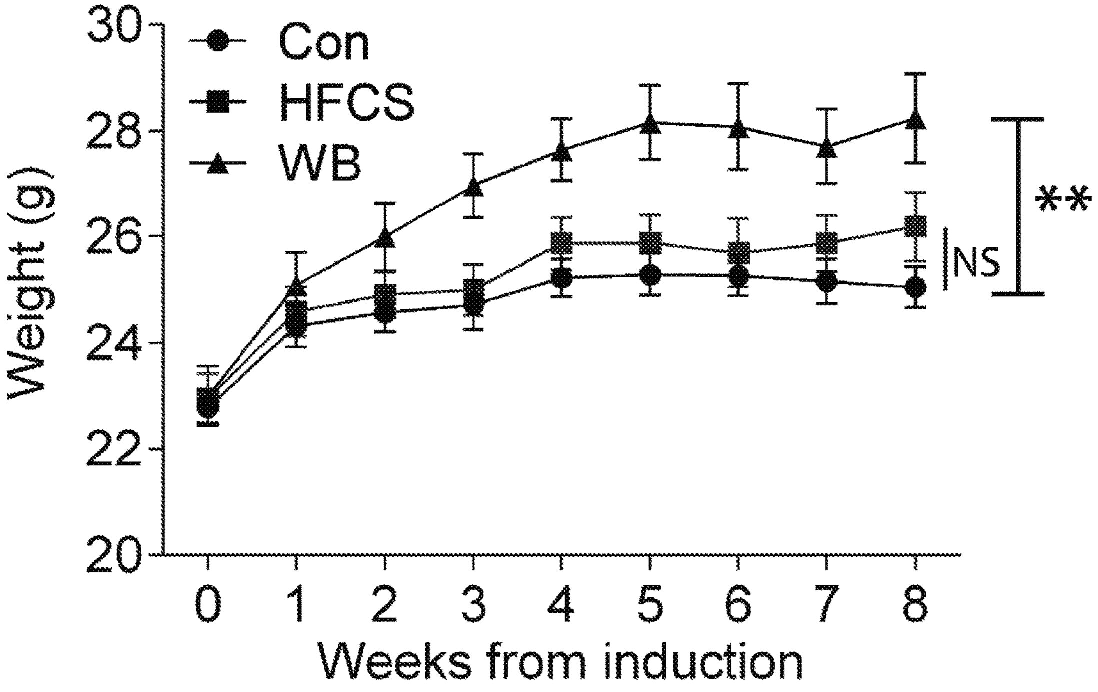
FIGS. 1A-1L illustrate that high-fructose corn syrup (HFCS) enhances intestinal tumor growth in APC-deficient mice independent of obesity.
Figure 1B:
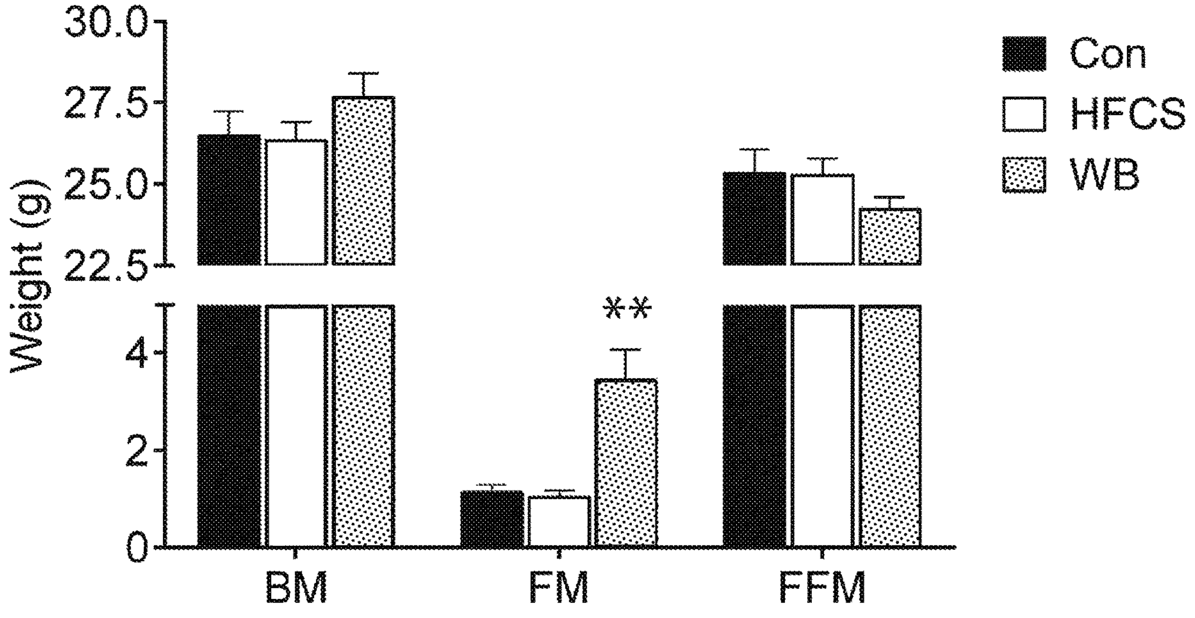
Figure 1C:
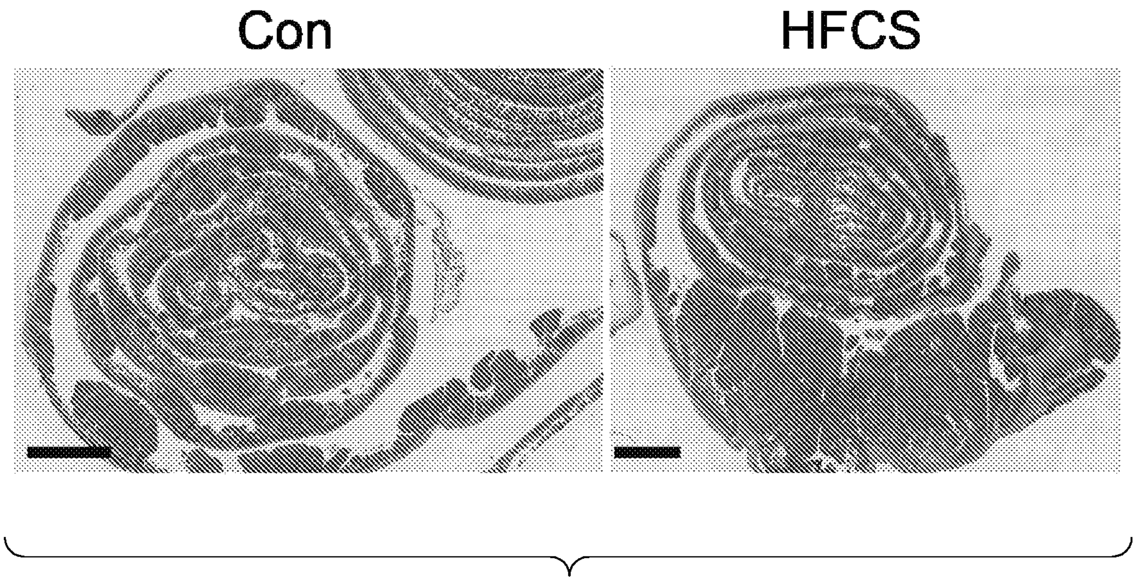
Figure 1D:
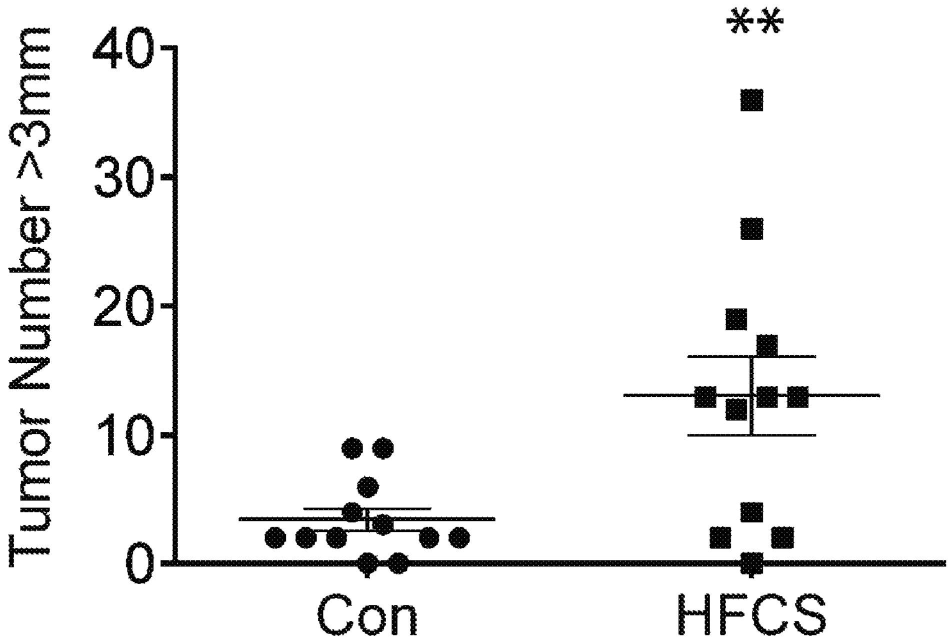
Figure 1E:
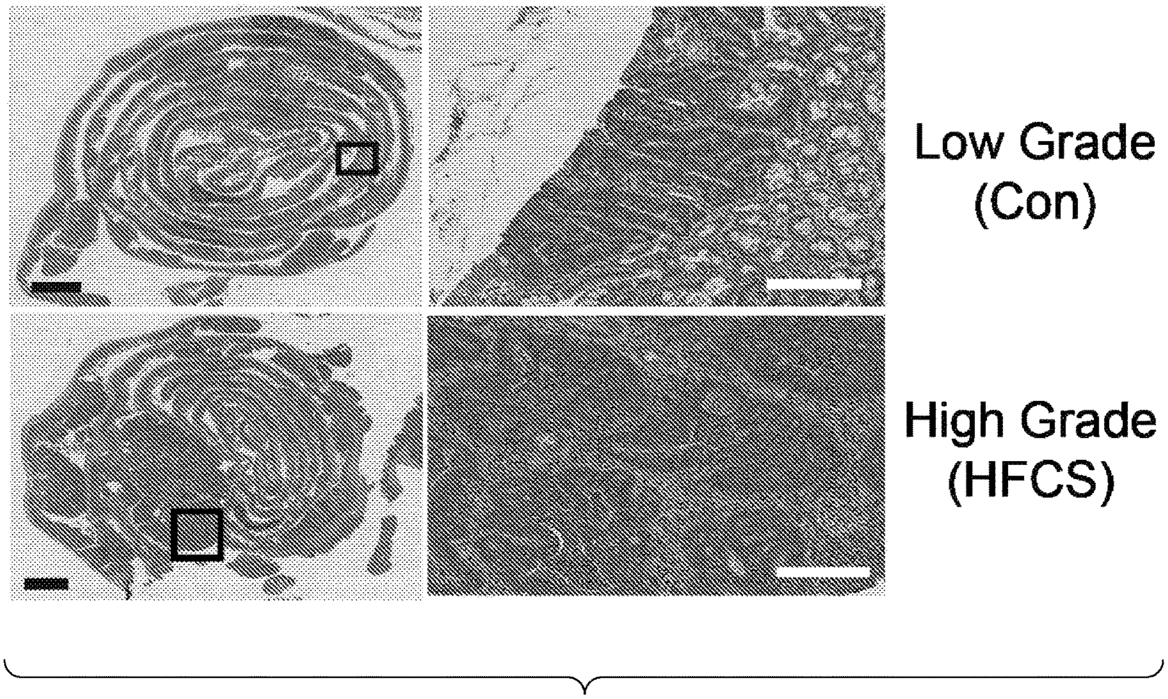
Figure 1F:
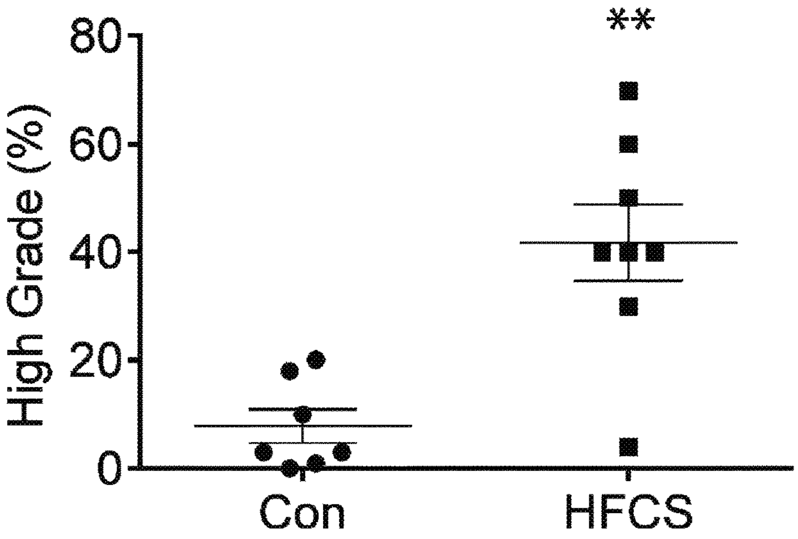
Figure 1G:
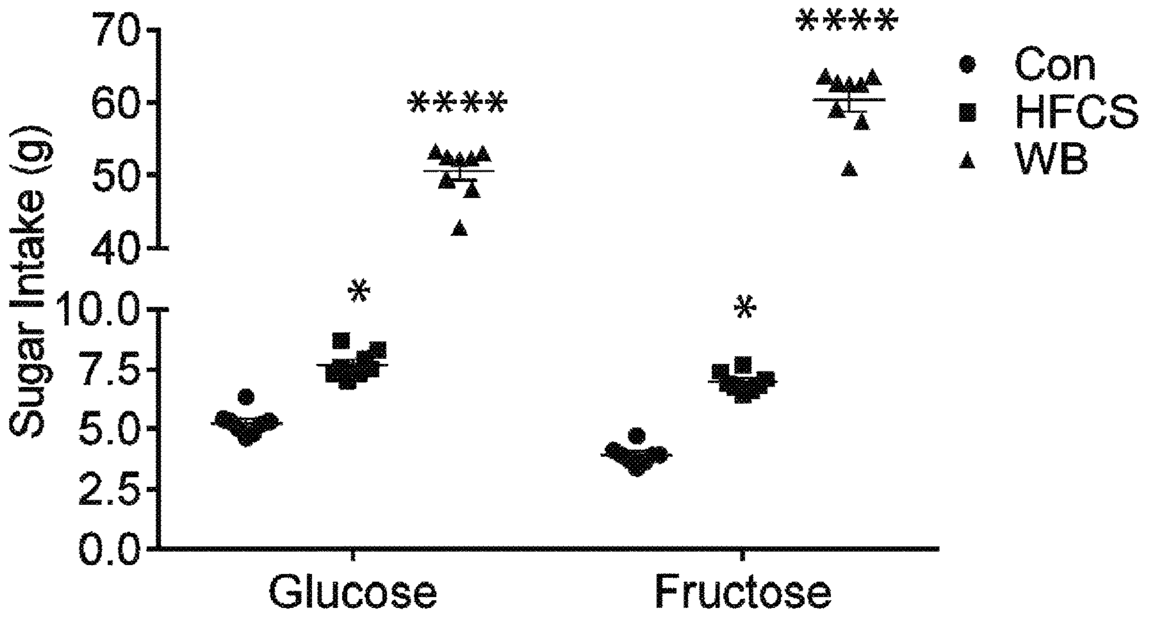
Figure 1H:
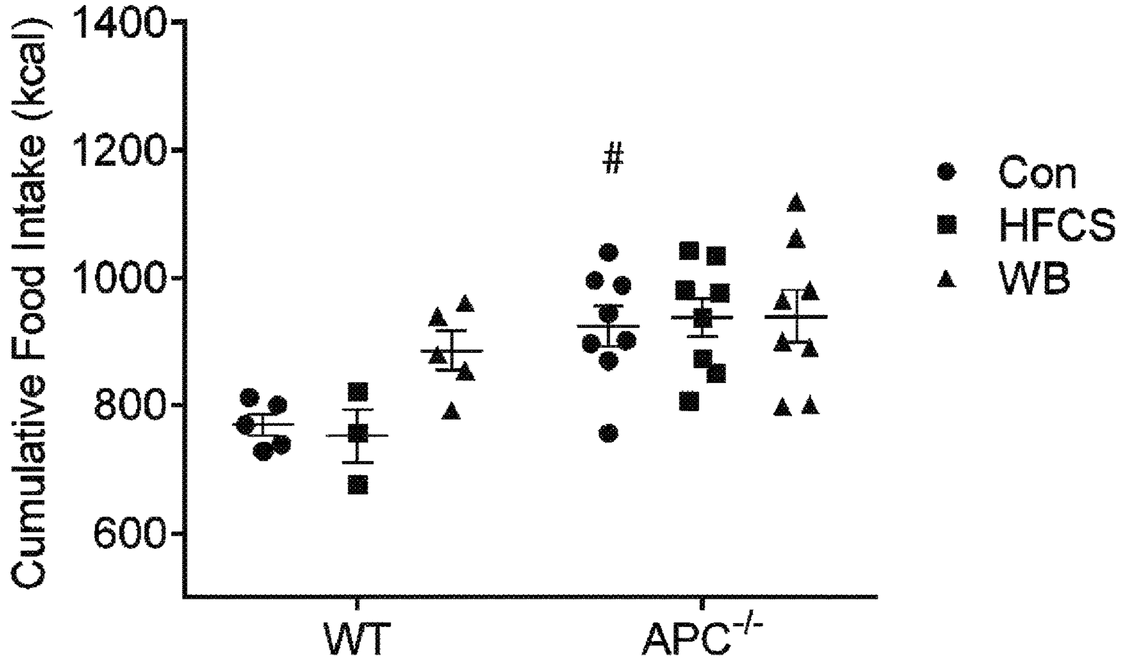
Figure 1I:
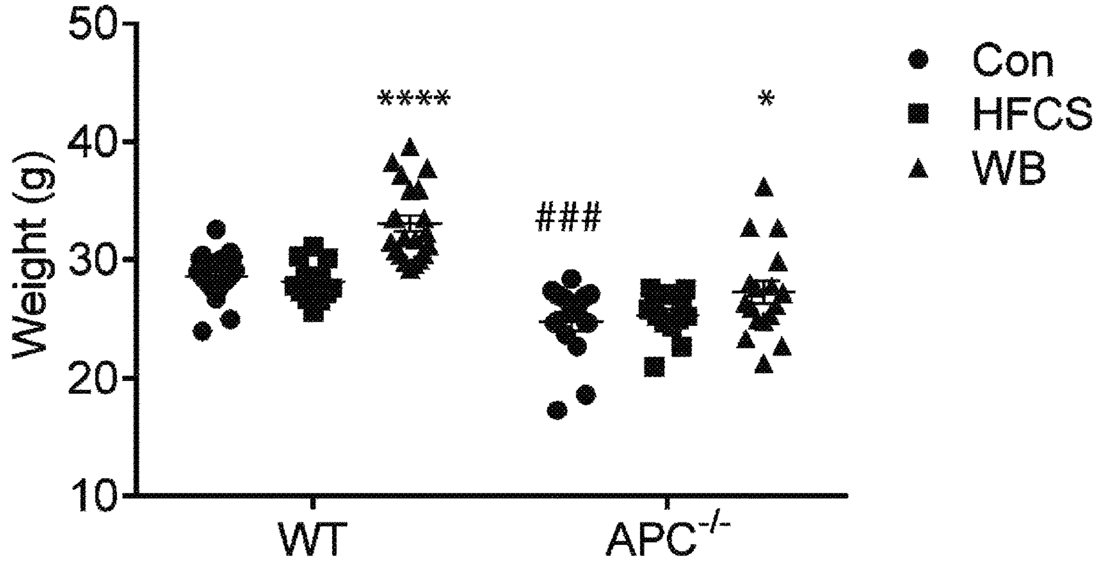
Figure 1J:
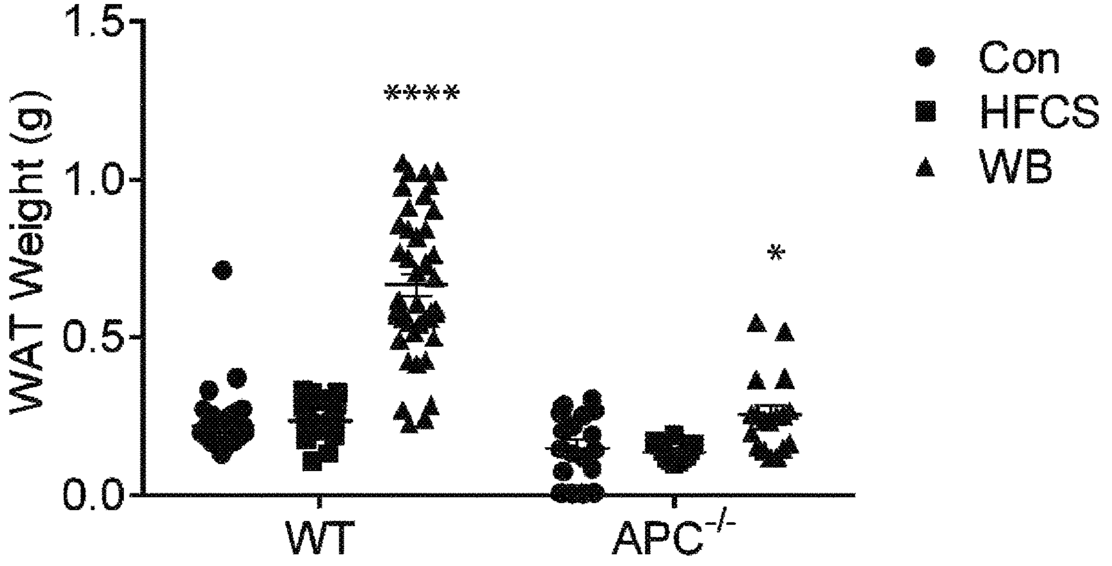
Figure 1K:
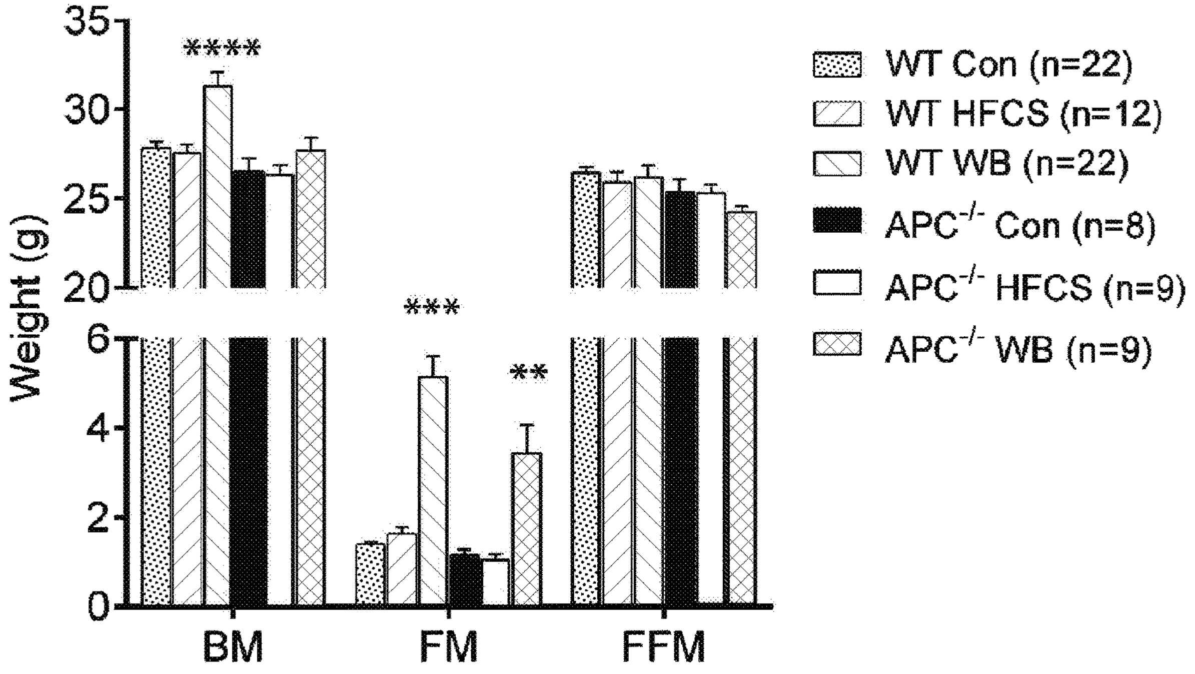
Figure 1L:
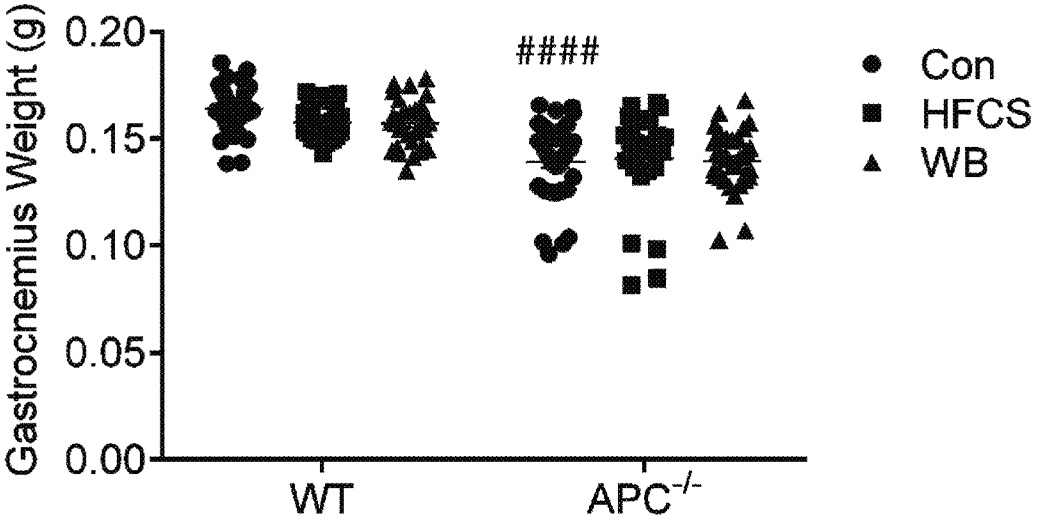

Methods and compositions are described herein that can be used to inhibit or delay the onset of certain types of cancer, including colorectal cancer and cancers of the small intestine. Colorectal cancer is one of cancer species which occurs in the large intestine (cecum, colon and rectum). Cancers that occur in the anal canal are also included in the definition of colorectal cancer, as well as intestinal polyps or adenomas that may eventually turn into cancer. In general, the colorectal cancer is divided into cecum cancer, colon cancer and rectum cancer. In some cases, the patient or subject that is treated has an adenomatous polyposis coli (APC) genetic mutation. The methods and compositions described herein can be used to inhibit or treat patients with APC mutations and/or any of these cancer types.

The methods and compositions described herein can inhibit (1) fructose transport (e.g., via GLUT5), (2) metabolism (e.g., via ketohexokinase, KHK), (3) fatty acid synthesis (e.g., via FASN), (4) phosphoinositide 3-kinase (PI3K), or (5) a combination thereof to inhibit and/or prevent tumor growth. The methods can include modifications of diet such as reducing or eliminating fructose from the diet, reducing or eliminating sugars from the diet, reducing or eliminating certain amino acids from the diet, reducing or eliminating carbohydrates from the diet, or combinations thereof. For example, the methods can include use of a ketogenic diet, a diet with a low glycemic index, or a sugar-free diet.

Diet

The methods described herein can include reducing or eliminating certain sugars, carbohydrates, amino acids, and combinations thereof.

Sugars and carbohydrates that include high amounts of sucrose, glucose, and especially fructose, can be reduced or eliminated from the diet to reduce the incidence and progression of cancers such as colorectal cancers and cancers of the small intestine. In general, to reduce the incidence and progression of cancers such as colorectal cancers and cancers of the small intestine the diet should have less than about 25 grains of sugar per day, or less than about 20 grains of sugar per day, or less than about 15 grams of sugar per day, or less than about 10 grams of sugar per day, or less than about 5 grams of sugar per day.

Some types of sugar are more problematic than other types. High fructose corn syrup consists of glucose and fructose in a 45:55 ratio and the amounts ingested should be reduced because it contains so much fructose. Honey and tapioca syrup also contain significant amounts of fructose. High levels of fructose are problematic because such levels accelerate glycolysis and de novo lipogenesis that support tumor growth.

Examples of foods that contain fructose and should be avoided include high fructose corn syrup, sugar-sweetened beverages (SSBs, which are primarily sweetened with high-fructose corn syrup), honey, tapioca syrup, candy, sweetened yogurt, salad dressings sweetened with sugars or high fructose corn syrup, frozen or boxed dinners dressings sweetened with sugars or high fructose corn syrup, frozen pizzas sweetened with sugars or high fructose corn syrup, breads dressings sweetened with sugars or high fructose corn syrup, canned fruit sweetened with sugars or high fructose corn syrup, fruit juices, and granola bars sweetened with sugars or high fructose corn syrup. However, some types of fruits and vegetables also contain significant amounts of fructose including apples, grapes, watermelon, asparagus, peas, and zucchini, which should also be avoided in some cases.

In some cases, the subject's diet can be a fructose-free diet, or a diet that is substantially reduced in fructose, combined with a KHK inhibitor (e.g., any of these described herein). One example of a KHK inhibitor that can be used is a PF-06835919 inhibitor.

Foods that include high amounts of the amino acid glycine can be reduced or eliminated from the diet to reduce the incidence and progression of cancers such as colorectal cancers and cancers of the small intestine. In general, a diet to reduce the incidence and progression of cancers can include less than 10 grams per day, or less than 7 grams per day, or less than 5 grams per clay, or less than 4 grams per day, or less than 3 grains per day, or less than 2 grams per day, or less than 1 gram per day of glycine.

Glycine is abundant in cartilage, collagen, bones, tendons, and gelatin. Examples of foods containing significant amounts of glycine that can be avoided to reduce the incidence and progression of cancers include gelatin, pork skins, pork ears, pork feet, meat-by-products, jellied beef luncheon meat, chicken breast, corned beef, ostrich, crustaceans (crab, Alaska king crab, mollusks, lobsters), etc. The following website provides a listing of foods high in glycine nutritiondata.self.com/foods-000094000000000000000.html. The following website provides listings of low glycine foods: eatthismuch.com/food/browse/low-glycine-foods/?q=&type=food&page=3&order_by=glycine&show_nutrient=glycine.

Foods that include high amounts of the amino acid serine can be reduced or eliminated from the diet to reduce the incidence and progression of cancers such as colorectal cancers and cancers of the small intestine. In general, a diet to reduce the incidence and progression of cancers can include less than 10 grams per day, or less than 7 grams per day, or less than 5 grams per day, or less than 4 grams per day, or less than 3 grams per day, or less than 2 grains per day, or less than 1 gram per day of serine.

Foods containing significant amounts of serine include fish (salmon, hake, monkfish, cod, and fish broth), milk, eggs, cheeses, beans, carob seeds, soy (tofu, tempeh, soymilk), peanuts, asparagus, yogurt, and lentils. The following website provides a listing of foods high in serine: nutritiondata.self.com/foods-000096000000000000000.html.

In some cases, the diet can be a serine/glycine depleted diet together with one or more phosphoglycerate dehydrogenase (PHGDH) inhibitors. Such PHGDH inhibitors include any of the following: PH719, NCT-502, NCT-503, TDI-8077, TDI-6570, CBR-5884, CBR-5807, CBR-6936, CBR-9480, PKUMDL-WQ-2201, PKUMDL-WQ-2101, alpha-ketothiomide inhibitor, AZ compound, Raze compound.

Some examples of PHGDH inhibitors are shown below.

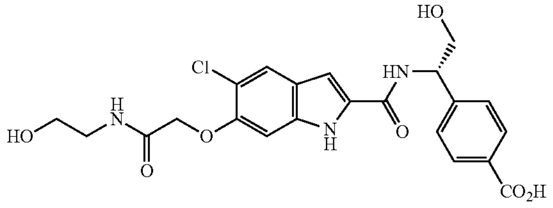

Astra Zeneca PHGDH inhibitor
SPR $K_D$ = 0.18 μM

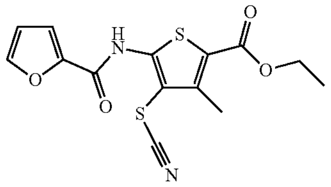

CBR-5884
$IC_{50}$ = 33 μM

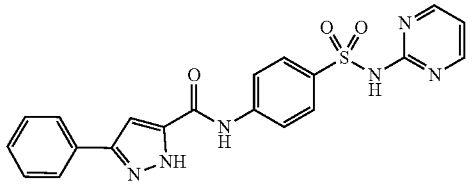

Representative Raze Inhibitor
$IC_{50}$ < 50 μM

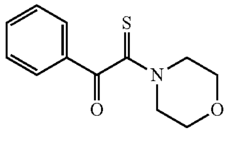

α-Ketothioamide inhibitor
$IC_{50}$ = 30.9 μM

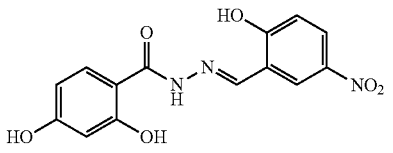

PKUMDL-WQ-2101
$IC_{50}$ = 34.8 μM

-continued

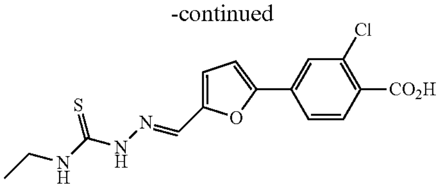

PKUMDL-WQ-2201
$IC_{50}$ = 35.7 μM

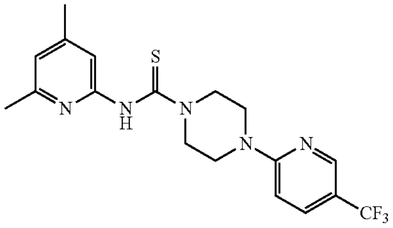

NCT-502
$IC_{50}$ = 3.7 μM

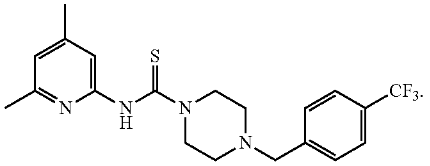

NCT-503
$IC_{50}$ = 2.5 μM

In some cases, the diet can be a ketogenic dict that is highly palatable and easy to consume. A ketogenic diet involves ingestion of more calories from fat and less from carbohydrates. Hence a ketogenic diet is classified as a low, or very low carbohydrate diet. Sugars are generally eliminated or significantly reduced from a ketogenic diet. For example, a subject's ketogenic diet can involve ingestion of less than 30 grams carbohydrate per day, less than 20 grains carbohydrates, less than 15 grams carbohydrate per day, less than 10 grams carbohydrates, less than 7 grams carbohydrate per day, less than 5 grams carbohydrates, or less than 3 grams of carbohydrates per day. In some cases, the Atkins diet (an example of a high fat and high protein diet) can be used as a ketogenic diet.

In some cases, such a ketogenic diet can involve ingestion of a 3:1 ratio of ketogenic-to-antiketogenic macromolecules, which results in approximately 85% fat, 12% protein, and 3% carbohydrates. There is a diverse mixture of fats. For example, the fats can include those from plants, nuts, and animal products. The diet can be actively managed by dieticians who interact with patients on the diet on a weekly basis. Such a diet can obtain up to 80% compliance, up to 90% compliance, up to 95% compliance, up to 96% compliance, up to 98% compliance, up to 99% compliance, or even up to 100% compliance. For example, 100% compliance over 4 weeks was achieved in an ongoing pilot study in women with endometrial cancer.

In some embodiments, the ketogenic diet includes at most 5%, 6%, 7%, 8%, 9%, 10%, 11%, 12%, 13%, 14%, or 15% protein, with the remainder of the diet made up of fat, fiber, ash, and carbohydrates. In some embodiments, the ketogenic diet includes at most 2%, 3%, 4%, 5%, 6%, 7%, 8%, 9%, or 10% carbohydrates, with the remainder of the diet made up of fat, fiber, ash, and protein. In some embodiments, the ketogenic diet includes fat measured in grams and carbohydrates and proteins collectively measured in grams in a ratio of 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, or 4.5 to one (1) of fat to carbohydrate/protein. A comparison of a ketogenic diet with a normal diet is shown below as Table 1.

TABLE 1

| | Normal Diet | Ketogenic Diet |
|---|---|---|
| Protein | 21% | 8.60% |
| Fat | 11.30% | 75.10% |
| Fiber | 4.60% | 4.80% |
| Ash | 7% | 3.00% |
| Carbohydrate | 62% | 3.20% |

The methods described herein can include such a ketogenic diet with administration of PI3 kinase, GLUT5, KHK, FASN, PHGDH inhibitors, including any of those described herein.

In some cases, for any of the methods disclosed herein, "administration" includes providing one or more of a PI3 kinase inhibitor, GLUT5 inhibitor, KHK inhibitor, FASN inhibitor, PHGDH inhibitor, and/or ketogenic diet to the subject, e.g., to be ingested or administered at the same or a later time, or providing a prescription for one or more of a PI3 kinase inhibitor, GLUT5 inhibitor, KHK inhibitor, FASN inhibitor, PHGDH inhibitor, and/or ketogenic diet to the subject. In certain embodiments, "administration" of the ketogenic diet comprises instructing the subject to follow a ketogenic diet.

GLUT5

GLUT5 is a fructose-transporter, and a member of the facilitative glucose transporter (GLUT, SLC2) family. One example of a *Homo sapiens* GLUT5 protein sequence is shown below as SEQ ID NO:1 (NCBI accession no. NP_001315548.1).

```
  1 MEQQDQSMKE GRLTLVLALA TLIAAFGSSF QYGYNVAAVN
 41 SPALLMQQFY NETYYGRTGE FMEDFPLTLL WSVTVSMFPF
 81 GGFIGSLLVG PLVNKFGRKG ALLFNNIFSI VPAILMGCSR
121 VATSFELIII SRLLVGICAG VSSNVVPMYL GELAPKNLRG
161 ALGVVPQLFI TVGILVAQIF GLRNLLANVD GWPILLGLTG
201 VPAALQLLLL PFFPESPRYL LIQKKDEAAA KKALQTLRGW
241 DSVDREVAEI RQEDEAEKAA GFISVLKLFR MRSLRWQLLS
281 IIVLMGGQQL SGVNAIYYYA DQIYLSAGVP EEHVQYVTAG
321 TGAVNVVMTF CAVFVVELLG RRLLLLLGFS ICLIACCVLT
361 AALALQDTVS WMPYISIVCV ISYVIGHALG PSPIPALLIT
401 EIFLQSSRPS AFMVGGSVHW LSNFTVGLIE PFIQEGLGPY
441 SFIVFAVICL LTTIYIFLIV PETKAKTFIE INQIFTKMNK
481 VSEVYPEKEE LKELPPVTSE Q
```

An example of a cDNA that encodes the GLUT5 protein with SEQ ID NO:1 is shown below as SEQ ID NO:2 (with NCBI accession no. NM_001328619.1).

```
   1 GCTTCTCACA GTCTCCCACC CCGCCCTGCT CGCGGAGCCT
  41 GCAGGCCTCG GCCTCATGGC GGCCTGAGGC AGGGGCCTGG
  81 AGGCTGGTCC GCCCGCCACG AAGGTTGGGG GGTCCCTGGC
 121 CAGAAGCAGG ACCCGGGCGA GGCTGAGGGG GACTCTGGCA
 161 GAAGCTGAAG GGGACCCGGT GCACGCGTTA CTTTGGCTAA
 201 AAGGAGGTGA GCGGCACTCT GCCCTTCCAG AGCAAGCATG
 241 GAGCAACAGG ATCAGAGCAT GAAGGAAGGG AGGCTGACGC
 281 TTGTGCTTGC CCTGGCAACC CTGATAGCTG CCTTTGGGTC
 321 ATCCTTCCAG TATGGGTACA ACGTGGCTGC TGTCAACTCC
 361 CCAGCACTGC TCATGCAACA ATTTTACAAT GAGACTTACT
 401 ATGGTAGGAC CGGTGAATTC ATGGAAGACT TCCCCTTGAC
 441 GTTGCTGTGG TCTGTAACCG TGTCCATGTT TCCATTTGGA
 481 GGGTTTATCG GATCCCTCCT GGTCGGCCCC TTGGTGAATA
 521 AATTTGGCAG AAAAGGGGCC TTGCTGTTCA ACAACATATT
 561 TTCTATCGTG CCTGCGATCT TAATGGGATG CAGCAGAGTC
 601 GCCACATCAT TTGAGCTTAT CATTATTTCC AGACTTTTGG
 641 TGGGAATATG TGCAGGTGTA TCTTCCAACG TGGTCCCCAT
 681 GTACTTAGGG GAGCTGGCCC CTAAAAACCT GCGGGGGGCT
 721 CTCGGGGTGG TGCCCCAGCT CTTCATCACT GTTGGCATCC
 761 TTGTGGCCCA GATCTTTGGT CTTCGGAATC TCCTTGCAAA
 801 CGTAGATGGC TGGCCGATCC TGCTGGGGCT GACCGGGGTC
 841 CCCGCGGCGC TGCAGCTCCT TCTGCTGCCC TTCTTCCCCG
 881 AGAGCCCCAG GTACCTGCTG ATTCAGAAGA AAGACGAAGC
 921 GGCCGCCAAG AAAGCCCTAC AGACGCTGCG CGGCTGGGAC
 961 TCTGTGGACA GGGAGGTGGC CGAGATCCGG CAGGAGGATG
1001 AGGCAGAGAA GGCCGCGGGC TTCATCTCCG TGCTGAAGCT
1041 GTTCCGGATG CGCTCGCTGC GCTGGCAGCT GCTGTCCATC
1081 ATCGTCCTCA TGGGCGGCCA GCAGCTGTCG GGCGTCAACG
1121 CTATCTACTA CTACGCGGAC CAGATCTACC TGAGCGCCGG
1161 CGTGCCGGAG GAGCACGTGC AGTACGTGAC GGCCGGCACC
1201 GGSGGCGTGA ACGTGGTCAT GACCTTCTGC GCCGTGTTCG
1241 TGGTGGAGCT CCTGGGTCGG AGGCTGCTGC TGCTGCTGGG
1281 CTTCTCCATC TGCCTCATAG CCTGCTGCGT GCTCACTGCA
1321 GCTCTGGCAC TGCAGGACAC AGTGTCCTGG ATGCCATACA
1361 TCAGCATCGT CTGTGTCATC TCCTACGTCA TAGGACATGC
1401 CCTCGGGCCC AGTCCCATAC CCGCGCTGCT CATCACTGAG
1441 ATCTTCCTGC AGTCCTCTCG GCCATCTGCC TTCATGGTGG
1481 GGGGCAGTGT GCACTGGCTC TCCAACTTCA CCGTGGGCTT
1521 GATCTTCCCG TTCATCCAGG AGGGCCTCGG CCCGTACAGC
1561 TTCATTGTCT TCGCCGTGAT CTGCCTCCTC ACCACCATCT
1601 ACATCTTCTT GATTGTCCCG GAGACCAAGG CCAAGACGTT
```

-continued

```
1641 CATAGAGATC AACCAGATTT TCACCAAGAT GAATAAGGTG
1681 TCTGAAGTGT ACCCGGAAAA GGAGGAACTG AAAGAGCTTC
1721 CACCTGTCAC TTCGGAACAG TGACTCTGGA GAGGAAGCCA
1761 GTGGAGCTGG TCTGCCAGGG GCTTCCCACT TTGGCTTATT
1801 TTTCTGACTT CTAGCTGTCT GTGAATATCC AGAAATAAAA
1841 CAACTCTGAT GTGGAATGCA GTCCTCATCT CCAGCCTCCC
1881 CACCCCAGTG GGAACTGTGC AAAGGGCTGC CTTGCTGTTC
1921 TTGAAGCTGG GCTGTCTCTC TCCATGTTGG CCTGTCACCA
1961 GACCCGAGTC AATTAAACAG CTGGTCCTCC ACTTTGCTGG
2001 TTCAGCCTTC GTGTGGCTCC TGGTAACGTG GCTCCACCTT
2041 GATGGGTCAA CCTTTGTGTG GCTCCTGGTA ACATAACAAC
2081 AACAGTTACT ATAGTGGTGA GATGGAAGGA ATCAAATTTT
2121 GCCAGAGAAA CTAACTTGGT GGCCCCGACA GGTCTTCCGG
2161 GGCCATGGGC ATTTGTTTAG AGCCAAATTC ATCCTCTTAC
2201 CAGATCCTTT TCCAGAAATA CCTGTCTAGG AAGGTGTGAT
2241 GTCAGAAACA ATGACATCCA GAAAGCTGAG GAACAGGTTC
2281 CTGTGGAGAC ACTGAGTCAG AATTCTTCAT CCTAAATTAT
2321 TTTGTTAGTG GAAAATGGAA TTGCTTCTGT GTAGTCAATA
2361 AAATGAACCT GATCACTTTT CAA
```

Another example of a *Homo sapiens* GLUT5 protein sequence is shown below as SEQ ID NO:3 (NCBI accession no. AAA52570.1).

```
  1 MEQQDOSMKE GRLTLVLALA TLIAAFGSSE QYGYNVAAVN
 41 SPALLMQQFY NETYYGRTGE FMEDEPLTLL WSVTVSMFPF
 81 GGFIGSLLVG PLVNKFGRKG ALLFNNIFSI VPAILMGCSR
121 VATSFELIII SRLLVGICAG VSSNVVPMYL GELAPKNLRG
141 ALGVVPQLFI TVGILVAQIF GLRNLLANVD GWPILLGLTG
181 VPAALQLLLL PFFPESPRYL LIQKKDEAAA KKALQTLRGW
241 DSVDREVAEI RQEDEAEKAA GFISVLKLFR MRSLRWQLLS
281 IIVLMGGQQL SGVNAIYYYA DQIYLSAGVP EEHVQYVTAG
321 TGAVNVVMTF CAVFVVELLG RRLLLLLGFS ICLIACCVLT
361 AALALQDTVS WMPYISIVCV ISYVIGHALG PSPIPALLIT
401 EIFLQSSRPS AFMVGGSVHW LSNFTVGLIF PFIQEGLGPY
441 SFIVFAVICL LTTIYIFLIV PETKAKTFIE INQIFTKMNK
481 VSEVYPEKEE LKELPPVTSE Q
```

An example of a cDNA that encodes the GLUT5 protein with SEQ ID NO:3 is shown below as SEQ ID NO:4 (with NCBI accession no. M55531.1).

```
  1 CTTCTCTCTC CATTCAGTGC ACGCGTTACT TTGGCTAAAA
 41 GGAGGTGAGC GGCACTCTGC CCTTCCAGAG CAAGCATGGA
```

-continued

```
  81 GCAACAGGAT CAGAGCATGA AGGAAGGGAG GCTGACGCTT
 121 GTGCTTGCCC TGGCAACCCT GATAGCTGCC TTTGGGTCAT
 161 CCTTCCAGTA TGGGTACAAC GTGGCTGCTG TCAACTCCCC
 201 AGCACTGCTC ATGCAACAAT TTTACAATGA GACTTACTAT
 241 GGTAGGACCG GTGAATTCAT GGAAGACTTC CCCTTGACGT
 281 TGCTGTGGTC TGTAACCGTG TCCATGTTTC CATTTGGAGG
 321 GTTTATCGGA TCCCTCCTGG TCGGCCCCTT GGTGAATAAA
 361 TTTGGCAGAA AAGGGGCCTT GCTGTTCAAC AACATATTTT
 401 CTATCGTGCC TGCGATCTTA ATGGGATGCA GCAGAGTCGC
 441 CACATCATTT GAGCTTATCA TTATTTCCAG ACTTTTGGTG
 481 GGAATATGTG CAGGTGTATC TTCCAACGTG GTCCCCATGT
 521 ACTTAGGGGA GCTGGCCCCT AAAAACCTGC GGGGGGCTCT
 561 CGGGGTGGTG CCCCAGCTCT TCATCACTGT TGGCATCCTT
 601 GTGGCCCAGA TCTTTGGTCT TCGGAATCTC CTTGCAAACG
 641 TAGATGGCTG GCCGATCCTG CTGGGGCTGA CCGGGGTCCC
 681 CGCGGCGCTG CAGCTCCTTC TGCTGCCCTT CTTCCCCGAG
 721 AGCCCCAGGT ACCTGCTGAT TCAGAAGAAA GACGAAGCGG
 761 CCGCCAAGAA AGCCCTACAG ACGCTGCGCG GCTGGGACTC
 801 TGTGGACAGG GAGGTGGCCG AGATCCGGCA GGAGGATGAG
 841 GCAGAGAAGG CCGCGGGCTT CATCTCCGTG CTGAAGCTGT
 881 TCCGGATGCG CTCGCTGCGC TGGCAGCTGC TGTCCATCAT
 921 CGTCCTCATG GGCGGCCAGC AGCTGTCGGG CGTCAACGCT
 961 ATCTACTACT ACGCGGACCA GATCTACCTG AGCGCCGGCG
1001 TGCCGGAGGA GCACGTGGAG TAGGTGACGG CCGGCACCGG
1041 GGCCGTGAAC GTGGTCATGA CCTTCTGCGC CGTGTTCGTG
1081 GTGGAGCTCC TGGGTCGGAG GCTGCTGCTG CTGCTGGGCT
1121 TCTCCATCTG CCTCATAGCC TGCTGCGTGC TCACTGCAGC
1161 TCTGGCACTG CAGGACACAG TGTCCTGGAT GCCATACATC
1201 AGCATCGTCT GTGTCATCTC CTACGTCATA GGACATGCCC
1241 TCGGGCCCAG TCCCATACCC GCGCTGCTCA TCACTGAGAT
1281 CTTCCTGCAG TCCTCTCGGC CATCTGCCTT CATGGTGGGG
1321 GGCAGTGTGC ACTGGCTCTC CAACTTCACC GTGGGCTTGA
1361 TCTTCCCGTT CATCCAGGAG GGCCTCGGCC CGTACAGCTT
1401 CATTGTCTTC GCCGTGATCT GCCTCCTCAC CACCATCTAC
1441 ATCTTCTTGA TTGTCCCGGA GACCAAGGCC AAGACGTTCA
1481 TAGAGATCAA CCAGATTTTC ACCAAGATGA ATAAGGTGTC
1521 TGAAGTGTAC CCGGAAAAGG AGGAACTGAA AGAGCTTCCA
1561 CCTGTCACTT CGGAACAGTG ACTCTGGAGA GGAAGCCAGT
1601 GGAGCTGGTC TGCCAGGGGC TTCCCACTTT GGCTTATTTT
1641 TCTGACTTCT AGCTGTCTGT GAATATCCAG AAATAAAACA
1681 ACTCTGATGT GGAATGCAGT CCTCATCTCC AGCCTCCCCA
```

-continued

```
1721 CCCCAGTGGG AACTGTGCAA AGGGCTGCCT TGCTGTTCTT
1761 GAAGCTGGGC TGTCTCTCTC CATGTTGGCC TGTCACCAGA
1801 CCCGAGTCAA TTAAACAGCT GGTCCTCCAC TTTGCTGGTT
1841 CAGCCTTCGT GTGGCTCCTG GTAACGTGGC TCCACCTTGA
1881 TGGGTCAACC TTTGTGTGGC TCCTGGTAAC ATAACAACAA
1921 CAGTTACTAT AGTGGTGAGA TGGAAGGAAT CAAATTTTGC
1961 CAGAGAAACT AACTCGGTGG CCCCAACAGG TCTTCCGGGG
2001 CCATGGGCAT TTGTTTAGAG CCAAATTCAT CCTCTTACCA
2041 GATCCTTTTC CAGAAATACC TGTCTAGGAA GGTGTGATGT
2081 CAGAAACAAT GACATCCAGA AAGCTGAGGA ACAGGTTCCT
2121 GTGGAGACAC TGAGTCAGAA TTCTTCATCC AAATTATTTT
2161 GTTAGTGGAA AATGGAATTG CTTCTGTGTA GTCAATAAAA
2201 TGAACCTGAT CACTTTTC
```

Subjects can express a GLUT5 enzyme that can have one or more amino acid differences compared to the sequences described herein. For example, subjects can express a GLUT5 enzyme at least 80%, at least 85%, at least 90%, at least 95%, at least 96%, at least 97%, at least 99% amino acid sequence identity or similarity with the GLUT5 amino acid sequences described herein. Similarly, subjects can express GLUT5 RNA with one or more nucleotide differences compared to the GLUT5 nucleic acids described herein. For example, subjects can express a GLUT5 RNA at least 80%, at least 85%, at least 90%, at least 95%, at least 96%, at least 97%, at least 99% amino acid sequence identity or similarity with the GLUT5 nucleic acid sequences described herein.

As described herein, inhibition of GLUT5 can inhibit cancer, including colorectal cancer and cancers of the small intestine. One example of an inhibitor of GLUT5 is N-[4-(methylsulfonyl)-2-nitrophenyl]-1,3-benzodioxol-5-amine (MSNBA), with the following structure. See WO2016201214A1.

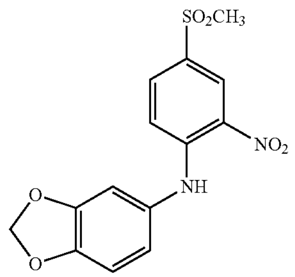 [SMILES: CS(=O)(=O)c1ccc(Nc2ccc3c(c2)OCO3)c([N+](=O)[O-])c1]

Other examples of GLUT5 inhibitors include N-(2,5-dimethoxybenzyl)-N-[4-(methylsulfonyl)-2-nitrophenyl] amine; N-(3,4-dimethoxyphenyl)-4-(methylsulfonyl)-2-nitroaniline; N-[1-(3-fluoro-4-methoxypheny 1) ethyl]-4-(methylsulfonyl)-2-nitroaniline; N-[1-(1,3-benzodioxol-5-yl) ethyl]-4-(methylsulfonyl)-2-nitroaniline; and N-(3,5-dimethoxyphenyl)-4-(methylsulfonyl)-2-nitroaniline. See WO2016201214A1. Structures of some GLUT5 inhibitors are shown below.

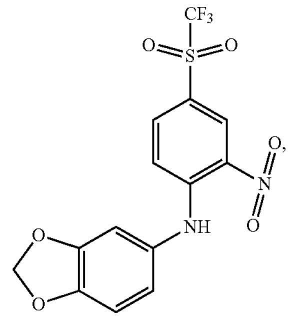

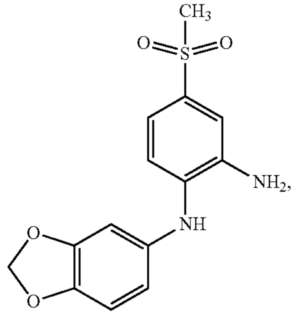

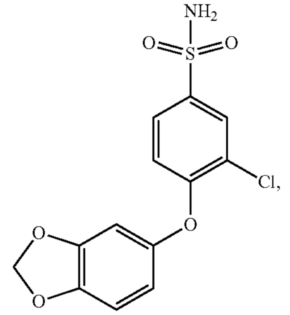

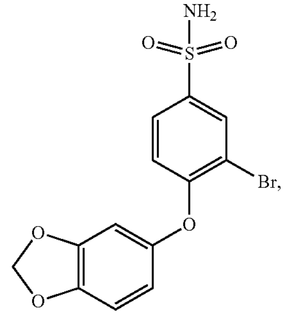

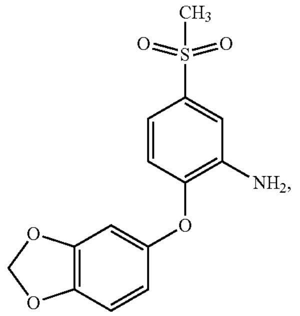

-continued

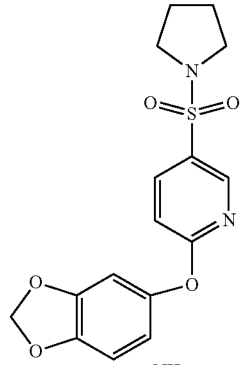

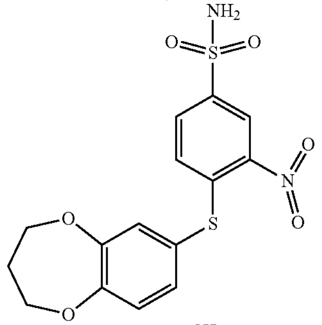

or

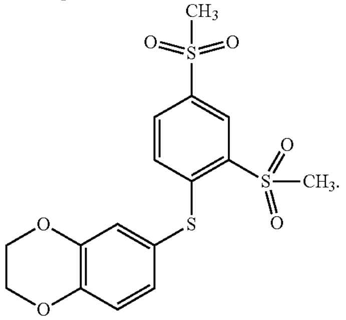

Additional inhibitors of GLUT5 are provided in JP 2015-205827 A.

Ketohexokinase (KHK)

Ketohexokinase (KHK) is a fructokinase that catalyzes the phosphorylation of fructose to fructose-1-phosphate (F1P) in the first step in fructolysis. The C isoform of fructokinase is the predominant form of the enzyme in the liver, kidney and intestine, whereas the fructokinase A splice variant is expressed in most tumors and throughout the body. There are at least 12 other KHK isoforms expressed in humans.

One example of an amino acid sequence for a *Homo sapiens* isoform C of fructokinase (KHK) is shown below as SEQ ID NO:5 (NCBI accession no. NP_006479.1).

```
  1 MEEKQILCVG LVVLDVISLV DKYPKEDSEI RCLSQRWQRG
 41 GNASNSCTVL SLLGAPCAFM GSMAPGHVAD FLVADFRRRG
 81 VDVSQVAWQS KGDTPSSCCI INNSNGNRTI VLHDTSLPDV
121 SATDFEKVDL TQFKWIHIEG RNASEQVKML QRIDAHNTRQ
161 PPEQKIRVSV EVEKPREELF QLFGYGDVVF VSKDVAKHLG
201 FQSAEEALRG LYGRVRKGAV LVCAWAEEGA DALGPDGKLL
```

-continued

```
241  HSDAFPPPRV VDTLGAGDTF NASVIFSLSQ GRSVQEALRF

281  GCQVAGRRCG LQGPDGIV
```

An example of a cDNA that encodes the KHK protein with SEQ ID NO:5 is shown below as SEQ ID NO:6 (with NCBI accession no. NM_006488.3).

```
   1 AGGCAGGGCT GCAGATGCGA GGCCCAGCTG TACCTCGCGT
  41 GTCCCGGGTC GGGAGTCGGA GACGCAGGTG CAGGAGAGTG
  81 CGGGGCAAGT AGGGGATTTT CTCTTTGCAT TCTCGAGATC
 121 GCTTAGCCGC GCTTTAAAAA GGTTTGCATC AGCTGTGAGT
 161 CCATCTGACA AGCGAGGAAA CTAAGGCTGA GAAGTGGGAG
 201 GCGTTGCCAT CTGCAGGCCC AGGCAACCTG CTACGGGAAG
 241 ACCGGGGACC AAGACCTCTG GGTTGGCTTT CCTAGACCCG
 281 CTCGGGTCTT CGGGTGTCGC GAGGAAGGGC CCTGCTCCTT
 321 TCGTTCCCTG CACCCCTGGC CGCTGCAGGT GGCTCCCTGG
 361 AGGAGGAGCT CCCACGCGGA GGAGGAGCCA GGGCAGCTGG
 401 GAGCGGGGAC ACCATCCTCC TGGATAAGAG GCAGAGGCCG
 441 GGAGGAACCC CGTCAGCCGG GCGGGCAGGA AGCTCTGGGA
 481 GTAGCCTCAT GGAAGAGAAG CAGATCCTGT GCGTGGGGCT
 521 AGTGGTGCTG GACGTCATCA GCCTGGTGGA CAAGTACCCT
 561 AAGGAGGACT CGGAGATAAG GTGTTTGTCC CAGAGATGGC
 601 AGCGCGGAGG CAACGCGTCC AACTCCTGCA CCGTTCTCTC
 641 CCTGCTCGGA GCCCCCTGTG CCTTCATGGG CTCAATGGCT
 681 CCTGGCCATG TTGCTGACTT CCTGGTGGCC GACTTCAGGC
 721 GGCGGGGCGT GGACGTGTCT CAGGTGGCCT GGCAGAGCAA
 761 GGGGGACACC CCCAGCTCCT GCTGCATCAT CAACAACTCC
 801 AATGGCAACC GTACCATTGT GCTCCATGAC ACGAGCCTGC
 841 GAGATGTGTC TGCTACAGAC TTTGAGAAGG TTGATCTGAC
 881 CCAGTTCAAG TGGATCCACA TTGAGGGCCG GAACGCATCG
 921 GAGCAGGTGA AGATGCTGCA GCGGATAGAC GCACACAACA
 961 CCAGGCAGCC TCCAGAGCAG AAGATCCGGG TGTCCGTGGA
1001 GGTGGAGAAG CCACGAGAGG AGCTCTTCCA GCTGTTTGGC
1041 TACGGAGACG TGGTGTTTGT CAGCAAAGAT GTGGCCAAGC
1081 ACTTGGGGTT CCAGTCAGCA GAGGAAGCCT TGAGGGGCTT
1121 GTATGGTCGT GTGAGGAAAG GGGCTGTGCT TGTCTGTGCC
1161 TGGGCTGAGG AGGGCGCCGA CGCCCTGGGC CCTGATGGCA
1201 AATTGCTCCA CTCGGATGCT TTCCCGCCAC CCCGCGTGGT
1241 GGATACACTG GGAGCTGGAG ACACCTTCAA TGCCTCCGTC
1281 ATCTTCAGCC TCTCCCAGGG GAGGAGCGTG CAGGAAGCAC
1321 TGAGATTCGG GTGCCAGGTG GCCGGCAAGA AGTGTGGCCT
1361 GCAGGGCTTT GATGGCATCG TGTGAGAGCA GGTGCCGGCT
1401 CCTCACACAC CATGGAGACT ACCATTGCGG CTGCATCGCC
```

-continued

```
1441 TTCTCCCCTC CATCCAGCCT GGCGTCCAGG TTGCCCTGTT
1481 CAGGGGACAG ATGCAAGCTG TGGGGAGGAC TCTGCCTGTG
1521 TCCTGTGTTC CCCACAGGGA GAGGCTCTGG GGGGATGGCT
1561 GGGGGATGCA GAGCCTCAGA GCAAATAAAT CTTCCTCAGA
1601 GCCAGCTTCT CCTCTCAATG TCTGAACTGC TCTGGCTGGG
1641 CATTCCTGAG GCTCTGACTC TTCGATCCTC CCTCTTTGTG
1681 TCCATTCCCC AAATTAACCT CTCCGCCCAG GCCCAGAGGA
1721 GGGGCTGCCT GGGCTAGAGC AGCGAGAAGT GCCCTGGGCT
1761 TGCCACCAGC TCTGCCCTGG CTGGGGAGGA CACTCGGTGC
1801 CCCACACCCA GTGAACCTGC CAAAGAAACC GTGAGAGCTC
1841 TTCGGGGCCC TGCGTTGTGC AGACTCTATT CCCACAGCTC
1881 AGAAGCTGGG AGTCCACACC GCTGAGCTGA ACTGACAGGC
1921 CAGTGGGGGG CAGGGGTGCG CCTCCTCTGC CCTGCCCACC
1961 AGCCTGTGAT TTGATGGGGT CTTCATTGTC CAGAAATACC
2001 TCCTCCCGCT GACTGCCCCA GAGCCTGAAA GTCTCACCCT
2041 TGGAGCCCAC CTTGGAATTA AGGGCGTGCC TCAGCCACAA
2081 ATGTGACCCA GGATACAGAG TGTTGCTGTC CTCAGGGAGG
2121 TCCGATCTGG AACACATATT GGAATTGGGG CCAACTCCAA
2161 TATAGGGTGG GTAAGGCCTT ATAATGTAAA GAGCATATAA
2201 TGTAAAGGGC TTTAGAGTGA GACAGACCTG GATTAAAATC
2241 TGCCATTTAA TTAGCTGCAT ATCACCTTAG GGTACAGCAC
2281 TTAACGCAAT CTGCCTCAAT TTCTTCATCT GTCAAATGGA
2321 ACCAATTCTG CTTGGCTACA GAATTATTGT GAGGATAAAA
2361 TCATATATAA AATGCCCAGC ATGATGCCTG ATGTGTA
```

Another example of a *Homo sapiens* KUM protein sequence is shown below as 110 SEQ ID NO:7.

```
  1 MGSSHHHHHH SSGEVPRGSQ ILCVGLVVLD VISLVDKYPK
 41 EDSEIRCLSQ RWQRGGNASN SCTVLSLLGA PCAFMGSMAP
 81 GHVADFLVAD FRRRGVDVSQ VAWQSKGDTP SSCCIINNSN
121 GNRTIVLHDT SLPDVSATDF EKVDLTQFKW IHIEGRNASE
161 QVKMLQRIDA HNTRQPPEQK IRVSVEVEKP REELFQLFGY
201 GDVVFVSKDV AKHLGFQSAE EALRGLYGRV RKGAVLVCAW
241 AEEGADALGP DGKLLHSDAF PPPRVVDTLG AGDTFNASVI
281 FSLSQGRSVQ EALRFGCQVA GKKCGLQGFD GIV
```

Another example of a *Homo sapiens* KHK protein sequence is shown below as SEQ IF) NO:8 (NCBI accession no. P50053.2).

```
  1 MEEKQILCVG LVVLDVISLV DKYPKEDSEI RCLSQRWQRG
 41 GNASNSCTVI SLLGAPCAFM GSMAPGHVAD FLVADFRRRG
 81 VDVSQVAWQS KGDTPSSCCI INNSNGNRTI VLHDTSLPDV
```

-continued

```
121  SATDFEKVDL TQFKWIHIEG RNASEQVKML QRIDAHNTRQ

161  PPEQKIRVSV EVEKPKEELF QLFGYGDVVF VSKDVAKHLG

201  FQSAEEALRG LYGRVRKGAV LVCAWAEEGA DALGPDGKLL

241  HSDAFPPPRV VDTLGAGDTF NASVIFSLSQ GRSVQEALRF

281  GCQVAGKKCG LQGFDGIV
```

An example of a cDNA that encodes the KHK protein with SEQ ID NO:8 is shown below as SEQ ID NO:9 (with EMBL accession no. X78678.1).

```
  4  GTAGCCTCAT GGAAGAGAAG CAGATCCTGT GCGTGGGGCT

 41  AGTGGTGCTG GACGTCATCA GCCTGGTGGA CAAGTACCCT

 81  AAGGAGGACT CGGAGATAAG GTGTTTGTCC CAGAGATGGC

121  AGCGCGGAGG CAACGCGTCC AACTCCTGCA CCGTTCTCTC

161  CCTGCTCGGA GCCCCCTGTG CCTTCATGGG CTCAATGGCT

201  CCTGGCCATG TTGCTGATTT TGTCCTGGAT GACCTCCGCC

241  GCTATTCTGT GGACCTACGC TACACAGTCT TTCAGACCAC

281  AGGCTCCGTC CCCATCGCCA CGGTCATCAT CAACGAGGCC

321  AGTGGTAGCC GCACGATCCT ATACTATGAC AGGAGCCTGC

361  CAGATGTGTC TGCTACAGAC TTTGAGAAGG TTGATCTGAC

401  CCAGTTCAAG TGGATCCACA TTGAGGGCCG GAACGCATCG

441  GAGCAGGTGA AGATGCTGCA GCGGATAGAC GCACACAACA

481  CCAGGCAGCC TCAAGAGCAG AAGATCCGGG TGTCCGTGGA

521  GGTGGAGAAG CCACGAGAGG AGCTCTTCCA GCTGTTTGGC

561  TACGGAGACG TGGTGTTTGT CAGCAAAGAT GTGGCCAAGC

601  ACTTGGGGTT CCAGTCAGCA GAGGAAGCCT TGAGGGGCTT

641  GTATGGTCGT GTGAGGAAAG GGGCTGTGCT TGTCTGTGCC

681  TGGGCTGAGG AGGGCGCCGA CGCCCTGGGC CCTGATGGCA

721  AATTGCTCCA CTCGGATGCT TTCCCGCCAC CCCGCGTGGT

761  GGATACACTG GGAGCTGGAG ACACCTTCAA TGCCTCCGTC

801  ATCTTCAGCC TCTCCCAGGG GAGGAGCGTG CAGGAAGCAC

841  TGAGATTCGG GTGCCAGGTG GCCGGCAAGA AGTGTGGCCT

881  GCAGGGCTTT GATGGCATCG TGTGAGAGCA GGTGCCGGCT

921  CCTCACACAC CATGGAGACT ACCATTGCGG CTGCATCGCC

961  TTCTCCCCTC CATCCAGCCT GGCGTCCAGG TTGCCCTGTT
```

One example of an amino acid sequence for a *Homo sapiens* isoform A of fructokinase ((KHK) is shown below as SEQ ID NO:10 (NCBI accession no. NP_000212).

```
  1  MEEKQILCVG LVVLDVISLV DKYPKEDSEI RCLSQRWQRG

 41  GNASNSCTVL SLLGAPCAFM GSMAPGHVAD FVLDDLRRYS

 81  VDLRYTVFQT TGSVPIATVI INEASGSRTI LYYDRSLPDV

121  SATDFEKVDL TQFKWIHIEG RNASEQVKML QRIDAHNTRQ
```

-continued

```
161  PPEQKIRVSV EVEKPREELF QLFGYGDVVF VSKDVAKHLG

201  FQSAEEALRG LYGRVRKGAV LVCAWAEEGA DALGPDGKLL

241  HSDAFPPPRV VDTLGAGDTF NASVIFSLSQ GRSVQEALRF

281  GCQVAGKKCG LQGFDGIV
```

An example of a cDNA that encodes the KHK protein with SEQ ID NO:10 is shown below as SEQ ID NO:11 (with NCBI accession no. NM_000221.3).

```
   1  AGGCAGGGCT GCAGATGCGA GGCCCAGCTG TACCTCGCGT

  41  GTCCCGGGTC GGGAGTCGGA GACGCAGGTG CAGGAGAGTG

  81  CGGGGCAAGT AGCGCATTTT CTCTTTGCAT TCTCGAGATC

 121  GCTTAGCCGC GCTTTAAAAA GGTTTGCATC AGCTGTGAGT

 161  CCATCTGACA AGCGAGGAAA CTAAGGCTGA GAAGTGGGAG

 201  GCGTTGCCAT CTGCAGGCCC AGGCAACCTG CTACGGGAAG

 241  ACCGGGGACC AAGACCTCTG GGTTGGCTTT CCTAGACCCG

 281  CTCGGGTCTT CGGGTGTCGC GAGGAAGGGC CCTGCTCCTT

 321  TCGTTCCCTG CACCCCTGGC CGCTGCAGGT GGCTCCCTGG

 361  AGGAGGAGCT CCCACGCGGA GGAGGAGCGA GGGCAGCTGG

 401  GAGCGGGGAC ACCATCCTCC TGGATAAGAG GCAGAGGCCG

 441  GGAGGAACCC CGTCAGCCGG GCGGGCAGGA AGCTCTGGGA

 481  GTAGCCTCAT GGAAGAGAAG CAGATCCTGT GCGTGGGGCT

 521  AGTGGTGCTG GACGTCATCA GCCTGGTGGA CAAGTACCCT

 561  AAGGAGGACT CGGAGATAAG GTGTTTGTCC CAGAGATGGC

 601  AGCGCGGAGG CAACGCGTCC AACTCCTGCA CCGTTCTCTC

 641  CCTGCTCGGA GCCCCCTGTG CCTTCATGGG CTCAATGGCT

 681  CCTGGCCATG TTGCTGATTT TGTCCTGGAT GACCTCCGCC

 721  GCTATTCTGT GGACCTACGC TACACAGTCT TTCAGACCAC

 761  AGGCTCCGTC CCCATCGCCA CGGTCATCAT CAACGAGGCC

 801  AGTGGTAGCC GCACCATCCT ATACTATGAC AGGAGCCTGC

 841  CAGATGTGTC TGCTACAGAC TTTGAGAAGG TTGATCTGAC

 881  CCAGTTCAAG TGGATCCACA TTGAGGGCCG GAACGCATCG

 921  GAGCAGGTGA AGATGCTGCA GCGGATAGAC GCACACAACA

 961  CCAGGCAGCC TCCAGAGCAG AAGATCCGGG TGTCCGTGGA

1001  GGTGGAGAAG CCACGAGAGG AGCTCTTCCA GCTGTTTGGC

1041  TACGGAGACG TGGTGTTTGT CAGCAAAGAT GTGGCCAAGC

1081  ACTTGGGGTT CCAGTCAGCA GAGGAAGCCT TGAGGGGCTT

1121  GTATGGTCGT GTGAGGAAAG GGGCTGTGCT TGTCTGTGCC

1161  TGGGCTGAGG AGGGGGCCGA CGCCCTGGGC CCTGATGGCA

1201  AATTGCTCCA CTCGGATGCT TTCCCGCCAC CCCGGGTGGT

1241  GGATACACTG GGAGCTGGAG ACACCTTCAA TGCCTCCGTC

1281  ATCTTCAGCC TCTCCCAGGG GAGGAGCGTG CAGGAAGCAC

1321  TGAGATTCGG GTGCCAGGTG GCCGGCAAGA AGTGTGGCCT
```

-continued

```
1361 GCAGGGCTTT GATGGCATCG TGTGAGAGCA GGTGCCGGCT
1401 CCTCACACAC CATGGAGACT ACCATTGCGG CTGCATCGCC
1441 TTCTCCCCTC CATCCAGCCT GGCGTCCAGG TTGCCCTGTT
1481 CAGGGGACAG ATGCAAGCTG TGGGGAGGAC TCTGCCTGTG
1521 TCCTGTGTTC CCCACAGGGA GAGGCTCTGG GGGGATGGCT
1561 GGGGGATGCA GAGCCTCAGA GCAAATAAAT CTTCCTCAGA
1601 GCCAGCTTCT CCTCTCAATG TCTGAACTGC TCTGGCTGGG
1641 CATTCCTGAG GCTCTGACTC TTCGATCCTC CCTCTTTGTG
1681 TCCATTCCCC AAATTAACCT CTCCGCCCAG GCCCAGAGGA
1721 GGGGCTGCCT GGGCTAGAGC AGCGAGAAGT GCCGTGGGCT
1761 TGCCACCAGC TCTGCCCTGG CTGGGGAGGA CACTCGGTGC
1801 CCCACACCCA GTGAACCTGC CAAAGAAACC GTGAGAGCTC
1841 TTCGGGGCCC TGCGTTGTGC AGACTCTATT CCCACAGCTC
1881 AGAAGCTGGG AGTCCACACC GCTGAGCTGA ACTGACAGGC
1921 CAGTGGGGGG CAGGGGTGCG CCTCCTCTGC CCTGCCCACC
1961 AGCCTGTGAT TTGATGGGGT CTTCATTGTC CAGAAATACC
2001 TCCTCCCGCT GACTGCCCCA GAGCCTGAAA GTCTCACCCT
2041 TGGAGCCCAC CTTGGAATTA AGGGCGTGCC TCAGCCACAA
2081 ATGTGACCCA GGATACAGAG TGTTGCTGTC CTCAGGGAGG
2121 TCCGATCTGG AACACATATT GGAATTGGGG CCAACTCCAA
2161 TATAGGGTGG GTAAGGCCTT ATAATGTAAA GAGCATATAA
2201 TGTAAAGGGC TTTAGAGTGA GAGAGACCTG GATTAAAATC
2241 TGCCATTTAA TTAGCTGCAT ATCACCTTAG GGTACAGCAC
2281 TTAACGCAAT CTGCCTCAAT TTCTTCATCT GTCAAATGGA
2321 ACCAATTCTG CTTGGCTACA GAATTATTGT GAGGATAAAA
2361 TCATATATAA AATGCCCAGC ATGATGCCTG ATGTGTA
```

Subjects can express a KHK enzyme can have one or more amino acid differences compared to the sequences described herein. For example, subjects can express a KHK enzyme at least 80%, at least 85%, at least 90%, at least 95%, at least 96%, at least 97%, at least 99% amino acid sequence identity or similarity with the KHK amino acid sequences described herein. Similarly, subjects can express KHK RNA with one or more nucleotide differences compared to the KHK nucleic acids described herein. For example, subjects can express a KHK RNA at least 80%, at least 85%, at least 90%, a least 95%, at least 96%, at least 97%, at least 99% amino acid sequence identity or similarity with the KHK nucleic acid sequences described herein.

As described herein, inhibition of KHK isoforms can inhibit cancer, including colorectal cancer and cancers of the small intestine, as well as intestinal polyps or adenomas that may eventually turn into cancer. In some cases, the KHK inhibitors employed in the compositions and methods described herein inhibit one isoform (e.g. KHK-C), but do not the others (e.g. KHK-A). In some cases, the KIRK inhibitors employed in the compositions and methods described herein inhibit one isoform (e.g. KHK-A), but do not the others (e.g. KHK-C). The KHK inhibitor can be used alone to inhibit cancer, including colorectal cancer and cancers of the small intestine, or the KHK inhibitor(s) can be used in combination with a diet that does not include ingestion of substantial amounts of fructose, glycine, serine, or a combination thereof.

Examples of inhibitors of KHK that can be used include those described by Maryanoff et al. (ACS Med. Chem, Lett, 2: 538-543 (2011)) such as the following compounds of Formula I:

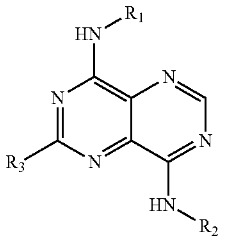

wherein:

$R_1$ is alkyl, cycloalkyl, phenyl, alkylphenyl, alkoxyphenyl, alkylthiophenyl, alkylsulfinylphenyl, aminoalkyl, or halophenyl:

$R_2$ is alkyl, aminoalkyl, alkylamino, alkenylamino, aminoalkenyl, alkynylamino, aminoalkynyl, aminophenyl, aminoalkylphenyl, aminoalkylthienyl, aminoalkylthiazolyl, alkylalkoxy, or alkylheterocyclyl; and $R_3$ is alkylamino, aminoalkylamino, aminoalkylaminoalkyl, piperazino, homopiperazino, alkylpiperazino, piperazinoalkyl, morpholino, aminopiperidino, aminoalkylpiperidino, alkyhaninopiperidino, azetidino, aminoalkylazetidino, alkylaminoazetidino, diazaspiroalkyl, alkylaminoalkylpiperidino, or alkylpiperazino.

Examples of KHK inhibitors include those with the $R_1$ and $R_2$ substituents shown in Table 2.

TABLE 2

Examples of $R_1$ and $R_2$ substituents

| Compound | $R_1$ | $R_2$ | $R_3$ |
|---|---|---|---|
| 1 | 2-$MeC_6H_4$ | Me | piperazino |
| 2 | 2-$MeC_6H_4$ | $CH_2$—c-Pr | piperazino |
| 3 | Phenyl | $CH_2$—c-Pr | piperazino |
| 4 | 3-$MeC_6H_4$ | $CH_2$—c-Pr | piperazino |
| 5 | 2-$MeOC_6H_4$ | $CH_2$—c-Pr | piperazino |
| 6 | 2-$EtOC_6H_4$ | $CH_2$—c-Pr | piperazino |
| 7 | 2-$MeSC_6H_4$ | $CH_2$—c-Pr | piperazino |
| 8 | 3-$MeSC_6H_4$ | $CH_2$—c-Pr | piperazino |
| 9 | 4-$MeSC_6H_4$ | $CH_2$—c-Pr | piperazino |
| 10 | 2-$MeSO_2C_6H_4$ | $CH_2$—c-Pr | piperazino |

TABLE 2-continued

| Examples of $R_1$ and $R_2$ substituents | | | |
|---|---|---|---|
| Compound | $R_1$ | $R_2$ | $R_3$ |
| 11 | 2-$EtSC_6H_4$ | $CH_2$—c-Pr | piperazino |
| 12 | 2-$CF_3SC_6H_4$ | $CH_2$—c-Pr | piperazino |
| 13 | 2-$EtC_6H_4$ | $CH_2$—c-Pr | piperazino |
| 14 | 2-(i-Pr)$C_6H_4$ | $CH_2$—c-Pr | piperazino |
| 15 | 2-(c-Pr)$C_6H_4$ | $CH_2$—c-Pr | piperazino |
| 16 | 2-$FC_6H_4$ | $CH_2$—c-Pr | piperazino |
| 17 | 2-$ClC_6H_4$ | $CH_2$—c-Pr | piperazino |
| 18 | 2-$BrC_6H_4$ | $CH_2$—c-Pr | piperazino |
| 19 | c-Pr | $CH_2$—c-Pr | piperazino |
| 20 | c-hexyl | $CH_2$—c-Pr | piperazino |
| 21 | phenylalkyl | NH—Me | piperazino |
| 22 | phenylalkyl | NH—Pr | piperazino |
| 23 | phenylalkyl | NH—hexyl | piperazino |
| 24 | phenylalkyl | NH—(c-hexyl) | piperazino |
| 25 | phenylalkyl | N(ethyl)$_2$ | piperazino |
| 26 | phenylalkyl | NH—$CH_2C{\equiv}CH$ | piperazino |
| 27 | phenylalkyl | NH—$CH_2Ph$ | piperazino |
| 28 | phenylalkyl | NH—$CH_2$(2-thienyl) | piperazino |
| 29 | phenylalkyl | NH—$CH_2$(2-thiazolyl) | piperazino |
| 30 | phenylalkyl | NH($CH_2$-c-Pr) | homopiperazino |
| 31 | phenylalkyl | NH($CH_2$-c-Pr) | N—Me-piperazino |
| 32 | phenylalkyl | NH($CH_2$-c-Pr) | morpholino |
| 33 | phenylalkyl | NH($CH_2$-c-Pr) | 4-($NH_2CH_2$)-piperidino |
| 34 | phenylalkyl | NH($CH_2$-c-Pr) | 4-($NH_2$)-piperidino |
| 35 | phenylalkyl | NH($CH_2$-c-Pr) | 4-piperidinyl-NH |
| 36 | 2-$MeSC_6H_4$ | $CH_2$—c-Bu | piperazino |
| 37 | 2-$MeSC_6H_4$ | $CH_2CH_2$—c-Pr | piperazino |
| 38 | 2-$MeSC_6H_4$ | $CH_2CH_2OMe$ | piperazino |
| 39 | 2-$MeSC_6H_4$ | $CH_2$(2-thienyl) | piperazine |
| 40 | 2-$MeSC_6H_4$ | $CH_2$(2-thiazolyl) | piperazino |
| 41 | 2-$MeSC_6H_4$ | $CH_2$(2-pyridyl) | piperazino |
| 42 | 2-$MeSC_6H_4$ | H | piperazino |
| 43 | 2-$MeSC_6H_4$ | $CH_2$—c-Pr | (R)-3-($NH_2$)-piperidino |
| 44 | 2-$MeSC_6H_4$ | $CH_2$—c-Pr | (S)-3-($NH_2$)-piperidino |
| 45 | 2-$MeSC_6H_4$ | $CH_2$—c-Pr | 4-($NH_2CH_2$)-piperidino |
| 46 | 2-$MeSC_6H_4$ | $CH_2$—c-Pr | 3-($NH_2CH_2$)-azetidino |
| 47 | 2-$MeSC_6H_4$ | $CH_2$—c-Pr | 2,6-diazaspiro [3.3]hept-2-yl |
| 48 | 2-$MeSC_6H_4$ | $CH_2$—c-Pr | $MeNHCH_2CH_2NMe$ |
| 49 | 2-$MeSC_6H_4$ | $CH_2$—c-Pr | 4-($Me_2NCH_2$)-piperidino |
| 50 | 2-$MeSC_6H_4$ | $CH_2$—c-Pr | N-Me-piperazino |

Another example of a KHK inhibitor is the following compound (see. e.g., Huard et al. J. Med, Chem, 60 (18): 7835-7849 (2017)):

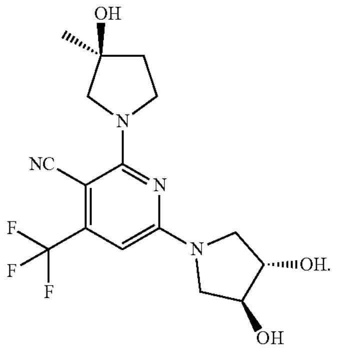 [SMILES: C[C@]1(O)CCN(c2nc(N3C[C@H](O)[C@@H](O)C3)cc(C(F)(F)F)c2C#N)C1]

Another example of a KUM inhibitor is shown below (available from Millipore Sigma, see webpage at emdmillipore.com/US/en/product/Ketohexoinase-Inhibitor-Calbiochem, EMD_BIO-420640).

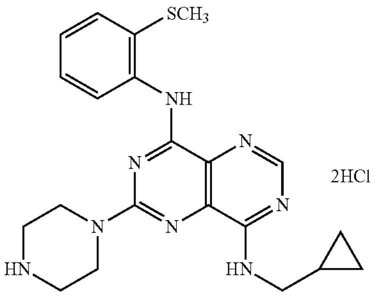 [SMILES: CSc1ccccc1Nc1nc(N2CCNCC2)nc2c(NCC3CC3)ncnc12]

Other KHK inhibitors that can be used are any of those described in WO2011133750A1. For example, the KHK inhibitor can be a compound of formula II:

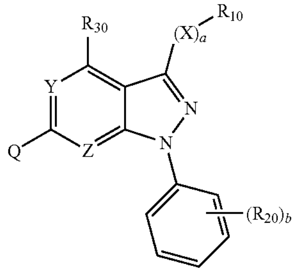

wherein:

a is an integer from 0 to 1;

X is —O— or —S—;

$R_{10}$ is C(1-4)alkyl or a halogenated C(1-4)alkyl;

h is an integer from 0 to 2;

$R_{20}$ is halogen, hydroxy, cyano, nitro, $NR^AR^B$, —O—C(1-4)alkyl, thioalkyl (e.g., —S—C(1-4)alkyl) or halogenated C(1-4)alkyl; wherein $R^A$ and $R^8$ are independently hydrogen or C(1-4)alkyl;

$R_{30}$ is hydrogen, halogen, hydroxy, —O—C(1-4)alkyl, or $NR^CR^D$; wherein $R^c$ and $R^D$ are each independently hydrogen or C(1-4)alkyl;

Y is CH; Z is CH; or alternatively Y is CH and Z is N; or alternatively Y is N and Z is N;

Q is $-(L^1)_c$-(Ring, A), $-(L^1)_c$-(Ring B)-(Ring C) or -(Ring B)-$L^1$-(Ring C);

c is art integer from 0 to 1;

$L^1$ is —$CH_2$—, —CH(OH)—, —$CH_2CH_2$—, —$CH_2CH_2CH_2$—, —CH═CH—, —CH═CH—$CH_2$—, or —O—, —O—$CH_2$—, —C(O)—, —C(0)-C(0)-, —C(0)-$CH_2$—, —C(0)-N($R^4$)—, —N($R^4$)—, —N($R^4$)—$CH_2$—, —N($R^1$)—$CH_2CH_2$—, —N($R^4$)—(CO)—, —N($R^4$)—C(O)—$CH_2$—, —N($R_4$)—C(O)—$CH_2$—$CH_2$— and —N($R_4$)—C(O)—N($R^5$)—; wherein $R^4$ and $R^5$ are each independently hydrogen or C(1-2)alkyl;

(Ring A) is phenyl or 4-10 membered nitrogen containing ring; wherein (Ring A) is optionally substituted with halogen, C(1-4)alkyl, cyano, $NR^ER^F$, —C(═NH)—$NR^ER^F$, —C(O)—$CH_2$—$NR^ER^F$, —C(O)—$CH_2CH_2$—$NR^ER^P$ or phenyl; wherein $R^E$ and $R^F$ are each independently hydrogen or C(1-4)alkyl;

(Ring B) is phenyl or 410 membered nitrogen containing ring;

(Ring C) is 4-10 membered nitrogen containing ring wherein (Ring C) is optionally substituted with one to two C(1-4)alkyl.

Phosphoinositide 3-Kinase (PI3K)

The phosphoinositide 3-kinase (PI3K) signaling pathway is a key regulator in cancer proliferation (rapid increase or spread) and metastasis (development of secondary growths away from a primary site of cancer). The PI3K pathway includes four Class I isoforms: alpha, beta, delta and gamma (a, (3, (3, and 7). The four isoforms play unique roles in the survival of different tumor types and in the creation of supportive tumor microenvironments.

One example of an amino acid sequence for a *Homo sapiens* phosphoinositide 3-kinase (PI3K) is shown below as SEQ ID NO:12 (NCBI accession no. CAA72168.1).

```
   1 MSSTQDNGEH WKSLESVGIS RKELAMAEAL QMEYDALSRL
  41 RHDKEENRAK QNADPSLISW DEPGVDFYSK PAGRRTDLKL
```

-continued

```
  81 LRGLSGSDPT LNYNSLSPQE GPPNHSTSQG PQPGSDPWPK
 121 GSLSGDYLYI FDGSDGGVSS SPGPGDIEGS CKKLSPPPLP
 161 PRASIWDTPP LPPRKGSPSS SKISQPSDIN TFSLVEQLPG
 201 KLLEHRILEE EEVLGGGGQG RLLGSVDYDG INDAIRTLNL
 241 KSTYDVEMLR DATRGWKEGR GPLDFSKDTS GKPVARSKTM
 281 PPQVPPRTYA SRYGNRKNAT PGKNRRISAA PVGSRPHTVA
 321 NGHELFEVSE ERDEEVAAFC HMLDILRSGS DIQDYFLTGY
 361 VWSAVTPSPE HLGDEVNLKV TVLCDRLQEA LTFTCNCSST
 401 VDLLIYQTLC YTHDDLRNVD VGDFVLKPCG LEEFLQNKHA
 441 LGSHEYIQYC RKFDIDIRLQ LMEQKVVRSD LARTVNDDQS
 481 PSTLNYLVHL QERPVKQTIS RQALSLLFDT YHNEVDAFLL
 521 ADGDFPLKAD RVVQSVKAIC NALAAVETPE ITSALNQLPP
 561 CPSRMQPKIQ KDPSVLAVRE NREKVVEALT AAILDLVELY
 601 CNTFNADFQT AVPGSRKHDL VQEACHFARS LAFTVYATHR
 641 IPIIWATSYE DFYLSCSLSH GGKDMCSPLQ TRRAHFSKYL
 681 FHLIVWDQQI CFPVQVNRLP RETLLCATLY ALPIPPPGSS
 721 SEANKQRRVP EALGWVTTPL FNFRQVLTCG RKLLGLWPAT
 761 QENPSARWSA PNFHQPDSVI LQIDFPTSAF DIKFTSPPGD
 801 KFSPRYEFGS LREEDQRKLK DIMQKESLYW LTDADKKRLW
 841 EKRYYCHSEV SSLPLVLASA PSWEWACLPD IYVLLKQWTH
 881 MNHQDALGLL HATFPDQEVR RMAVQWISGL SDAELLDYLP
 921 QLVQALKYEC YLDSPLVRFL LKRAVSDLRV THYFFWLLKD
 961 GLKDSQFSIR YQYLLAALLC CCGKGLREEF NRQCWLVNAL
1001 AKLAQQVREA APSARQGILR TGLEEVKQFF ALNGSCRLPL
1041 SPSLLVKGIV PRDCSYFNSN AVPLKLSGQN VDPLGENIRV
1081 IFKCGDDLRQ DMLTLQMIRI MSKIWVQEGL DMRMVIFRCF
1121 STGRGRGMVE MIPNAETLRK IQVHEGVTGS FKDRPLADWL
1161 QKHNPGEDEY EKAVENFIYS CAGCCVATYV LGICKRHNDN
1201 IMLKTTGHMF HIDFGRFLGH AQMFGNIKRD RAPFVFTSDM
1241 AYVINGGDKP SSRFHDFVDL CCQAYNLIRK HTHLFLNLLG
1281 LMLSCGIPEL SDLEDLKYVY DALRPQDTEA NATTYFTRLI
1321 ESSLGSVATK LNFFIHNLAQ MKFTGSDDRL TLSFASRTHT
1361 LKSSGRISDV FLCRHEKIFH PNKGYIYVVK VMRENTHEAT
1401 YIQRTFEEFQ ELHNKLRLLF PSSHLPSFPS RFVIGRSRGE
1441 AVAERRREEL NGYIWHLIHA PPEVAECDLV YTFFHPLPRD
1481 EKAMGTSPAP KSSDGTWARP VGKVGGEVKL SISYKNNKLF
1521 IMVMHIRGLQ LLQDGNDPDP YVKIYLLPDP QKTTKRKTKV
1561 ARKTCNPTYN EMLVYDGIPK GDLQQRELQL SVLSEQGFWE
1601 NVLLGEVNIR LRELDLAQEK TGWFALGSRS HGTL
```

An example of a cDNA that encodes the *Homo sapiens* phosphoinositide 3-kinase (PI3K) protein with SEQ ID NO:12 is shown below as SEQ ID NO:13 (with NCBI accession no. Y11312.1).

```
   1 ACTCACTATA GGGCTCGAGC GGCCGCCCGG GCAGGTAAGA
  41 ATCAGAAGAC ATTTGTGCTT TGGGGAGCAG AGGCCCTCAG
  81 GGTATAGAGA AGGAAGAAGA GAGAGGTTCA CTGTAGTCCT
 121 GAAGCAGAAA TAAGACCTGT GGCTGAAGGA AGCCTTAGCA
 161 ATTCACTCCT TCCTCTTCCT GAGAACTCTC TGTAGGAAGT
 201 CTCACCTAGC AGAGGCTTCA CAGTATTTCA GAGAAGCCAA
 241 AGATTGTTTG CCTCTTTGGA AACTGTTATC CTTCCATCAT
 281 GACTGTGTCA CTCCTGCCAC TGTTCCACCA TAGAGATGGC
 321 GTCCTTTGCA GCAAACCGTA AGTTATAAGG ATGAGGGAAG
 361 AAGAGTAGAG GGCCAAAAGG ATTCCATTTT GAGGAAAAAC
 401 TACAGTTTGC CTTGCCAGGT AGAAGAATCA GGCGCCCAGA
 441 CACCATGTCA CAACCCTCCA GAACTGACGT TGGCAGGAAG
 481 TAGAGACTTT GTTGCCTGTG TCCCCCATCC TCACCATGTC
 521 TTCGACTCAG GACAATGGGG AACACTGGAA GTCCCTGGAG
 561 TCTGTGGGCA TCAGCCGCAA AGAACTAGCG ATGGCCGAAG
 601 CCCTGCAGAT GGAGTATGAT GCCCTGTCCC GGCTCCGGCA
 641 TGACAAGGAG GAGAACAGAG CCAAGCAGAA CGCAGACCCC
 681 TCTCTCATCA GCTGGGATGA GCCTGGGGTA GACTTTTACA
 721 GCAAGCCAGC AGGAAGGCGG ACCGACCTCA AGCTGTTACG
 761 CGGTCTCTCT GGCTCTGATC CTACCCTTAA CTACAACTCA
 801 CTATCCCCAC AGGAAGGGCC GCCCAACCAC TCTACCTCCC
 841 AAGGGCCACA GCCTGGCTCA GATCCCTGGC CCAAAGGCTC
 881 CCTGTCTGGA GACTATCTCT ACATTTTTGA TGGTTCAGAT
 921 GGGGGAGTCT CTTCGTCCCC AGGACCAGGG GACATAGAGG
 961 GCTCTTGCAA GAAACTATCC CCACCTCCTC TGCCTCCCCG
1001 AGCTTCTATC TGGGATACCC CTCCCCTGCC TCCCAGAAAG
1041 GGGTCCCCCT CATCCTCCAA GATCTCCCAG CCCAGTGACA
1081 TCAACACTTT CTCTTTGGTC GAACAATTGC CAGGCAAACT
1121 GCTAGAGCAT CGGATCCTAG AAGAGGAAGA GGTGCTGGGA
1161 GGTGGGGGTC AGGGGCGCCT ACTGGGGTCT GTGGACTATG
1201 ATGGTATCAA TGATGCAATT ACTAGGCTCA ACTTGAAATC
1241 GACCTATGAT GTGGAGATGT TGCGGGATGC CACCAGGGGC
1281 TGGAAGGAGG GCCGAGGGCC GCTGGACTTC AGCAAAGACA
1321 CCTCTGGAAA ACCCGTGGCC AGGAGCAAGA CTATGCCCCC
1361 TCAGGTGCCC CCCCGCACCT ATGCCTCCCG CTATGGCAAC
1401 CGAAAGAATG CGACGCCTGG CAAGAACCGC CGGATTTCTG
1441 CAGCCCCGGT GGGCTCCCGG CCCCACACTG TTGCCAATGG
1481 CCATGAGTTG TTTGAGGTCT CAGAAGAGAG AGATGAGGAG
```

-continued

```
1521 GTTGCTGCAT TTTGCCACAT GCTGGATATC CTTCGATCTG
1561 GCTCTGACAT CCAAGACTAC TTCCTCACTG GCTATGTCTG
1601 GAGTGCTGTC ACCCCTAGCC CAGAGCACCT CGGGGATGAG
1641 GTCAACCTGA AGGTGACTGT GTTGTGTGAC AGGCTTCAAG
1681 AGGCACTCAC TTTCACCTGC AACTGTTCCT CCACTGTAGA
1721 CTTGCTTATC TACCAGACCC TGTGCTACAC CCATGATGAC
1761 CTGAGGAATG TGGACGTGGG TGACTTTGTG CTAAAGCCCT
1801 GCGGGCTGGA GGAGTTCCTG CAGAACAAGC ATGCCTTGGG
1841 CAGTCATGAG TACATCCAAT ACTGCCGCAA GTTTGACATT
1881 GACATTCGGC TACAGCTGAT GGAGCAGAAG GTTGTGCGCA
1921 GTGACCTGGC CCGGACGGTG AATGATGACC AGAGCCCCTC
1961 CACCTTGAAC TACCTCGTCC ATCTCCAAGA GAGGCCTGTC
2001 AAGCAGACCA TCAGCAGGCA GGCCCTGAGT CTTCTGTTCG
2041 ACACTTACCA CAATGAGGTG GATGCCTTCC TGCTGGCTGA
2081 TGGAGACTTC CCACTGAAGG CTGACAGGGT GGTCCAGTCC
2121 GTCAAGGCCA TCTGCAACGC CCTGGCCGCC GTGGAAACCC
2161 CTGAGATCAC CAGTGCTCTC AACCAGCTGC CCCCCTGCCC
2201 CTCCCGCATG CAGCCTAAAA TTCAGAAGGA TCCCAGTGTC
2241 TTGGCTGTGA GGGAAAACCG AGAGAAGGTC GTGGAAGCCC
2281 TGACCGCTGC CATCTTGGAC CTGGTGGAGC TGTACTGCAA
2321 CACATTCAAC GCAGACTTCC AGACGGCAGT GCCCGGGAGC
2361 CGCAAGCATG ACCTGGTCCA GGAGGCCTGC CATTTCGCCA
2401 GGTCCCTGGC CTTCACTGTC TATGCCACCC ACCGCATCCC
2441 CATCATCTGG GCTACCAGCT ATGAAGATTT CTACCTCTCC
2481 TGCTCCCTCA GCCATGGCGG CAAGGACATG TGCAGCCCCC
2521 TGCAGACCCG AAGAGCTCAC TTCTCCAAGT ACCTCTTCCA
2561 CCTCATCGTC TGGGACCAGC AGATCTGCTT CCCAGTGCAG
2601 GTGAACCGGC TGCCTCGGGA GACACTGCTG TGTGCCACTC
2641 TCTATGCTCT GCCCATCCCC CCACCGGGGA GCTCCTCAGA
2681 GGCCAATAAG CAGCGGCGGG TGCCTGAAGC CCTGGGCTGG
2721 GTCACTACCC CACTCTTCAA CTTCAGGCAG GTCCTGACCT
2761 GTGGCCGGAA GCTTCTGGGT TTGTGGCCAG CAACACAGGA
2801 AAATCCCAGC GCCCGTTGGA GTGCACCTAA TTTCCACCAG
2841 CCAGACAGTG TCATCCTGCA GATTGACTTC CCCACCTCGG
2881 CCTTTGACAT CAAGTTCACC AGCCCCCCTG GAGACAAGTT
2921 CAGCCCCCGC TATGAGTTTG GCAGCCTCCG GGAAGAAGAC
2961 CAGCGCAAGC TTAAAGACAT CATGCAGAAA GAGTCCTTGT
3001 ACTGGCTCAC TGATGCTGAC AAGAAGCGCC TGTGGGAGAA
3041 GCGATATTAC TGCCACTCGG AGGTGAGCTC GCTCCCCCTG
3081 GTGCTCGCCA GCGCCCCCAG CTGGGAGTGG GCTTGCCTGC
```

-continued

```
3121 CTGACATCTA TGTTCTCCTG AAGCAGTGGA CCCACATGAA
3161 CCACCAGGAT GCCCTGGGGC TCCTGCATGC CACCTTCCCG
3201 GACCAGGAGG TGCGTCGTAT GGCTGTGCAG TGGATTGGCT
3241 CACTCTCAGA TGCTGAGCTG CTAGACTACC TGCCCCAGCT
3281 GGTACAGGCC CTGAAGTATG AATGCTACCT GGACAGCCCG
3321 TTGGTGCGCT TCCTCCTGAA ACGAGCTGTG TCTGACTTGA
3361 GAGTGACTCA CTACTTCTTC TGGTTACTGA AGGACGGCCT
3401 CAAGGACTCT CAGTTCAGCA TCCGCTACCA GTATCTGCTG
3441 GCAGCCTTAC TGTGCTGCTG TGGCAAGGGG CTGAGAGAAG
3481 AGTTTAACCG CCAGTGCTGG CTTGTCAATG CCCTGGCCAA
3521 ACTGGCCCAG CAGGTCCGGG AGGCAGCCCC ATCTGCAAGG
3561 CAGGGAATCC TCCGCACGGG CCTGGAGGAG GTGAAGCAGT
3601 TCTTTGCCCT CAATGGCTCG TGCCGCTTGC CACTCAGCCC
3641 CAGTCTGCTG GTTAAGGGAA TTGTGCCCAG GGACTGTTCC
3681 TACTTCAACT CCAATGCTGT CCCCCTCAAA CTCTCCTTCC
3721 AAAATGTGGA TCCCCTGGGT GAGAACATCC GTGTCATCTT
3761 CAAGTGTGGG GACGACCTTC GCCAGGACAT GCTAACGCTG
3801 CAGATGATTC GCATCATGAG CAAGATCTGG GTCCAGGAGG
3841 GGCTGGACAT GCGCATGGTC ATCTTCCGCT GCTTCTCCAC
3881 CGGCCGGGGC AGAGGGATGG TGGAGATGAT CCCTAATGCT
3921 GAGACCCTGC GTAAGATCCA GGTGGAGCAT GGGGTGACCG
3961 GCTCGTTCAA GGACCGGCCC CTGGCAGACT GGCTGCAGAA
4001 ACACAACCCT GGGGAGGACG AGTATGAGAA GGCTGTGGAG
4041 AACTTTATCT ACTCCTGCGC TGGCTGCTGC GTGGCCACGT
4081 ACGTCTTGGG CATCTGTGAC CGACATAATG ACAACATCAT
4121 GCTGAAGACC ACTGGTCACA TGTTCCACAT TGATTTTGGC
4161 CGCTTCCTGG GCCATGCCCA GATGTTTGGC AACATCAAGC
4201 GGGACCGTGC CCCCTTTGTC TTCACCTCGG ACATGGCGTA
4241 TGTCATCAAC GGGGGTGACA AGCCTTCCAG CCGCTTCCAT
4281 GATTTTGTTG ACCTTTGCTG CCAAGCCTAC AACCTCATTC
4321 GCAAGCACAC CCACCTCTTC CTCAACCTTC TGGGCCTGAT
4361 GTTGTCCTGT GGGATCCCTG AACTCTCAGA CCTGGAGGAC
4401 CTCAAGTATG TGTACGATGC CCTGAGGCCT CAGGATACAG
4441 AGGCCAATGC CACTACCTAC TTCACTAGGT TGATTGAGTC
4481 CAGCCTGGGC AGTGTAGCCA CAAAGCTCAA TTTTTTCATC
4521 CATAATCTGG CTCAGATGAA GTTCACGGGC TCAGATGACC
4561 GGCTGACCCT CTCCTTTGCC TCCCGAACAC ACACTCTCAA
4601 GAGCTCTGGC CGAATCAGTG ATGTTTTCCT CTGCCGCCAT
4641 GAGAAGATCT TCCACCCCAA CAAAGGCTAT ATATATGTGG
4681 TAAAGGTGAT GCGAGAGAAC ACTCACGAGG CCACCTACAT
4721 CCAGCGGACC TTTGAGGAGT TCCAGGAATT ACACAATAAG
4761 TTGCGGCTGC TCTTCCCTTC TTCCCACTTG CCCAGCTTCC
4801 CTAGTCGCTT CGTGATCGGC CGCTCCCGGG GAGAGGCGGT
4841 GGCCGAGCGG CGGAGGGAGG AGCTAAACGG TTACATCTGG
4881 CACTTGATCC ACGCACCCCC TGAGGTGGCC GAGTGTGATT
4921 TGGTGTACAC CTTCTTCCAC CCACTGCCCC GGGATGAGAA
4961 GGCTATGGGC ACCAGCCCAG CTCCTAAGTC CTCAGATGGC
5001 ACATGGGCCC GGCCCGTCGG AAAGGTGGGA GGGGAGGTGA
5041 AGCTGTCCAT CTCCTACAAA AACAATAAAC TCTTCATCAT
5081 GGTGATGCAT ATTCGGGGCT TGCAACTGCT CCAGGATGGA
5121 AATGACCCTG ACCCCTATGT GAAAATTTAC CTCCTTCCTG
5161 ACCCTCAGAA AACCACTAAG AGGAAAACCA AAGTGGCCCG
5201 GAAAACCTGC AATCCTACCT ACAATGAGAT GTTGGTATAT
5241 GATGGGATCC CCAAGGGTGA CCTGCAGCAG CGGGAGCTCC
5281 AGCTGAGCGT GCTGAGTGAG CAGGGATTCT GGGAGAACGT
5321 CCTCCTCGGT GAGGTGAACA TCCGCCTGCG AGAGCTGGAC
5361 CTGGCTCAGG AGAAGACCGG CTGGTTCGCC CTGGGATCTC
5401 GAAGTCATGG CACCTTGTGA GCCCAGCAGA GCCACCACCC
5441 AGCATCCCAG GCTGGTGGCA GGAGCTGGGG GAGAGGACTC
5481 TCCCCTGTGA GACTCCTCCT TGTGAAGGGC CAGGGCCCTG
5521 GGCAGGCCTC CAGCTCGGTC CAGGTGATTC TGGCCTCTGT
5561 GGTAGGAGGC AGGGAGAGTA AGACATGCTC TGCTGTCTCT
5601 TCCTCTGGAG ACTGAACTTG GGTTGGTTGT GATGAGCAGC
5641 CCCTTGGAGG CTGTGAGGTT GCAGCAAAGT TTTAAGTTTA
5681 CCTTGTGTCA AGGGAGCAAT GCTTGGTTTG GGGAATGTGT
5721 GGGGTGGGCT GTATGAAGTA CCATTTTGGG GGTGGGTGGG
5761 TGGATATCTT AATTTTTATT TTTAAAAAAT GAAATAGTGA
5801 TGTTGTCCTA ACTGGGACAG GAAGCCTTGC GAGAAGGGAC
5841 GTACCTATGC CCCACAAGGC AAGAGAGGAA CACTATTTGG
5881 ACTTTTTGTA TGATTAAGGT TCTTATTGGA CTTTTCCCTA
5921 GGTTTTTTTT TTTTGTTATT GTTGTTGTTG TTCCGTTTTC
5961 TAGCTATAGG AACTATCTGG GGAGGGGCCC AGTGGGTCCT
6001 CGGCCAGAGC CCTCTCTAAG GACAGGTTGG GGAGGGTTGG
6041 GGAGGGCTGC CTGTGCTGGA CTGAGGCTTG TGCCACTGGG
6081 CCTTTCTGAT TTTGCCTCCA AAGGAGAGCG CTGTGATACC
6121 TACATGTGTA AGGAAGGGCC TTCCGTATTG GGGTTCTGCC
6161 AAGGACCCGT ATTCAGGGAC CCATGCTCTT TTGGGGGGAC
6201 TTTTCCTCTT GTCTTCCCTA CTTTATTAGG ACTTGCCCTG
6241 AATACCATTT TCTACCCCTT GCCCCTCCAT TCTCCTGGCC
6281 CTTCTGGGGG TCAGCTGGTC TCTATGAATA TGCTGGGGGT
6321 GCTTCCCCAT AGGTCTCTCC CTTCATTTGT CTCTGGTGGG
```

-continued

```
6361 ACAAAATACT GACTCAGTCC TTAGATGTAG TTTCACCCAA
6401 GAGCATCTTG GCCCTGGGAA GAGGTCCCTA GGCTGCAGAT
6441 GCTACTGACT GCTTGCTAGG TAGCCTCTGG AAAGCATTCC
6481 CCATCCATCA CTCCCCACTT CTTTCTGCTG TGCTGCTTCC
6521 CTCCCAAACT CCATTTCTGT CACCCTTTTT ATAAGACTTT
6561 TCCTCATTCT GTGGGGCCAT AAACCTATTT AGTCTGGAGC
6601 CAAAGGGATG CCCTATCTGA AGGAAAGGGG CATGGGGTGG
6641 GGGATTCCAT CAAAACTGTT GTTTTTTGCC CCATGATTTT
6681 TCTTTGGTCA GTAGGAGGCT GGATTGGAGT GGTGATTATT
6721 CCCCTGGAGC TAAGCTCAGG AGCCCGAAGG GAGAGACTGA
6761 GACTGACTCC CTTATCTCTT CATATTCTTT ATTCCCTACC
6801 AGATGGATTT TTTTTTTTTT TTTTGGAGAC GGAGTCTCGC
6841 CCTGTCGCCA GGCTGGAGTG TAGTGGCATG ATCTCGACTC
6881 ACTGCAAAAT CTGCCTCCCG GGTTCAAGCG ATTCTCCTAC
6921 CTCAGCCTCC CGAGTAGCTG GGATTACAGG CATGTGCCAC
6961 CACGCCAAGC TAATTTTTGT ATTTTTAGTA GAGACGGGGT
7001 TTCACCATGT TGGCCAGGAT GGTCTCGATC TCTTGACCTC
7041 GTGATCTGCC TGCCTTGGCC TCCCAAAGTG CTGGGATTAC
7081 AGGCGTGAGC CACCATGCCC CGCCCCAGAT GGATTTTACA
7121 TTTGCTCTTT TGTGTTTCGC TCCAAAGGGT TGTCTTCCTC
7161 GCCAAAAGGA GGGAGGGACT TTGAATTTGA TATGAATCTT
7201 TAAAACCAGA ATTGGCTGGA TATTTCCCAT GATTGGGAAA
7241 AGAGTGAAAT GAGGACATTC TGTAAACTGT CCCTCCCTAA
7281 TTCCAAGGAT CAGAAACTCC CCGTTTTGCT GACTCATTCC
7321 ATAACTGGAG AAAGAAGCTC CATTGACCGA AGCCACAGGG
7361 CAGCATGGAA GTTTAAATTT TCTCTAAAAT TAAAATGCCA
7401 AGGATAAAGC TGGCTGCTTC CAGGAGGGGG AAGAGGAGTG
7441 GGGAGTGGGC GGTGAAACTT TTCCAGATGA ACGGACCATA
7481 AATGTGTTAC TGGCTTTGTG CCTGTAGCTC ATTTTATTAT
7521 GACCTATATG CTCCTGATTT AAAGAGATCT GTGTACTGTT
7561 TACTTCCCAC TTCCCAGAAT CCCTTGTATC TCCTTTCTCG
7601 GGAATTGTAT TTTCTAATAA ATGACATTTG AGAAAAAAAA
7641 AAAAAAAAAA AAAA
```

Subjects can express a phosphoinositide 3-kinase PI3K) enzyme can have one or more amino acid differences compared to the sequences described herein. For example, subjects can express a PI3K enzyme at least 80%, at least 85%, at least 90%, at least 95%, at least 96%, at least 97%, at least 99% amino acid sequence identity or similarity with the PI3K amino acid sequences described herein. Similarly, subjects can express PI3K RNA with one or more nucleotide differences compared to the PI3K nucleic acids described herein. For example, subjects can express a PI3K RNA at least 80%, at least 85%, at least 90%, at least 95%, at least 96%, at least 97%, at least 99% amino acid sequence identity or similarity with the PI3K nucleic acid sequences described herein.

As described herein, inhibition of PI3K can inhibit cancer, including colorectal cancer and cancers of the small intestine, as well as intestinal polyps or adenomas that may eventually turn into cancer. Examples of inhibitors of PI3K that can be used include the following compounds:

Pan-inhibitors such as Buparlisib/BKM-120, Copanlisib/Bay80-6946, TAK-117, Pictilisib/GDC-0941, Pilaralisib/XL-147/SAR245408, Zstk474, CH5132799;

- p110a inhibitors such as Taselisib/GDC-0032, Alpelisib/BYL-719, Serabelisib/MLN1117;
- p110b inhibitors such as GSK2636771;
- p110d inhibitors such as Idelalisib/CAL-101, Duvelisib/IPI-145;
- PI3K/mTOR inhibitors such as BEZ235, GDC-0980, PKI-587, 765/SAR245409, BGT226, DS-7423, PLVT33597, or SF1126.

Fatty Acid Synthase (FASN)

Fatty acid synthase is a multi-enzyme protein that catalyzes fatty acid synthesis. It is not a single enzyme but a whole enzymatic system composed of two identical 272 kDa multifunctional polypeptides, in which substrates are handed from one functional domain to the next.

One example of an amino acid sequence for a *Homo sapiens* fatty acid synthase (FASN) is shown below as SEQ ID NO:14 (NCBI accession no. NP_004095.4).

```
  1 MEEVVIAGMS GKLPESENLQ EFWDNLIGGV DMVTDDDRRW
 41 KAGLYGLPRR SGKLKDLSRF DASFFGVHPK QHATMDPQLR
 81 LLLEVTYEAI VDGGINPDSL RGTHTGVWVG VSGSETSEAL
121 SRDPETLVGY SMVGCQRAMM ANRLSFFFDF RGPSIALDTA
161 CSSSLMALQN AYQAIHSGQC PAAIVGGINV LLKPNTSVQF
201 LRLGMLSPEG TCKAFDTAGN GYCRSEGVVA VLLTKKSLAR
241 RVYATILNAG TNTDGFKEQG VTFPSGDIQE QLIRSLYQSA
281 GVAPESFEYI EAHGTGTKVG DPQELNGITR ALCARTQEPL
321 LIGSTKSNMG HPEPASGLAA LAKVLLSLEH GLWAPNLHFH
361 SPNPEIPALL DGRLQVVDQP LPVRGGNVGI NSFGFGGSVN
401 HIILRPNTQP PPAPAPHATL PRLLRASGRT PEAVQKLLEQ
441 GLRHSQDLAF LSMLNDIAAV PATAMPFRGY AVLGGERGGP
481 EVQQVPAGER PLWFICSGMG TQWRGMGLSL MRLDRFRDSI
521 LRSDEAVKPF GLKVSQLLLS TDESTFDDIV HSFVSLTAIQ
561 IGLIDLLSCM GLRPDGIVGH SLGEVACGYA DGCLSQEEAV
601 LAAYWRGQCI KEAHLPPGAM AAVGLSWEEC KQRCPPGVVP
641 ACHNSKDTVT ISGPQAPVFE FVEQLRKEGV FAKEVRTGGM
681 AFHSYFMEAI APPLLQELKK VIREPKPRSA RWLSTSIPEA
721 QWHSSLARTS SAEYNVNNLN SPVLFQEALW HVPEHAVVLE
761 IAPHALLQAV LKRGLKPSCT IIPLMKKDHR DNLEFFLAGI
801 GRLHLSGIDA NPNALFPPVE FPAPRGTPLI SPLIKWDHLS
841 AWDVPAAEDF PNGSGSPSAA IYNIDTSSES PDHYLVDHTL
881 DGRVLFPATG YLSIVWKTLA RALGLGVEQL PVVFEDVVLH
921 QATILPKTGT VSLEVRLLEA SRAFEVSENG NLVVSGKVYQ
```

-continued

961 WDDPDPRLFD HPESPTPNPT EPLFLAQAEV YKELRLRGYD

1001 YGPHFQGILE ASLEGDSGRL LWKDNWVSFM DTMLQMSILG

1041 SAKHGLYLPT RVTAIHIDPA THRQKLYTLQ DKAQVADVVV

1081 SRWLRVTVAG GVHISGLHTE SAPRRQQEQQ VPILEKFCFT

1121 PHTEEGCLSE RAALQEELQL CKGLVQALQT KVTQQGLKMV

1161 VPGLDGAQIP RDPSQQELPR LLSAACRLQL NGNLQLELAQ

1201 VLAQERPKLP EDPLLSGLLD SPALKACLDT AVENMPSLKM

1241 KVVEVLAGHG HLYSRIPGLL SPHPLLQLSY TATDRHPQAL

1281 EAAQAELQQH DVAQGQWDPA DPAPSALGSA DLLVCNCAVA

1321 ALGDPASALS NMVAALREGG FLLLHTLLRG HPLGDIVAFL

1361 TSTEPQYGQG ILSQDAWESL FSRVSLRLVG LKKSFYGSTL

1401 FLCRRPTPQD SPIFLPVDDT SFRWVESLKG ILADEDSSRP

1441 VWLKAINCAT SGVVGLVNCL RREPGGNRLR CVLLSNLSST

1481 SHVPEVDPGS AELQKVLQGD LVMNVYRDGA WGAFRHFLLE

1521 EDKPEEPTAH AFVSTLTRGD LSSIRWVCSS LRHAQPTCPG

1561 AQLCTVYYAS LNFRDIMALT GKLSPDAIPG KWTSQDSLLG

1601 MEFSGRDASG KRVMGLVPAK GLATSVLLSP DFLWDVPSNW

1641 TLEEAASVPV VYSTAYYALV VRGRVRPGET LLIHSGSGGV

1681 GQAAIAIALS LGCRVFTTVG SAEKRAYLQA RFPQLDSTSF

1721 ANSRDTSFEQ HVLWHTGGKG VDLVLNSLAE EKLQASVRCL

1761 ATHGRFLEIG KFDLSQNHPL GMAIFLKNVT FHGVLLDAFF

1801 NESSADWREV WALVQAGIRD GVVRPLKCTV FHGAWVEDAF

1841 RYAMQGKHIG KVVVQVLAEE PEAVLKGAKP KLMSAISKTF

1881 CPAHKSYIIA GGLGGFGLEL AQWLIQRGVQ KLVLTSRSGI

1921 RTGYQAKQVR RWRRQGVQVQ VSTSNISSLE GARGLIAEAA

1961 QLGPVGGVFN LAVVLRDGLL NEQTPEFFQD VCKPKYSGTL

2001 NLDRVTREAC PELDYFVVFS SVSCGRGNAG QSNYGFANSA

2041 MERICEKRRH EGLPGLAVQW GAIGDVGILV ETMSTNDTIV

2081 SGTLPQRMAS CLEVLDLFLN QPHMVLSSFV LAEKAAAYRD

2121 RDSQRDLVEA VAHILGIRDL AAVNLDSSLA DLGLDSLMSV

2161 EVRQTLEREL NLVLSVREVR QLTLRKLQEL SSKADEASEL

2201 ACPTPKEDGL AQQQTQLNLR SLLVNPEGPT LMRLNSVQSS

2241 ERPLFLVHPI EGSTTVFHSL ASRLSIPTYG LQCTRAAPLD

2281 SIHSLAAYYI DCIRQVQPEG PYRVAGYSYG ACVAFEMCSQ

2321 LQAQQSPAPT HNSLFLFDGS PTYVLAYTQS YRAKLTPGCE

2361 AEAETEAICF FVQQFTDMEH NRVLEALLPL KGLEERVAAA

2401 VDLIIKSHQG LDRQELSFAA RSFYYKLRAA EQYTPKAKYH

2441 GNVMLLRAKT GGAYGEDLGA DYNLSQVCDG GVSVHVIEGD

2481 HRTLLEGSGL ESIISIIHSS LAEPRVSVRE G

An example of a cDNA that encodes the Home *sapiens* fatty acid synthase (FASN) protein with SEQ ID NO: 14 is shown below as SEQ ID NO:15 (with NCBI accession no. NM_004104.5).

1 GAGCCAGAGA GACGGCAGCG GCCCCGGCCT CCCTCTCCGC

41 CGCGCTTCAG CCTCCCGCTC CGCCGCGCTC CAGCCTCGCT

81 CTCCGCCGCC CGCACCGCCG CCCGCGCCCT CACCAGAGCA

121 GCCATGGAGG AGGTGGTGAT TGCCGGCATG TCCGGGAAGC

161 TGCCAGAGTC GGAGAACTTG CAGGAGTTCT GGGACAACCT

201 CATCGGCGGT GTGGACATGG TCACGGACGA TGACCGTCGC

241 TGGAAGGCGG GGCTCTACGG CCTGCCCCGG CGGTCCGGCA

281 AGCTGAAGGA CCTGTCTAGG TTTGATGCCT CCTTCTTCGG

321 AGTCCACCCC AAGCAGGCAC ACACGATGGA CCCTCAGCTG

361 CGGCTGCTGC TGGAAGTCAC CTATGAAGCC ATCGTGGACG

401 GAGGCATCAA CCCAGATTCA CTCCGAGGAA CACACACTGG

441 CGTCTGGGTG GGCGTGAGCG GCTCTGAGAC CTCGGAGGCC

481 CTGAGCCGAG ACCCCGAGAC ACTCGTGGGC TACAGCATGG

521 TGGGCTGCCA GCGAGCGATG ATGGCCAACC GGCTCTCCTT

561 CTTCTTCGAC TTCAGAGGGC CCAGCATCGC ACTGGACACA

601 GCCTGCTCCT CCAGCCTGAT GGCCCTGCAG AACGCCTACC

641 AGGCCATCCA CAGCGGGCAG TGCCCTGCCG CCATCGTGGG

681 GGGCATCAAT GTCCTGCTGA AGCCCAACAC CTCCGTGCAG

721 TTCTTGAGGC TGGGGATGCT CAGCCCCGAG GGCACCTGCA

761 AGGCCTTCGA CACAGCGGGG AATGGGTACT GCCGCTCGGA

801 GGGTGTGGTG GCCGTCCTGC TGACCAAGAA GTCCCTGGCC

841 CGGCGGGTGT ACGCCACCAT CCTGAACGCC GGCACCAATA

881 CAGATGGCTT CAAGGAGCAA GGCGTGACCT TCCCCTCAGG

921 GGATATCCAG GAGCAGCTCA TCCGCTCGTT GTACCAGTCG

961 GCCGGAGTGG CCCCTGAGTC ATTTGAATAC ATCGAAGCCC

1001 ACGGCACAGG CACCAAGGTG GGCGACCCCC AGGAGCTGAA

1041 TGGCATCACC CGAGCCCTGT GCGCCACCCG CCAGGAGCCG

1081 CTGCTCATCG GCTCCACCAA GTCCAACATG GGGCACCCGG

1121 AGCCAGCCTC GGGGCTGGCA GCCCTGGCCA AGGTGCTGCT

1161 GTCCCTGGAG CACGGGCTCT GGGCCCCCAA CCTGCACTTC

1201 CATAGCCCCA ACCCTGAGAT CCCAGCGCTG TTGGATGGGC

1241 GGCTGCAGGT GGTGGACCAG CCCCTGCCCG TCCGTGGCGG

1281 CAACGTGGGC ATCAACTCCT TTGGCTTCGG GGCTCCAAC

1321 GTGCACATCA TCCTGAGGCC CAACACGCAG CCGCCCCCCG

1361 CACCCGCCCC ACATGCCACC CTGCCCCGTC TGCTGCGGGC

1401 CAGCGGACGC ACCCCTGAGG CCGTGCAGAA GCTGCTGGAG

1441 CAGGGCCTCC GGCACAGCCA GGACCTGGCT TTCCTGAGCA

1481 TGCTGAACGA CATCGCGGCT GTCCCCGCCA CCGCCATGCC

-continued

1521 CTTCCGTGGC TACGCTGTGC TGGGTGGTGA GCGCGGTGGC

1561 CCAGAGGTGC AGCAGGTGCC CGCTGGCGAG CGCCCGCTCT

1601 GGTTCATCTG CTCTGGGATG GGCACACAGT GGCGCGGGAT

1641 GGGGCTGAGC CTCATGCGCC TGGACCGCTT CCGAGATTCC

1681 ATCCTACGCT CCGATGAGGC TGTGAAGCCA TTCGGCCTGA

1721 AGGTGTCACA GCTGCTGCTG AGCACAGACG AGAGCACCTT

1761 TGATGACATC GTCCATTCGT TTGTGAGCCT GACTGCCATC

1801 CAGATAGGCC TCATAGACCT GCTGAGCTGC ATGGGGCTGA

1841 GGCCAGATGG CATCGTCGGC CACTCCCTGG GGGAGGTGGC

1881 CTGTGGCTAC GCCGACGGCT GCCTGTCCCA GGAGGAGGCC

1921 GTCCTCGCTG CCTACTGGAG GGGACAGTGC ATCAAAGAAG

1961 CCCATCTCCC GCCGGGCGCC ATGGCAGCCG TGGGCTTGTC

2001 CTGGGAGGAG TGTAAACAGC GCTGCCCCCC GGGCGTGGTG

2041 CCCGCCTGCC ACAACTCCAA GGACACAGTC ACCATCTCGG

2081 GACCTCAGGC CCCGGTGTTT GAGTTCGTGG AGCAGCTGAG

2121 GAAGGAGGGT GTGTTTGCCA AGGAGGTGCG GACCGGCGGT

2161 ATGGCCTTCC ACTCCTACTT CATGGAGGCC ATCGCACCCC

2201 CACTGCTGCA GGAGCTCAAG AAGGTGATCC GGGAGCCGAA

2241 GCCACGTTCA GCCCGCTGGC TCAGCACCTC TATCCCCGAG

2281 GCCCAGTGGC ACAGCAGCCT GGCACGCACG TCCTCCGCCG

2321 AGTACAATGT CAACAACCTG GTGAGCCCTG TGCTGTTCCA

2361 GGAGGCCCTG TGGCACGTGC CTGAGCACGC GGTGGTGCTG

2401 GAGATCGCGC CCCACGCCCT GCTGCAGGCT GTCCTGAAGC

2441 GTGGCCTGAA GCCGAGCTGC ACCATCATCC CCCTGATGAA

2481 GAAGGATCAC AGGGACAACC TGGAGTTCTT CCTGGCCGGC

2521 ATCGGCAGGC TGCACCTCTC AGGCATCGAC GCCAACCCCA

2561 ATGCCTTGTT CCCACCTGTG GAGTTCCCAG CTCCCCGAGG

2601 AACTCCCCTC ATCTCCCCAC TCATCAAGTG GGACCACAGC

2641 CTGGCCTGGG ACGTGCCGGC CGCCGAGGAC TTCCCCAACG

2681 GTTCAGGTTC CCCCTCAGCC GCCATCTACA ACATCGACAC

2721 CAGCTCCGAG TCTCCTGACC ACTACCTGGT GGACCACACC

2761 CTCGACGGTC GCGTCCTCTT CCCCGCCACT GGCTACCTGA

2801 GCATAGTGTG GAAGACGCTG GCCCGCGCCC TGGGCCTGGG

2841 CGTCGAGCAG CTGCCTGTGG TGTTTGAGGA TGTGGTGCTG

2881 CACCAGGCCA CCATCCTGCC CAAGACTGGG ACAGTGTCCC

2921 TGGAGGTACG GCTCCTGGAG GCCTCCCGTG CCTTCGAGGT

2961 GTCAGAGAAC GGCAACCTGG TAGTGAGTGG GAAGGTGTAC

3001 CAGTGGGATG ACCCTGACCC CAGGCTCTTC GACCACCCGG

3041 AAAGCCCCAC CCCCAACCCC ACGGAGCCCC TCTTCCTGGC

3081 CCAGGCTGAA GTTTACAAGG AGCTGCGTCT GCGTGGCTAC

-continued

3121 GACTACGGCC CTCATTTCCA GGGCATCCTG GAGGCCAGCC

3161 TGGAAGGTGA CTCGGGGAGG CTGCTGTGGA AGGATAACTG

3201 GGTGAGCTTC ATGGACACCA TGCTGCAGAT GTCCATCCTG

3241 GGCTCGGCCA AGCACGGCCT GTACCTGCCC ACCCGTGTCA

3281 CCGCCATCCA CATCGACCCT GCCACCCACA GGCAGAAGCT

3321 GTACACACTG CAGGACAAGG CCCAAGTGGC TGACGTGGTG

3361 GTGAGCAGGT GGCTGAGGGT CACAGTGGCC GGAGGCGTCC

3401 ACATCTCCGG GCTCCACACT GAGTCGGCCC CGCGGCGGCA

3441 GCAGGAGCAG CAGGTGCCCA TCCTGGAGAA GTTTTGCTTC

3481 ACTCCCCACA CGGAGGAGGG GTGCCTGTCT GAGCGCGCTG

3521 CCCTGCAGGA GGAGCTGCAA CTGTGCAAGG GGCTGGTGCA

3561 GGCACTGCAG ACCAAGGTGA CCCAGCAGGG GCTGAAGATG

3601 GTGGTGCCCG GACTGGATGG GGCCCAGATC CCCCGGGACC

3641 CCTCACAGCA GGAACTGCCC CGGCTGTTGT CGGCTGCCTG

3681 CAGGCTTCAG CTCAACGGGA ACCTGCAGCT GGAGCTGGCG

3721 CAGGTGCTGG CCCAGGAGAG GCCCAAGCTG CCAGAGGACC

3761 CTCTGCTCAG CGGCCTCCTG GACTCCCCGG CACTCAAGGC

3801 CTGCCTGGAC ACTGCCGTGG AGAACATGCC CAGCCTGAAG

3841 ATGAAGGTGG TGGAGGTGCT GGCTGGCCAC GGTCACCTGT

3881 ATTCCCGCAT CCCAGGCCTG CTCAGCCCCC ATCCCCTGCT

3921 GCAGCTGAGC TACACGGCCA CCGACCGCCA CCCCCAGGCC

3961 CTGGAGGCTG CCCAGGCCGA GCTGCAGCAG CACGACGTTG

4001 CCCAGGGCCA GTGGGATCCC GCAGACCCTG CCCCCAGCGC

4041 CCTGGGCAGC GCCGACCTCC TGGTGTGCAA CTGTGCTGTG

4081 GCTGCCCTCG GGGACCCGGC CTCAGCTCTC AGCAACATGG

4121 TGGCTGCCCT GAGAGAAGGG GGCTTTCTGC TCCTGCACAC

4161 ACTGCTCCGG GGGCACCCCC TCGGGGACAT CGTGGCCTTC

4201 CTCACCTCCA CTGAGCCGCA GTATGGCCAG GGCATCCTGA

4241 GCCAGGACGC GTGGGAGAGC CTCTTCTCCA GGGTGTCGCT

4281 GCGCCTGGTG GGCCTGAAGA AGTCCTTCTA CGGCTCCACG

4321 CTCTTCCTGT GCCGCCGGCC CACCCCGCAG GACAGCCCCA

4361 TCTTCCTGCC GGTGGACGAT ACCAGCTTCC GCTGGGTGGA

4441 GTCTCTGAAG GGCATCCTGG CTGACGAAGA CTCTTCCCGG

4441 CCTGTGTGGC TGAAGGCCAT CAACTGTGCC ACCTCGGGCG

4481 TGGTGGGCTT GGTGAACTGT CTCCGCCGAG AGCCCGGCGG

4521 GAACCGCCTC CGGTGTGTGC TGCTCTCCAA CCTCAGCAGC

4561 ACCTCCCACG TCCCGGAGGT GGACCCGGGC TCCGCAGAAC

4601 TGCAGAAGGT GTTGCAGGGA GACCTGGTGA TGAACGTCTA

4641 CCGCGACGGG GCCTGGGGGG CTTTCCGCCA CTTCCTGCTG

4681 GAGGAGGACA AGCCTGAGGA GCCGACGGCA CATGCCTTTG

4721 TGAGCACCCT CACCCGGGGG GACCTGTCCT CCATCCGCTG

-continued

4761 GGTCTGCTCC TCGCTGCGCC ATGCCCAGCC CACCTGCCCT
4801 GGCGCCCAGC TCTGCACGGT CTACTACGCC TCCCTCAACT
4841 TCCGCGACAT CATGCTGGCC ACTGGCAAGC TGTCCCCTGA
4881 TGCCATCCCA GGGAAGTGGA CCTCCCAGGA CAGCCTGCTA
4921 GGTATGGAGT TCTCGGGCCG AGACGCCAGC GGCAAGCGTG
4961 TGATGGGACT GGTGCCTGCC AAGGGCCTGG CCACCTCTGT
5001 CCTGCTGTCA CCGGACTTCC TCTGGGATGT GCCTTCCAAC
5041 TGGACGCTGG AGGAGGCGGC CTCGGTGCCT GTCGTCTACA
5081 GCACGGCCTA CTACGCGCTG GTGGTGCGTG GGCGGGTGCG
5121 CCCCGGGGAG ACGCTGCTCA TCCACTCGGG CTCGGGCGGC
5161 GTGGGCCAGG CCGCCATCGC CATCGCCCTC AGTCTGGGCT
5201 GCCGCGTCTT CACCACCGTG GGGTCGGCTG AGAAGCGGGC
5241 GTACCTCCAG GCCAGGTTCC CCCAGCTCGA CAGCACCAGC
5281 TTCGCCAACT CCCGGGACAC ATCCTTCGAG CAGCATGTGC
5321 TGTGGCACAC GGGCGGGAAG GGCGTTGACC TGGTCTTGAA
5361 CTCCTTGGCG GAAGAGAAGC TGCAGGCCAG CGTGAGGTGC
5401 TTGGCTACGC ACGGTCGCTT CCTGGAAATT GGCAAATTCG
5441 ACCTTTCTCA GAACCACCCG CTCGGCATGG CTATCTTCCT
5481 GAAGAACGTG ACATTCCACG GGGTCCTACT GGATGCGTTC
5521 TTCAACGAGA GCAGTGCTGA CTGGCGGGAG GTGTGGGCGC
5561 TTGTGCAGGC CGGCATCCGG GATGGGGTGG TACGGCCCCT
5601 CAAGTGCACG GTGTTCCATG GGGCCCAGGT GGAGGACGCC
5641 TTCCGCTACA TGGCCCAAGG GAAGCACATT GGCAAAGTCG
5681 TCGTGCAGGT GCTTGCGGAG GAGCCGGAGG CAGTGCTGAA
5721 GGGGGCCAAA CCCAAGCTGA TGTCGGCCAT CTCCAAGACC
5761 TTCTGCCCGG CCCACAAGAG CTACATCATC GCTGGTGGTC
5801 TGGGTGGCTT CGGCCTGGAG TTGGCGCAGT GGCTGATACA
5841 GCGTGGGGTG CAGAAGCTCG TGTTGACTTC TCGCTCCGGG
5881 ATCCGGACAG GCTACCAGGC CAAGCAGGTC CGCCGGTGGA
5921 GGCGCCAGGG CGTACAGGTG CAGGTGTCCA CCAGCAACAT
5961 CAGCTCACTG GAGGGGGCCC GGGGCCTCAT TGCCGAGGCG
6001 GCGCAGCTTG GGCCCGTGGG CGGCGTCTTC AACCTGGCCG
6041 TGGTCTTGAG AGATGGCTTG CTGGAGAACC AGACCCCAGA
6081 GTTCTTCCAG GACGTCTGCA AGCCCAAGTA CAGCGGCACC
6121 CTGAACCTGG ACAGGGTGAC CCGAGAGGCG TGCCCTGAGC
6161 TGGACTACTT TGTGGTCTTC TCCTCTGTGA GCTGCGGGCG
6201 TGGCAATGCG GGACAGAGCA ACTACGGCTT TGCCAATTCC
6241 GCCATGGAGC GTATCTGTGA GAAACGCCGG CACGAAGGCC
6281 TCCCAGGCCT GGCCGTGCAG TGGGGCGCCA TCGGCGACGT
6321 GGGCATTTTG GTGGAGACGA TGAGCACCAA CGACACGATC

-continued

6361 GTCAGTGGCA CGCTGCCCCA GCGCATGGCG TCCTGCCTGG
6401 AGGTGCTGGA CCTCTTCCTG AACCAGCCCC ACATGGTCCT
6441 GAGCAGCTTT GTGCTGGCTG AGAAGGCTGC GGCCTATAGG
6481 GACAGGGACA GCCAGCGGGA CCTGGTGGAG GCCGTGGCAC
6521 ACATCCTGGG CATCCGCGAC TTGGCTGCTG TCAACCTGGA
6561 CAGCTCACTG GCGGACCTGG GCCTGGACTC GCTCATGAGC
6601 GTGGAGGTGC GCCAGACGCT GGAGCGTGAG CTCAACCTGG
6641 TGCTGTCCGT GCGCGAGGTG CGGCAACTCA CGCTCCGGAA
6681 ACTGCAGGAG CTGTCCTCAA AGGCGGATGA GGCCAGCGAG
6721 CTGGCATGCC CCACGCCCAA GGAGGATGGT CTGGCCCAGC
6761 AGCAGACTCA GCTGAACCTG CGCTCCCTGC TGGTGAACCC
6801 GGAGGGCCCC ACCCTGATGC GGCTCAACTC CGTGCAGAGC
6841 TCGGAGCGGC CCCTGTTCCT GGTGCACCCA ATCGAGGGCT
6881 CCACCACCGT GTTCCACAGC CTGGCCTCCC GGCTCAGCAT
6921 CCCCACCTAT GGCCTGCAGT GCACCCGAGC TGCGCCCCTT
6961 GACAGCATCC ACAGCCTGGC TGCCTACTAC ATCGACTGCA
7001 TCAGGCAGGT GCAGCCCGAG GGCCCCTACC GCGTGGCCGG
7041 CTACTCCTAC GGGGCCTGCG TGGCCTTTGA AATGTGCTCC
7081 CAGCTGCAGG CCCAGCAGAG CCCAGCCCCC ACCCACAACA
7121 GCCTCTTCCT GTTCGACGGC TCGCCCACCT ACGTACTGGC
7161 CTACACCCAG AGCTACCGGG CAAAGCTGAC CCCAGGCTGT
7201 GAGGCTGAGG CTGAGACGGA GGCCATATGC TTCTTCGTGC
7241 AGCAGTTCAC GGACATGGAG CACAACAGGG TGCTGGAGGC
7281 GCTGCTGCCG CTGAAGGGCC TAGAGGAGCG TGTGGCAGCC
7321 GCCGTGGACC TGATCATCAA GAGCCACCAG GGCCTGGACC
7361 GCCAGGAGCT GAGCTTTGCG GCCCGGTCCT TCTACTACAA
7401 GCTGCGTGCC GCTGAGCAGT ACACACCCAA GGCCAAGTAC
7441 CATGGCAACG TGATGCTACT GCGCGCCAAG ACGGGTGGCG
7481 CCTACGGCGA GGACCTGGGC GCGGACTACA ACCTCTCCCA
7521 GGTATGCGAC GGGAAAGTAT CCGTCCACGT CATCGAGGGT
7561 GACCACCGCA CGCTGCTGGA GGGCAGCGGC CTGGAGTCCA
7601 TCATCAGCAT CATCCACAGC TCCCTGGCTG AGCCACGCGT
7641 GAGCGTGCGG GAGGGCTAGG CCCGTGCCCC CGCCTGCCAC
7681 CGGAGGTCAC TCCACCATCC CCACCCCACC CCACCCCACC
7721 CCCGCCATGC AACGGGATTG AAGGGTCCTG CCGGTGGGAC
7761 CCTGTCCGGC CCAGTGCCAC TGCCCCCCGA GGCTGCTAGA
7801 TGTAGGTGTT AGGCATGTCC CACCCACCCG CCGCCTCCCA
7841 CGGCACCTCG GGGACACCAG AGCTGCCGAC TTGGAGACTC
7881 CTGGTCTGTG AAGAGCCGGT GGTGCCCGTG CCCGCAGGAA
7921 CTGGGCTGGG CCTCGTGCGC CCGTGGGGTC TGCGCTTGGT
7961 CTTTCTGTGC TTGGATTTGC ATATTTATTG CATTGCTGGT

-continued

```
8001 AGAGACCCCC AGGCCTGTCC ACCCTGCCAA GACTCCTCAG

8041 GCAGCGTGTG GGTCCCGCAC TCTGCCCCCA TTTCCCCGAT

8081 GTCCCCTGCG GGCGCGGGCA GCCACCCAAG CCTGCTGGCT

8121 GCGGCCCCCT CTCGGCCAGG CATTGGCTCA GCCCGCTGAG

8161 TGGGGGGTCG TGGGCCAGTC CCCGAGGAGC TGGGCCCCTG

8201 CACAGGCACA CAGGGCCCGG CCACACCCAG CGGCCCCCCG

8241 CACAGCCACC CGTGGGGTGC TGCCCTTATG CCCGGCGCCG

8281 GGCACCAACT CCATGTTTGG TGTTTGTCTG TGTTTGTTTT

8321 TCAAGAAATG ATTCAAATTG CTGCTTGGAT TTTGAAATTT

8361 ACTGTAACTG TCAGTGTACA CGTCTGGACC CCGTTTCATT

8401 TTTACACCAA TTTGGTAAAA ATGCTGCTCT CAGCCTCCCA

8441 CAATTAAACC GCATGTGATC TCCA
```

Subjects can express a tarty acid synthase enzyme can have one or more amino acid differences compared to the sequences described herein. For example, subjects can express a FASN enzyme at least 80%, at least 85%, at least 90%, at least 95%, at least 96%, at least 97%, at least 99% amino acid sequence identity or similarity with the FASN amino acid sequences described herein. Similarly, subjects can express FASN RNA with one or more nucleotide differences compared to the FASN nucleic acids described herein. For example, subjects can express a FASN RNA at least 80%, at least 85%, at least 90%, at least 95%, at least 96%, at least 97%, at least 99% amino acid sequence identity or similarly with the FASN nucleic acid sequences described herein.

As described herein, inhibition of FASN can inhibit cancer, including colorectal cancer and cancers of the small intestine, as well as intestinal polyps or adenomas that may eventually turn into cancer. Examples of inhibitors of FASN that can be used include the following compounds:

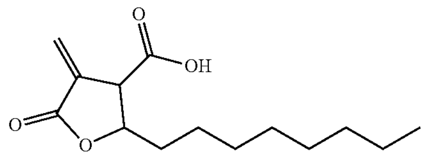

C75 (CAS No. 218137-86-1)

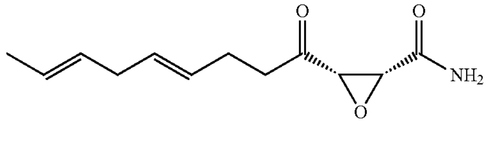

Cerulenin (CAS No. 17397-89-6)

-continued

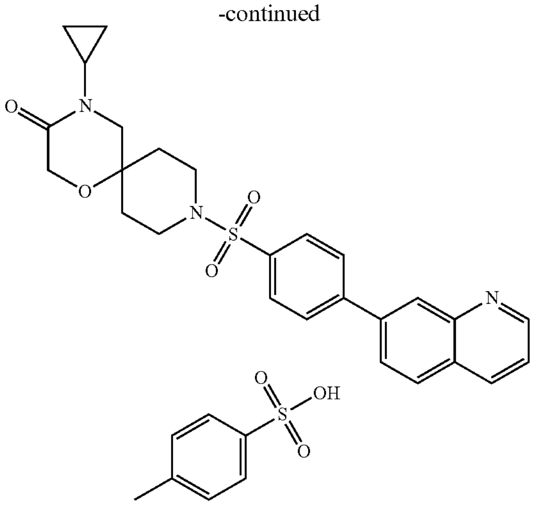

FAS-IN-1 Tosylate

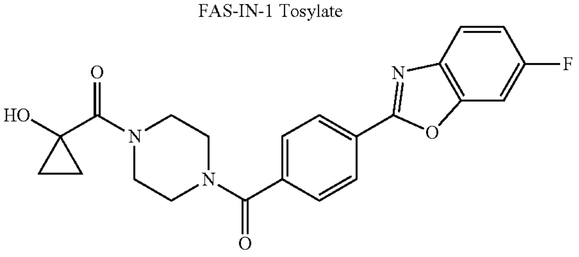

FT113 CAS No. 1630808-89-7

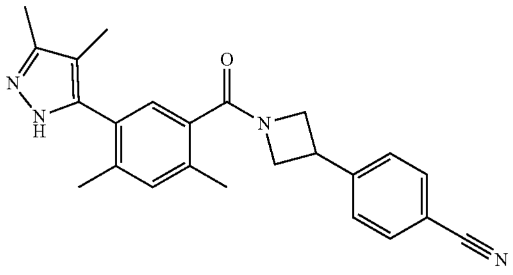

FASN Inhibitor 1 CAS No. 2097262-60-5

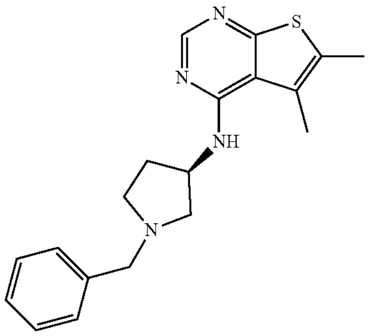

HS79 CAS No. 2138838-56-7

Nucleic Acids that Inhibit GLUT5, FASN, PI3 Kinase, or KHK

Various inhibitors of GLUT5, FASN, PI3 kinase, or KHK function can be employed in the compositions and methods described herein. For example, one type of GLUT5, FASN, PI3 kinase, or KHK inhibitor can be an inhibitory nucleic acid. See, e.g., Liu et al. *Targeting Ketohexokinase* (*KHK*)

*with a Novel Antisense Oligonucleotide (ASO) Decreases De Novo Lipogenesis and Improves Insulin—Mediated Whole Body Glucose Metabolism*, Diabetes J. 67 (1): (July 2018)). The expression or translation of an endogenous GLUT5, FASN, PI3 kinase, or KHK can be inhibited, for example, by use of an inhibitory nucleic acid that specifically binds to an endogenous (target) nucleic acid that encodes GLUT5, FASN, PI3 kinase, or KHK.

An inhibitory nucleic acid can have at least one segment that will hybridize to GLUT5, FASN, PI3 kinase, or KHK nucleic acid under intracellular or stringent conditions. The inhibitory nucleic acid can reduce expression of a nucleic acid encoding GLUT5, FASN, PI3 kinase, or KHK. An inhibitory nucleic acid may hybridize to a genomic DNA, a messenger RNA, or a combination thereof. An inhibitory nucleic acid may be incorporated into a plasmid vector or viral DNA. It may be single stranded or double stranded, circular or linear.

An inhibitory nucleic acid is a polymer of ribose nucleotides or deoxyribose nucleotides having more than 13 nucleotides in length. An inhibitory nucleic acid may include naturally occurring nucleotides synthetic, modified, or pseudo-nucleotides such as phosphorothiolates; as well as nucleotides having a detectable label such as $P^{32}$, biotin or digoxigenin. An inhibitory nucleic acid can reduce the expression and/or activity of a GLUT5, FASN, PI3 kinase, or KHK nucleic acid. Such an inhibitory nucleic acid may be completely complementary to a segment of GLUT5, FASN, PI3 kinase, or KHK nucleic acid (e.g., to a GLUT5, FASN, PI3 kinase, or KHK mRNA). Alternatively, some variability is permitted in the inhibitory nucleic acid sequences relative to GLUT5, FASN, PI3 kinase, or KHK sequences. For example, the GLUT5, TAW PI3 kinase, or KHK nucleic acids or GLUT5, FASN, PI3 kinase, or KHK proteins can have at least 85% sequence identity and/or complementary, or at least 90% sequence identity and/or complementary, or at least 95% sequence identity and/or complementary, or at least 96% sequence identity and/or complementary, or at least 97% sequence identity and/or complementary, or at least 98% sequence identity and/or complementary, or at least 99% sequence identity and/or complementary to the target GLUT5, FASN, PI3 kinase, or KHK nucleic acid.

An inhibitory nucleic acid can hybridize to a GLUT5, FASN, PI3 kinase, or KHK nucleic acid under intracellular conditions or under stringent hybridization conditions and in amounts sufficient to inhibit expression of a GLUT5, FASN, PI3 kinase, or KHK nucleic acid. Intracellular conditions refer to conditions such as temperature, pH and salt concentrations typically found inside a cell, e.g. an animal or mammalian cell. One example of such an animal or mammalian cell is a cancer cell such as a colorectal or small intestine cancer cell. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory oligonucleotides that comprise, for example, 2, 3, 4, or 5 or more stretches of contiguous nucleotides that are precisely complementary to a GLUT5, FASN, PI3 kinase, or KHK coding or flanking sequence, can each be separated by a stretch of contiguous nucleotides that are not complementary to adjacent coding sequences, and such an inhibitory nucleic acid can still inhibit the function of a GLUT5, FASN, PI3 kinase, or KHK nucleic acid. In general, each stretch of contiguous nucleotides is at least 4, 5, 6, 7, or 8 or more nucleotides in length. Non-complementary intervening sequences may be 1, 2, 3, or 4 nucleotides in length.

One skilled in the art can easily use the calculated melting point of an inhibitory nucleic acid hybridized to a sense nucleic acid to estimate the degree of mismatching that will be tolerated for inhibiting expression of a particular target nucleic acid. Inhibitory nucleic acids of the invention include, for example, a short hairpin RNA, a small interfering RNA, a ribozyme or an antisense nucleic acid molecule.

The inhibitory nucleic acid molecule may be single or double stranded (e.g. a small interfering RNA (siRNA)) and may function in an enzyme-dependent manner or by steric blocking. Inhibitory nucleic acid molecules that function in an enzyme-dependent manner include forms dependent on RNase H activity to degrade target mRNA. These include single-stranded DNA, RNA, and phosphorothioate molecules, as well as the double-stranded RNAi/siRNA system that involves target mRNA recognition through sense-antisense stand pairing followed by degradation of the target mRNA by the RNA-induced silencing complex. Steric blocking inhibitory nucleic acids, which are RNase-H independent, interfere with gene expression or other mRNA-dependent cellular processes by binding to a target mRNA and getting in the way of other processes. Steric blocking inhibitory nucleic acids include 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce GLUT5, FASN, PI3 kinase, or KHK, translation such that translation of the encoded polypeptide is reduced. SiRNAs mediate post-transcriptional gene silencing in a sequence-specific manner. See, for example, website at invitrogen.com/site/us/enlhome/Products-and-Services/Applicationstrnai.html. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the GLUT5, FASN, PI3 kinase, or KIM mRNA transcript. The region of homology may be 30 nucleotides or less in length, such as less than 25 nucleotides, or for example about 21 to 23 nucleotides in length. SiRNA is typically double stranded and may have two-nucleotide 3' overhangs, for example, 3' overhanging UU dinucleotides. Methods for designing siRNAs are available, see, for example, Elbashir et al. *Nature* 411: 494-498 (2001); Harborth et al. *Antisense Nucleic Acid Drug Dev.* 13: 83-106 (2003).

One example of KHK nucleic acid inhibitor is described in Liu et al. *Targeting Ketohexokinase (KHK) with a Novel Antisense Oligonucleotide (ASO) Decreases De Nova Lipogenesis and Improves Insulin-Mediated Whole Body Glucose Metabolism*, Diabetes J. 67(1): (July 2018)).

The pSuppressorNeo vector for expressing hairpin siRNA, commercially available from IMGENEX (San Diego, California), can be used to make siRNA for inhibiting GLUT, PI3 kinase, or KHK expression. The construction of the siRNA expression plasmid involves the selection of the target region of the mRNA, which can be a trial-and-error process. However, Elbashir et al. have provided guidelines that appear to work ~80% of the time. Elbashir, S. M., et al. *Analysis of gene function in somatic mammalian cells using small interfering RNAs*. Methods, 2002. 26 (2): p. 199-213. Accordingly, for synthesis of synthetic siRNA, a target region may be selected preferably 50 to 100 nucleotides downstream of the start codon. The 5' and 3' untranslated regions and regions close to the start codon should be avoided as these may be richer in regulatory protein binding sites. As siRNA can begin with AA, have 3' UU overhangs for both the sense and antisense siRNA strands, and have an approximate 50% G/C content. An example of a sequence for a synthetic siRNA is 5'-AA(N19)UU, where N is any nucleotide in the mRNA sequence and should be approximately 50% G-C content. The selected sequence(s) can be compared to others in the human genome database to mini mite homology to other known coding sequences (e.g., by Blast search, for example, through the NCBI website).

SiRNAs may be chemically synthesized, created by in vitro transcription, or expressed from an siRNA expression vector or a PCR expression cassette. See, e.g., website at invitrogen.com/site/us/en/home/Products-and-Services/Applications/rnai.html. When an siRNA is expressed from an expression vector or a PCR expression cassette, the insert encoding the siRNA may be expressed as an RNA transcript that folds into an siRNA hairpin or a shRNA. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, or about 3 to 23 nucleotides in length, and may include various nucleotide sequences including for example, AUG, CCC, UUCG, CCACC, CTCGAG, AAGCUU, and CCACACC. SiRNAs also may be produced in vivo by cleavage of double-stranded RNA introduced directly or via a transgene or virus. Amplification by an RNA-dependent RNA polymerase may occur in some organisms.

An inhibitory nucleic acid such as a short hairpin RNA siRNA or an antisense oligonucleotide may be prepared using methods such as by expression from an expression vector or expression cassette that includes the sequence of the inhibitory nucleic acid. Alternatively, it may be prepared by chemical synthesis using naturally occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the inhibitory nucleic acid and the target GLUT, PI3 kinase, or KHK nucleic acid.

Antibodies that Inhibit GLUT5, FASN, PI3 Kinase, or KHK

In some cases, isolated antibodies that hind specifically to GLUT5, FASN, PI3 kinase, or KHK can be used as inhibitors of GLUT5, FASN, PI3 kinase, or KHK in the compositions and methods described herein. Such antibodies may be monoclonal antibodies. In some cases, the antibodies can be polyclonal antibodies. Such antibodies may also be humanized or fully human antibodies. The antibodies can exhibit one or more desirable functional properties, such as high affinity or specific binding to GLUT5, FASN, PI3 kinase, or KHK.

Methods and compositions described herein can include GLUT5, FASN, PI3 kinase, or KHK antibodies, or a combination of GLUT5, FASN, PI3 kinase, or KHK antibodies with inhibitory nucleic acids, and/or small molecule inhibitors of GLUT5, FASN. PI3 kinase, or KHK.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VII) and a heavy chain constant region. The heavy chain constant region is comprised of three domains, CHI, $CH_2$ and $CH_3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g. an epitope or a domain of GLUT5, FASN, PI3 kinase, or KHK). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$, and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g. Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody." as used herein, is intended to refer to an antibody that is substantially free of other antibodies having different antigenic specificities (e.g., an isolated antibody that specifically binds GLUT5, FASN, PI3 kinase, or KHK is substantially free of antibodies that specifically bind antigens other than GLUT5, FASN, PI3 kinase, or KHK. In some cases, the antibodies ay however, have cross-reactivity to other antigens, such as GLUT5, FASN, PI3 kinase, or KHK protein variants or GLUT5, FASN, PI3 kinase, or KHK from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody." as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody." as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody." as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma. (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_L$ and $V_H$ regions of the recombinant antibodies are sequences that, while derived from and related to human germline $V_L$ and $V_H$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human GLUT5, FASN, PI3 kinase, or KHK is intended to refer to an antibody that binds to human GLUT, PI3 kinase, or KHK with a Ku of $1\times10^{-7}$M or less, more preferably $5\times10^{-8}$ M or less, more preferably $1\times10^{-8}$ M or less, more preferably $5\times10^{-9}$ M or less, even more preferably between $1\times10^{-8}$ M and 1x1 M or less.

The term "$K_{asscc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "Ku," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The antibodies of the invention are characterized by particular functional features or properties of the antibodies. For example, the antibodies bind specifically to human GLUT5, FASN, PI3 kinase, or KHK. Preferably, an antibody of the invention binds to GLUT, PI3 kinase, or KHK with high affinity, for example with a $K_D$ of $1\times10^{-7}$ M or less (e.g., less than $1\times10^{-8}$ M or less than $1\times10^{9}$ M). The antibodies can exhibit one or more of the following characteristics:

(a) binds to human GLUT5, FASN, PI3 kinase, or HK with a $K_D$ of $1\times10^{-7}$ M or less;
(b) inhibits the function or activity of GLUT, PI3 kinase, or HK proteins;
(c) reduces tumor growth;
(d) inhibits the onset of colorectal or small intestine cancer;
(e) inhibits intestinal polyps or adenomas that can turn into cancer; or
(e) a combination thereof.

Assays to evaluate the binding ability of the antibodies toward GLUT5, FASN, PI3 kinase, or KHK can be used, including for example, ELISAs, Western blots and RIAs. The binding kinetics (e.g., binding affinity) of the antibodies also can be assessed by standard assays known in the art, such as by Biacore™. analysis.

Given that the subject antibody preparations can bind to GLUT5, FASN, PI3 kinase, or KHK, the $V_L$ and $V_H$ sequences can be "mixed and matched" to create other binding molecules that bind to GLUT5, FASN, PI3 kinase, cr KHK. The binding properties of such "mixed and matched" antibodies can be tested using the binding assays (e.g., ELISAs). When $V_L$ and $V_H$ chains are mixed and matched, a $V_H$ sequence from a particular $V_H/V_L$ pairing can be replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence; and (b) a light chain variable region comprising an amino acid sequence;

wherein the antibody specifically hinds GLUT5, FASN, PI3 kinase, or KHK.

In some cases, the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., British J. of Cancer 83 (21:252-260 (2000) (describing the production of a humanized anti-CD30 antibody using only the heavy chain variable domain CDR3 of murine anti-CD30 antibody Ki-4); Beiboer et al., J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al., Proc. Natl. Acad. Sci. U.S.A. 95:8910-8915 (1998) (describing a panel of humanized anti-integrin alpha$_v$beta$_3$ antibodies using a heavy and light chain variable CDR3 domain. Hence, in some cases a mixed and matched antibody or a humanized antibody contains a CDR3 antigen binding domain that is specific for GLUT5, FASN, PI3 kinase, or KHK.

Genomic Modification to Reduce Susceptibility to Cancer

In some cases, GLUT5, FASN, PI3 kinase, or KHK expression of functioning can be reduced by genomic modification of GLUT5, FASN, PI3K, and/or KHK genes.

Non-limiting examples of methods of introducing a modification into the genome of a cell can include use of microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

For example, nucleases such as zinc finger nucleases (ZEN s) transcription activator like effector nucleases (TALENs), and/or meganucleases can be employed with a guide nucleic acid that allows the nuclease to target the genomic GLUT5, FASN, PI3K, and/or KHK site(s). In some cases, a targeting vector can be used to introduce a deletion or modification of one or more genomic GLUT5, FASN, and/or KHK site(s).

A "targeting vector" is a vector generally has a 5' flanking region and a 3' flanking region homologous to segments of the gene of interest. The 5' flanking region and a 3' flanking region can surround a DNA sequence comprising a modification and/or a foreign DNA sequence to be inserted into the gene. For example, the foreign DNA sequence may encode a selectable marker. In some cases, the targeting vector does not comprise a selectable marker but such a selectable marker can facilitate identification and selection of cells with desirable mutations. Examples of suitable selectable markers include antibiotics resistance genes such as chloramphenicol resistance, gentamycin resistance, kanamycin resistance, spectinomycin resistance (SpecR), neomycin resistance gene (NEO), and/or the hygromycin β-phosphotransferase genes. The 5' flanking region and the 3' flanking region can be homologous to regions within the gene, or to regions flanking the gene to be deleted, modified, or replaced with the unrelated DNA sequence. The targeting vector is contacted with the native gene of interest in vivo (e.g., within the cell) under conditions that favor homologous recombination. For example, the cell can be contacted with the targeting vector under conditions that result in transformation of the cyanobacterial cell(s) with the targeting vector.

A typical targeting vector contains nucleic acid fragments of not less than about 0.1 kb nor more than about 10.0 kb from both the 5' and the 3' ends of the genomic locus which encodes the gene to be modified (e.g. the genomic GLUT5, FASN, PI3K, and/or KHK site(s)). These two fragments are separated by an intervening fragment of nucleic acid which encodes the modification to be introduced. When the resulting construct recombines homologously with the chromosome at this locus, it results in the introduction of the modification, e.g. a deletion of a portion of the genomic GLUT5, FASN, PI3K, and/or KHK site(s), replacement of the genomic GLUT5, FASN, PI3K, and/or KIM promoter or coding region site(s) or the insertion of non-conserved codon or a stop codon.

In some cases, a Cas9/CRISPR system can be used to create a modification in genomic GLUT5, FASN, PI3K, and/or KHK that reduces the expression or functioning of the GLUT5, FASN, PI3K, and/or KHK gene products. Clustered regularly interspaced short palindromic repeats (CRISPR)/CRISPR-associated (Cas) systems are useful for, e.g. RNA-programmable genome editing (see e.g., Marraffini and Sontheimer, Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010:45:292-302; Jinek et al. Science 2012 337:815-820; Bikard and Marraffini Curr Opin Immunol 2012 24:15-20; Bikard et al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is described, for example, by Mali et al. Science 2013 339:823-6; which is incorporated by reference herein in its entirety. Kits for the design and use of CRISPR-mediated genome editing are commercially available, e.g. the PRECISION X CAS9 SMART NUCLEASE™ System (Cat No. CAS900A-1) from System Biosciences, Mountain View, CA In other cases, a cre-lox recombination system of bacteriophage P1, described by Abremski et al. 1983. *Cell* 32:1301 (1983), Sternberg et al., *Cold Spring Harbor Symposia on Quantitative Biology*, Vol. XLV 297 (1981) and others, can be used to promote recombination and alteration of the genomic GLUT5, FASN, PI3K, and/or KHK site(s). The cre-lox system utilizes the cre recombinase isolated from bacteriophage P1 in conjunction with the DNA sequences that the recombinase recognizes (termed lox sites). This recombination system has been effective for achieving recombination in plant cells (see, e.g., U.S. Pat. No. 5,658,772), animal cells (U.S. Pat. Nos. 4,959,317 and 5,801,030), and in viral vectors (Hardy et al., *J. Virology* 71:1842 (1997).

The genomic mutations so incorporated can alter one or more amino acids in the encoded GLUT5, FASN, PI3K, and/or KHK gene products. For example, genomic sites modified so that in the encoded GLUT5, FASN, PI3K, and/or KHK protein is more prone to degradation, or is less stable, so that the half-life of such protein(s) is reduced. In another example, genomic sites can be modified so that at least one amino acid of a GLUT5, FASN, PI3K, and/or KHK polypeptide is deleted or mutated to reduce the enzymatic activity at least one of GLUT5, FASN, PI3K, and/or KHK. In some cases, a conserved amino acid or a conserved domain of the GLUT5, FASN, PI3K, and/or KHK polypeptide is modified. For example, a conserved amino acid or several amino acids in a conserved domain of the GLUT5, FASN, PI3K, and/or KHK polypeptide can be replaced with one or more amino acids having physical and/or chemical properties that are different from the conserved amino acid(s). For example, to change the physical and/or chemical properties of the conserved amino acid(s), the conserved amino acid(s) can be deleted or replaced by amino acid(s) of another class, where the classes are identified in the following Table 3.

TABLE 3

| Classification | Genetically Encoded |
|---|---|
| Hydrophobic | A, G, F, I, L, M, P, V, W |
| Aromatic | F, Y, W |
| Apolar | M, G, P |
| Aliphatic | A, V, L, I |
| Hydrophilic | C, D, E, H, K, N, Q, R, S, T, Y |
| Acidic | D, E |
| Basic | H, K, R |
| Polar | Q, N, S, T, Y |
| Cysteine-Like | C |

Different types of amino acids can be employed in the GLUT5, FASN, and/or KHK polypeptide. Examples are shown in Table 4.

TABLE 4

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| N-Methylglycine (sarcosine) | | MeGly |
| Ornithine | | Orn |
| Norleucine | | Nle |
| Penicillamine | | Pen |
| Homoarginine | | hArg |
| N-methylvaline | | MeVal |
| Homocysteine | | hCys |
| Homoserine | | hSer |

Such genomic modifications can reduce the expression or functioning of GLUT5, FASN, PI3K, and/or KHK gene products by at least 10%, or at least 15%, or at least 20%, or at least 25%, or at least 30%, or at least 35%, or at least 40%, or at least 45%, or at least 50% compared to the unmodified G FASN, PI3K, and/or KHK gene product expression or functioning.

Methods of Identifying Agents that can Inhibit or Treat Cancer Growth

The invention further provides screening assays that are useful for generating or identifying therapeutic agents for prevention and treatment of cancer or tumor growth, and assays for generating or identifying agents that inhibit GLUT5, FASN, PI3 kinase, or KHK. In particular, GLUT5, FASN, PI3 kinase, or KHK may be used in a variety of assays for identifying factors that inhibit tumor growth.

In some cases, the methods can be performed in vitro. For example, WO/2008/024902 and US20130195886 describe some methods for identifying agents that can inhibit KHK.

For example, in one embodiment, the invention relates to a method of identifying a therapeutic agent that can inhibit GLUT5, FASN, PI3 kinase, or KHK-mediated tumor growth. Such a method can involve use of an animal model for colorectal or small intestinal cancer. For example, a method of identifying a therapeutic agent can involve administering a test agent to an experimental animal that expresses GLUT5, FASN, PI3 kinase, or KHK in tumor cells and observing whether one or more tumors in the experimental animal increase in size. In some embodiments, the method also includes comparing the number of tumors that increase in size compared to a control experimental animal has not been administered the test agent or a control experimental animal that has also been administered the test agent but that does not express GLUT5, FASN, PI3 kinase, or KHK.

Examples of experimental animals that can be employed include mice, rats, dogs, goats, monkeys, and chimpanzees. In general, any experimental animal can be employed se long as it is susceptible to tumor growth, particularly if the animal is susceptible to tumor growth of human cancer cells that have been administered to the experimental animal. One type of mouse strain that can be used is the, Lgr5-EGFP-IRES-creERT2; $Apc^{flox/flox}$ (referred as $APC^{-/-}$) mice, in C57BL/6 background or other mouse strains described in the Examples.

Dosages of known and newly identified therapeutic agents can also be determined by use of such methods. For example, in one embodiment, the invention includes a method of identifying dosage of a therapeutic agent that can inhibit GLUT5, FASN, PI3 kinase, or KHK-mediated tumor growth. Such a method can e administering a series of test dosages of a therapeutic agent to an experimental animal that expresses GLUT5, FASN, PI3 kinase, or KHK in tumor cells and observing which dosage(s) inhibit tumor growth in the experimental animal.

The present invention also provides a method of evaluating a therapeutically effective dosage for treating a cancer with a GLUT5, FASN, PI3 kinase, cr KHK inhibitor or a test agent that includes determining the LD100 or ED50 of the agent in vitro. Such a method permits calculation of the approximate amount of agent needed per volume to inhibit cancer cell growth or to kill 50% to 100% of the cancer cells. Such amounts can be determined, for example, by standard microdilution methods in cultured cells or by administration of varying amounts of a GLUT5, FASN, PI3 kinase, or KHK inhibitor or a test agent to an experimental animal.

Test agents and test dosages that can successfully inhibit GLUT5, FASN, PI3 kinase, or KHK-mediated tumor growth can reduce the tumor growth of a primary tumor by any amount such as, for example, by at least 2%, 5%, 10%, 20%, 40%, 50%, 60%, 70%, 80%, 90%, 95% or more than 95%. A therapeutically effective dosage is also one that is substantially non-toxic. For example, a therapeutically effective dosage is a dosage that does not adversely affect the production of differentiated cells from the bone marrow such as immune cells (e.g., T cells and/or B cells), erythrocytes, lymphocytes, or combinations thereof.

Subjects for Treatment

The methods and compositions described herein can be administered to an animal or a human subject in need of treatment, for prevention, elimination, alleviation or amelioration of a cancer. The cancer can for example be a colorectal cancer or a cancer of the small intestine. The cancer can occur in the small intestine, the large intestine (cecum, colon and rectum), or the anal canal. The cancer can be an intestinal polyp or intestinal adenoma that could eventually turn into cancer.

In some cases, the patient or subject that is treated has an adenomatous polyposis coli (APC) genetic mutation. The APC gene in humans is located on chromosome 5, see NCBI accession number NC_00005.10 in band q22.2 (5q22.2) (chromosome 5 location 112707498 . . . 112846239). Missense mutations, nonsense mutations, silent mutations, and frameshift deletions in the APC gene can lead to cancers such as intestinal cancer, stomach cancer, and thymus cancer. For example, the APC gene is deleted in polyposis 2.5 (DP2.5). Germline defects in the APC gene cause an autosomal dominant syndrome called familial adenomatous polyposis (FAP).

The APC gene encodes a tumor suppressor protein that is involved in the β-Catenin/Wnt signaling pathway. An example of a sequence for a human APC protein is shown below as SEQ If) NO:16.

```
   1 MASSGQIDLL ERLKELNLDS SNFPGVKLRS KMSLRSYGSR
  41 EGSVSSRSGE CSPVPMGSFP RRGFVNGSRE STGYLEELEK
  81 ERSLLLADLD KEEKEKDWYY AQLQNLTKRI DSLPLTENFS
 121 LQTDMTRRQL EYEARQIRVA MEEQLGTCQD MEKRAQRRIA
 161 RIQQIEKDIL RIRQLLQSQA TEAERSSQNK HETGSHDAER
 201 QNEGQGVGEI NMATSGNGQG STTRMDHETA SVLSSSSTHS
 241 APRRLTSHLG TKIRAYCETC WEWQEAHEPG MDQDKNPMPA
 281 PVEHQICPAV CVLMKLSFDE EHRHAMNELG GLQAIAELLQ
 321 VDCEMYGLTN DHYSITLRRY AGMALTNLTF GDVANKATLC
 361 SMKGCMRALV AQLKSESEDL QQVIASVLRN LSWRADVNSK
 401 KTLREVGSVK ALMECALEVK KESTLKSVLS ALWNLSAHCT
 441 ENKADICAVD GALAFLVGTL TYRSQTNTLA IIESGGGILR
 481 NVSSLIATNE DHRQILRENN CLQTLLQHLK SHSLTIVSNA
 521 CGTLWNLSAR NPKDQEALWD MGAVSMLKNL IHSKHKMIAM
 561 GSAAALRNLM ANRPAKYKDA NIMSPGSSLP SLHVRKQKAL
 601 EAELDAQHLS ETFDNIDNLS PKASHRSKQR HKQSLYGDYV
 641 FDTNRHDDNR SDNFNTGNMT VLSPYLNTTV LPSSSSSRGS
 681 LDSSRSEKDR SLERERGIGL GNYHPATENP GTSSKRGLQI
 721 STTAAQIAKV MEEVSAIHTS QEDRSSGSTT ELHCVTDERN
 761 ALRRSSAAHT HSNTYNFTKS ENSNRTCSMP YAKLEYKRSS
 801 NDSLNSVSSS DGYGKRGQMK PSIESYSEDD ESKFCSYGQY
 841 PADLAHKIHS ANHMDDNDGE LDTPINYSLK YSDEQLNSGR
 881 QSPSQNERWA RPKHIIEDEI KQSEQRQSRN QSTTYPVYTE
 921 STDDKHLKFQ PHFGQQECVS PYRSRGANGS ETNRVGSNHG
```

-continued

```
 961 INQNVSQSLC QEDDYEDDKP TNYSERYSEE EQHEEEERPT
1001 NYSIKYNEEK RHVDQPIDYS LKYATDIPSS QKQSFSFSKS
1041 SSGQSSKTEH MSSSSENTST PSSNAKRQNQ LHPSSAQSRS
1081 GQPQKAATCK VSSINQETIQ TYCVEDTPIC FSRCSSLSSL
1121 SSAEDEIGCN QTTQEADSAN TLQIAEIKEK IGTRSAEDPV
1161 SEVPAVSQHP RTKSSRLQGS SLSSESARHK AVEFSSGAKS
1201 PSKSGAQTPK SPPEHYVQET PLMFSRCTSV SSLDSFESRS
1241 IASSVQSEPC SGMVSGIISP SDLPDSPGQT MPPSRSKTPP
1281 PPPQTAQTKR EVPKNKAPTA EKRESGPKQA AVNAAVQRVQ
1321 VLPDADTLLH FATESTPDGF SCSSSLSALS LDEPFIQKDV
1361 ELRIMPPVQE NDNGNETESE QPKESNENQE KEAEKTIDSE
1401 KDLLDDSDDD DIEILEECII SAMPTKSSRK AKKPAQTASK
1441 LPPPVARKPS QLPVYKLLPS QNRLQPQKHV SFTPGDDMPR
1481 VYCVEGTPIN FSTATSLSDL TIESPPNELA AGEGVRGGAQ
1521 SGEFEKRDTI PTEGRSTDEA QGGKTSSVTI PELDDNKAEE
1561 GDILAECINS AMPKGKSHKP FRVKKIMDQV QQASASSSAP
1601 NKNQLDGKKK KPTSPVKPIP QNTEYRTRVR KNADSKNNLN
1641 AERVFSDNKD SKKQNLKNNS KVFNDKLPNN EDRVRGSFAF
1681 DSPHHYTPIE GTPYCFSRND SLSSLDFDDD DVDLSREKAE
1721 LRKAKENKES EAKVTSHTEL TSNQQSANKT QAIAKQPINR
1761 GQPKPILQKQ STFPQSSKDI PDRGAATDEK LQNFAIENTP
1801 VCFSHNSSLS SLSDISQENN NKENEPIKET EPPDSQGEPS
1841 KPQASGYAPK SFHVEDTPVC FSRNSSLSSL SIDSEDDLLQ
1881 ECISSAMPKK KKPSRLKGDN EKHSPRNMGG ILGEDLTLDL
1921 KDIQRPDSEH GLSPDSENFD WKAIQEGANS IVSSLHQAAA
1961 AACLSRQASS DSDSILSLKS GISLGSPFHL TPDQEEKPFT
2001 SNKGPRILKP GEKSTLETKK IESESKGIKG GKKVYKSLIT
2041 GKVRSNSEIS GQMKQPLQAN MPSISRGRTM IHIPGVRNSS
2081 SSTSPVSKKG PPKLTPASKS PSEGQTATTS PRGAKPSVKS
2121 ELSPVARQTS QIGGSSKAPS RSGSRDSTPS RPAQQPLSRP
2161 IQSPGRNSIS PGRNGISPPN KLSQLPRTSS PSTASTKSSG
2201 SGKMSYTSPG RQMSQQNLTK QTGLSKNASS IPRSESASKG
2241 LNQMNNGNGA NKKVELSRMS STKSSGSESD RSERPVLVRQ
2281 STFIKEAPSP TLRRKLEESA SFESLSPSSR PASPTRSQAQ
2321 TPVLSPSLPD MSLSTHSSVQ AGGWRKLPPN LSPTIEYNDG
2361 RPAKRHDIAR SHSESPSRLP INRSGTWKRE HSKHSSSLPR
2401 VSTWRRTGSS SSILSASSES SEKAKSEDEK HVNSISGTKQ
2441 SKENQVSAKG TWRKIKENEF SPTNSTSQTV SSGATNGAES
2481 KTLIYQMAPA VSKTEDVWVR IEDCPINNPR SGRSPTGNTP
2521 PVIDSVSEKA NPNIKDSKDN QAKQNVGNGS VPMRTVGLEN
```

-continued

```
2561 RLNSFIQVDA PDQKGTEIKP GQNNPVPVSE TNESSIVERT

2601 PFSSSSSSKH SSPSGTVAAR VTPFNYNPSP RKSSADSTSA

2641 RPSQIPTPVN NNTKKRDSKT DSTESSGTQS PKRHSGSYLV

2681 TSV
```

A cDNA sequence encoding the APC protein shown above (as SEQ ID NO:16) is provided below as SEQ ID NO:17

```
   1 ACTGGAGACA GAATGGAGGT GCTGCCGGAC TCGGAAATGG

  41 GGAAGTACTT AAACAACTAC AAGGAAGTAT TGAAGATGAA

  81 GCTATGGCTT CTTCTGGACA GATTGATTTA TTAGAGCGTC

 121 TTAAAGAGCT TAACTTAGAT AGCAGTAATT TCCCTGGAGT

 161 AAAACTGCGG TCAAAAATGT CCCTCCGTTC TTATGGAAGC

 201 CGGGAAGGAT CTGTATCAAG CCGTTCTGGA GAGTGCAGTC

 241 CTGTTCCTAT GGGTTCATTT CCAAGAAGAG GGTTTGTAAA

 281 TGGAAGCAGA GAAAGTACTG GATATTTAGA AGAACTTGAG

 321 AAAGAGAGGT CATTGCTTCT TGCTGATCTT GACAAAGAAG

 361 AAAAGGAAAA AGACTGGTAT TACGCTCAAC TTCAGAATCT

 401 CACTAAAAGA ATAGATAGTC TTCCTTTAAC TGAAAATTTT

 441 TCCTTACAAA CAGATATGAC CAGAAGGCAA TTGGAATATG

 481 AAGCAAGGCA AATCAGAGTT GCGATGGAAG AACAACTAGG

 521 TACCTGCCAG GATATGGAAA AACGAGCACA GCGAAGAATA

 561 GCCAGAATTC AGCAAATCGA AAAGGACATA CTTCGTATAC

 601 GACAGCTTTT ACAGTCCCAA GCAACAGAAG CAGAGAGGTC

 641 ATCTCAGAAC AAGCATGAAA CCGGCTCACA TGATGCTGAG

 681 CGGCAGAATG AAGGTCAAGG AGTGGGAGAA ATCAACATGG

 721 CAACTTCTGG TAATGGTCAG GGTTCAACTA CACGAATGGA

 761 CCATGAAACA GCCAGTGTTT TGAGTTCTAG TAGCACACAC

 801 TCTGCACCTC GAAGGCTGAC AAGTCATCTG GGAACCAAGA

 841 TACGCGCTTA CTGTGAAACC TGTTGGGAGT GGCAGGAAGC

 881 TCATGAACCA GGCATGGACC AGGACAAAAA TCCAATGCCA

 921 GCTCCTGTTG AACATCAGAT CTGTCCTGCT GTGTGTGTTC

 961 TAATGAAACT TTCATTTGAT GAAGAGCATA GACATGCAAT

1001 GAATGAACTA GGGGGACTAC AGGCCATTGC AGAATTATTG

1041 CAAGTGGACT GTGAAATGTA TGGGCTTACT AATGACCACT

1081 ACAGTATTAC ACTAAGACGA TATGCTGGAA TGGCTTTGAC

1121 AAACTTGACT TTTGGAGATG TAGCCAACAA GGCTACGCTA

1161 TGCTCTATGA AAGGCTGCAT GAGAGCACTT GTGGCCCAAC

1201 TAAAATCTGA AAGTGAAGAC TTACAGCAGG TTATTGCGAG

1241 TGTTTTGAGG AATTTGTCTT GGCGAGCAGA TGTAAATAGT

1281 AAAAAGACGT TGCGAGAAGT TGGAAGTGTG AAAGCATTGA

1321 TGGAATGTGC TTTAGAAGTT AAAAAGGAAT CAACCCTCAA
```

-continued

```
1361 AAGCGTATTG AGTGCCTTAT GGAATTTGTC AGCACATTGC

1401 ACTGAGAATA AAGCTGATAT ATGTGCTGTA GATGGTGCAC

1441 TTGCATTTTT GGTTGGCACT CTTACTTACC GGAGCCAGAC

1481 AAACACTTTA GCCATTATTG AAAGTGGAGG TGGGATATTA

1521 CGGAATGTGT CCAGCTTGAT AGCTACAAAT GAGGACCACA

1561 GGCAAATCCT AAGAGAGAAC AACTGTCTAC AAACTTTATT

1601 ACAACACTTA AAATCTCATA GTTTGACAAT AGTCAGTAAT

1641 GCATGTGGAA CTTTGTGGAA TCTCTCAGCA AGAAATCCTA

1681 AAGACCAGGA AGCATTATGG GACATGGGGG CAGTTAGCAT

1721 GCTCAAGAAC CTCATTCATT CAAAGCACAA AATGATTGCT

1761 ATGGGAAGTG CTGCAGCTTT AAGGAATCTC ATGGCAAATA

1801 GGCCTGCGAA GTACAAGGAT GCCAATATTA TGTCTCCTGG

1841 CTCAAGCTTG CCATCTCTTC ATGTTAGGAA ACAAAAAGCC

1881 CTAGAAGCAG AATTAGATGC TCAGCACTTA TCAGAAACTT

1921 TTGACAATAT AGACAATTTA AGTCCCAAGG CATCTCATCG

1961 TAGTAAGCAG AGACACAAGC AAAGTCTCTA TGGTGATTAT

2001 GTTTTTGACA CCAATCGACA TGATGATAAT AGGTCAGACA

2041 ATTTTAATAC TGGCAACATG ACTGTCCTTT CACCATATTT

2081 GAATACTACA GTGTTACCCA GCTCCTCTTC ATCAAGAGGA

2121 AGCTTAGATA GTTCTCGTTC TGAAAAAGAT AGAAGTTTGG

2161 AGAGAGAACG CGGAATTGGT CTAGGCAACT ACCATCCAGC

2201 AACAGAAAAT CCAGGAACTT CTTCAAAGCG AGGTTTGCAG

2241 ATCTCCACCA CTGCAGCCCA GATTGCCAAA GTCATGGAAG

2281 AAGTGTCAGC CATTCATACC TCTCAGGAAG ACAGAAGTTC

2321 TGGGTCTACC ACTGAATTAC ATTGTGTGAC AGATGAGAGA

2361 AATGCACTTA GAAGAAGCTC TGCTGCCCAT ACACATTCAA

2401 ACACTTACAA TTTCACTAAG TCGGAAAATT CAAATAGGAC

2441 ATGTTCTATG CCTTATGCCA AATTAGAATA CAAGAGATCT

2481 TCAAATGATA GTTTAAATAG TGTCAGTAGT AGTGATGGTT

2521 ATGGTAAAAG AGGTCAAATG AAACCCTCGA TTGAATCCTA

2561 TTCTGAAGAT GATGAAAGTA AGTTTTGCAG TTATGGTCAA

2601 TACCCAGCCG ACCTAGCCCA TAAAATACAT AGTGCAAATC

2641 ATATGGATGA TAATGATGGA GAACTAGATA CACCAATAAA

2681 TTATAGTCTT AAATATTCAG ATGAGCAGTT GAACTCTGGA

2721 AGGCAAAGTC CTTCACAGAA TGAAAGATGG GCAAGACCCA

2761 AACACATAAT AGAAGATGAA ATAAAACAAA GTGAGCAAAG

2801 ACAATCAAGG AATCAAAGTA CAACTTATCC TGTTTATACT

2841 GAGAGCACTG ATGATAAACA CCTCAAGTTG CAACCACATT

2881 TTGGACAGCA GGAATGTGTT TCTCCATACA GGTCACGGGG

2921 AGCCAATGGT TCAGAAACAA ATCGAGTGGG TTCTAATCAT
```

-continued

```
2961 GGAATTAATC AAAATGTAAG CCAGTCTTTG TGTCAAGAAG
3001 ATGACTATGA AGATGATAAG CCTACCAATT ATAGTGAACG
3041 TTACTCTGAA GAAGAACAGC ATGAAGAAGA AGAGAGACCA
3081 ACAAATTATA GCATAAAATA TAATGAAGAG AAACGTCATG
3121 TGGATCAGCC TATTGATTAT AGTTTAAAAT ATGCCACAGA
3161 TATTCCTTCA TCACAGAAAC AGTCATTTTC ATTCTCAAAG
3201 AGTTCATCTG GACAAAGCAG TAAAACCGAA CATATGTCTT
3241 CAAGCAGTGA GAATACGTCC ACACCTTCAT CTAATGCCAA
3281 GAGGCAGAAT CAGCTCCATC CAAGTTCTGC ACAGAGTAGA
3321 AGTGGTCAGC CTCAAAAGGC TGCCACTTGC AAAGTTTCTT
3361 CTATTAACCA AGAAACAATA CAGACTTATT GTGTAGAAGA
3401 TACTCCAATA TGTTTTTCAA GATGTAGTTC ATTATCATCT
3441 TTGTCATCAG CTGAAGATGA AATAGGATGT AATCAGACGA
3481 CACAGGAAGC AGATTCTGCT AATACCCTGC AAATAGCAGA
3521 AATAAAAGAA AAGATTGGAA CTAGGTCAGC TGAAGATCCT
3561 GTGAGCGAAG TTCCAGCAGT GTCACAGCAC CCTAGAACCA
3601 AATCCAGCAG ACTGCAGGGT TCTAGTTTAT CTTCAGAATC
3641 AGCCAGGCAC AAAGCTGTTG AATTTTCTTC AGGAGCGAAA
3681 TCTCCCTCCA AAAGTGGTGC TCAGACACCC AAAAGTCCAC
3721 CTGAACACTA TGTTCAGGAG ACCCCACTCA TGTTTAGCAG
3761 ATGTACTTCT GTCAGTTCAC TTGATAGTTT TGAGAGTCGT
3801 TCGATTGCCA GCTCCGTTCA GAGTGAACCA TGCAGTGGAA
3841 TGGTAAGTGG CATTATAAGC CCCAGTGATC TTCCAGATAG
3881 CCCTGGACAA ACCATGCCAC CAAGCAGAAG TAAAACACCT
3921 CCACCACCTC CTCAAACAGC TCAAACCAAG CGAGAAGTAC
3961 CTAAAAATAA AGCACCTACT GCTGAAAAGA GAGAGAGTGG
4001 ACCTAAGCAA GCTGCAGTAA ATGCTGCAGT TCAGAGGGTC
4041 CAGGTTCTTC CAGATGCTGA TACTTTATTA CATTTTGCCA
4081 CGGAAAGTAC TCCAGATGGA TTTTCTTGTT CATCCAGCCT
4121 GAGTGCTCTG AGCCTCGATG AGCCATTTAT ACAGAAAGAT
4161 GTGGAATTAA GAATAATGCC TCCAGTTCAG GAAAATGACA
4201 ATGGGAATGA AACAGAATCA GAGCAGCCTA AAGAATCAAA
4241 TGAAAACCAA GAGAAAGAGG CAGAAAAAAC TATTGATTCT
4281 GAAAAGGACC TATTAGATGA TTCAGATGAT GATGATATTG
4321 AAATACTAGA AGAATGTATT ATTTCTGCCA TGCCAACAAA
4361 GTCATCACGT AAAGCAAAAA AGCCAGCCCA GACTGCTTCA
4441 AAATTACCTC CACCTGTGGC AAGGAAACCA AGTCAGCTGC
4441 CTGTGTACAA ACTTCTACCA TCACAAAACA GGTTGCAACC
4481 CCAAAAGCAT GTTAGTTTTA CACCGGGGGA TGATATGCCA
4521 CGGGTGTATT GTGTTGAAGG GACACCTATA AACTTTTCCA
4561 CAGCTACATC TCTAAGTGAT CTAACAATCG AATCCCCTCC
4601 AAATGAGTTA GCTGCTGGAG AAGGAGTTAG AGGAGGGGCA
4641 CAGTCAGGTG AATTTGAAAA ACGAGATACC ATTCCTACAG
4681 AAGGCAGAAG TACAGATGAG GCTCAAGGAG GAAAAACCTC
4721 ATCTGTAACC ATACCTGAAT TGGATGACAA TAAAGCAGAG
4761 GAAGGTGATA TTCTTGCAGA ATGCATTAAT TCTGCTATGC
4801 CCAAAGGGAA AAGTCACAAG CCTTTCCGTG TGAAAAAGAT
4841 AATGGACCAG GTCCAGCAAG CATCTGCGTC TTCTTCTGCA
4881 CCCAACAAAA ATCAGTTAGA TGGTAAGAAA AAGAAACCAA
4921 CTTCACCAGT AAAACCTATA CCACAAAATA CTGAATATAG
4961 GACACGTGTA AGAAAAAATG CAGACTCAAA AAATAATTTA
5001 AATGCTGAGA GAGTTTTCTC AGACAACAAA GATTCAAAGA
5041 AACAGAATTT GAAAAATAAT TCCAAGGTCT TCAATGATAA
5081 GCTCCCAAAT AATGAAGATA GAGTCAGAGG AAGTTTTGCT
5121 TTTGATTCAC CTCATCATTA CACGCCTATT GAAGGAACTC
5161 CTTACTGTTT TTCACGAAAT GATTCTTTGA GTTCTCTAGA
5201 TTTTGATGAT GATGATGTTG ACCTTTCCAG GGAAAAGGCT
5241 GAATTAAGAA AGGCAAAAGA AAATAAGGAA TCAGAGGCTA
5281 AAGTTACCAG CCACACAGAA CTAACCTCCA ACCAACAATC
5321 AGCTAATAAG ACACAAGCTA TTGCAAAGCA GCCAATAAAT
5361 CGAGGTCAGC CTAAACCCAT ACTTCAGAAA CAATCCACTT
5401 TTCCCCAGTC ATCCAAAGAC ATACCAGACA GAGGGGCAGC
5441 AACTGATGAA AAGTTACAGA ATTTTGCTAT TGAAAATACT
5481 CCGGTTTGCT TTTCTCATAA TTCCTCTCTG AGTTCTCTCA
5521 GTGACATTGA CCAAGAAAAC AACAATAAAG AAAATGAACC
5561 TATCAAAGAG ACTGAGCCCC CTGACTCACA GGGAGAACCA
5601 AGTAAACCTC AAGCATCAGG CTATGCTCCT AAATCATTTC
5641 ATGTTGAAGA TACCCCAGTT TGTTTCTCAA GAAACAGTTC
5681 TCTCAGTTCT CTTAGTATTG ACTCTGAAGA TGACCTGTTG
5721 CAGGAATGTA TAAGCTCCGC AATGCCAAAA AAGAAAAAGC
5761 CTTCAAGACT CAAGGGTGAT AATGAAAAAC ATAGTCCCAG
5801 AAATATGGGT GGCATATTAG GTGAAGATCT GACACTTGAT
5841 TTGAAAGATA TACAGAGACC AGATTCAGAA CATGGTCTAT
5881 CCCCTGATTC AGAAAATTTT GATTGGAAAG CTATTCAGGA
5921 AGGTGCAAAT TCCATAGTAA GTAGTTTACA TCAAGCTGCT
5961 GCTGCTGCAT GTTTATCTAG ACAAGCTTCG TCTGATTCAG
6001 ATTCCATCCT TTCCCTGAAA TCAGGAATCT CTCTGGGATC
6041 ACCATTTCAT CTTACACCTG ATCAAGAAGA AAAACCCTTT
6081 ACAAGTAATA AAGGCCCACG AATTCTAAAA CCAGGGGAGA
6121 AAAGTACATT GGAAACTAAA AAGATAGAAT CTGAAAGTAA
6161 AGGAATCAAA GGAGGAAAAA AAGTTTATAA AAGTTTGATT
```

-continued

6201 ACTGGAAAAG TTCGATCTAA TTCAGAAATT TCAGGCCAAA

6241 TGAAACAGCC CCTTCAAGCA AACATGCCTT CAATCTCTCG

6281 AGGCAGGACA ATGATTCATA TTCCAGGAGT TCGAAATAGC

6321 TCCTCAAGTA CAAGTCCTGT TTCTAAAAAA GGCCCACCCC

6361 TTAAGACTCC AGCCTCCAAA AGCCCTAGTG AAGGTCAAAG

6401 AGCCACCACT TCTCCTAGAG GAGCCAAGCC ATCTGTGAAA

6441 TCAGAATTAA GCCCTGTTGC CAGGCAGACA TCCCAAATAG

6481 GTGGGTCAAG TAAAGCACCT TCTAGATCAG GATCTAGAGA

6521 TTCGACCCCT TCAAGACCTG CCCAGCAACC ATTAAGTAGA

6561 CCTATACAGT CTCCTGGCCG AAACTCAATT TCCCCTGGTA

6601 GAAATGGAAT AAGTCCTCCT AACAAATTAT CTCAACTTCC

6641 AAGGACATCA TCCCCTAGTA CTGCTTCAAC TAAGTCCTCA

6681 GGTTCTGGAA AAATGTCATA TACATCTCCA GGTAGACAGA

6721 TGAGCCAACA GAACCTTACC AAACAAACAG GTTTATCCAA

6761 GAATGCCAGT AGTATTCCAA GAAGTGAGTC TGCCTCCAAA

6801 GGACTAAATC AGATGAATAA TGGTAATGGA GCCAATAAAA

6841 AGGTAGAACT TTCTAGAATG TCTTCAACTA AATCAAGTGG

6881 AAGTGAATCT GATAGATCAG AAAGACCTGT ATTAGTACGC

6921 CAGTCAACTT TCATCAAAGA AGCTCCAAGC CCAACCTTAA

6961 GAAGAAAATT GGAGGAATCT GCTTCATTTG AATCTCTTTC

7001 TCCATCATCT AGACCAGCTT CTCCCACTAG GTCCCAGGCA

7041 CAAACTCCAG TTTTAAGTCC TTCCCTTCCT GATATGTCTC

7081 TATCCACACA TTCGTCTGTT CAGGCTGGTG GATGGCGAAA

7121 ACTCCCACCT AATCTCAGTC CCACTATAGA GTATAATGAT

7161 GGAAGACCAG CAAAGCGCCA TGATATTGCA CGGTCTCATT

7201 CTGAAAGTCC TTCTAGACTT CCAATCAATA GGTCAGGAAC

7241 CTGGAAACGT GAGCACAGCA AACATTCATC ATCCCTTCCT

7281 CGAGTAAGCA CTTGGAGAAG AACTGGAAGT TCATCTTCAA

7321 TTCTTTCTGC TTCATCAGAA TCCAGTGAAA AAGCAAAAAG

7361 TGAGGATGAA AAACATGTGA ACTCTATTTC AGGAACCAAA

7401 CAAAGTAAAG AAAACCAAGT ATCCGCAAAA GGAACATGGA

7441 GAAAAATAAA AGAAAATGAA TTTTCTCCCA CAAATAGTAC

7481 TTCTCAGACC GTTTCCTCAG GTGCTACAAA TGGTGCTGAA

7521 TCAAAGACTC TAATTTATCA AATGGCACCT GCTGTTTCTA

7561 AAACAGAGGA TGTTTGGGTG AGAATTGAGG ACTGTCCCAT

7601 TAACAATCCT AGATCTGGAA GATCTCCCAC AGGTAATACT

7641 CCCCCGGTGA TTGACAGTGT TTCAGAAAAG GCAAATCCAA

7681 ACATTAAAGA TTCAAAAGAT AATCAGGCAA AACAAAATGT

7721 GGGTAATGGC AGTGTTCCCA TGCGTACCGT GGGTTTGGAA

7761 AATCGCCTGA ACTCCTTTAT TCAGGTGGAT GCCCCTGACC

7801 AAAAAGGAAC TGAGATAAAA CCAGGACAAA ATAATCCTGT

-continued

7841 CCCTGTATCA GAGACTAATG AAAGTTCTAT AGTGGAACGT

7881 ACCCCATTCA GTTCTAGCAG CTCAAGCAAA CACAGTTCAC

7921 CTAGTGGGAC TGTTGCTGCC AGAGTGACTC CTTTTAATTA

7661 CAACCCAAGC CCTAGGAAAA GCAGCGCAGA TAGCACTTCA

8001 GCTCGGCCAT CTCAGATCCC AACTCCAGTG AATAACAACA

8041 CAAAGAAGCG AGATTCCAAA ACTGACAGCA CAGAATCCAG

8081 TGGAACCCAA AGTCCTAAGC GCCATTCTGG GTCTTACCTT

8121 GTGACATCTG TTTAAAAGAG AGGAAGAATG AAACTAAGAA

8161 AATTCTATGT TAATTACAAC TGCTATATAG ACATTTTGTT

8201 TCAAATGAAA CTTTAAAAGA CTGAAAAATT TTGTAAATAG

8241 GTTTGATTCT TGTTAGAGGG TTTTTGTTCT GGAAGCCATA

8281 TTTGATAGTA TACTTTGTCT TCACTGGTCT TATTTTGGGA

8321 GGCACTCTTG ATGGTTAGGA AAAAAATAGT AAAGCCAAGT

8361 ATGTTTGTAC AGTATGTTTT ACATGTATTT AAAGTAGCAT

8401 CCCATCCCAA CTTCCTTTAA TTATTGCTTG TCTTAAAATA

8441 ATGAACACTA CAGATAGAAA ATATGATATA TTGCTGTTAT

8481 CAATCATTTC TAGATTATAA ACTGACTAAA CTTACATCAG

8521 GGAAAAATTG GTATTTATGC AAAAAAAAAT GTTTTTGTCC

8561 TTGTGAGTCC ATCTAACATC ATAATTAATC ATGTGGCTGT

8601 GAAATTCACA GTAATATGGT TCCCGATGAA CAAGTTTACC

8641 CAGCCTGCTT TGCTTTACTG CATGAATGAA ACTGATGGTT

8681 CAATTTCAGA AGTAATGATT AACAGTTATG TGGTCACATG

8721 ATGTGCATAG AGATAGCTAC AGTGTAATAA TTTACACTAT

8761 TTTGTGCTCC AAACAAAACA AAAATCTGTG TAACTGTAAA

8801 ACATTGAATG AAACTATTTT ACCTGAACTA GATTTTATCT

8841 GAAAGTAGGT AGAATTTTTG CTATGCTGTA ATTTGTTGTA

8881 TATTCTGGTA TTTGAGGTGA GATGGCTGCT CTTTTATTAA

8921 TGAGACATGA ATTGTGTCTC AACAGAAACT AAATGAACAT

8961 TTCAGAATAA ATTATTGCTG TATGTAAACT GTTACTGAAA

9001 TTGGTATTTG TTTGAAGGGT CTTGTTTCAC ATTTGTATTA

9041 ATAATTGTTT AAAATGCCTC TTTTAAAAGC TTATATAAAT

9081 TTTTTTCTTC AGCTTCTATG CATTAAGAGT AAAATTCCTC

9121 TTACTGTAAT AAAAACAATT GAAGAAGACT GTTGCCACTT

9161 AACCATTCCA TGCGTTGGCA CTTATCTATT CCTGAAATTT

9201 CTTTTATGTG ATTAGCTCAT CTTGATTTTT AATATTTTTC

9241 CACTTAAACT TTTTTTTCTT ACTCCACTGG AGCTCAGTAA

9281 AAGTAAATTC ATGTAATAGC AATGCAAGCA GCCTAGCACA

9321 GACTAAGCAT TGAGCATAAT AGGCCCACAT AATTTCCTCT

9361 TTCTTAATAT TATAGAATTC TGTACTTGAA ATTGATTCTT

9401 AGACATTGCA GTCTCTTCGA GGCTTTACAG TGTAAACTGT

-continued

```
 9441 CTTGCCCCTT CATCTTCTTG TTGCAACTGG GTCTGACATG
 9481 AACACTTTTT ATCACCCTGT ATGTTAGGGC AAGATCTCAG
 9521 CAGTGAAGTA TAATCAGCAC TTTGCCATGC TCAGAAAATT
 9561 CAAATCACAT GGAACTTTAG AGGTAGATTT AATACGATTA
 9601 AGATATTCAG AAGTATATTT TAGAATCCCT GCCTGTTAAG
 9641 GAAACTTTAT TTGTGGTAGG TACAGTTCTG GGGTACATGT
 9681 TAAGTGTCCC CTTATACAGT GGAGGGAAGT CTTCCTTCCT
 9721 GAAGGAAAAT AAACTGACAC TTATTAACTA AGATAATTTA
 9761 CTTAATATAT CTTCCCTGAT TTGTTTTAAA AGATCAGAGG
 9801 GTGACTGATG ATACATGCAT ACATATTTGT TGAATAAATG
 9841 AAAATTTATT TTTAGTGATA AGATTCATAC ACTCTGTATT
 9881 TGGGGAGGGA AAACCTTTTT AAGCATGGTG GGGCACTCAG
 9921 ATAGGAGTGA ATACACCTAC CTGGTGCCTT GAAAATCACA
 9961 TCAAGTAGTT AATTATCTAC CCCTTACCTG TGTTTATAAC
10001 TTCCAGGTAA TGAGAATGAT TTTTTTTAAA GCTAAAATGC
10041 CAGTAAATAA AAGTGCTATG ACTTGAGCTA AGATATTTGA
10081 CTCCAATGCC TGTACTGTGT CTACTGCACC ACTTTGTAAA
10121 CACTTCAATT TACTATCTTT GAAATGATTG ACCTTTAAAT
10161 TTTTGCCAAA TGTTATCTGA AATTGTCTAT GAATACCATC
10201 TACTTCTGTT GTTTTCCCAG GCTTCCATAA ACAATGGAGA
10241 TACATGCA
```

SEQ ID NOs:16 and 17 are merely examples of some APC sequences. There are number of variations in APC genes and APC proteins that do not adversely affect their functions.

However, subjects with APC mutations that reduce the expression or functioning of their APC gene or the APC protein can lead to cancer. Hence, subjects treated by the methods and compositions described herein can have a variety of mutations in the APC gene such that a defective amount or type an APC protein is present in the subject. Subjects with missense mutations, nonsense mutations, silent mutations, and frameshift deletions in the APC gene can have cancers such as intestinal cancer, stomach cancer, and thymus cancer. Hence, use of the methods and compositions described herein can treat, prevent or ameliorate the incidence, progression, and severity of cancers such as cancers related to APC mutations.

The Examples illustrate the effects of the methods and compositions described herein on various animal models. For example, the animal models employed in the experimental work described herein included the following:

Lgr5-EGFP-CreER$^{T2}$; Apc$^{flox/flox}$ (WT)

Lgr5-EGFP-CreER$^{T2}$; Apc$^{flox/flox}$ (APC$^{-/-}$)

I.gr5-EGFP-CreER$^{T2}$; Apc$^{flox/flox}$; KHK$^{-/-}$ (APC$^{-/-}$ KHK$^{-/-}$)

Lgr5-EGFP-CreER$^{T2}$; Apc$^{flox/flox}$; Fasn$^{flox/flox}$ (APC$^{-/-}$ FASN$^{-/-}$)

Cdx2P-CreER$^{T2}$; Apo$^{flox/flox}$

Balb/c+azoxymethane (AOM) and dextran sodium sulfate (DSS)

Therefore, the methods, uses and compositions described herein are effective for treatment of subjects that have an APC mutation and that have symptoms of colorectal cancer, as well as intestinal polyps or adenomas that may eventually turn into cancer.

In some cases, the patient or subject that is treated has one or more activating mutations in beta catenin. The beta catenin protein in humans is encoded by the CTNNB1 gene. Mutations and overexpression of beta-catenin are associated with cancers such as hepatocellular carcinoma, colorectal carcinoma, lung cancer, malignant breast tumors, ovarian and endometrial cancer.

The CTNNB1 gene is located on chromosome 3 (see NCBI accession number NC_000003.12) at positions 41199422 . . . 41240445. The beta-catenin protein binds to the product of the APC gene, which is mutated in adenomatous polyposis of the colon. Mutations in this gene are a cause of colorectal cancer (CRC), pilomatrixoma (PTR), medulloblastoma (MDB), and ovarian cancer.

An example of a sequence for a human beta-catenin protein is shown below as SEQ ID NO:18.

```
  1 MELDMAMEPD RKAAVSHWQQ QSYLDSGIHS GATTTAPSLS
 41 GKGNPEEEDV DTSQVLYEWE QGFSQSFTQE QVADIDGQYA
 81 MTRAQRVRAA MFPETLDEGM QIPSTQFDAA HPTNVQRLAE
121 PSQMLKHAVV NLINYQDDAE LATRAIPELT KLLNDEDQVV
161 VNKAAVMVHQ LSKKEASRHA IMRSPQMVSA IVRTMQNTND
201 VETARCTAGT LHNLSHHREG LLAIFKSGGI PALVKMLGSP
241 VDSVLFYAIT TLHNLLLHQE GAKMAVRLAG GLQKMVALLN
281 KTNVKFLAIT TDVLQILAYG NQESKLIILA SGGPQALVNI
321 MRTYTYEKLL WTTSRVLKVL SVCSSNKPAI VEAGGMQALG
361 LHLTDPSQRL VNQCLWTLRN LSDAATKQEG MEGLLGTLVQ
401 LLGSDDINVV TCAAGILSNL TCNNYKNKMM VCQVGGIEAL
441 VRTVLRAGDR EDITEPAICA LRHLTSRHQE AEMAQNAVRL
481 HYGLPVVVKL LHPPSHWPLI KATVGLIRNL ALCPANHAPL
521 REQGAIPRLV QLLVRAHQDT QRRTSMGGTQ QQFVEGVRME
561 EIVEGCTGAL HILARDVHNR IVIRGLNTIP LFVQLLYSPI
601 ENIQRVAAGV LCELAQDKEA AEAIEAEGAT APLTELLHSR
641 NEGVATYAAA VLFRMSEDKP QDYKKRLSVE LTSSLFRTEP
681 MAWNETADLG LDIGAQGEPL GYRQDDPSYR SFHSGGYGQD
721 ALGMDPMMEH EMGGHHPGAD YPVDGLPDLG HAQDLMDGLP
761 PGDSNQLAWF DTDL
```

A cDNA sequence for the human beta-catenin protein (SEQ ID NO:18) is shown below as SEQ ID NO:19.

```
  1 AAGCCTCTCG GTCTGTGGCA GCAGCGTTGG CCCGGCCCCG
 41 GGAGCGGAGA GCGAGGGGAG GCGGAGACGG AGGAAGGTCT
 81 GAGGAGCAGC TTCAGTCCCC GCCGAGCCGC CACCGCAGGT
121 CGAGGACGGT CGGACTCCCG CGGCGGGAGG AGCCTGTTCC
161 CCTGAGGGTA TTTGAAGTAT ACCATACAAC TGTTTTGAAA
201 ATCCAGCGTG GACAATGGCT ACTCAAGGCT ACCTTTTGCT
```

-continued

241 CCATTTTCTG CTCACTCCTC CTAATGGCTT GGTGAAATAG
281 CAAACAAGCC ACCAGCAGGA ATCTAGTCTG GATGACTGCT
321 TCTGGAGCCT GGATGCAGTA CCATTCTTCC ACTGATTCAC
361 TGATTTGATG GAGTTGGACA TGGCCATGGA ACCAGACAGA
401 AAAGCGGCTG TTAGTCACTG GCAGCAACAG TCTTACCTGG
441 ACTCTGGAAT CCATTCTGGT GCCACTACCA CAGCTCCTTC
481 TCTGAGTGGT AAAGGCAATC CTGAGGAAGA GGATGTGGAT
521 ACCTCCCAAG TCCTGTATGA GTGGGAACAG GGATTTTCTC
561 AGTCCTTCAC TCAAGAACAA GTAGCTGATA TTGATGGACA
601 GTATGCAATG ACTCGAGCTC AGAGGGTACG AGCTGCTATG
641 TTCCCTGAGA CATTAGATGA GGGCATGCAG ATCCCATCTA
681 CACAGTTTGA TGCTGCTCAT CCCACTAATG TCCAGCGTTT
721 GGCTGAACCA TCACAGATGC TGAAACATGC AGTTGTAAAC
761 TTGATTAACT ATCAAGATGA TGCAGAACTT GCCACACGTG
801 CAATCCCTGA ACTGACAAAA CTGCTAAATG ACGAGGACCA
841 GGTGGTGGTT AATAAGGCTG CAGTTATGGT CCATCAGCTT
881 TCTAAAAAGG AAGCTTCCAG ACACGCTATC ATGCGTTCTC
921 CTCAGATGGT GTCTGCTATT GTACGTACCA TGCAGAATAC
961 AAATGATGTA GAAACAGCTC GTTGTACCGC TGGGACCTTG
1001 CATAACCTTT CCCATCATCG TGAGGGCTTA CTGGCCATCT
1041 TTAAGTCTGG AGGCATTCCT GCCCTGGTGA AAATGCTTGG
1081 TTCACCAGTG GATTCTGTGT TGTTTTATGC CATTACAACT
1121 CTCCACAACC TTTTATTACA TCAAGAAGGA GCTAAAATGG
1161 CAGTGCGTTT AGCTGGTGGG CTGCAGAAAA TGGTTGCCTT
1201 GCTCAACAAA ACAAATGTTA AATTCTTGGC TATTACGACA
1241 GACTGCCTTC AAATTTTAGC TTATGGCAAC CAAGAAAGCA
1281 AGCTCATCAT ACTGGCTAGT GGTGGACCCC AAGCTTTAGT
1321 AAATATAATG AGGACCTATA CTTACGAAAA ACTACTGTGG
1361 ACCACAAGCA GAGTGCTGAA GGTGCTATCT GTCTGCTCTA
1401 GTAATAAGCC GGCTATTGTA GAAGCTGGTG GAATGCAAGC
1441 TTTAGGACTT CACCTGACAG ATCCAAGTCA ACGTCTTGTT
1481 CAGAACTGTC TTTGGACTCT CAGGAATCTT TCAGATGCTG
1521 CAACTAAACA GGAAGGGATG GAAGGTCTCC TTGGGACTCT
1561 TGTTCAGCTT CTGGGTTCAG ATGATATAAA TGTGGTCACC
1601 TGTGCAGCTG GAATTCTTTC TAACCTCACT TGCAATAATT
1641 ATAAGAACAA GATGATGGTC TGCCAAGTGG GTGGTATAGA
1681 GGCTCTTGTG CGTACTGTCC TTCGGGCTGG TGACAGGGAA
1721 GACATCACTG AGCCTGCCAT CTGTGCTCTT CGTCATCTGA
1761 CCAGCCGACA CCAAGAAGCA GAGATGGCCC AGAATGCAGT
1801 TCGCCTTCAC TATGGACTAC CAGTTGTGGT TAAGCTCTTA

-continued

1841 CACCCACCAT CCCACTGGCC TCTGATAAAG GCTACTGTTG
1881 GATTGATTCG AAATCTTGCC CTTTGTCCCG CAAATCATGC
1921 ACCTTTGCGT GAGCAGGGTG CCATTCCACG ACTAGTTCAG
1961 TTGCTTGTTC GTGCACATCA GGATACCCAG CGCCGTACGT
2001 CCATGGGTGG GACACAGCAG CAATTTGTGG AGGGGGTCCG
2041 CATGGAAGAA ATAGTTGAAG GTTGTACCGG AGCCCTTCAC
2081 ATCCTAGCTC GGGATGTTCA CAACCGAATT GTTATCAGAG
2121 GACTAAATAC CATTCCATTG TTTGTGCAGC TGCTTTATTC
2161 TCCCATTGAA AACATCCAAA GAGTAGCTGC AGGGGTCCTC
2201 TGTGAACTTG CTCAGGACAA GGAAGCTGCA GAAGCTATTG
2241 AAGCTGAGGG AGCCACAGCT CCTCTGACAG AGTTACTTCA
2281 CTCTAGGAAT GAAGGTGTGG CGACATATGC AGCTGCTGTT
2321 TTGTTCCGAA TGTCTGAGGA CAAGCCACAA GATTACAAGA
2361 AACGGCTTTC AGTTGAGCTG ACCAGCTCTC TCTTCAGAAC
2401 AGAGCCAATG GCTTGGAATG AGACTGCTGA TCTTGGACTT
2441 GATATTGGTG CCCAGGGAGA ACCCCTTGGA TATCGCCAGG
2481 ATGATCCTAG CTATCGTTCT TTTCACTCTG GTGGATATGG
2521 CCAGGATGCC TTGGGTATGG ACCCCATGAT GGAACATGAG
2561 ATGGGTGGCC ACCACCCTGG TGCTGACTAT CCAGTTGATG
2601 GGCTGCCAGA TCTGGGGCAT GCCCAGGACC TCATGGATGG
2641 GCTGCCTCCA GGTGACAGCA ATCAGCTGGC CTGGTTTGAT
2681 ACTGACCTGT AAATCATCCT TTAGCTGTAT TGTCTGAACT
2721 TGCATTGTGA TTGGCCTGTA GAGTTGCTGA GAGGGCTCGA
2761 GGGGTGGGCT GGTATCTCAG AAAGTGCCTG ACACACTAAC
2801 CAAGCTGAGT TTCCTATGGG AACAATTGAA GTAAACTTTT
2841 TGTTCTGGTC CTTTTTGGTC GAGGAGTAAC AATACAAATG
2881 GATTTTGGGA GTGACTCAAG AAGTGAAGAA TGCACAAGAA
2921 TGGATCACAA GATGGAATTT ATCAAACCCT AGCCTTGCTT
2961 GTTAAATTTT TTTTTTTTTT TTTTTAAGAA TATCTGTAAT
3001 GGTACTGACT TTGCTTGCTT AGAAGTAGCT CTTTTTTTTT
3041 TTTTTTTTTT TTTTTTGCAG TAACTGTTTT TTAAGTCTCT
3081 CGTAGTGTTA AGTTATAGTG AATACTGCTA CAGCAATTTC
3121 TAATTTTTAA GAATTGAGTA ATGGTGTAGA ACACTAATTC
3161 ATAATCACTC TAATTAATTG TAATCTGAAT AAAGTGTAAC
3201 AATTGTGTAG CCTTTTTGTA TAAAATAGAC AAATAGAAAA
3241 TGGTCCAATT AGTTTCCTTT TTAATATGCT TAAAATAAGC
3281 AGGTGGATCT ATTTCATGTT TTTGATCAAA AACTATTTGG
3321 GATATGTATG GGTAGGGTAA ATCAGTAAGA GGTGTTATTT
3361 GGAACCTTGT TTTGGACAGT TTACCAGTTG CCTTTTATCC

-continued

```
3401 CAAAGTTGTT GTAACCTGCT GTGATACGAT GCTTCAAGAG

3441 AAAATGCGGT TATAAAAAAT GGTTCAGAAT TAAACTTTTA

3481 ATTCATTC
```

SEQ ID NOs:18 and 19 are merely examples of some beta-catenin sequences. There are a number of variations in CTNNB1 genes and beta-catenin proteins that do not adversely affect their functions.

However, subjects with mutations that increase the expression or functioning of their CTNNB1 gene or the beta-catenin protein can lead to cancer. Hence, subjects treated by the methods and compositions described herein can have a variety of mutations such that the amount or activity of a beta-catenin protein is present in the subject. Subjects with missense mutations, nonsense mutations, silent mutations, and frameshift deletions that affect the expression of the CTNNB1 gene or the activity of a beta-catenin protein can have cancers such as intestinal cancer, stomach cancer, and thymus cancer. Hence, use of the methods and compositions described herein can neat, prevent or ameliorate the incidence, progression, and severity of cancers such as cancers related to mutations that increase the expression or the activity of a beta-catenin protein.

Compositions

The GLUT5, FASN, PI3 kinase, or KHK inhibitors and/or GLUT5, FASN, PI3 kinase, or KHK binding agents can be formulated as compositions with or without additional therapeutic agents, and administered to an animal, such as a human patient, in a variety of forms adapted to the chosen route of administration. Routes for administration include, for example, oral, local, parenteral, intraperitoneal, intravenous and intraarterial routes.

The compositions can be formulated as pharmaceutical dosage forms. Such pharmaceutical dosage forms can include (a) liquid solutions; (b) tablets, sachets, or capsules containing liquids, solids, granules, or gelatin; (c) suspensions in an appropriate liquid; and (d) suitable emulsions.

Solutions of the active agents (GLUT5, FASN, PI3 kinase, or KHK inhibitors, other therapeutic agents and/or GLUT5, FASN, PI3 kinase, or KHK binding agents) can be prepared in water or saline, and optionally mixed with other agents. For example, formulations for intravenous or intraarterial administration may include sterile aqueous solutions that may also contain buffers, diluents, stabilizing agents, nontoxic surfactants, chelating agents, polymers and/or other suitable additives. Sterile injectable solutions are prepared by incorporating the active agents in the required amount in the appropriate solvent with various of the other ingredients, in a sterile manner or followed by sterilization (e.g., filter sterilization) after assembly.

In another embodiment, active agent-lipid particles can be prepared and incorporated into a broad range of lipid-containing dosage forms. For instance, the suspension containing the active agent-lipid particles can be formulated and administered as liposomes, gels, oils, emulsions, topical creams, pastes, ointments, lotions, foams, mousses, and the like.

In some embodiments, the active agents may be formulated in liposome compositions. Sterile aqueous solutions, active agent-lipid particles or dispersions comprising the active agent(s) are adapted for administration by encapsulation in liposomes. Such liposomal formulations can include an effective amount of the liposomally packaged active agent(s) suspended in diluents such as water, saline, or PEG 400.

The liposomes may be unilamellar or multilamellar and are formed of constituents selected from phosphatidylcholine, dipalmitoylphosphatidylcholine, cholesterol, phosphatidylethanolamine, phosphatidylserine, demyristoylphosphatidylcholine and combinations thereof. The multilamellar liposomes comprise multilamellar vesicles of similar composition to unilamellar vesicles but are prepared to provide a plurality of compartments in which the silver component in solution or emulsion is entrapped. Additionally, other adjuvants and modifiers may be included in the liposomal formulation such as polyethyleneglycol, or other materials.

While a suitable formulation of liposome includes dipalmitoylphosphatidylcholine:cholesterol (1:1) it is understood by those skilled in the art that any number of liposome bilayer compositions can be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101.

The liposomes containing the active agents may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules which preferentially target the liposome to specific organs or cell types include for example antibodies which target the liposomes to cells bearing specific antigens. Techniques for coupling such molecules are available (see for example U.S. Pat. No. 4,762,915 the disclosure of which is incorporated herein by reference). Alternatively, or in conjunction, one skilled in the art would understand that any number of lipids bearing a positive or negative net charge may be used to alter the surface charge or surface charge density of the liposome membrane. The liposomes can also incorporate thermal sensitive or pH sensitive lipids as a component of the lipid bilayer to provide controlled degradation of the lipid vesicle membrane.

Liposome formulations for use with active agents may also be formulated as disclosed in WO 2005/105152 (the disclosure of which is incorporated herein in its entirety). Briefly, such formulations comprise phospholipids and steroids as the lipid component. These formulations help to target the molecules associated therewith to in vivo locations without the use of an antibody or other molecule.

Antibody-conjugated liposomes, termed immunoliposomes, can be used to carry active agent(s) within their aqueous compartments. Compositions of active agent(s) provided within antibody labeled liposomes (immunoliposomes) can specifically target the active agent(s) to a particular cell or tissue type to elicit a localized effect. Methods for making of such immunoliposomal compositions are available, for example, in Selvam M. P., et al., 1996. Antiviral Res. Dec; 33(1):11-20 (the disclosure of which is incorporated herein in its entirety).

For example, immunoliposomes can specifically deliver active agents to the cells possessing a unique antigenic marker recognized by the antibody portion of the immunoliposome. Immunoliposomes are ideal for the in vivo delivery of active agent(s) to target tissues due to simplicity of manufacture and cell-specific specificity.

Tumor-specific antibodies can be used in conjunction with the inhibitors or liposomes containing inhibitors. Other active agents can also be included in such liposomes. Antibodies such as anti-CD1 lb antibodies, anti-CD33 antibodies, anti-VEGF receptor antibodies, anti-alphafetoprotein (AFP) antibodies, anti-carcinoembryonic antigen (CEA) antibodies, anti-CA-125 antibodies, anti-MUC-1 antibodies, anti-epithelial tumor antigen (ETA) antibodies, anti-tyrosinase antibodies, anti-ras antibodies, anti-p53 antibodies and antibodies directed against melanoma-associated antigen 1 (MAGE1) can be used in liposomes. For example, the antibodies can be mixed with or tethered to the lipids making up the liposomal shell. VEGF receptor is highly expressed in various tumor-related cells. The entire coding sequences for all MAGE genes are located within the last exon, which exhibits 64 to 85% homology with the sequence of MAGE1. Active agents including GLUT5, FASN. PI3 kinase, or KHK inhibitors can be loaded into liposomes following conjugation of liposomal lipids with antibodies that specifically bind CD11b, CD33, VEGF receptor, AFT, CEA, CA-125, MUC-1, ETA, tyrosinase, ras, p53, MAGE1, or combinations of antibodies directed against these or other tumor antigens.

In some instances, the active agents can be administered orally, in combination with a pharmaceutically acceptable vehicle such as an inert diluent or an assimilable edible carrier. They may be enclosed in hard or softshell gelatin capsules, may be compressed into tablets, or may be incorporated directly with the food of the patient's diet. For oral therapeutic administration, they may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied. The amount of compound in such therapeutically useful compositions is such that an effective dosage level will be obtained.

The active agents can also be incorporated into dosage forms such as tablets, troches, pills, and capsules. These dosage forms may also contain any of the following: binders such as gum tragacanth, acacia, corn starch or gelatin; excipients such as dicalcium phosphate; a disintegrating agent such as corn starch, potato starch, alginic acid and the like; a lubricant such as magnesium stearate; polymers such as cellulose-containing polymers (e.g., hydroxypropyl methylcellulose, methylcellulose, ethylcellulose), polyethylene glycol, poly-glutamic acid, poly-aspartic acid or poly-lysine; and a sweetening agent such as lactose or aspartame or a flavoring agent such as peppermint, oil of wintergreen, or cherry flavoring may be added.

Tablet formulations can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active agents in a flavoring or sweetener, e.g., as well as pastilles comprising the active a (s) in an inert base, such as gelatin and glycerin or sucrose and acacia emulsions, gels, and the like containing carriers available in the art.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compounds and agents may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In some embodiments, one or more of the active agents are linked to polyethylene glycol (PEG). For example, one of skill in the art may choose to link an active agent to PEG to form the following pegylated drug.

Useful dosages of the active agents (e.g., GLUT5, FASN, PI3 kinase, or KHK inhibitors) can be determined by comparing their in vitro activity, and in vivo activity in animal models, for example, as described herein. Methods for the extrapolation of effective dosages in mice, and other animals, to humans are available to the art; for example, see U.S. Pat. No. 4,938,949. The agents can be conveniently administered in unit dosage form.

The desired dose may conveniently be presented in a single dose or as divided doses administered at appropriate intervals, for example, as two, three, four or more sub-doses per day. The sub-dose itself may be further divided, for example, into a number of discrete loosely spaced administrations; such as multiple oral, intraperitoneal or intravenous doses. For example, it can be desirable to administer the present compositions intravenously over an extended period, either by continuous infusion or in separate doses.

The therapeutically effective amount of the active agent(s) a GLUT5, FAS PI3 kinase, and/or KHK inhibitor) necessarily varies with the subject and the disease, disease severity, or physiological problem to be treated. As one skilled in the art would recognize, the amount can be varied depending on the method of administration. The amount of the active agent (e.g., inhibitor) for use in treatment will vary not only with the route of administration, but also the nature of the condition being treated and the age and condition of the patient and will be ultimately at the discretion of the attendant physician or clinician.

The pharmaceutical compositions of the invention can include an effective amount of at least one of the active agents of the invention (e.g., GLUT5, FASN, PI3 kinase, or KHK inhibitors), or two or more different agents of the invention (e.g., two or more GLUT5, FASN, PI3 kinase, or KHK inhibitors). These compositions can also include a pharmaceutically effective carrier.

The components of the compositions are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can be beneficial to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge. The bioactivity of the components can be determined by use of an in vitro assay system which measures the activity the component and can be determined by various methods. Such bioactivities can be expressed as $EC_{50}$ or $IC_{50}$ values.

Generally, the compounds are dispensed in unit dosage form including from about 0.05 mg to about 1000 mg of active ingredient together with a pharmaceutically acceptable carrier per unit dosage.

The pharmaceutical compositions of the invention can also include other active ingredients and therapeutic agents, for example, other chemotherapeutic agents, anti-inflammatory agents, analgesics, vitamins, and the like. It is also within the scope of the present invention to combine any of the methods and any of the compositions disclosed herein with conventional cancer therapies, anti-cancer agents and various drugs in order to enhance the efficacy of such methods and/or compositions. For example, methods and compositions containing combinations of active agents can act through different mechanisms to improve the efficacy or speed of treatment. Methods and compositions containing combinations of active agents can also reduce the doses/toxicity of conventional therapies and/or to increase the sensitivity of conventional therapies.

One conventional therapy that can be used in conjunction with the methods and compositions containing combinations of active agents is surgery to remove identified sites of tumors. Other conventional therapies that can be employed include radiation therapy or other types of chemotherapeutic drugs. Chemotherapeutic drugs that can be used include anti-cancer drugs available in the art, including but not limited to any radioactive drug, topoisomerase inhibitor, DNA binding agent, anti-metabolite, cytoskeletal-interacting drugs, ionizing radiation, or a combination of two or more of such known DNA damaging agents.

Cytoskeletal drugs are small molecules that interact with actin or tubulin. Any such cytoskeletal drug can be used in the methods and compositions described herein. Cytoskeletal drugs include paclitaxel, colchicine, cytochalasins, demecolcine, latsunculin, nocodazole, phalloidin, swinholide and vinblastine. Some cytoskeletal drugs stabilize a cytoskeletal component, for example, paclitaxel stabilizes microtubules. Other cytoskeletal drugs prevent polymerization. For example, cytochalasin D binds to actin monomers and prevents polymerization of actin filaments. In some embodiments, the anti-cancer agent is paclitaxel.

A topoisomerase inhibitor that can be used in conjunction with the invention can be, for example, a topoisomerase I (Topo I) inhibitor, a topoisomerase II (Topo II) inhibitor, or a dual topoisomerase I and II inhibitor. A topo I inhibitor can be from any of the following classes of compounds: camptothecin analogue (e.g., karenitecin, aminocamptothecin, lurtotecan, topotecan, irinotecan, BAY 56-3722, nibitecan, G114721, exatecan mesylate), rebeccamycin analogue, PNU 16614$, rebeccamycin, TAS-103, camptothecin (e.g., camptothecin polyglutamate, camptothecin sodium), intoplicine, ecteinascidin 743, J-107088, pibenzimol. Examples of preferred topo I inhibitors include but are not limited to camptothecin, topotecan (hycaptamine), irinotecan (irinotecan hydrochloride), belotecan, or an analogue or derivative thereof.

A topo II inhibitor that can be used in conjunction with the invention can be, for example, from any of the following classes of compounds: anthracycline antibiotics (e.g., carubicin, pirarubicin, daunorubicin citrate liposomal, daunomycin, 4-iodo-4-doxydoxorubicin, doxorubicin, docetaxel, n,n-dibenzyl daunomycin, morpholinodoxorubicin, aclacinomycin antibiotics, duborimycin, menogaril, nogalamycin, zorubicin, epirubicin, marcellomycin, detorubicin, annamycin, 7-cyanoquinocarcinol, deoxydoxorubicin, idarubicin, GPX-100, MEN-10755, valrubicin, KRN5500), epipodophyllotoxin compound (e.g., podophyllin, teniposide, etoposide, GL331, 2-ethylhydrazide), anthraquinone compound (e.g., ametantrone, bisantrene, mitoxantrone, anthraquinone), ciprofloxacin, acridine carboxamide, amonafide, anthrapyrazole antibiotics (e.g., teloxantrone, secloxantrone trihydrochloride, piroxantrone, anthrapyrazole, losoxantrone), TAS-103, fostriecin, razoxane, XK469R, XK469, chloroquinoxaline sulfonamide, merbarone, intoplicine, elsamitrucin, CI 921, pyrazoloacridine, elliptinium, amsacrine. Examples of preferred topo II inhibitors include but are not limited to doxorubicin (Adriamycin), etoposide phosphate (etopofos), teniposide, sobuzoxane, or an analogue or derivative thereof.

DNA binding agents that can be used in conjunction with the invention include but are not limited to DNA groove binding agent, e.g., DNA minor groove binding agent; DNA crosslinking agent; intercalating agent; and DNA adduct forming agent. A DNA minor groove binding agent can be an anthracycline antibiotic, mitomycin antibiotic (e.g., porfiromycin, KW-2149, mitomycin B, mitomycin A, mitomycin C), chromomycin A3, carzelesin, actinomycin antibiotic (e.g., cactinomycin, dactinomycin, actinomycin F1), brostallicin, echinomycin, bizelesin, duocarmycin antibiotic (e.g., KW 2189), adozelesin, olivomycin antibiotic, plicamycin, zinostatin, distamycin, MS-247, ecteinascidin 743, amsacrine, anthramycin, and pibenzimol, or an analogue or derivative thereof. DNA crosslinking agents include but are not limited to antineoplastic alkylating agent, methoxsalen, mitomycin antibiotic, psoralen. An antineoplastic alkylating agent can be a nitrosourea compound (e.g., cystemustine, tauromustine, semustine, PCNU, streptozocin, SarCNU, CGP-6809, carmustine, fotemustine, methylnitrosourea, nimustine, ranimustine, ethylnitrosourea, lomustine, chlorozotocin), mustard agent (e.g., nitrogen mustard compound, such as spiromustine, trofosfamide, chlorambucil, estramustine, 2,2,2-trichlorotriethylamine, prednimustine, novembichin, phenamet, glufosfamide, peptichemio, ifosfamide, defosfamide, nitrogen mustard, phenesterin, mannomustine, cyclophosphamide, melphalan, perfosfamide, mechlorethamine oxide hydrochloride, uracil mustard, bestrabucil, DHEA mustard, tallimustine, mafosfamide, aniline mustard, chlomaphazine; sulfur mustard compound, such as bischloroethylsulfide; mustard prodrug, such as TLK286 and ZD2767), ethylenimine compound (e.g., mitomycin antibiotic, ethylenimine, uredepa, thiotepa, diaziquone, hexamethylene bisacetamide, pentamethylmelamine, altretamine, carzinophilin, triaziquone, meturedepa, benzodepa, carboquone), alkylsulfonate compound (e.g., dimethylbusulfan, Yoshi-864, improsulfan, piposulfan, treosulfan, busulfan, hepsulfam), epoxide compound (e.g., anaxirone, mitolactol, dianhydrogalactitol, teroxirone), miscellaneous alkylating agent (e.g., ipomeanol, carzelesin, methylene dimethane sulfonate, mitobronitol, bizelesin, adozelesin, piperazinedione, VNP40101M, asaley, 6-hydroxymethylacylfulvene, EO9, etoglucid, ecteinascidin 743, pipobroman), platinum compound (e.g., ZD0473, liposomal-cisplatin analogue, satraplatin, BBR 3464, spiroplatin, ormaplatin, cisplatin, oxaliplatin, carboplatin, lobaplatin, zeniplatin, iproplatin), triazene compound (e.g., imidazole mustard, CB 10-277, mitozolomide, temozolomide, procarbazine, dacarbazine), picoline compound (e.g., penclomedine), or an analogue or derivative thereof. Examples of preferred alkylating agents include but are not limited to cisplatin, dibromoduicitol, fotemustine, ifosfamide (ifosfamid), ranimustine (ranomustine), nedaplatin (latoplatin), bendamustine (bendamustine hydrochloride), eptaplatin, temozolomide (methazolastone), carboplatin, altretamine (hexamethylmelamine), prednimustine, oxaliplatin (oxalaplatinum), carmustine, thiotepa, leusulfon (busulfan), lobaplatin, cyclophosphamide, bisulfan, melphalan, and chlorambucil, or analogues or derivatives thereof.

Intercalating agents can be an anthraquinone compound, bleomycin antibiotic, rebeccamycin analogue, acridine, acridine carboxamide, amonafide, rebeccamycin, anthrapyrazole antibiotic, echinomycin, psoralen, LU 79553, BW A773U, crisnatol mesylate, benzo(a)pyrene-7,8-diol-9,10-epoxide, acodazole, elliptinium, pixantrone, or an analogue or derivative thereof, etc.

DNA adduct forming agents include but are not limited to enediyne antitumor antibiotic (e.g., dynemicin A, esperamicin A1, zinostatin, dynemicin, calicheamicin gamma 11), platinum compound, carmustine, tamoxifen (e.g., 4-hydroxy-tamoxifen), psoralen, pyrazine diazohydroxide, benzo(a)pyrene-7,8-diol-9,10-epoxide, or an analogue or derivative thereof.

Anti-metabolites include but are not limited to cytosine, arabinoside, floxuridine, fluorouracil, mercaptopurine, Gemcitabine, and methotrexate (MTX).

Monoclonal antibodies, cancer vaccines, angiogenesis inhibitors, and gene therapy are targeted therapies that can also be combined into the GLUT5, FASN. PI3 kinase, or KHK inhibitor compositions and used in the methods described herein.

The ultimate dosage form should be sterile, fluid and stable under the conditions of manufacture and storage.

Kits

Another aspect of the invention is one or more kits for inhibiting or treating the cancer.

The kits of the present invention can include GLUT5, FASN, PI3 kinase, and/or KHK inhibitor, a chemotherapeutic agent, instructions for reducing or eliminating ingestion of certain sugars, polysaccharides, and/or amino acids, or a combination thereof. The kits can also include instructions for administering the GLUT5, FASN, PI3 kinase, and/or KHK inhibitor, and/or the chemotherapeutic agent.

The following non-limiting Examples illustrate materials and methods used for development of the invention.

Example 1: Materials and Methods

This Example describes some of the materials and methods used in the experiments described herein.

Animal Study

A genetically engineered mouse model of intestinal tumorigenesis, Lgr5-EGFP-IRES-creERT2; $Apc^{flox/flox}$ (referred as $APC^{-/-}$) mice, in C57BL/6 background were generated as described by Yun et al. (*Science*. 350, 1391-1396 (2015)). Compound mice, $APC^{-/-}$; FASN and $APC^{-/-}$; $KHK^{-/-}$ mice, were generated by crossing the $APC^{-/-}$ line with $FASN^{-/-}$ mice and mice deficient in ketohexokinase (KHK). $FASN^{flox/flox}$ mice were generously provided by Dr. Semenkovich at Washington University (Lodhi et al. *Cell Metab*, 16, 189-201 (2012)). $KHK^{-/-}$ mice lacking both KHK-A and KHK-C in a C57BL/6 background and were kindly shared by Dr. Bonthron at University of Leeds at UK and Drs. Lanaspa and Johnson at University of Colorado (Diggle et al. J. *Histochem, Cytochem,* 57, 763-774 (2009)). CDX2P-$CreER^{T2}$ mice were purchased from JAX stock #022390 (Feng et al., *Am, J. Pathol.* 183, 493-503 (2013)) and crossed to $APC^{flox/flox}$ mice to generate CDX2P-$CreER^{T2}$; $APC^{flox/flox}$ mice. Only male mice were used throughout the study to reflect the strong epidemiological evidence linking obesity or sugar consumption to colon cancer incidence in male but not female (Kim et al., *Cancer Causes Control CCC.* 28, 1-4 (2017)). Mice were maintained in temperature-controlled and humidity-controlled specific pathogen-free conditions on a 12-hour light/dark cycle and received rodent chow (PicoLab Rodent 20 5053 lab Diet St. Louis, MO) and free access to drinking water. Mice harboring Lgr5-EGFP-IRES-creERT2 allele ($APC^{-/-}$, APC $FASN^{-/-}$ and $APC^{-/-}$; $KHK^{-/-}$) were injected a single tamoxifen intraperitoneal injection (IP) (20 mg/kg, Sigma, Cat. #T5648) at 7 to 8 weeks of age to induce tumors. CDX2P-$CreER^{T2}$; $APC^{flox/flox}$ mice were injected a single tamoxifen IP injection (16 mg/kg) at 7 to 8 weeks of age. Littermates without tumor induction were used as wild-type (WT) controls. High-fructose corn syrup (HFCS) was prepared by combining D-(+)-Glucose (Sigma, Cat. #G8270) and D-(−)-Fructose (Sigma, Cat. #F0127) in a 45:55 ratio using tap water. Age-matched cohorts of WT and $APC^{-/-}$ were created with HFCS by two types of methods. The first is via ad libitum delivery in the drinking water (25% HFCS in water, referred as the Water Bottle or WB group). The other method is via daily oral gavage of HFCS (Glucose 45 mg+Fructose 55 mg, total 400 ul in tap water, referred as HFCS group). As a control for the HFCS group, mice were treated with 400 ul of tap water via daily oral gavage (referred as Con group). $APC^{-/-}$; $KHK^{-/-}$ mice were treated with HFCS or water via daily oral gavage (HFCS or Con groups). Treatments in $APC^{-/-}$ and $APC^{-/-}$; $KHK^{-/-}$ mice started the day after tamoxifen injection. Mice were longitudinally assessed for intestinal tumor progression by testing weekly for the presence of heme in the stool using the Hemocult Sensa test (Beckman Coulter). Animals were euthanized based on the degree weight loss and the Hemocult score. This resulted in all $APC^{-/-}$, $FASN^{-/-}$, and $APC^{-/-}$; $KHK^{-/-}$ mice being sacrificed between 8 and 9 weeks after treatment. Polyp number and volume were determined in whole mount tissue following methylene blue staining (0.2% methylene blue in $H_2O$, Sigma, Cat. #M9140) using a dissecting microscope in a blinded manner. Subsequently, intestines were Swiss-rolled, paraffin embedded, and subjected to histologic analysis following H&E staining. Experiments were repeated multiple times over 15 cohorts of 8-10 mice per group. All animal studies were approved by the Institutional Animal Care and Use Committee (IACUC) of Weill Cornell Medical College and Baylor College of Medicine.

Body Composition and Glucose Tolerance

Body Mass, Fat mass (FM) and fat-free mass (FFM) were measured and calculated using magnetic resonance spectroscopy (MRI) as described by Mystkowski et al. (*Int. J. Obes, Relat. Metab. Disord. J. Int. Assoc. Study Obes.* 24.719-724 (2000)). Skeletal muscle was assessed by measuring the weight of the gastrocnemius. Visceral fat was assessed by measuring the weight of the gonadal white adipose depot. Glucose tolerance testing was performed in WT and $APC^{-/-}$ mice with or without chronic treatment using WB or HFCS. Mice were fasted for six hours after which 2 g/kg intraperitoneal glucose solution was administered. Tail blood glucose was measured with a glucose meter over time. Mice were allowed to recover and resume their diets after completion of the testing.

Biochemical Analysis

The serum level of insulin was determined using the Ultra-Sensitive Mouse Insulin ELISA Kit (Crystal Chem Inc. Cat. #90080) after mice were fasted for six hours. Glucose and Fructose concentration in the serum and the intestinal lumen were measured with EnzyChrom glucose assay kit (BioAssay Systems, Cat. #EBGL-100) and EnzyChrom fructose assay kit (BioAssay Systems, Cat. #EFRU-100). For measurement of hepatic and stool triglyceride, the frozen liver or stool were weighed and digested in 6 volumes of alcoholic KOH (2:1 EtOH to 30% KOH) at 60° C. until tissue was completely dissolved. 500 μL of digest was added to 540 μL of 1M $MgCl_2$ and mixed well. After 10-minute incubation on ice, samples were centrifuged for 30 minutes at maximum speed. The supernatant was aspirated into a new tube and glycerol content was measured using calorimetric assay (Stanbio, Boerne, TX). Phosphofructokinase activity was measured using a commercial assay kit (Abcam ab155898). As per the vendor's instructions, tumors were homogenized by Dounce homogenizer in ice-cold assay buffer. It was determined that 5 ug of tumor homogenate was ideal per reaction. The kinetic change in absorbance was measured using a POLARstar Omega plate reader.

Metabolite Extraction for Targeted Metabolomics

Polar metabolites were extracted from the frozen liver, small intestinal epithelium, and tumor tissue using either 80% methanol (Yuan et al. *Nat. Protoc.* 7, 872-881 (2012)) or a 40:40:20 mixture of acetonitrile:methanol:water with 0.1M formic acid followed by neutralization with ammonium bicarbonate for ATP measurements (Lu et al. Anna, Rev, Biochem. 86, 277-304 (2017)). Briefly, each sample was crushed on dry ice using a mortar and pestle and transferred to a pre-cooled 2 mL homogenization tube. Pre-cooled exaction buffer (1 mL) was added to each sample and incubated on ice for 10 min. Samples were then centrifuged at 4° C. for 15 minutes at 14,000 rpm. The supernatants were removed, and pellets were re-extracted with 0.5 mL of extraction buffer. The pooled supernatants were then evaporated, and used for LC/MS. For fatty acid analysis, total tissue lipids were extracted and saponified using methods described by Kamphorst et al. (Anal. Chem. 83, 9114-9122 (2011)). Lipids were extracted from crushed tissue powder using 1 ml of cold 50:50 mnethanol:water containing 0.1M HCl followed by the addition of 0.5 ml of chloroform. The mixture was vortexed and centrifuged at 16.000×g for 5 min. The lower chloroform layer was transferred to a glass vial and pooled together with a subsequent 0.5 ml chloroform wash of the methanol:water phase. The chloroform phase was dried under nitrogen gas, resuspended in 1 ml of 90:10 MeOH:$H_2O$ containing 0.3M KOH, and incubated for 1 h at 80° C. to saponify fatty acids. The fatty acids were then extracted in 1 ml of hexanes, dried under nitrogen gas, and used for LC/MS.

Targeted Metabolomics Analysis

Analytical mass spectroscopy was carried out to quantify aqueous polar metabolites, fatty acids, and sugar phosphates. For polar metabolites, aqueous tissue extracts were separated via liquid chromatography on an Agilent 1290 LC system (Agilent Technologies, Santa Clara, CA) as detailed by de Carvalho et al. (Chem. Biol. 17, 323-332 (2010)). Briefly, solvent A ($ddH_2O$ with 0.2% formic acid) and solvent B (acetonitrile with 0.2% formic acid) mobile phase solvents are paired to a Cogent Diamond Hydride Type C column (MicroSolv Technology Corp, Leland, NC) with the following gradient applied at 0.4 mL/min flow rate: 0-2 min, 85% B; 3-5 min, 80% B; 6-7 min, 75%; 8-9 min, 70% B; 10-11.1 min, 50% B; 11.1-14 min 20% B; 14.1-24 min 5% B followed by a 10 min wash period at 85% B. The continuous infusion of twin reference masses for mass axis calibration achieved mass errors of <6 ppm.

Dried fatty acid pellets were resuspended in 50% methanol and 0.2% formic acid in $ddH_2O$ and transferred to glass autosampler vials. Mass spectrometry was based on methods described by Sana et al. (*J. Chromatogr. B Analyt. Technol. Biomed. Life. Sci,* 871, 314-321 (2008)). Briefly, a ZORBAX Eclipse Plus C18 column 4.6 mm×100 mm, 3.5 μm (Agilent Technologies, Santa Clara, CA) was paired with an Agilent 1200 Rapid Resolution system. The LC parameters were as follows: column temperature, 40° C.; injection volume, 4 μL; flow rate of 0.4 mL/min. Chromatography relied on a gradient of solvent A (0.2% formic acid in methanol) to solvent B (0.2% formic acid in $ddH_2O$), where a 2-minute equilibration period of 90% A was followed by a linear decrease over the course of 18-minutes to 2% followed by a 17-minute hold. Acquisition was performed on an Agilent 6224 TOE mass spectrometer in high resolution mode. The following settings were used: ESI capillary voltage, 4000 V (+) and 3500 V (−); fragmentor 170 V, the liquid nebulizer was set to 35 psig and the nitrogen drying gas was set to a flow rate of 12 L/min at 250° C. APCI capillary voltage was set at 4000 V (both ion modes), corona current was set to 4 μA and fragmentor at 170 V. The liquid nebulizer was set to 60 psig. Centroid mode was used for acquisition of 1.4 spectra/s for m/z's from 50-1300.

Sugar phosphate identification was done by a method that included an ion pairing chromatographic method that was developed for the resolution of phosphate-containing compounds from small molecule extracts (Hartman et al. Metabolomics Analysis of Tuberculosis Drug Activity Using an Agilent 6545 Q-TOF LC/MS (2017), (available at webpage agilent.com/cs/library/applications/5991-7970EN.pdf). Reproducible separation of individual hexose phosphate species was accomplished on an Agilent 1290 infinity LC system by injection of 5 μL of filtered extract through an Agilent ZORBAX Extend C18, 2.1×150 mm, 1.8 nm (Agilent Technologies, Santa Clara, CA) downstream of an Agilent ZORBAX SB-C8, 2.1 mm×30 mm, 3.5 nm (Agilent Technologies, Santa Clara, CA) guard column heated to 40° C. Solvent A (97% water/3% methanol containing 5 mM tetrabutylammonium hydroxide (TBA) and 5.5 mM acetic acid) and Solvent B (methanol containing 5 mM TBA and 5.5 mM acetic acid) were infused at a flow rate of 0.250 mL/min. The 24-minute reverse phase gradient was as follows: 0-3.5 min, 0% B; 4-7.5 min, 30% B; 8-15 min, 35% B: 20-24 min, 99% B; followed by a 7-minute post-run at 0% B. Acquisition was performed on an Agilent 6230 TOE mass spectrometer (Agilent Technologies, Santa Clara, CA) employing an Agilent Jet Stream electrospray ionization source (Agilent Technologies, Santa Clara, CA) operated at 4000 V Cap and 2000 V nozzle voltage in high resolution, negative mode. The following settings were used for acquisition: The sample nebulizer set to 45 prig with sheath gas flow of 12 L/min at 400° C. Drying gas was kept at 325° C. at 8 L/min. Fragmentor was set to 125 V, with the skimmer set to 50 V and Octopole Vpp at 400 V. Samples were acquired in centroid mode for 1.5 spectra/s for m/z's from 50-1100.

Collected data from the above methods was analyzed by batch processing with Agilent MassHunter Profinder software version 8.0SPI (Agilent Technologies, Santa Clara.

CA) for both targeted and untargeted analysis. Targeted metabolites were identified from m/z pairs by both retention time comparability with authentic standards and expected isotopomer distributions. Untargeted compounds were first identified as m/z:RT pairs using the Profinder Batch Targeted Feature Extraction. Candidate pairs were then processed through Agilent Mass Profiler Professional software version B14.5 (Agilent Technologies, Santa Clara, CA), where features were assessed for quality control measures (threshold m/z value peak height >10,000, coefficient of variation <25%) and statistically analyzed. When indicated mice or tumors were pre-treated with D-[$^{14}C$(U)]-Glucose (Perkin Elmer, Waltham, MA), D-[$^{14}C$(U)]-Fructose (American Radiolabeled Chemicals, St. Louis, MO), D-[U-$^{13}C_6$]-Glucose (Cambridge isotope Laboratories, Tewksbury, MA), or D-[U-$^{13}C_6$]-Fructose (Cambridge Isotope Laboratories, Tewksbury, MA). The various fatty acids are represented by "Cx:y" where x denotes the number of carbons and y the number of double bonds. For example, the symbol for palmitic acid is C16:0 and palmitoleic acid is C16:1. Eicosanoids were measured from total tumor lysates using the Comprehensive Eicosanoid Panel at the UCSD Lipidomics Core (Quehenberger et al. *J. Lipid Res.* 51, 3299-3305 (2010)).

Untargeted Metabolites Profiling

The excised animal tissues or tumors were added to 2 mL Eppendorf tubes containing 600 μL of 3 mM monobromobimane (MBB) in $CH_3OH$:$H_2O$ (80:20) at −20° C. and incubated for 2 h, followed by 1 h incubation at 0° C. Here, MBB was used to react with thiols and protect them for further oxidation. This initial incubation was followed by tissue disruption using stainless steel beads in a TissueLyser (Qiagen) and an additional 30 min at −20° C. Extracts were centrifuged for 15 min at 13000 rpm to pellet insoluble material and supernatants were transferred to clean tubes. This extraction was repeated two additional times and all three supernatants were dried in a speed-vac (Savant) and stored at −80° C. until analysis. For normalization of sample analyses, post-extracted tissue/tumor pellets were solubilized in 800 μL of 0.2 M aqueous NaOH at 95° C. for 60 min and the pellet protein was determined using the BioRad assay, relative to bovine serum albumin standards (0-1.5 mg/mL). For metabolite analysis, dried tissue/tumor extracts were reconstituted in $CH_3CN$:$H_2O$ (70:30) containing 0.025% acetic acid at a relative protein concentration of 10 μg/μL and 3 μL solution was injected for LC/MS. Plasma were incubated with 2.5 mM MBB in $CH_3OH$:$H_2O$ (80:20) at room temperature for 30 min, then diluted with same volume of $CH_3CN$:$H_2O$ (70:30) containing 0,025% acetic acid. The diluted samples were briefly vortexed and centrifuged for 25 min at 20,000 g to pellet precipitated proteins. The supernatants were transferred to autosampler vials with 3 μL solution injection for analysis by TOF LC/MS.

Metabolite profiling was performed using an Agilent Model 1200 liquid chromatography system coupled to an Agilent Model 6230 time-of-flight mass analyzer as described by Yun et al. (*Science.* 350, 1391-1396 (2015)). Chromatography of metabolites was performed using aqueous normal phase (ANP) gradient separation on a Diamond Hydride column (Microsolv, NJ). The mobile phases consisted of 6 EDTA and 0,025% acetic acid in isopropanol: $H_2O$ (50:50) (solvent A) and 6 μM EDTA and 5 mM ammonium acetate in $CH_3CN$: $H_2O$ (90:10) (solvent B). The following gradient was applied: 0-1.0 min, 99% B; 1.0-15.0 min, to 20% B; 15.1-29.0 min, 0% B; 29; 1-37 min, 99% B. Both positive and negative mass spectra were acquired in 2 GHz (extended dynamic range) mode with 1.41 spectra/sec sampled over a mass/charge range of 40-1400 Daltons. Data was saved in both centroid and profile mode using Agilent Mass Hunter Workstation B600 Data Acquisition Software.

Raw data files were analyzed using Mass Profiler Professional (Agilent, version B14.5) and Mass Hunter Profinder (version B08.00). Briefly, the molecular feature extraction (MFE) searches compounds based on the profile of identical m/z values and retention times, within a defined mass accuracy (<5 ppm). These features are further grouped into one or more "compounds" based on their isotope pattern, the formation of dimer, adduct ions (e.g. $H^+$, $Na^+$, $NH_4^+$ for positive mode and $H^-$, $CH_3COO^-$, $HCOO^-$ and $Cl^-$ for negative mode) and common neutral losses of $H_2O$ and $NH_3$. The identified features were manually validated following extraction. The identification is further confirmed by comparison to chemical standards.

Immunoblotting and immunohistochemistry

Liver, small intestine epithelium, and tumor tissue were lysed using lysis buffer containing 50 mM Tris·HCl (pH 7.4), 150 mM NaCl, 1 mM EDTA, 10% glycerol, 1% NP-40, 0.5% Triton X-100, and 1 tablet (per 10 mL) of protease and phosphatase inhibitor. Protein extracts (50 μg) were separated by 4-12% NuPAGE Bis-Tris gel (Invitrogen, Carlsbad, CA) and transferred to 0.45 nm PVDF membranes with wet transfer cells (Bio-Rad Laboratories, Hercules, CA). After 1 h of blocking with Tris-buffered saline with 0.1% (v/v) Tween 20 (TBST) containing 5% (w/v) BSA, membranes were incubated overnight at 4° C. with antibodies against GLUT1 (Millipore 07-1401), GLUT2 (abcamn ab192599), GLUT5 (abcam ab113931), SGLT1 (abcam ab14686), HK1 (CST 2024), HK2 (CST 2867), KHK (abcam ab154405), ALDOA (CST8060), ALDOB (abcam ab152828), ALDOC (proteintech 14884-1-AP), PKL (abcam ab171744), PKM1 (CST 7067), PKM2 (CST 4053), ENO1 (CST 3810) at a 1:1000 dilution in 5% BSA followed by a TBST wash and the appropriate secondary antibody (1:3000) for 1 h at room temperature. The signals were detected on HyBlot $C_L$ Autoradiography Film (Denville Scientific Holliston, MA) with SuperSignal Western Blot enhancer solution (Thermo Fisher, Waltham, MA). GLUT5 immunohistochemistry on Tumor Microarray (US Biomax Inc. Cat. #BC05002a) was done using the VENTANA BenchMark ULTRA stainer. Slides were deparaffinized with xylene and rehydrated in a graded ethanol series and water. Antigen retrieval was performed with 0.01 M citrate, pH 6.0 buffer by heating the samples in the microwave for 15 min. Sections were blocked with avidin/biotin blocking for 30 minutes. Sections were incubated with anti-SLC2A5 (Sigma, Cat. #AV42096, dilution 1:150) for 1 hour, followed by 60 minutes incubation with biotinylated goat anti-rabbit IgG (Vector labs, Cat. #PK6101, dilution 1:500). The detection was performed with the DAB detection kit (Ventana Medical Systems) according to manufacturer's instructions, followed by counterstaining with hematoxylin (Ventana Medical Systems) and cover slipping with Permount (Fisher Scientific).

Transcriptome Profiling Using RNA-Sect

Total RNA was extracted from small intestine epithelium and tumor tissue using RNeasy kit (Qiagen). 500 ug of total RNA of each sample was submitted to the Weill Cornell Medicine Genomics Resources Core Facility. Following isolation, total RNA integrity is checked using an Agilent Technologies 2100 Bioanalyzer with an RNA Integrity Number (RIN) value greater than 8. The library construction was followed by the protocol from Illumina TruSeq Stranded mRNA Sample Preparation kit. After the clot has generated clonal clusters of the DNA fragments, they were sequenced using HiSeq4000 using Paired End Clustering and 50×2 Cycles Sequencing (per lane). The quality of the raw FASTQ files were checked with FastQC, then mapped to mouse reference GRCm38 using STAR (v3.5.3a). FPKM (Fragments per Kilobase per million) was estimated using Cufflinks (v2.2.1) and HTSeq (v0.6.1) (Trapnell et al. Nat. Biotechnol. 28, 511-515 (2010) Anders et al. *Bioinforma. Oxf. Engl.* 31. 166-169 (2015)). Mouse gene symbols were converted to human gene symbols using the vertebrate homology list provided by Mouse Genome Informatics (Blake et al. *Nucleic Acids Res.* 45, D723-D729 (2017)). Differential expression analyses and variance stabilizing transformation for unsupervised analyses were performed using DESeq2 (v1.14.1) (Love et al. *Genome Biol.* 15, 550 (2014)). All custom code, statistical analysis, and visualizations were performed in Python or R, and used Nextflow to manage the computational pipelines (Di Tommaso et al. *Nat. Biotechnol.* 35, 316-319 (2017)). Code used for these analyses are available via the website: github.com/murphycj/manuscripts/tree/master/GoncalvesEtA12018.

Lipid Incorporation from Glucose

For in vivo measurement of glucose incorporation into lipids, mice were given a one-time bolus of HFCS (Glucose 45 mg ¢ Fructose 55 mg, total 400 ul in tap water) containing 5 μCi of D-[$^{14}$C(U)]-Glucose (Perkin Elmer, Waltham, MA). Four hours after the bolus, the mice were euthanized, and the small intestine epithelium and tumor tissue were harvested, then flash frozen in liquid nitrogen. Lipids were extracted and dried as described above using chloroform and methanol. The dried lipid extract was suspended in 4 mL of Ultima Gold liquid scintillation cocktail (PerkinElmer, Waltham, MA) and radioactivity was measured in disintegrations per minute (DPM) using a Tri-carb 2910 TR Liquid Scintillation Counter (PerkinElmer, Waltham, MA). Values were normalized to tissue mass.

RT-PCR

Total RNA was extracted from small intestine epithelium and tumor tissue using Trizol Thermo Fisher, Waltham, MA) followed by clean-up using RNeasy kit (Qiagen, Hilden, Germany). One microgram of total RNA was reversed transcribed using SuperScript VILO Master Mix (Thermo Fisher, Waltham, MA). Quantitative real time PCR was done using the Applied Biosystems TaqMan Gene Expression Assays (Thermo Fisher, Waltham, MA) with the following primers: ACACA (Mm01304257_m1), FASN, (Mm00662319_m1), SCD1 (Mm00772290_m1), and ACTB (Mm00607939_s1). The relative expression of each gene was calculated after normalizing to ACTB endogenous control and using the comparative $\Delta C_t$ method.

ATP Measurement in Tumors by HPLC

Polar metabolites were extracted from the tumor tissue using a 40:40:20 mixture of acetonitrile:methanol:water with 0.1 M formic acid followed by neutralization with ammonium bicarbonate (Lu et al. Anew, Rev. Biochem, 86, 277-304 (2017)). The dried extracts were then dissolved in 100 μl of 0.1 M $KH_2PO_4$ (pH 6.0) buffer and used in an ion-pair reversed-phase high-performance liquid chromatography (HPLC) method that was adapted from a method described by Zur Nedden et al. (Anal. Biochem, 388, 108-114 (2009)). Five microliters of dissolved extract were injected into an Agilent 1260 binary pump connected to a C18 column (Phenomnenex, 150 mm×4.6 mm, 5 μm; LUNA) with a 1 mL/min flow rate. ATP and ADP were separated using an isocratic mobile phase of 0.1 M $KH_2PO_4$ (pH 6.0) and absorbance was monitored by a diode array detector. Peaks were quantified at $A_{254}$ using Chemstation software (Agilent Technologies, Santa Clara, CA).

Statistics

All summary data are expressed as mean±SEM. When comparing means from two groups, a two-tailed, unpaired t-test was used following confirmation that the data was sampled from a Gaussian distribution by the D'Agostino-Pearson normality test. When comparing effects of genotype and treatment, a two-way ANOVA was done with post-test comparisons made by the Holm multiple comparisons test using Prism 6 (GraphPad La Jolla, CA). Statistical significance is indicated in figures using the following denotation: *P<0.05, P<0.01, *P<0.001, and ****P<0.0001.

Example 2: Larger and Higher-Grade Tumors are Present in Mice Fed High-Fructose Corn Syrup Increased consumption of sugar-sweetened beverages has been paralleled by an epidemic of obesity around the world, starting in the 1980s. During, this same time-period, period, the rate of colorectal cancer (CRC) incidence also increased among young and middle-aged adults, suggesting a potential link between sugar-sweetened beverages, obesity, and CRC development. Some studies have shown that excessive consumption of sugar-sweetened beverages causes obesity and that being obese increases the risk of CRC, especially in men (Fuchs et al. PLOS ONE 9: e99816 (2014); Bardou et al. 62:933-947 (2013)). However, whether sugar-sweetened beverages contribute directly to tumorigenesis is unclear. Two important confounders are obesity and metabolic syndrome, which can indirectly affect tumor development by changing a myriad of physiologic and endocrine systems in multiple organs (Hopkins et al. J. Clin. Oncol. 34:4277-4283 (2016)).

To untangle the link between sugar consumption, obesity, and cancer, the inventors mimicked sugar-sweetened beverage consumption in a genetically engineered mouse model of intestinal tumorigenesis. In this model, the adenomatous polyposis coli (APC) gene is deleted in $Lgr5^+$ intestinal stem cells upon systemic tamoxifen injection (Lgr5-EGFP-Cre-$ER^{T2}$; $APC^{flox/flox}$, hereafter $APC^{-/-}$ mice) (Yun et al. Science 350:1391-1396 (2015); Barker et al., Nature 457:608-611 (2009). APC is a negative regulator of Wnt signaling, and a tumor suppressor that is frequently mutated (75 to 80%) in the early stages of CRC development (Fearon & Vogelstein, Cell 61:759-767 (1990)). Sugar-sweetened beverages are primarily sweetened with high-fructose corn syrup (HFCS), which consists of glucose and fructose in a 45:55 ratio (Fulgoni 3rd, Am. J. Clin. Nutr. 88: 1715S (2008)). The physiological effects of HFCS administered to $APC^{-/-}$ and wild-type (WT) mice were first determined through ad libitum delivery in their drinking water (25% HFCS in water; referred to hereafter as the "water bottle" or WB group). The consumption of HFCS in this manner led to obesity in both WT and $APC^{-/-}$ mice (FIGS. 1G-1L), and to metabolic dysfunction in WT mice (FIGS. 2F-2K) over an 8-week period.

To uncouple the metabolic effects caused directly by HFCS from those caused by HFCS-induced obesity, $APC^{-/-}$ mice were treated with a restricted amount (400 ml of 25% HFCS) of HFCS daily via oral gavage starting the day after tamoxifen injection (referred to as the HFCS group). This modest amount of HFCS (~3% of total daily caloric intake) is calorically equivalent to human consumption of less than 12 ounces of sugar-sweetened beverage (~20 g of HFCS) per day. Chronic treatment of HFCS using this strategy did not induce obesity or metabolic dysfunction in $APC^{-/-}$ mice (FIG. 1A-1B and FIG. 2G-2K).

Although the total number of tumors was similar (FIGS. 3F-3G), HFCS treatment significantly increased the number of large adenomas (>3 mm in diameter) and high-grade tumors in the HFCS group compared to the Con group (FIG. 1C-1F, 3H). Similar results were observed in a study of another mouse model, CDX2P-CreER$^{T2}$; APC$^{flox/flox}$ (FIG. 31-3M), where intestinal tumors develop mainly in the colon instead of the small intestine. These results indicate that the chronic intake of modest amounts of HFCS in liquid form facilitates tumor growth in the setting of APC deficiency independent of obesity and the metabolic syndrome.

Figure 4A:
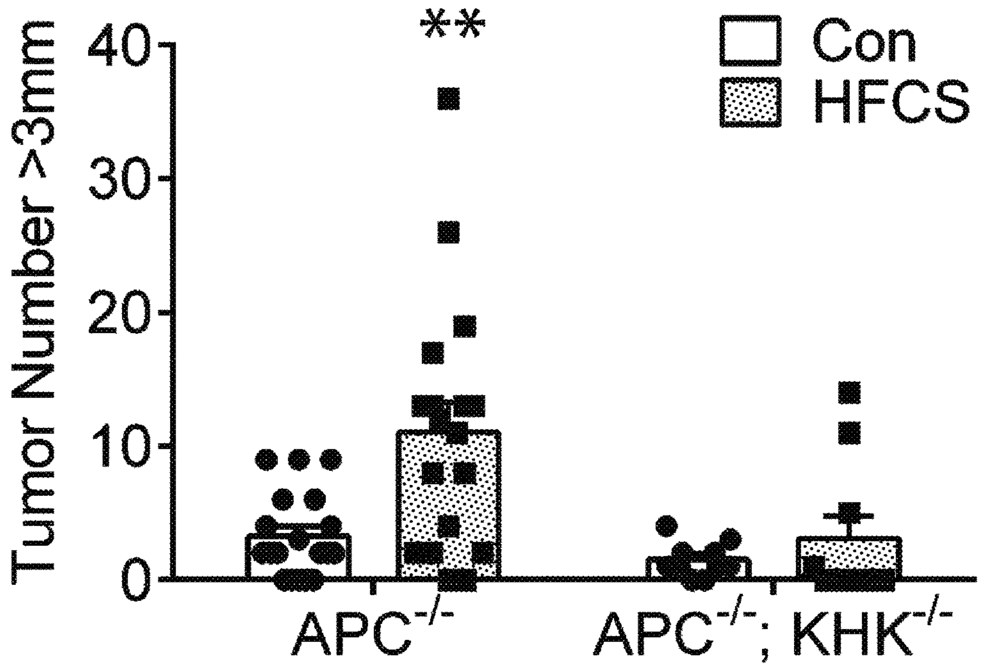
FIGS. 4A-4I illustrate that KHK deletions abolish tumor phenotypes in APC-deficient mice treated with HFCS.
Figure 4B:
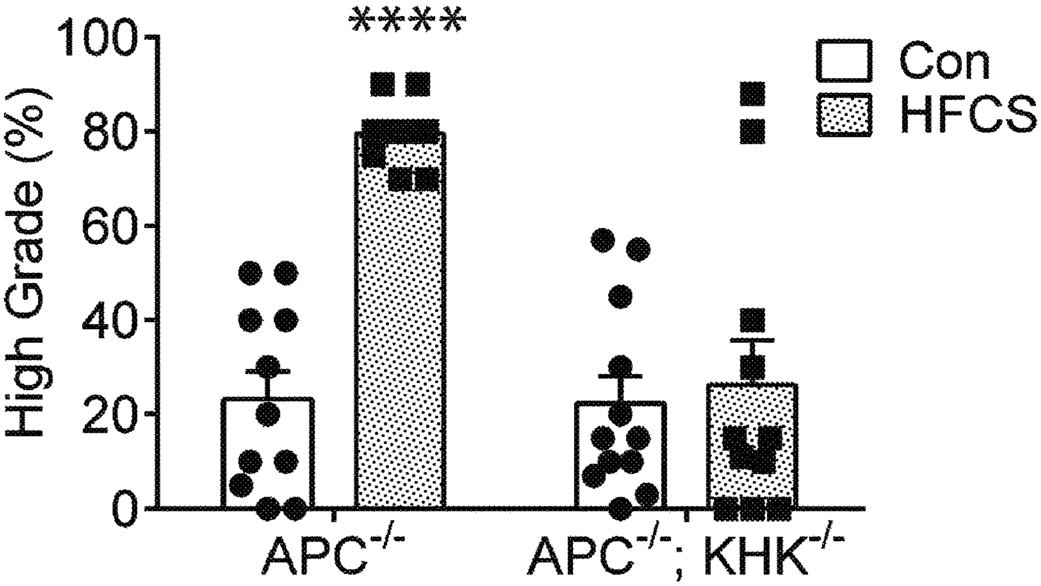
Figure 4C:
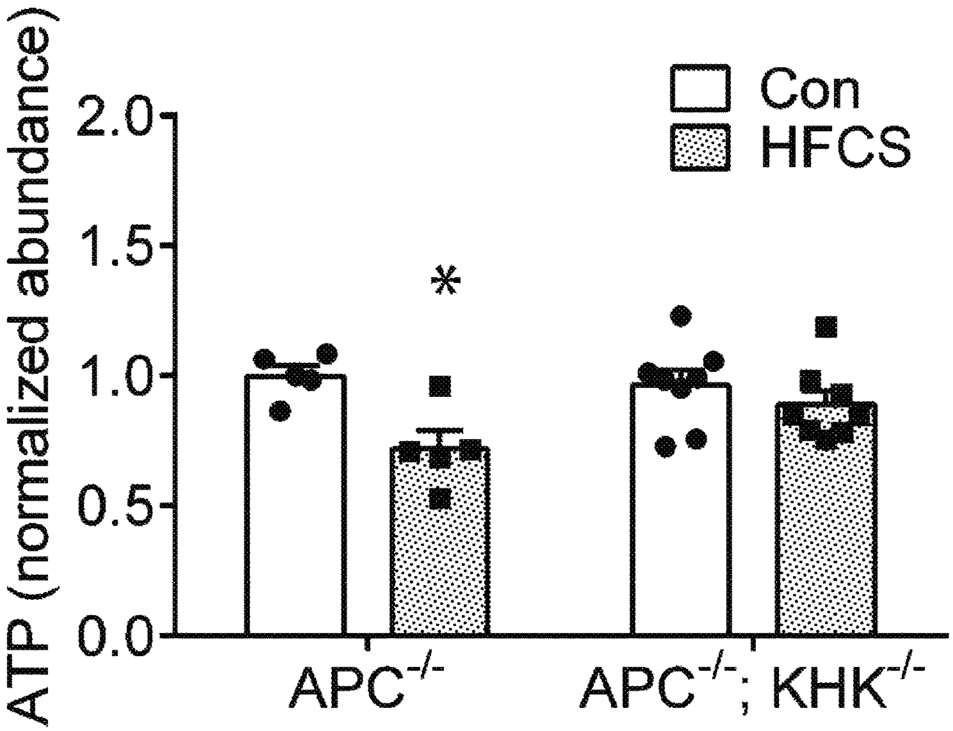
Figure 4D:
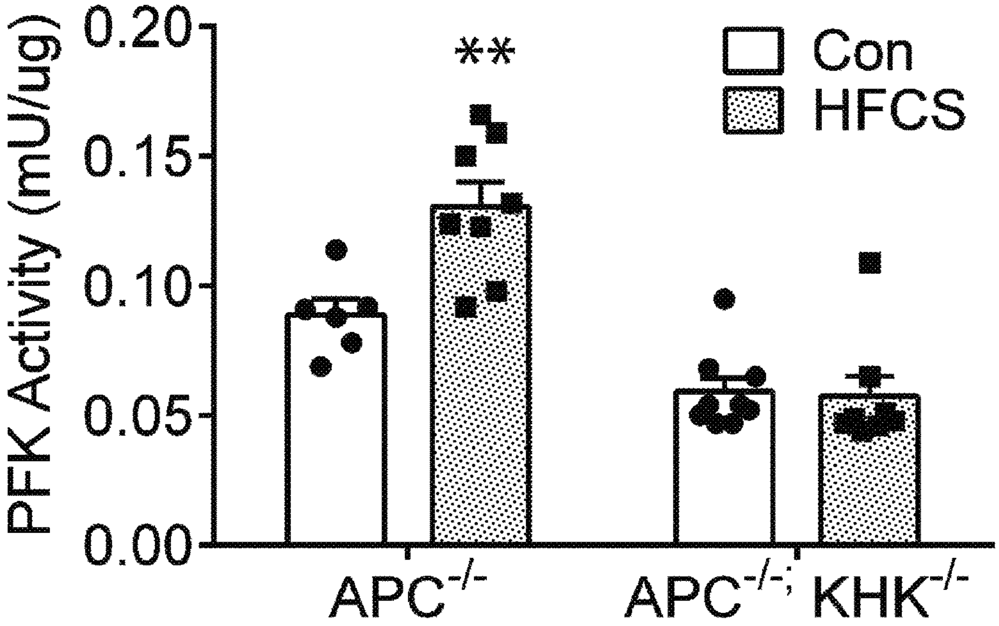
Figure 4E:
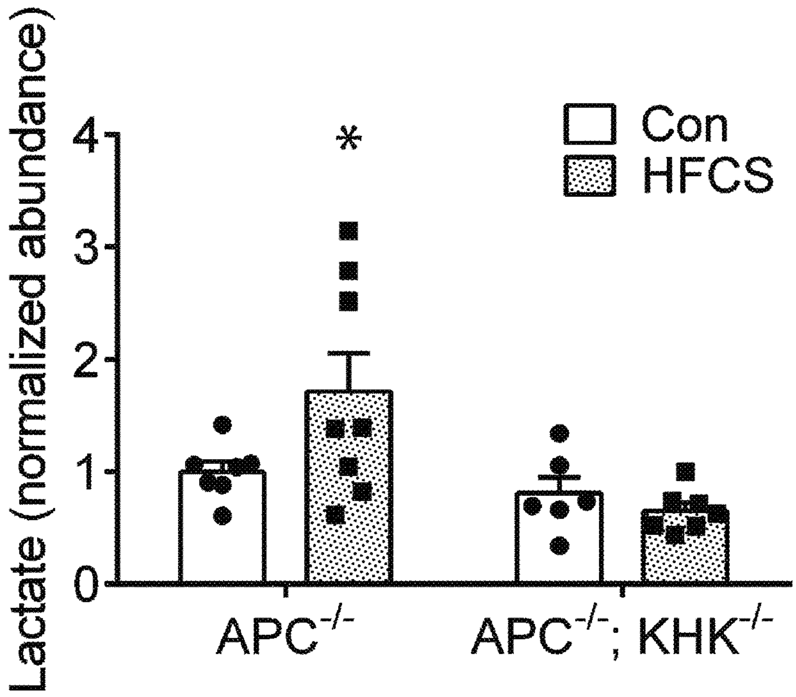
Figure 4F:
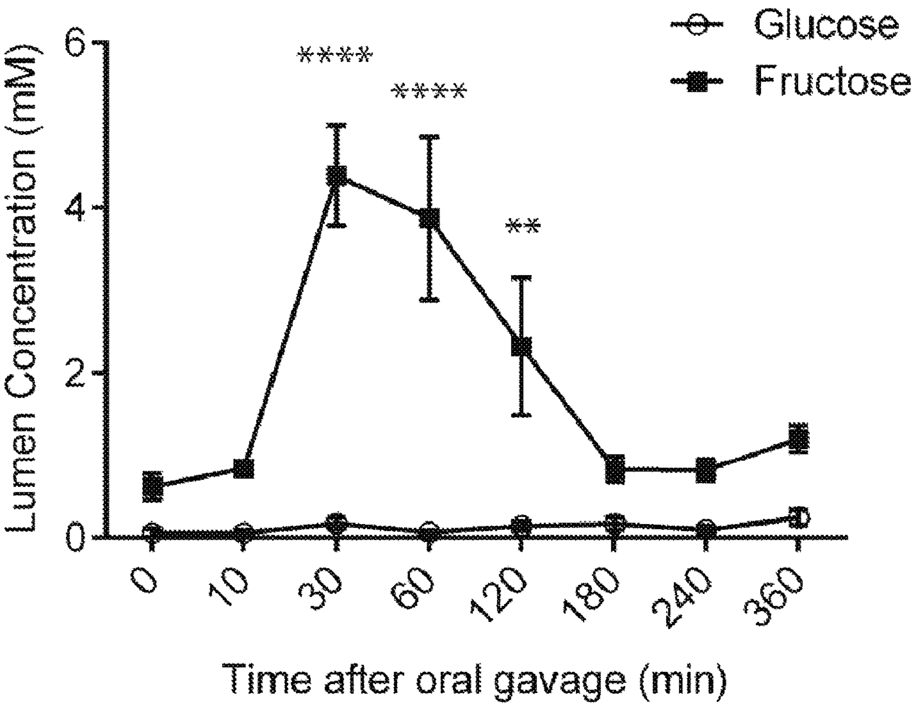
Figure 4G:
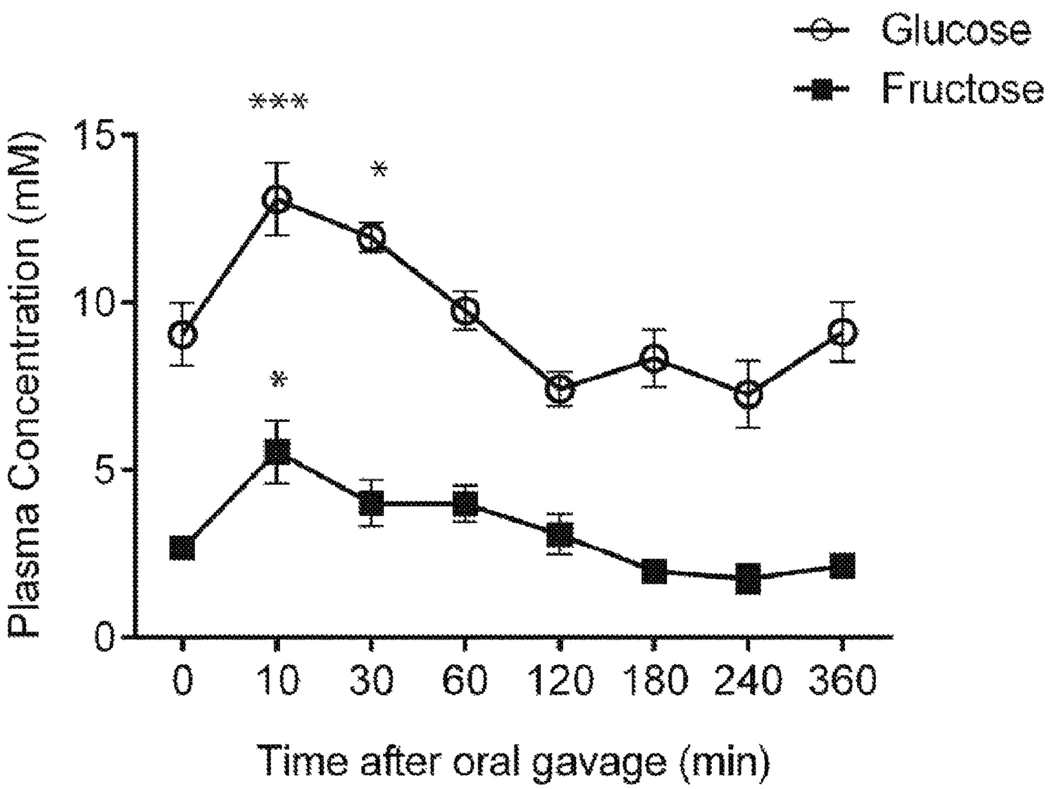
Figure 4H:
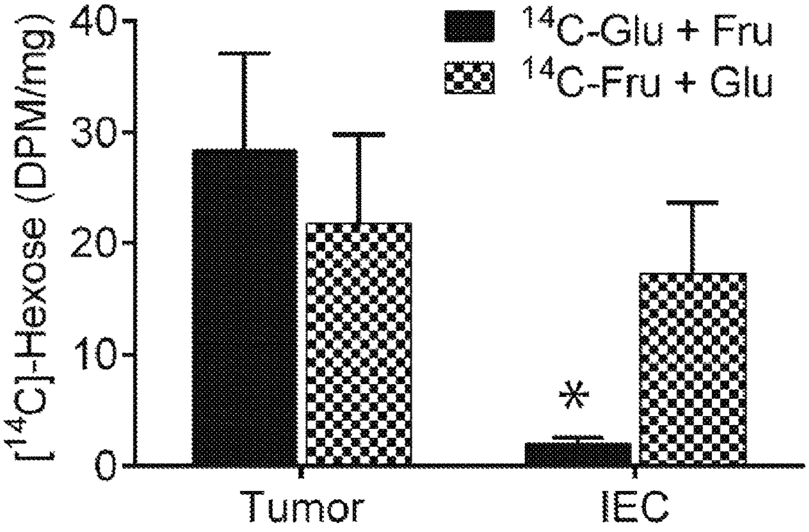
Figure 4I:
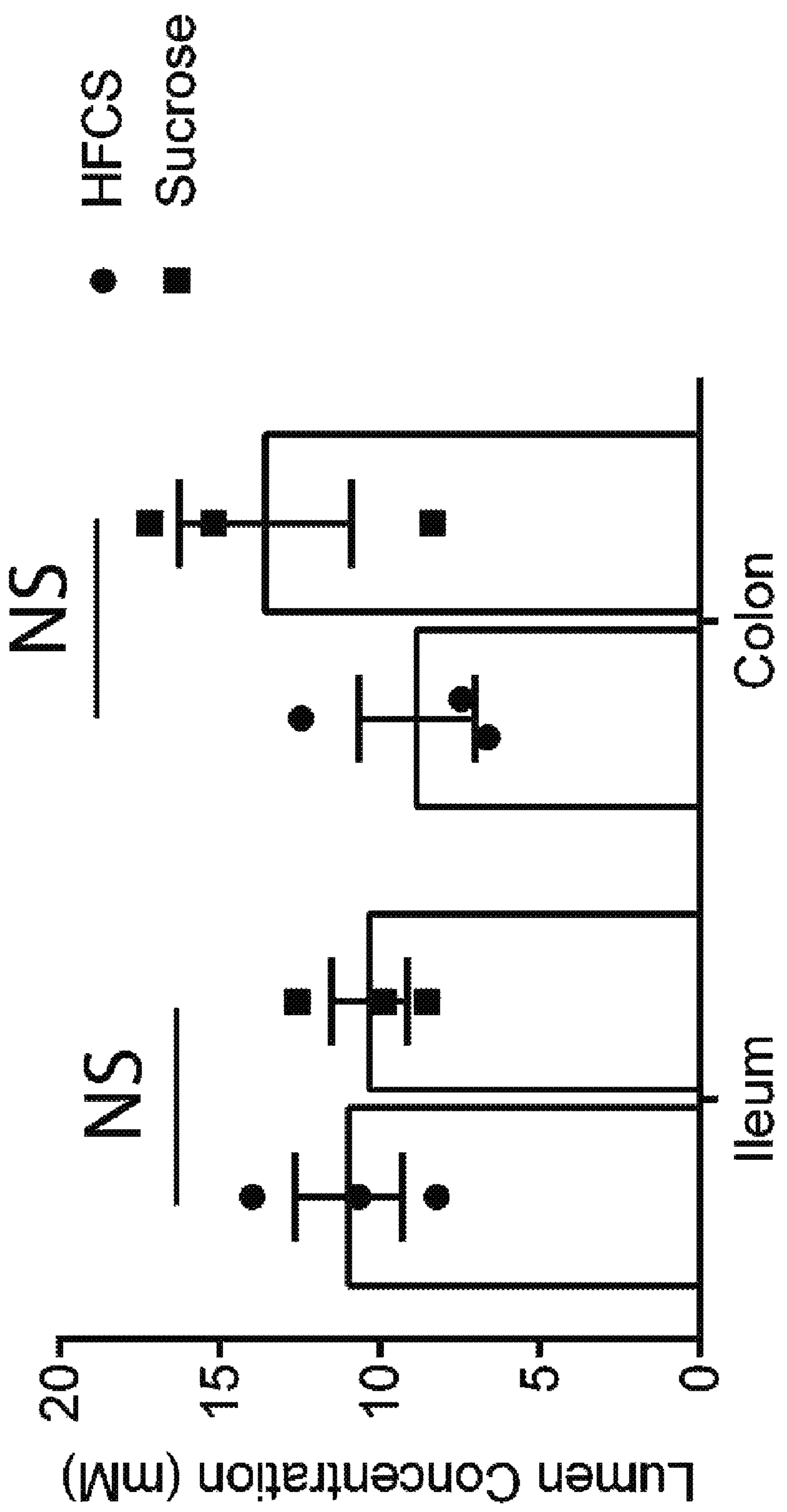
Figure 5A:
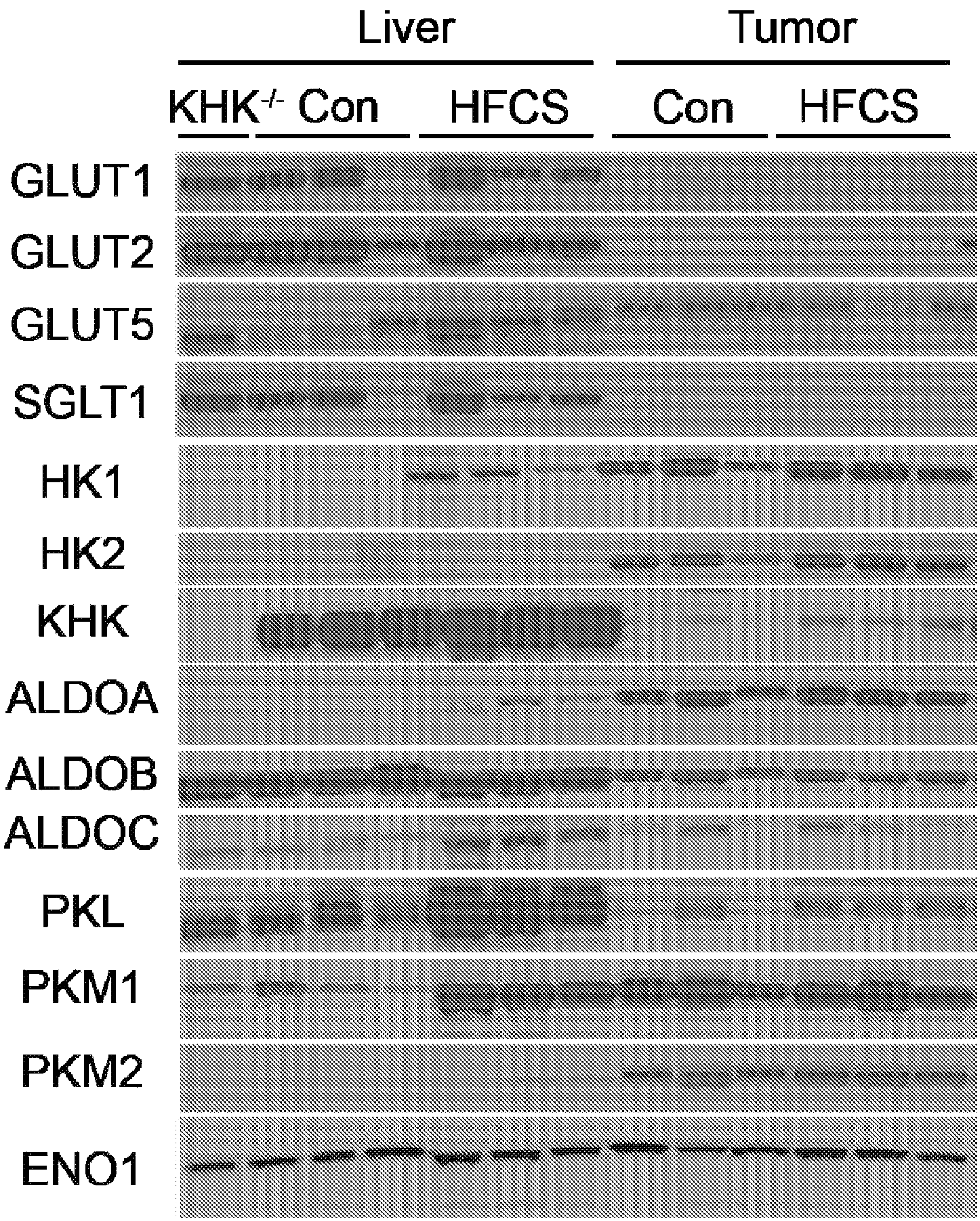
FIGS. 5A-5D illustrate the relative abundance of different proteins in various tissues.

Glucose is efficiently transported by the intestinal epithelial cells (IECs) in the small intestine via sodium-coupled glucose transporters (SGLTs) (Drozdowski & Thomson, World J. Gastroenterol. 12:1657-1670 (2006)). By contrast, fructose transport is mediated by a passive transporter (GLUT5) in IECs (Drozdowski & Thomson (2006)). The consumption of as little as 5 g of fructose can lead to the saturation of GLUT5 in the small intestine (i.e., malabsorption), resulting in an increased concentration of fructose in the lumen of the colon (large intestine) of healthy humans (Ravich et al. Gastroenterology 84, 26-29 (1983); Rumessen & Gudmand-Høyer, Gut 27:1161-1168 (1986); Beyer et al. J. Am. Dict. Assoc. 105:1559-1566 (2005)). One study in mice showed that fructose doses greater than 1 g/kg (~1% of daily calorie intake) overwhelm fructose absorption in the small intestine, resulting in a higher concentration of fructose in the colon (Jang et al., Cell Metab. 27:351-361.e3 (2018)). Fructose concentrations were significantly increased in the colonic lumen (4.4 mM at peak 30 min) in WT mice after an oral bolus of HFCS (FIG. 4F), consistent with impaired fructose uptake in the small intestine. Given these findings, the inventors hypothesized that fructose in the intestinal lumen might be efficiently transported and metabolized by tumors located in the distal small intestine and colon. Using glucose or fructose radio-labeled with $^{14}$C, the inventors confirmed that APC$^{-/-}$ tumors efficiently transported both fructose and glucose following a bolus of HICS (FIG. 4H). Furthermore, the amount of fructose reaching the liver and serum was reduced in tumor-bearing APC$^{-/-}$ mice compared to WT mice (FIG. 2A), implying F2 that fructose is trapped by the tumors instead of being transported to the liver and blood. Further supporting the inventors' hypothesis, GLUT5 was expressed at higher levels in APC$^{-/-}$ tumors as compared to intestinal epithelial cells (IECs) (FIG. 5A), and in human colon tumors as compared to adjacent normal IECs, on a tumor tissue microarray containing 25 cases of human colon tumors ranging from early-stage adenomas to metastatic carcinoma (Godoy et al., J. Cell. Physiol. 207: 614-627 (2006)). Similar results have been reported for other fructose-metabolizing enzymes, ketohexokinase (KHK) and aldolase B in human colon tumors (Li et al., Cell. Physiol. Biochem. 42: 397-406 (2017); Uzozie et al., Mol. Cell. Proteomics 13: 1198-1218 (2014)). In aggregate, these results indicate that intestinal tumors can transport fructose directly from the intestinal lumen, where the fructose concentration is high after oral administration of HFCS.

Glucose and fructose have the same caloric value and similar chemical structures; however, these two sugars are metabolized differently in both the liver and in intestinal epithelial cells (IECs (FIG. 2B) (Jensen et al., J. Hepatol. 68:1063-1075 (2018); Hannou et al. J. Clin. Invest. 128: 545-555 (2018)). The most notable difference begins with the initial phosphorylation step following absorption. Whereas glucose is phosphorylated by hexokinases Ks), generating glucose-6-phosphate (G6P), fructose is phosphorylated on the 1-position by KJ-1K (also known as fructokinase), producing fructose 1-phosphate (HP). The activity of HKs is tightly regulated by the concentration of G6P (product inhibition), whereas the activity of KHK is not subject to feedback inhibition. In the liver, this results in a rapid accumulation of F1P, coupled with a pronounced depletion of adenosine 5'-triphosphate (ATP) following fructose consumption. F1P can then be cleaved into three carbon units by aldolase B, bypassing phosphofructokinase (PFK). Despite the relatively well-studied pathway of fructose metabolism in the liver and in the small intestine, the role of fructose metabolism in tumors is mostly unknown.

Figures 1, 2A:
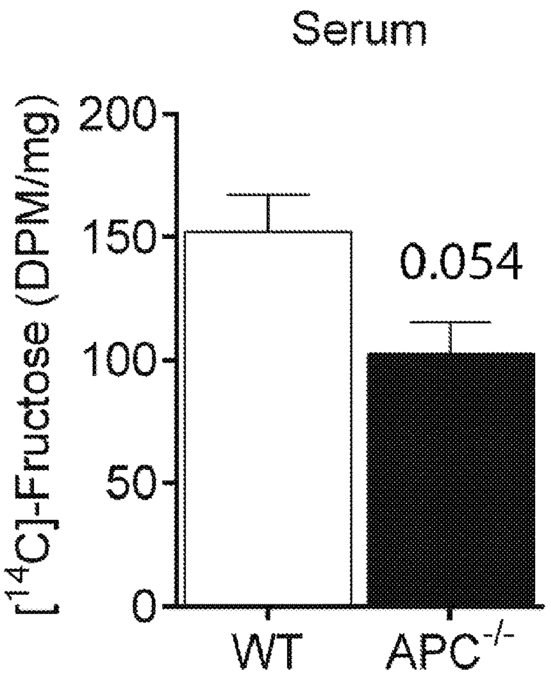
FIG. 1**G graphically illustrates cumulative sugar (glucose and fructose) intake as calculated by combining the consumption of sugar in the normal chow diet with supplemental HFCS (via a daily oral bolus by gavage or ad libitum access via the water bottle, WB) over 8 weeks in $APC^{-/-}$ mice. Sugar consumption in both $APC^{-/-}$ and WT mice increased by a factor of 10 in comparison to mice fed normal chow diet with non-sugared water (Con group) over an 8-week period. n=8 per group. Two-way ANOVA followed by Holm-Sidak post-test. *P<0.05, **P<0.0001 FIG. 1**H graphically illustrates cumulative food intake over 8 weeks of treatment in wild-type (WT) and tumor-bearing mice ($APC^{-/-}$) mice following 8 weeks of treatment with water (Con), a daily oral gavage of high-fructose corn syrup (HFCS), and mice supplied with unlimited high-fructose corn syrup via the water bottle (WB), Con, HFCS, and WB groups was calculated by measuring normal chow consumption plus supplemental HFCS (via daily oral gavage or WB). WT Con (n=5), HFCS (n=3), and WB (n=5). $APC^{-/-}$ (n=8 per group). Two-way ANOVA with Holm-Sidak post-test comparing HFCS and WB to Con showed no differences, comparisons between APC$^{-/-}$ Con to WT Con *P<0.05.
FIG. 2A-2K illustrates that intestinal tumors from APC-deficient mice facilitate glycolysis by using both glucose and fructose.
Figures 2, 2A:
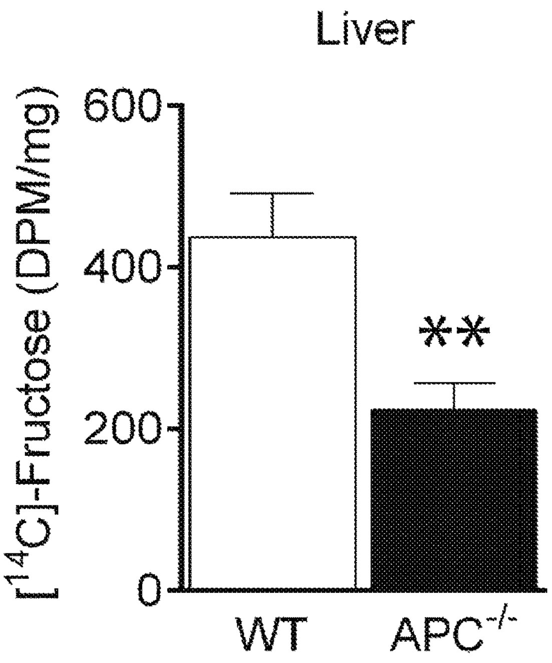
Figure 2B:
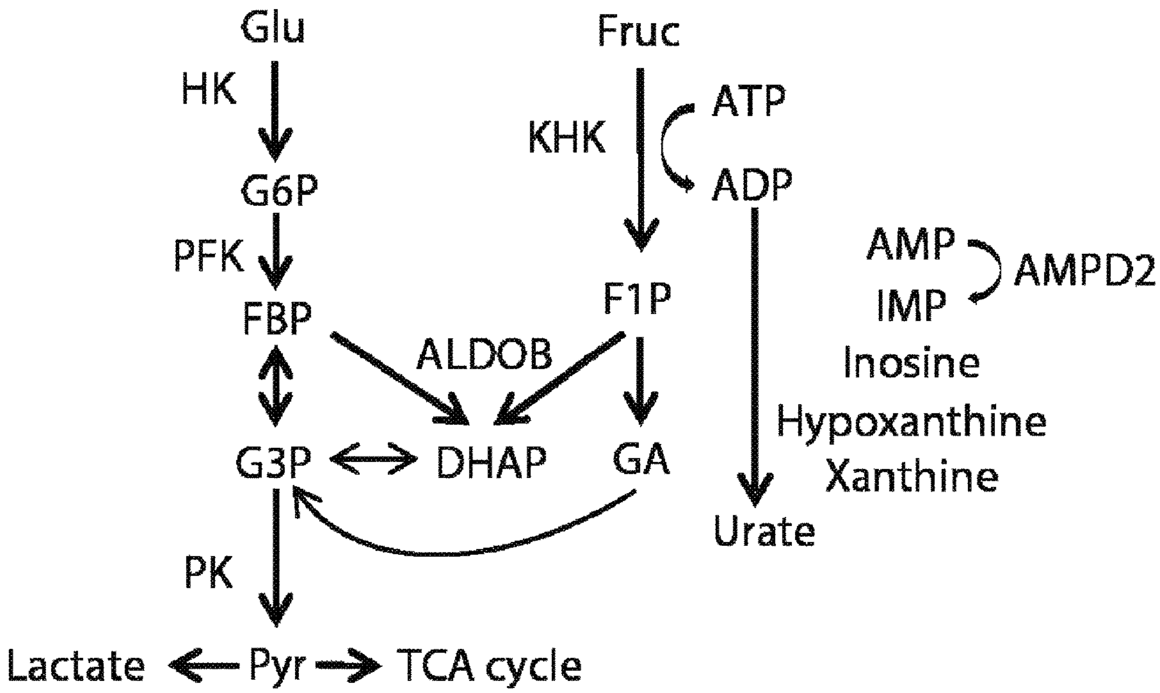
Figure 2C:
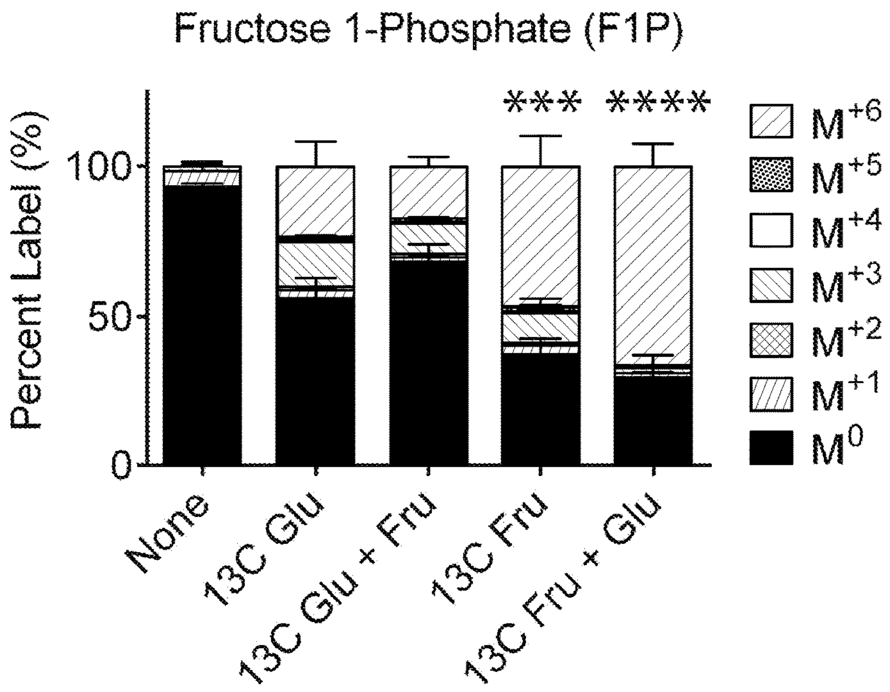
Figure 2D:
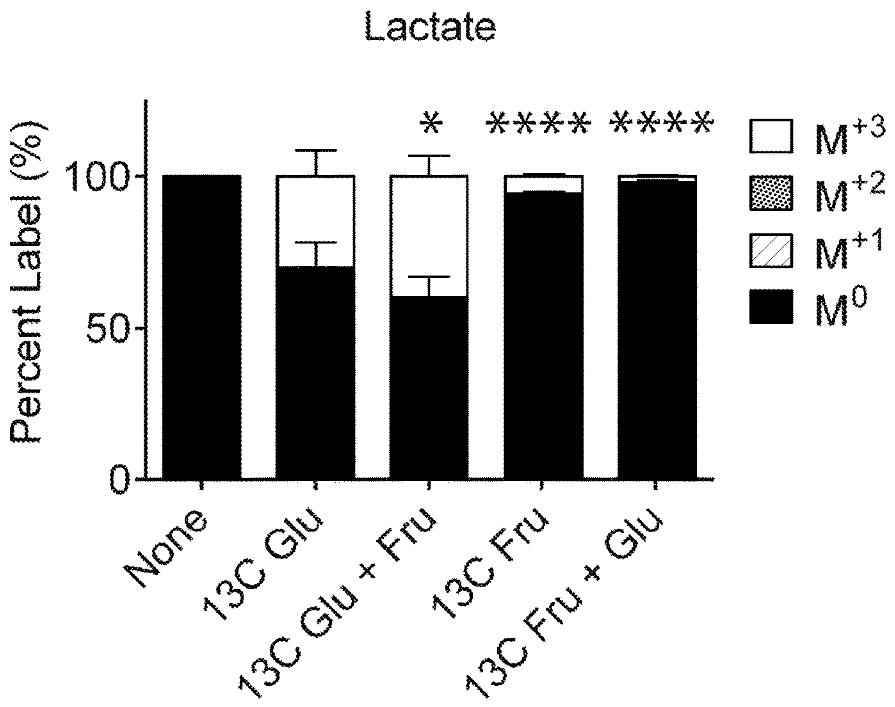
Figure 2E:
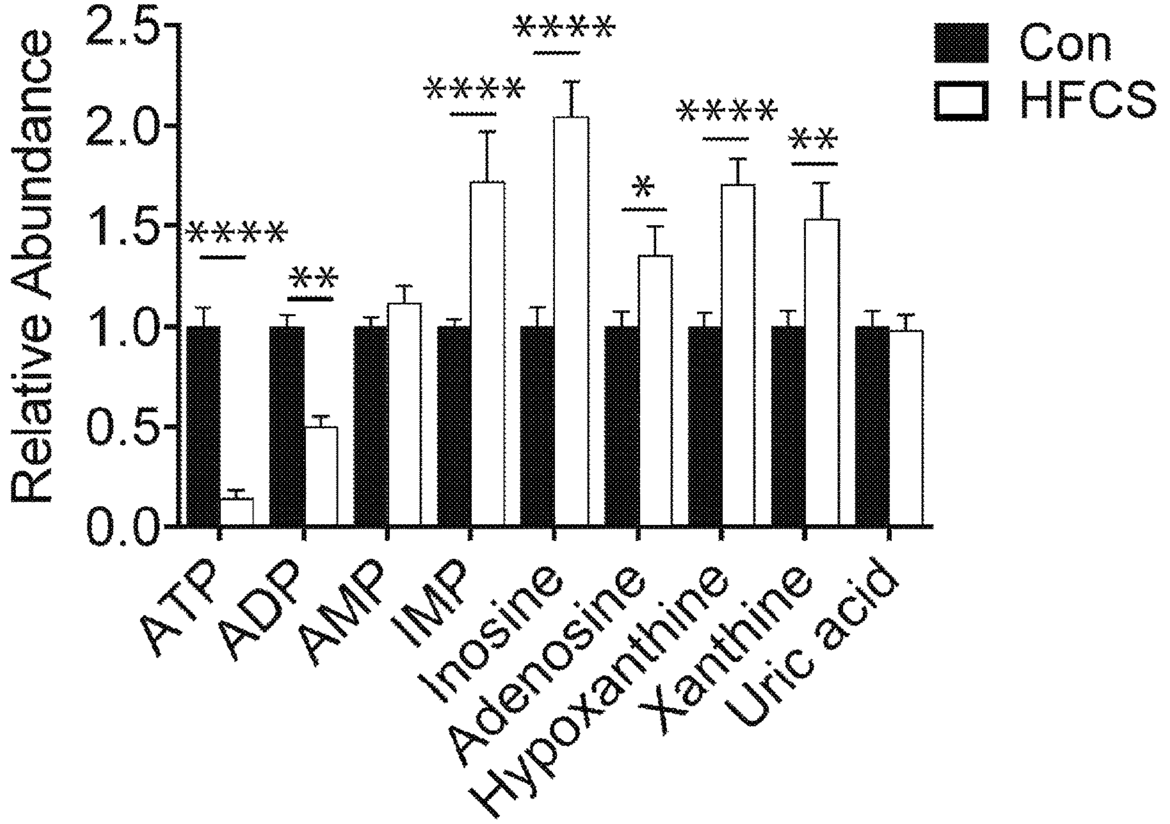
Figure 2F:
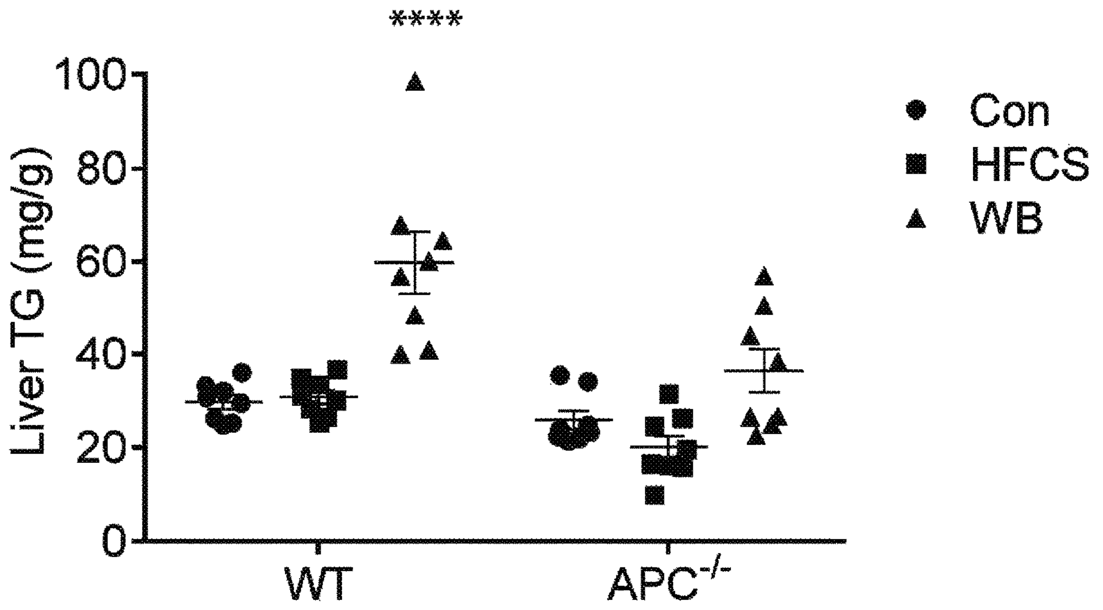
Figure 2G:
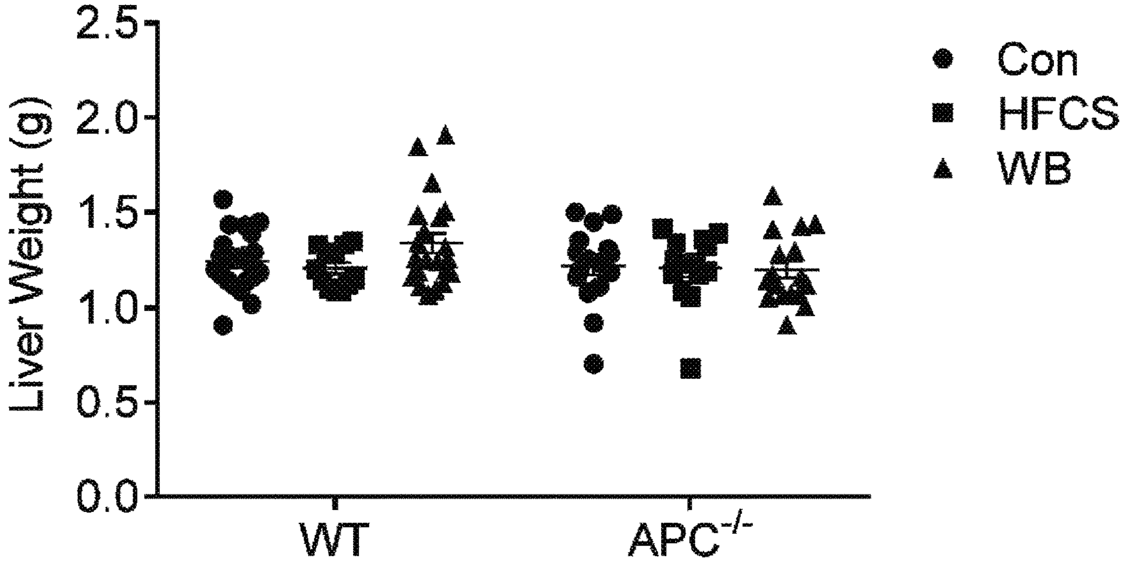
Figure 2H:
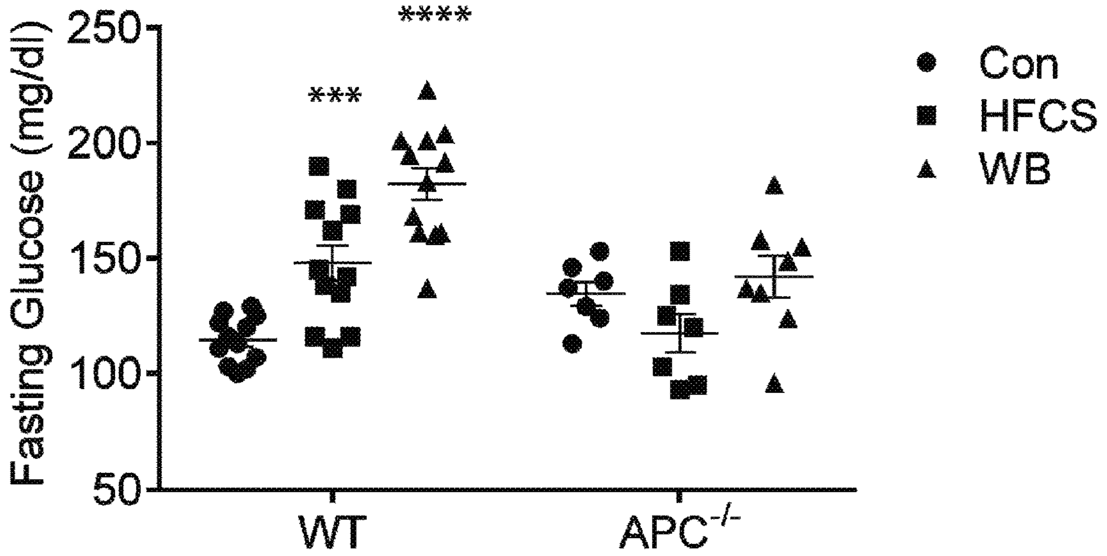
Figure 2I:
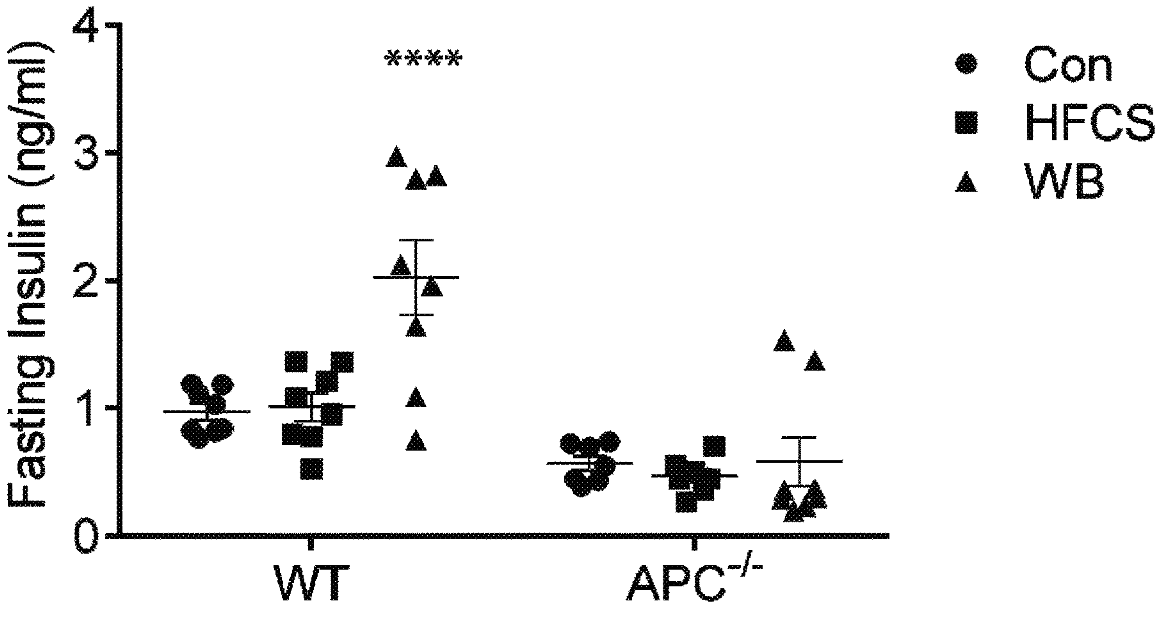
Figure 2J:
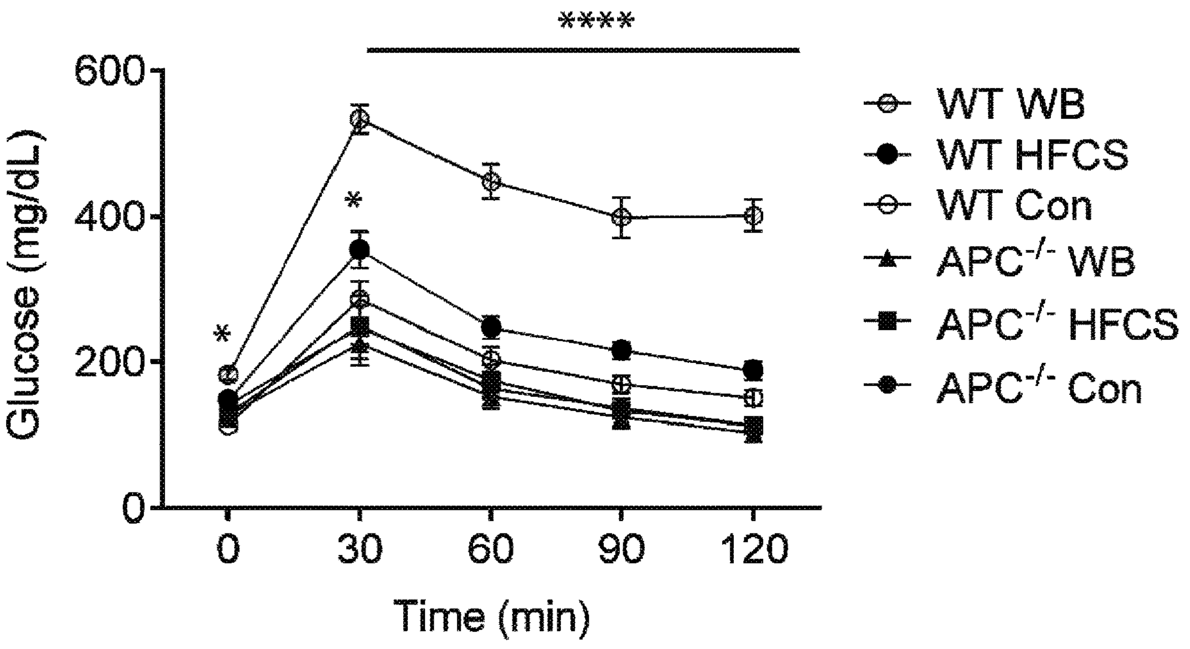
Figure 2K:
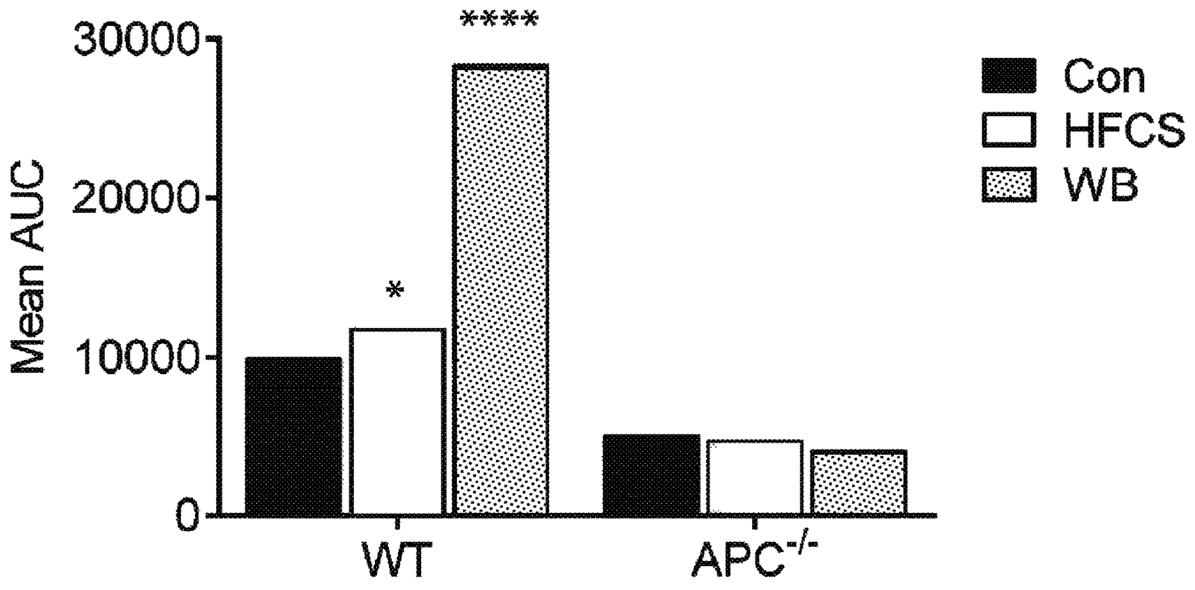
Figures 1, 5B:
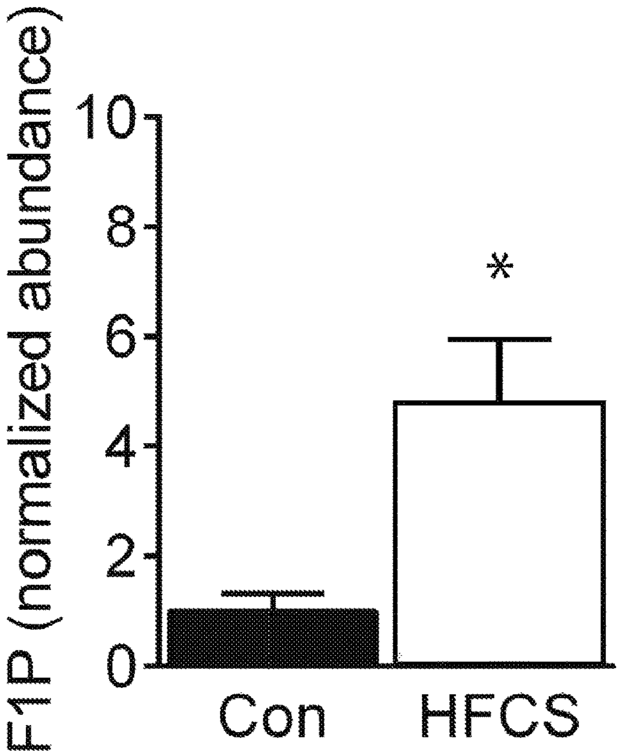
Figures 2, 5B:
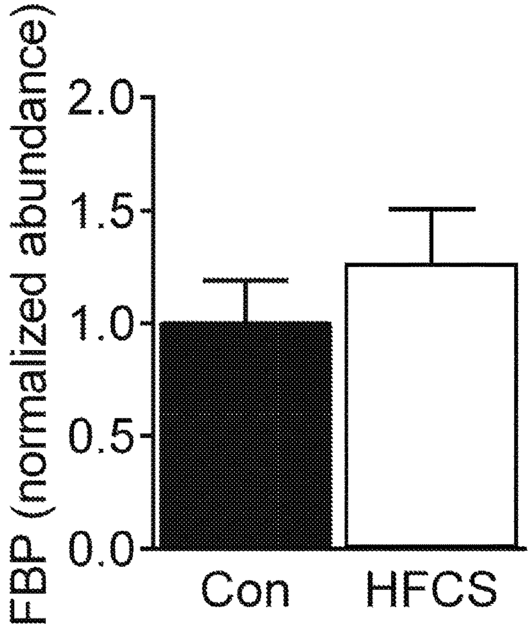
Figure 5C:
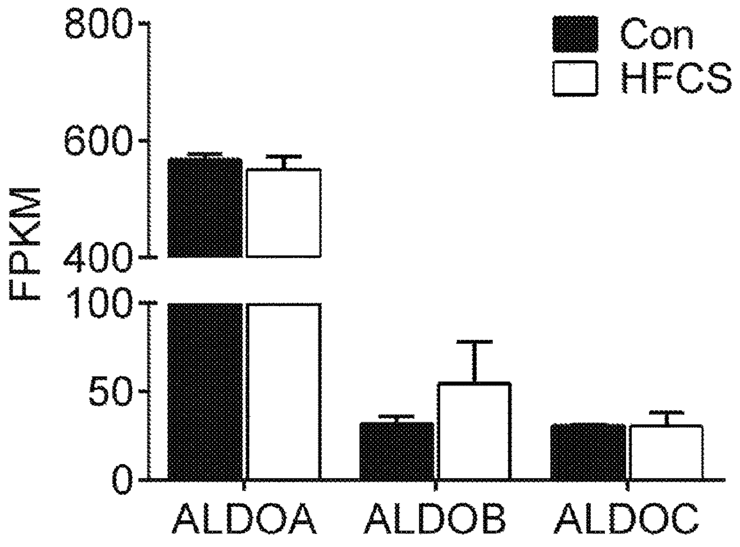

APC$^{-/-}$ tumors can efficiently transport both glucose and fructose. The inventors sought to determine the metabolic fate of glucose and fructose using $^{13}$C isotopic tracing. Tumors from APC$^{-/-}$ mice were isolated and exposed to four different labeling conditions for 10 min ex vivo: $^{13}$C-glucose (labeled at all six carbons), $^{13}$C-fructose (labeled at all six carbons), $^{13}$C-glucose+unlabeled fructose, and $^{13}$C-fructose+unlabeled glucose. The labeling pattern of metabolic intermediates from glucose and fructose was then determined using liquid chromatography with tandem mass spectrometry (LC-MS/MS). F1P was predominantly $^{13}$C-labeled at all six positions (M+6) in tumors treated with $^{13}$C-fructose or $^{13}$C-fructose+unlabeled glucose (47.1 and 67.1%, respectively), as assessed by the percentage of labeling (FIG. 2C). These findings confirm the activity and presence of KHK in the tumors. Notably, there was almost no labeling of downstream metabolites of F1P from $^{13}$C-fructose when unlabeled glucose was added to the medium (FIG. 2D), indicating that the presence of glucose saturates aldolase and prevents fructose from being cleaved into three carbon units in this dine frame. As shown in FIG. 5B-1, F1P accumulates because KHK produces F1P much faster than aldolase cleaves it. This results in an acute drop in cytosolic ATP in tumors from APC$^{-/-}$ mice that had received HFCS as a bolus compared to Con tumors (FIG. 2E).

Figure 5D:
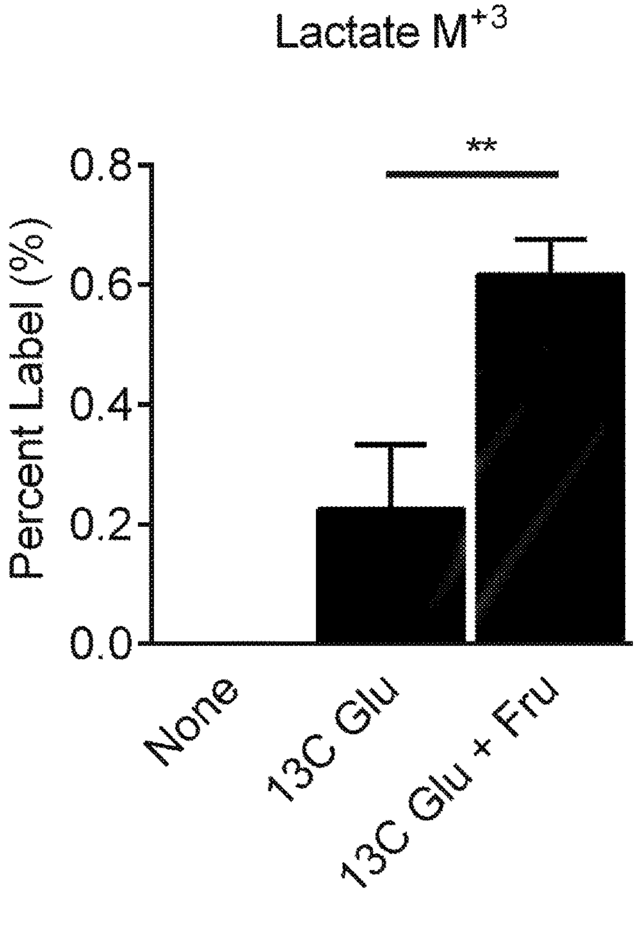

In the liver, the activity of the purine degradation pathway increases during fructose ingestion because AMP deaminase (AMPD2) is stimulated by the depletion of inorganic phosphate (Pi) that occurs in response to the high rate of glycolysis. In agreement with this mechanistic link between fructose and purine metabolism, the inventors found that the abundance of downstream metabolites of AMPD2 was higher in tumors from HFCS-treated APC$^{-/-}$ mice than in tumors from control APC mice (FIG. 2E). PFK is the most critical regulatory enzyme in glycolysis, and it is inhibited by ATP. The inventors therefore hypothesized that fructose-induced ATP depletion might result in the activation of PFK, thereby facilitating the metabolism of glucose via glycolysis in APC$^{-/-}$ tumors. As shown in FIG. 2D, tumors exposed to $^{13}$C-glucose+unlabeled fructose contained a higher percentage of fully labeled glycolytic metabolites than tumors exposed to $^{13}$C-glucose alone (e.g., 39.6% versus 30.2% for lactate, the end-product of glycolysis). The inventors also confirmed that in vivo lactate production in tumors was enhanced in APC$^{-/-}$ mice treated with an oral bolus of $^{13}$C-glucose+unlabeled fructose as compared to mice treated with a bolus of $^{13}$C-glucose alone (FIG. 5D). Together, these results indicate that fructose enhances glucose metabolism by depleting ATP levels, thereby activating PFK, an important glycolytic enzyme, in APC$^{-/-}$ tumors.

Figure 3A:
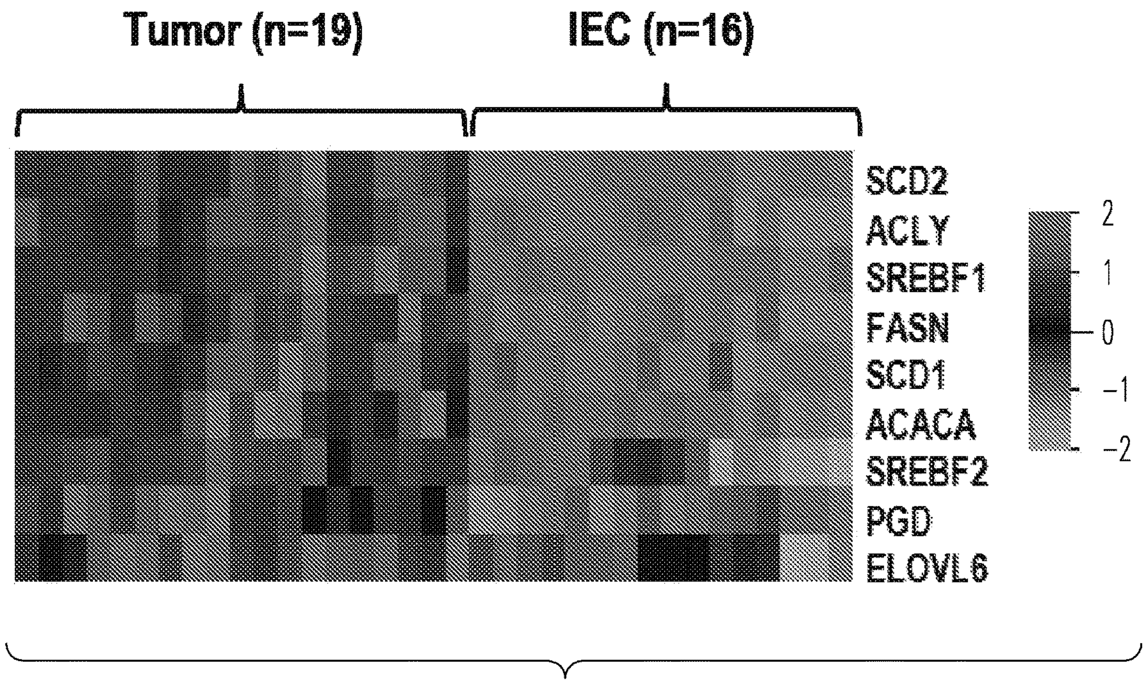
FIGS. 3A-3M illustrate that high-fructose corn syrup (HFCS) treatment accelerates de novo fatty acid synthesis in intestinal tumors from APC-deficient mice.
Figure 6A:
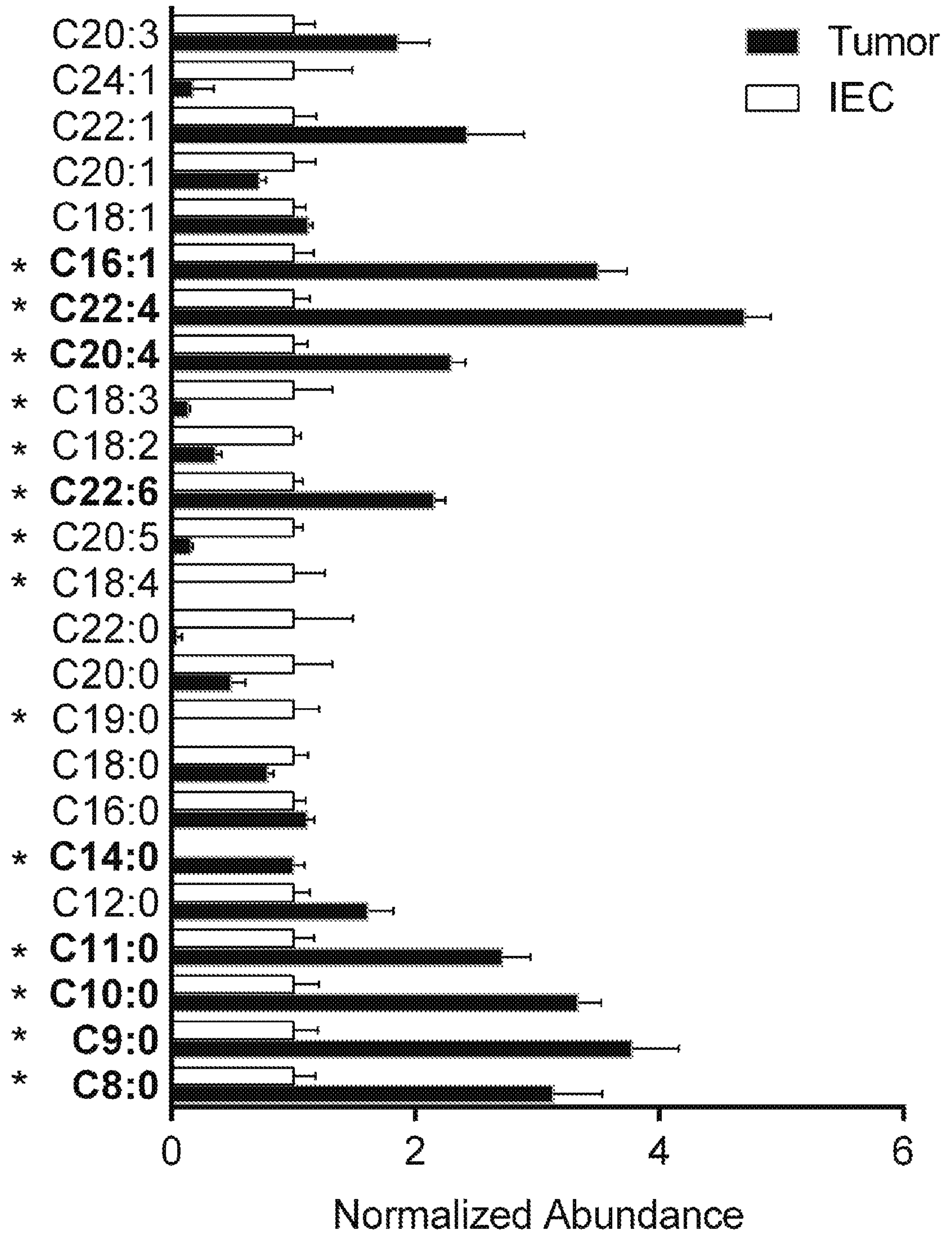
FIGS. 6A-6F illustrate that high-fructose corn syrup treatment increases de novo fatty acid synthesis in tumor.
Figure 6B:
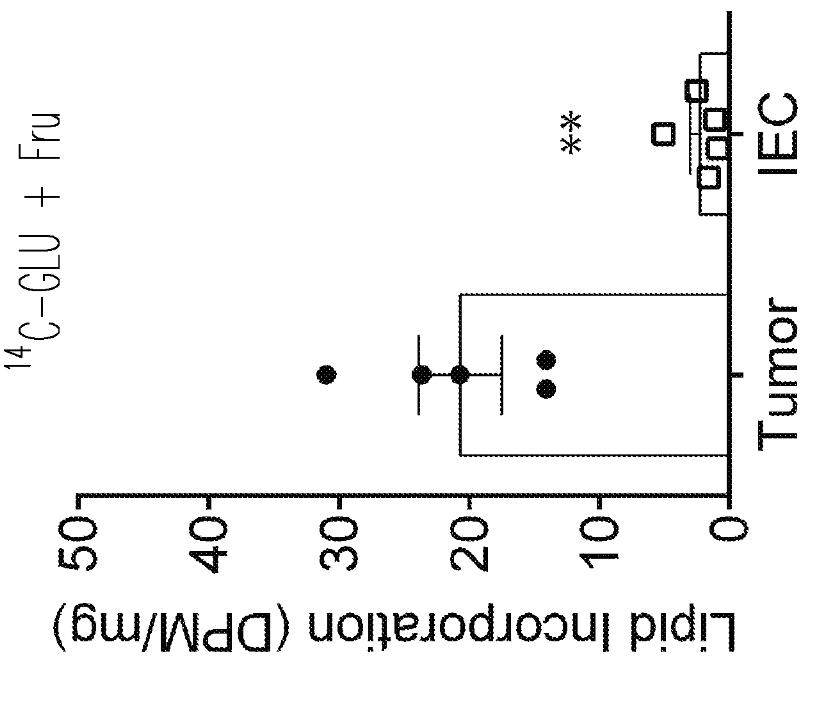

The inventors then explored the mechanism by which increased glycolysis enhances tumor growth in HFCS-treated APC$^{-/-}$ mice. In addition to generating ATP, glycolysis serves as a carbon source for de novo fatty acid synthesis. Cancer cells rely heavily on fatty acid synthesis (also known as "de novo lipogenesis") for cellular membrane formation, energy generation and storage, and intracellular signaling (Currie et al. Cell Metab. 18:153-161 (2013; Menendez et al. Cell Metab. 16, 189-201 (2012)). Next-generation RNA sequencing (RNA-seq) was used to evaluate the expression levels of all lipogenic enzymes, including acetyl-CoA (coenzyme A) carboxylase alpha (ACACA) and fatty acid synthase (FASN), were markedly increased in F3 $APC^{-/-}$ tumors in comparison to IECs (FIG. 3A). Accordingly, $APC^{-/-}$ tumors had an increased abundance of long-chain fatty acids, as measured by a LC-MS/MS analysis (FIG. 6A), and demonstrated increased incorporation of $^{14}C$-glucose into intracellular lipids as compared to the IECs following an oral bolus of HFCS (radiolabeled $^{14}C$-glucose together with unlabeled fructose) (FIG. 6B).

Figure 3B:
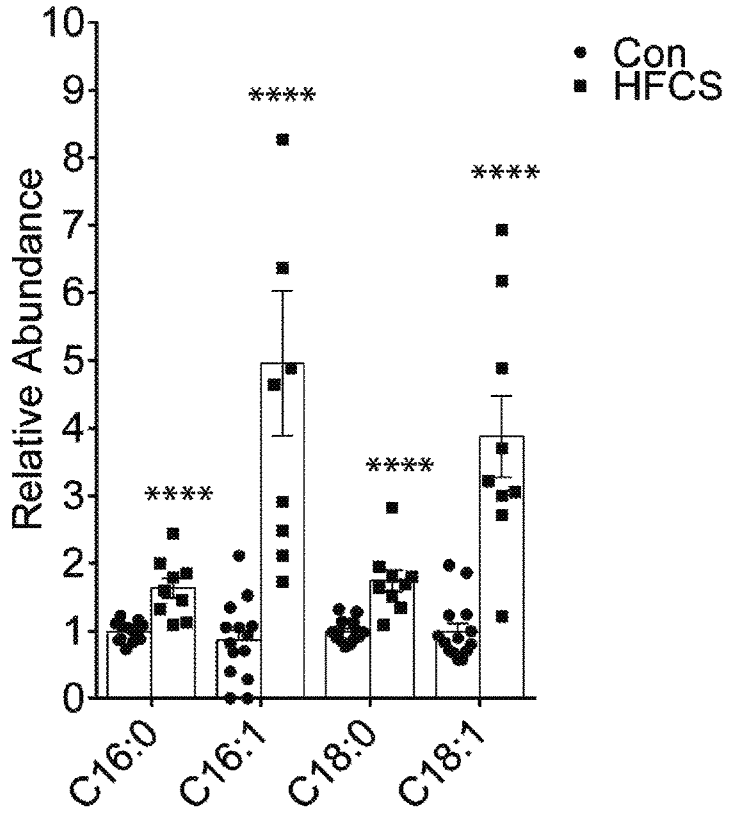
Figure 3C:
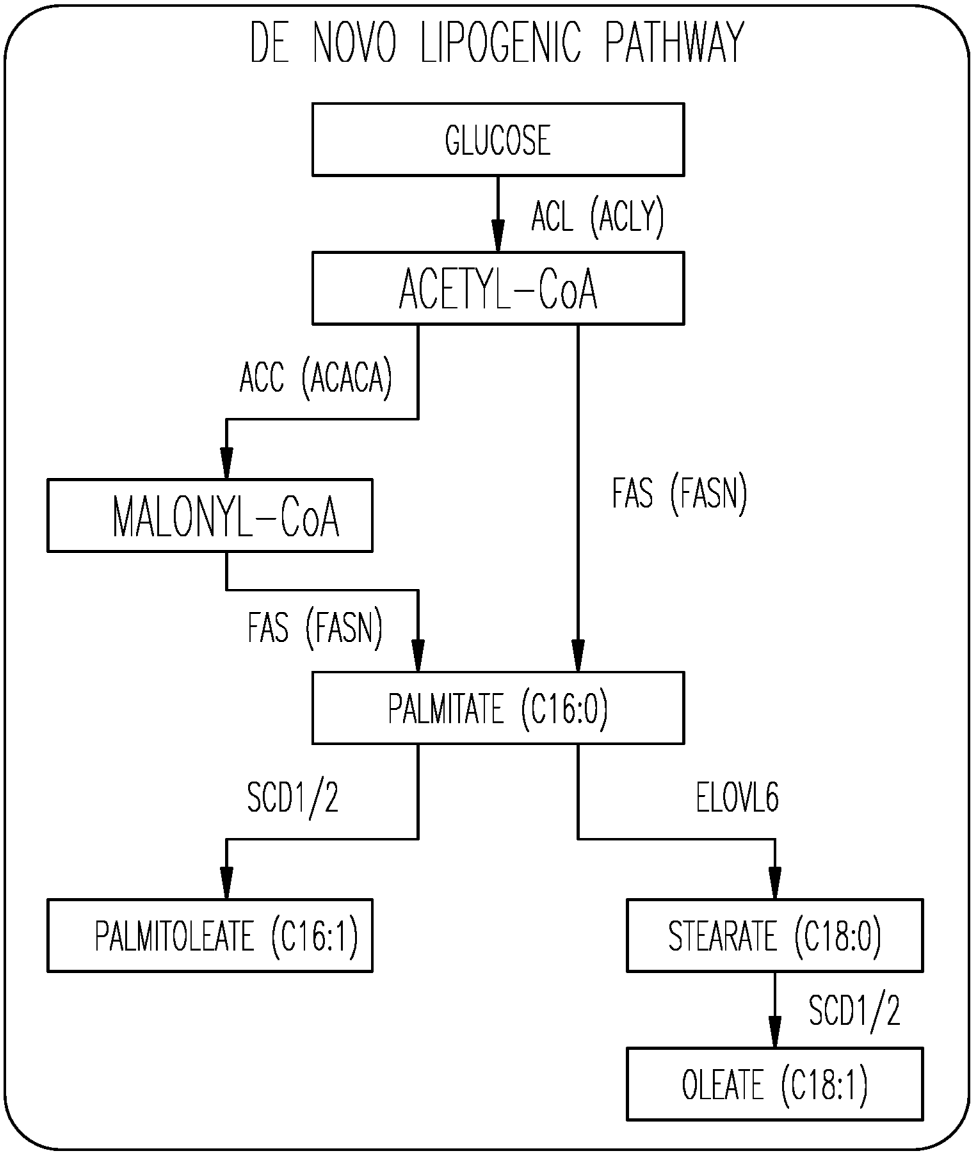
Figure 3D:
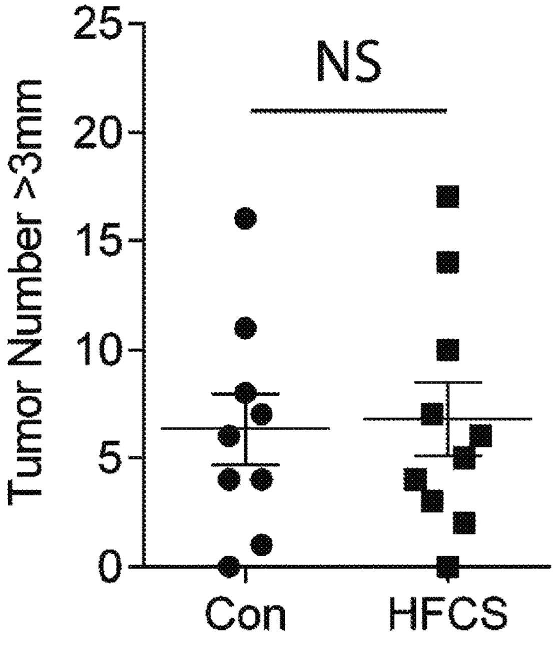
Figure 3E:
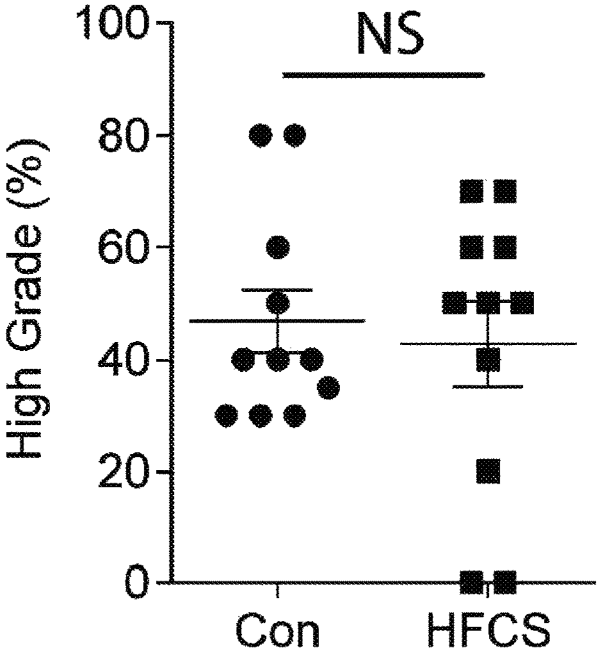
Figures 1, 3F:
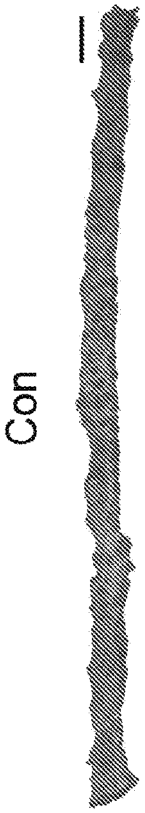
Figures 2, 3F:
Figure 3G:
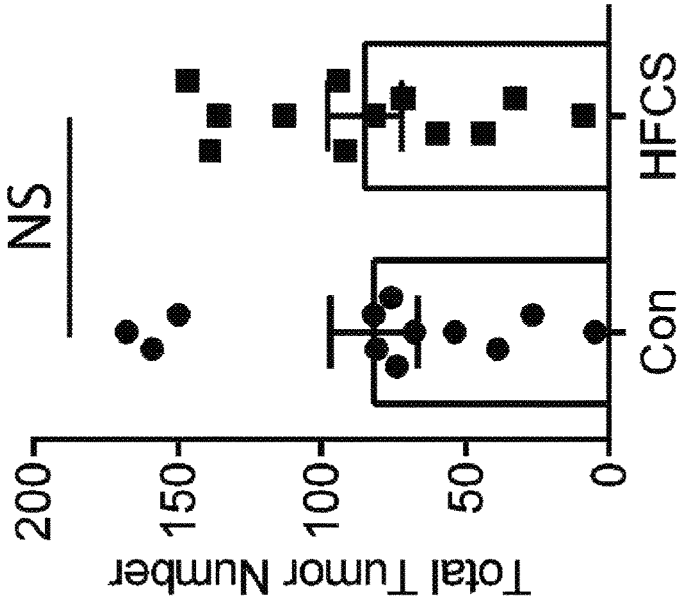
Figure 3H:
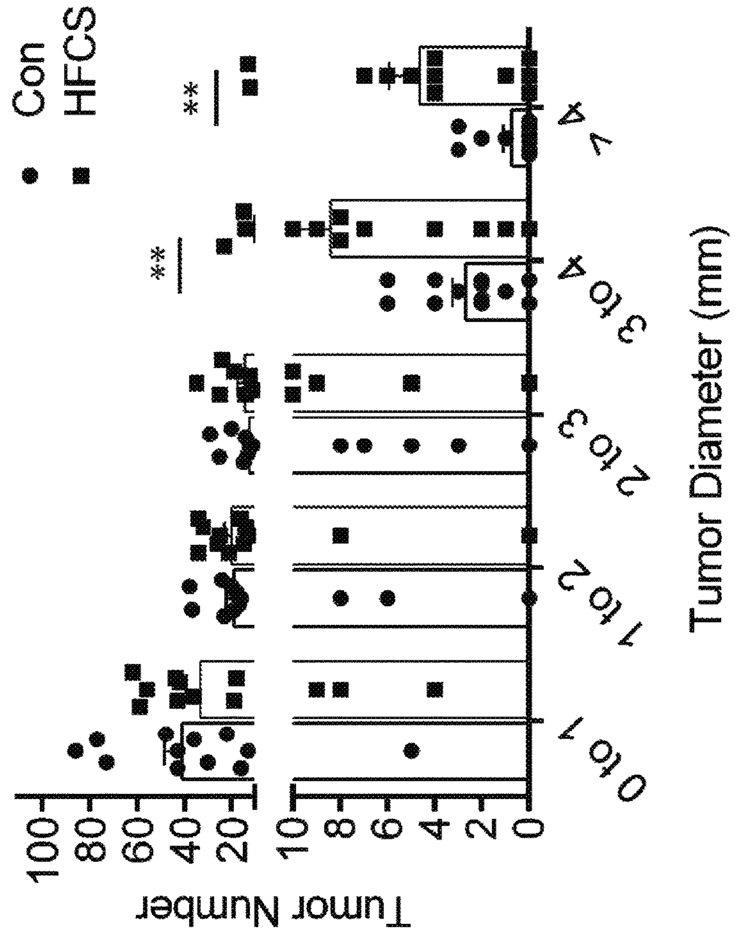
Figures 1, 3I:
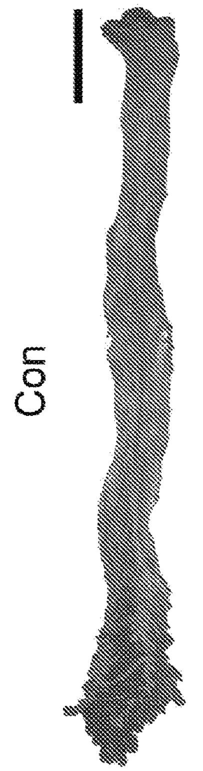
Figures 2, 3I:
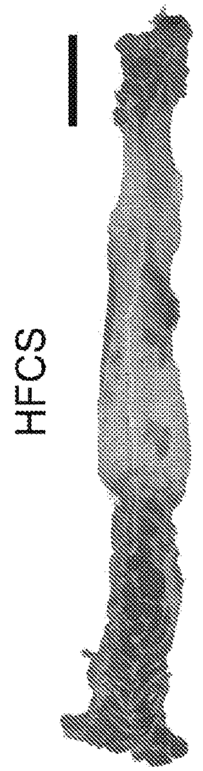
Figure 3J:
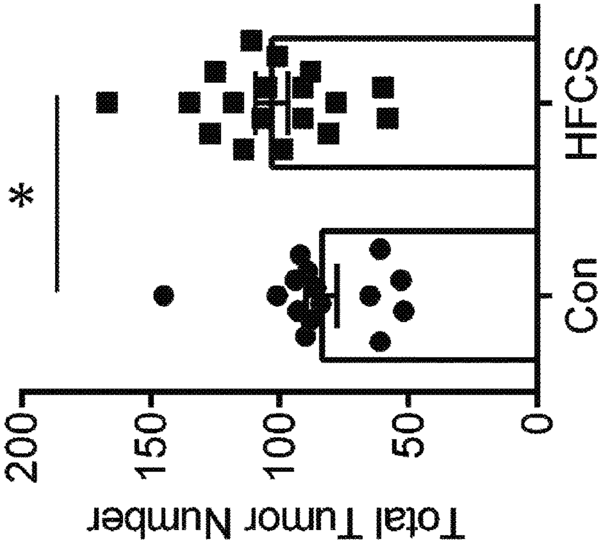
Figure 3K:
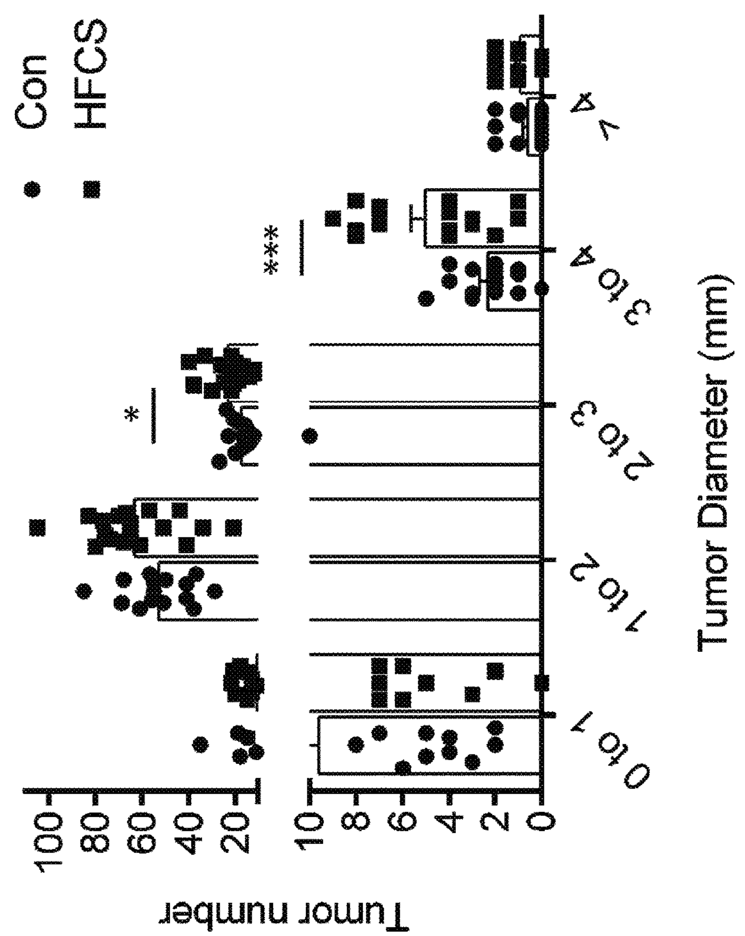
Figure 3L:
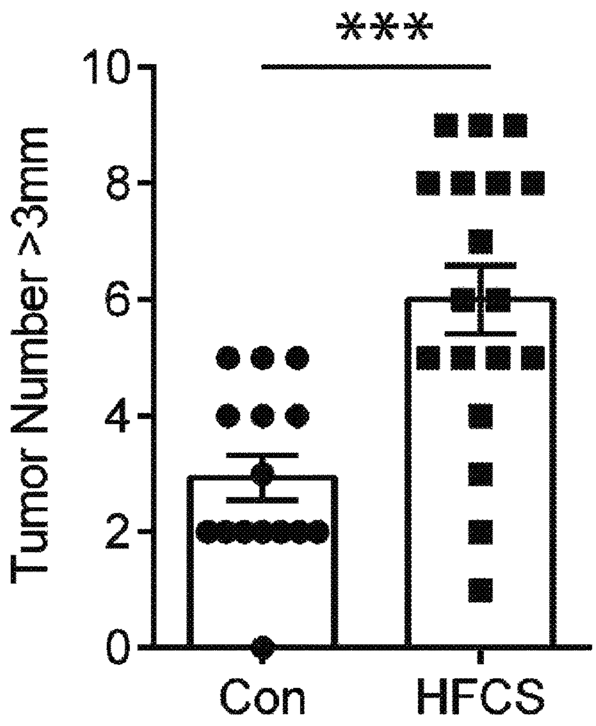
Figure 3M:
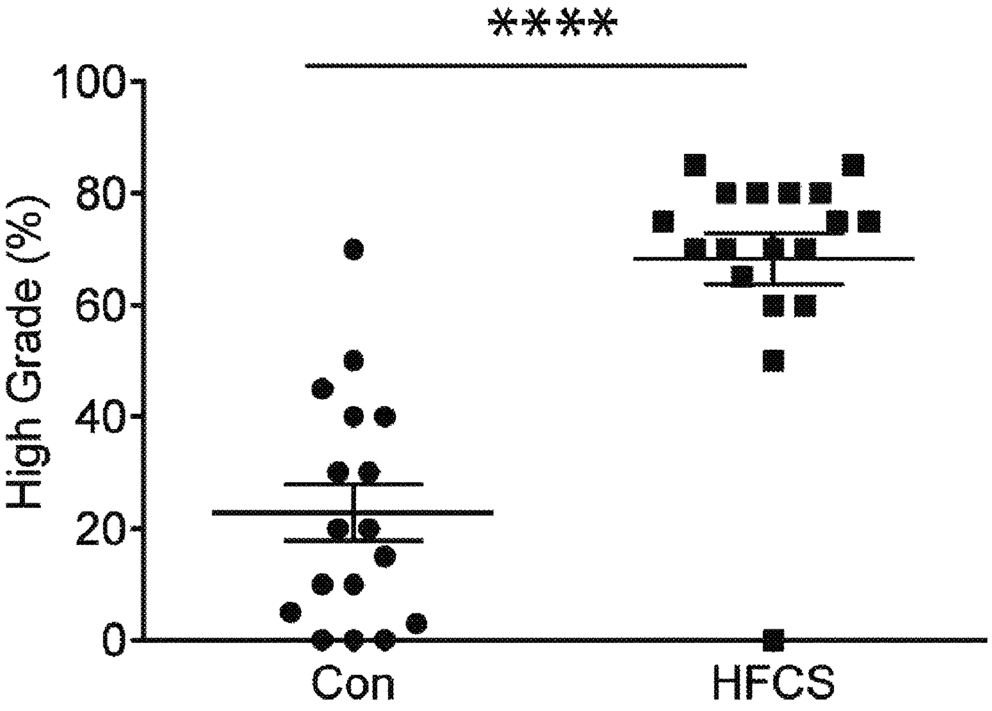
Figure 6C:
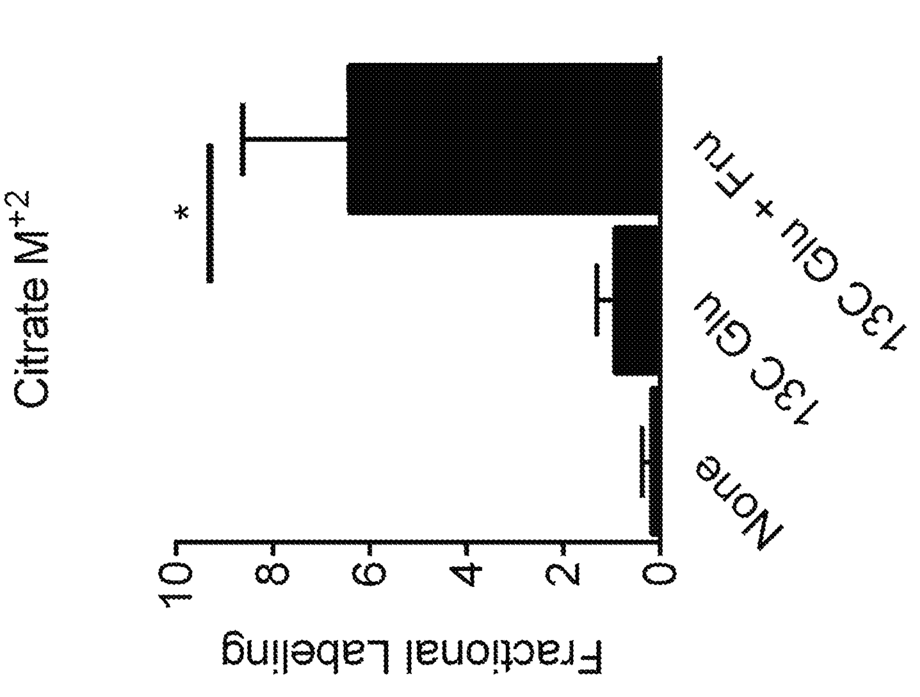
Figure 6D:
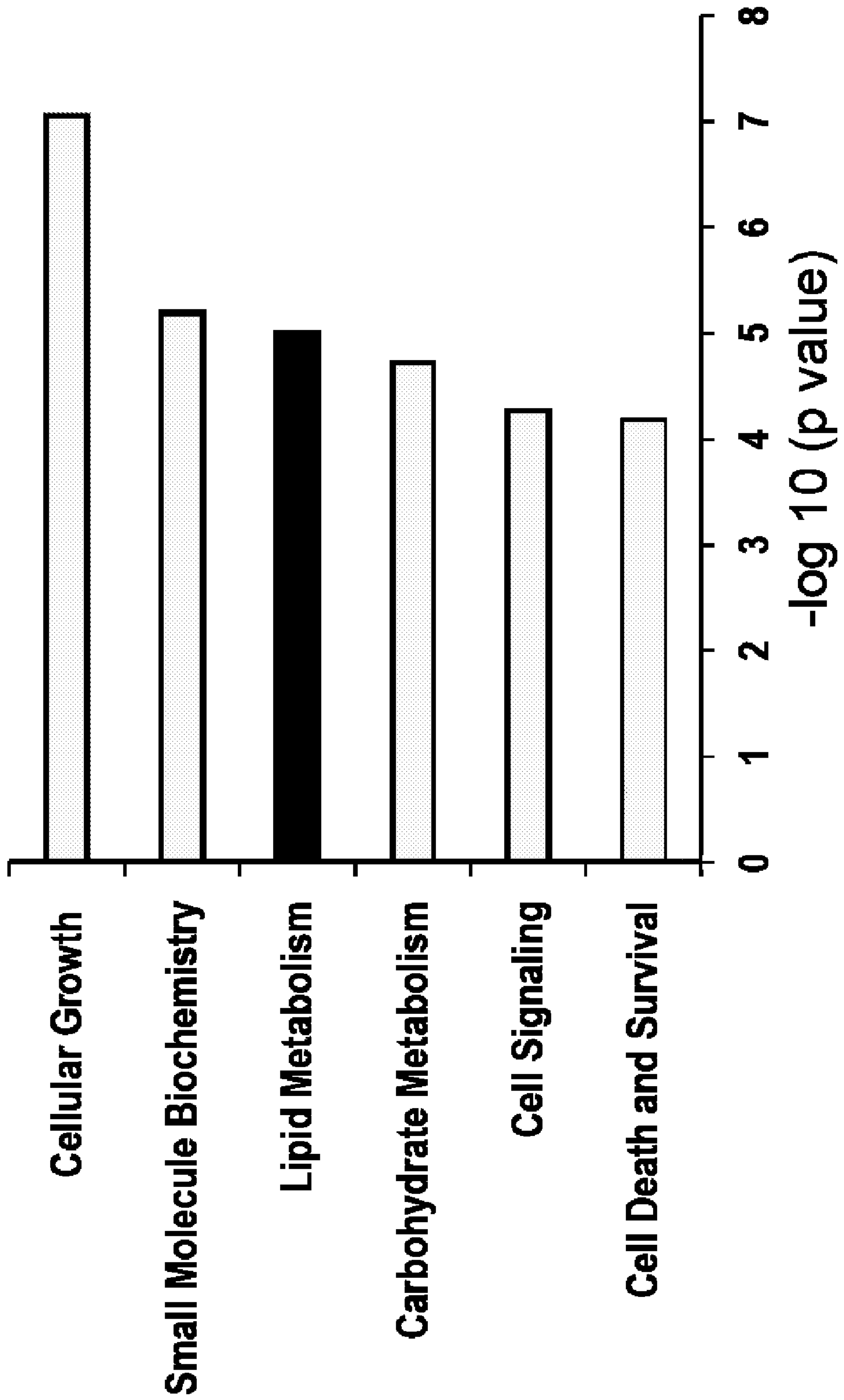
Figure 6E:
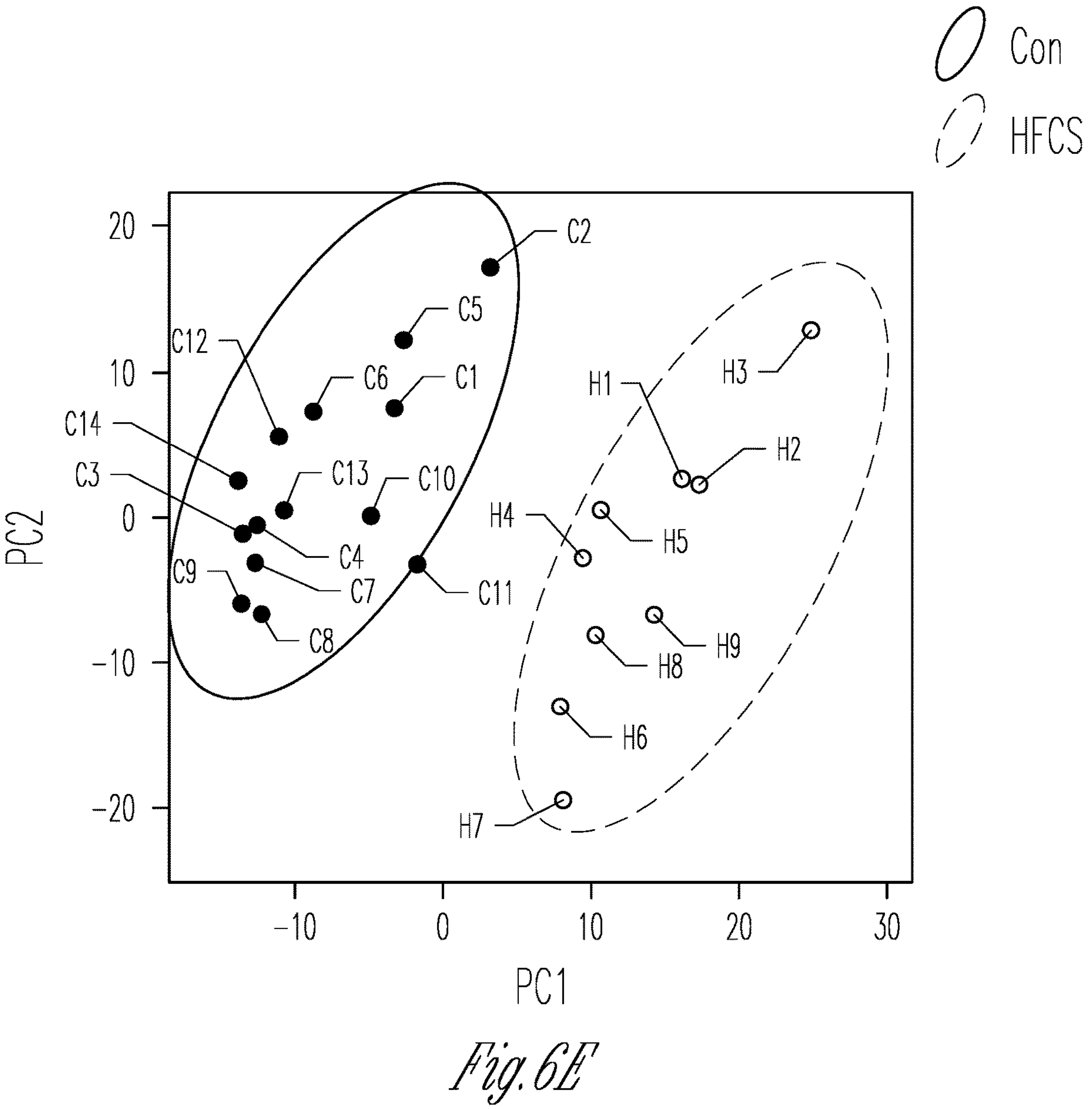
Figure 6F:
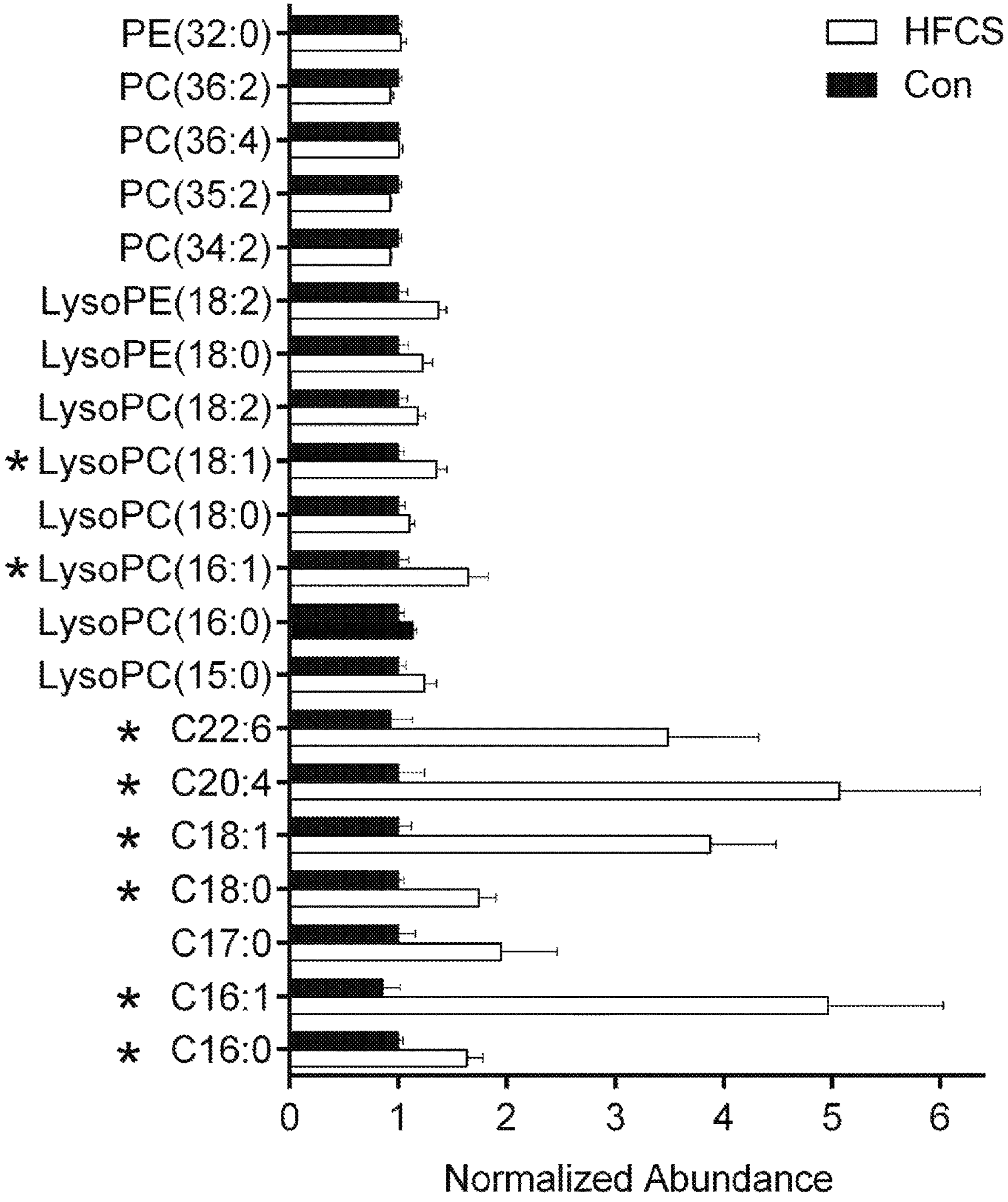
Figure 7A:
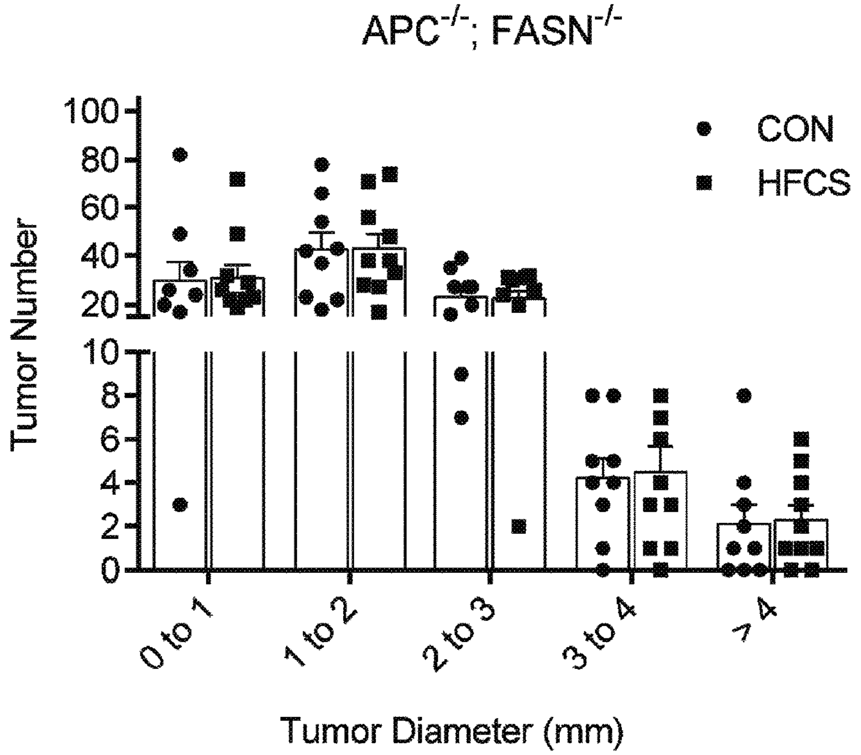
FIG. 7A-7D illustrate that genetic loss of FASN or KHK abrogates the HFCS-induced shift in tumor size distribution.

The above findings show that tumors in HFCS-treated $APC^{-/-}$ mice rewire their metabolic pathways in favor of fatty acid synthesis. The inventors postulated that chronic treatment of mice with HFCS would accelerate glycolysis and further increase the levels of fatty acids in tumors as compared to tumors from the Con group. To investigate this hypothesis, the inventors assessed the level of citrate, a key intermediate between glucose metabolism and fatty acid synthesis, in tumors by measuring its fractional labeling from $^{13}C$-glucose after tumors were exposed to either $^{13}C$-glucose or $^{13}C$-glucose+unlabeled fructose. The proportion of two-carbon—labeled ($M^{+2}$) citrate derived from glucose was significantly increased when fructose was added to the medium (FIG. 6C). Using a global metabolomics strategy, the inventors confirmed that the lipid metabolic pathway was one of the most enriched pathways in tumors from the HFCS-treated mice group compared to control group (FIG. 6D-6E). Notably, the levels of all four-major long-chain fatty acids—palmitic acid, palmitoleic acid, stearic acid, and oleic acid—were increased in tumors from HFCS-treated mice compared to tumors from water-treated mice (FIGS. 3B and 6F). In addition, many genes related to the production of eicosanoids from fatty acid precursors showed increased expression in $APC^{-/-}$ tumors as compared to IECs, and several eicosanoids increased in abundance in mice receiving chronic HFCS treatment. FASN encodes an enzyme that catalyzes the synthesis of palmitic acid from acetyl-CoA and malonyl-CoA, a critical step for de novo lipogenesis (FIG. 3C). To determine if de novo lipogenesis is necessary for enhancement of tumor growth by HFCS, $APC^{-/-}$; $FASN^{-/-}$ mice were generated by breeding $APC^{flox/flox}$ mice with $FASN^{flox/flox}$ mice (Lodhi et al., Cell Metab. 16, 189-201 (2012)) and the mice were treated with daily oral HFCS for 8 weeks. Indeed, the loss of FASN in $APC^{-/-}$ tumors abolished the ability of HFCS to enhance tumor growth (FIGS. 3D and 7A) as well as its effects on tumor grade (FIG. 3E), indicating that the increased fatty acid synthesis caused by HFCF treatment contributes to the tumorigenesis.

Figure 7B:
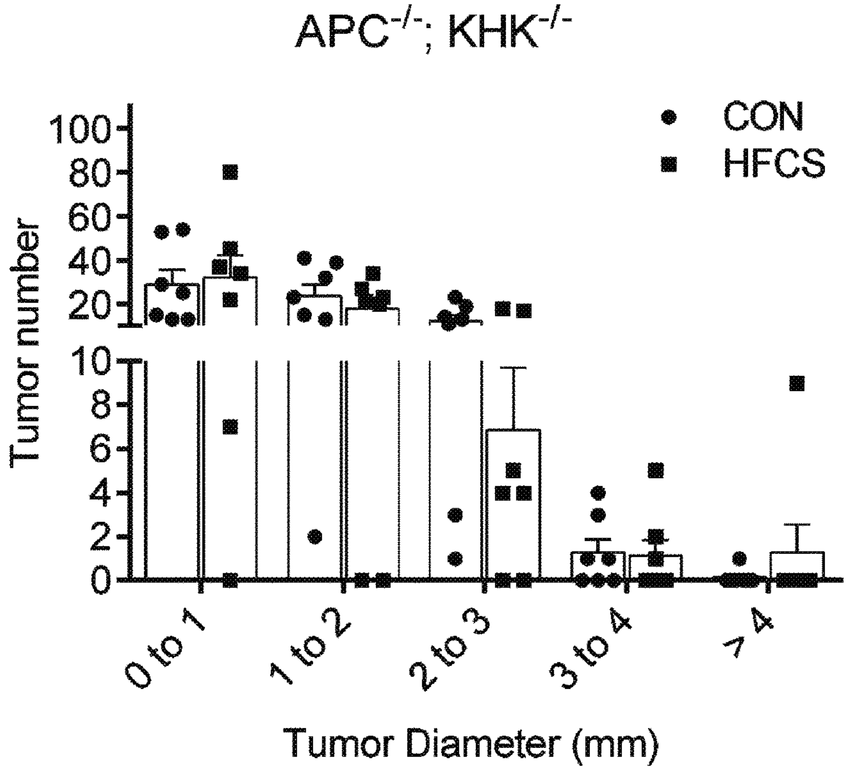
Figure 7C:
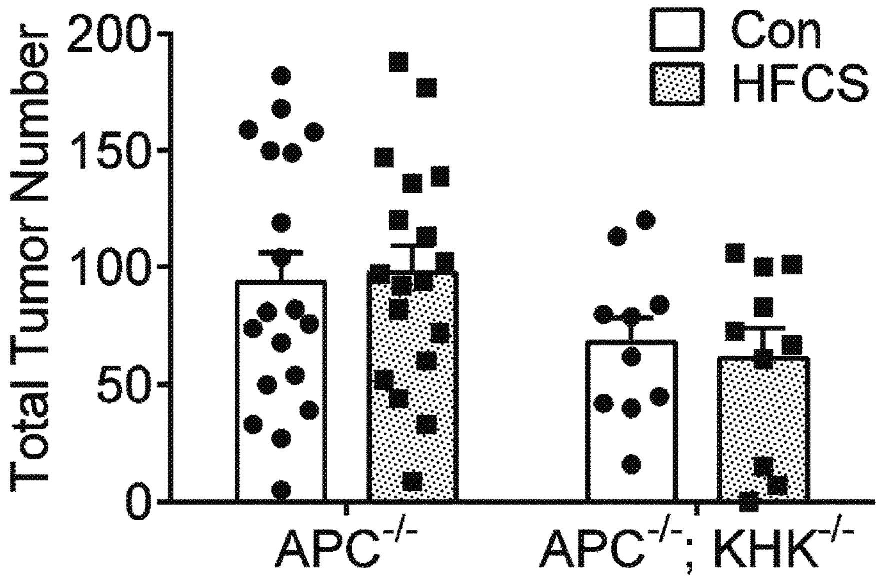
Figure 7D:
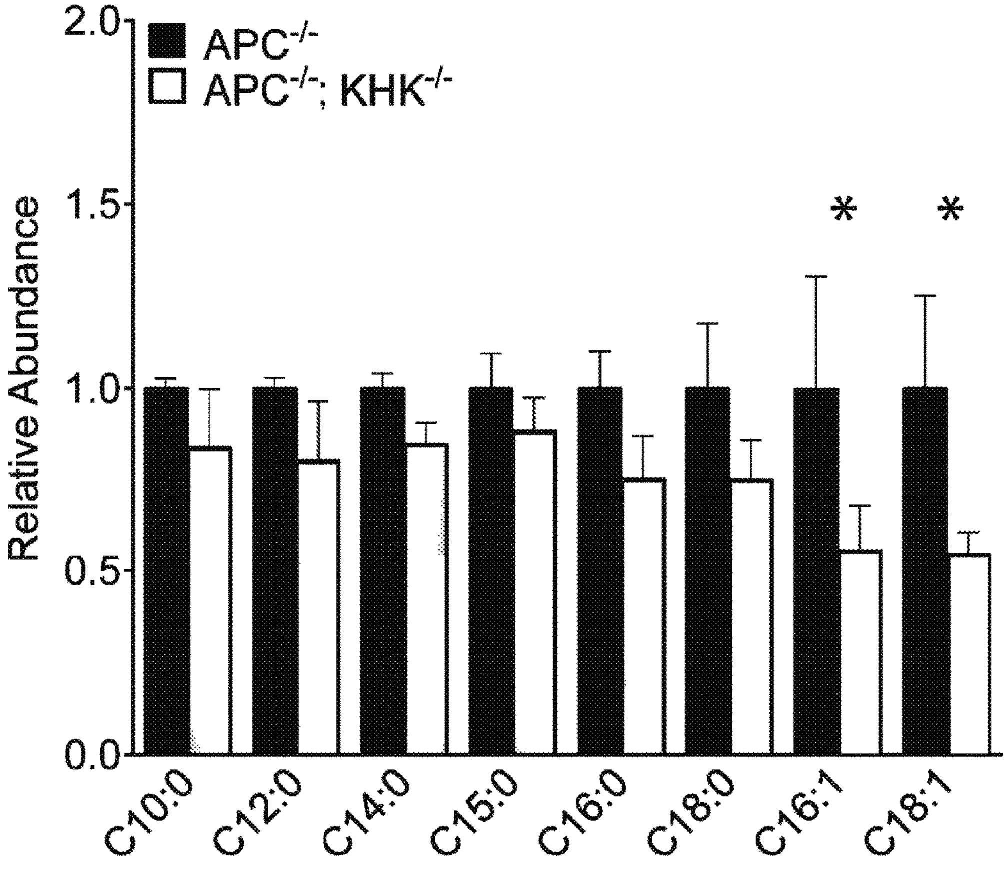

The inventors also investigated whether the increased tumor growth in the HFCS group was dependent on fructose metabolism. $APC^{-/-}$; $KHK^{-/-}$ mice were generated by crossing the $APC^{flox/flox}$ mice with mice deficient in KHK (T. Ishimoto et al., Proc. Natl. Acad. Sci. U.S.A. 109, 4320-4325 (2012); Diggle et al., J. Histochem. Cytochem. 57, 763-774 (2009)) and the mice were treated chronically by daily oral gavage with the modest amount of HFCS (3% of total daily caloric intake) for 8 weeks. The absence of KHK abolished HFCS enhancement of tumor growth and grade in APC−/− mice (FIGS. 4A-4B, and 7B). There was also a trend toward a reduction in overall tumor number (FIG. 7C). In contrast to the $APC^{-/-}$ tumors, the $APC^{-/-}$; $KHK^{-/-}$ tumors did not show changes in the abundance of ATP, PFK activity, or rate of glycolysis (as measured by lactate production) after HFCS treatment (FIG. 4C-4E). Finally, HFCS-treated $APC^{-/-}$; $KHK^{-/-}$ tumors had reduced levels of long-chain fatty acids relative to HFCS-treated $APC^{-/-}$ tumors (FIG. 7D), indicating that KHK activity is essential for the increased fatty acid synthesis following HFCS treatment.

Hence, the inventors have found that HFCS, the primary sweetener used in sugar-sweetened beverages, contributes to intestinal tumorigenesis in mice by accelerating glycolysis and de novo lipogenesis. These effects are independent of obesity and metabolic syndrome. HFCS in liquid form rapidly increases the levels of fructose and glucose in the intestinal lumen and serum, respectively, which allows intestinal tumors to take up these sugars for their growth. The results described herein also identify KHK as a key accelerator of tumor growth. When tumors are exposed to both glucose and fructose, KHK consumes fructose, rapidly depleting ATP, which in turn accelerates glycolysis and de novo lipogenesis. This reduction in ATP accelerates the flux of glucose through glycolysis by activating PFK. Such increased rate of glycolysis depletes Pi [at the step of glyceraldehyde 3-phosphate (GAPDH)] and results in activation of AMPD2, which degrades all forms of adenine nucleotides and further reduces cytosolic ATP in $APC^{-/-}$ tumors. Because fructose is not essential for the survival and growth of normal cells, inhibitors of GLUT5 or KHK may selectively impede the growth of colorectal cancer cells. These findings indicate that therapeutic targeting of fructose metabolism is a strategy for slowing the progression of colorectal cancer and that the combination of dietary glucose and fructose, even at moderate dose, can enhance intestinal tumor growth.

REFERENCES

1. V. S. Malik, M. B. Schulze, F. B. Hu, Am. J. Chu. Nutr. 84: 274-288 (2006).
2. A. M. Hodge, J. K. Bassett, R. L. Milne, D. R. English, G. G. Giles, Public Health Nutr. 21: 1618-1626 (2018).
3. L. Tappy, K. A. Lê, Physiol. Rev. 90: 23-46 (2010).
4. G. M. Singh et al., PLOS ONE 10, e0124845 (2015).
5. R. L. Siegel, K. D. Miller, A. Jemal, JAMA 318, 572-574 (2017).
6. M. Araghi et al int. J. Cancer ijc.32055 (2018),
7. H. Sung, R. L. Siegel, P. S. Rosenberg, A. Jemal, Lancet Public Health S2468-2667(18)30267-6 (2019).
8. M. A. Fuchs et al., PLOS ONE 9, e99816 (2014).
9. M. Bardou, N. Barkun, M. Martel, Gut 62, 933-947 (2013).
10. B. D. Hopkins, M. D. Goncalves, L. C. Cantley, J. Clin. Oncol. 34: 4277-4283 (2016).
11. J. Yun et al., Science 350: 1391-1396 (2015).
12. N. Barker et al., Nature 457: 608-611 (2009),
13. E. R. Fearon, B. Vogelstein, Cell 61: 759-767 (1990).
14. V. Fulgoni 3rd, Am. J. Clin. Nutr. 88: 1715S (2008).
15. Y. Feng et al., Am. J. Pathol. 183: 493-503 (2013).
16. L. A. Drozdowski, A. B. R. Thomson, World J. Gastroenterol. 12: 1657-1670 (2006).
17. W. J. Ravich, T. M. Bayless, M. Thomas, Gastroenterology 84: 26-29 (1983).
18. J. J. Rumessen, E. Gudmand-Høyer, Gut 27, 1161-1168 (1986).
19. P. L. Beyer, E. M. Caviar, R. W. McCallum, J. Am. Diet. Assoc. 105: 1559-1566 (2005).
20. C. Jang et al Cell Metab. 27: 351-361.e3 (2018).
21. A. Godoy et al., J. Cell. Physiol. 207: 614-627 (2006).
22. Q. Li et al., Cell. Physiol. Biochem. 42: 397-406 (2017).

23. A. Uzozie et al., Mol. Cell. Proteomics 13: 1198-1218 (2014).
24. T. Jensen et al., J. Hepatol. 68: 1063-1075 (2018).
25. S. A. Hannou, D. E. Haslam, N. M. McKeown, M. A. Herman, J. Clin. Invest. 128: 545-555 (2018).
26. G. Van den Berghe, Prog. Biochem. Pharmacol. 21: 1-32 (1986).
27. R. C. Morris Jr., K. Nigon, E. B. Reed, J. Clin. Invest. 61: 209-220 (1978).
28. R. G. Kemp, L. G. Foe, Mol. Cell. Biochem. 57: 147-154 (1983).
29. E. Currie, A. Schulze, R. Zechner. T. C. Walther, R. V. Farese Jr. Cell Metab. 18: 153-161(2013).
30. J. A. Menendez, R. Lupu, Nat. Rev. Cancer 7: 763-777 (2007).
31. I. J. Lodhi et al., Cell Metab. 16: 189-201 (2012).
32. T. Ishimoto et al., Proc. Natl. Acad. Sci. U.S.A. 109: 4320-4325 (2012).
33. C. P. Diggle et al., J. Histochem, Cytochem, 57: 763-774 (2009).
34. R. D. Feinman, E. J. Fine, Nutr. Metab. (Lond.) 10: 45 (2013).
35. G. Livesey, J. Nutr. 139: 1246S-1252S (2009).
36. E. IL Yau et al., Cancer Res. 77: 6330-6339 (2017).
37. J. Yun et al., Vitamin C selectively kills KRAS and BRAF mutant colorectal cancer cells by targeting GAPDH. *Science.* 350, 1391-1396 (2015).
38. I. J. Lodhi et al., Inhibiting adipose tissue lipogenesis reprograms thermogenesis and PPARγ activation to decrease diet-induced obesity. *Cell Metab.* 16, 189-201 (2012).
39. C. P. Diggle et al., Ketohexokinase: Expression and Localization of the Principal Fructose-metabolizing Enzyme. *J. Histochem. Cytochem.* 57, 763-774 (2009).
40. Y. Feng et al., Sox9 Induction, Ectopic Paneth Cells, and Mitotic Spindle Axis Defects in Mouse Colon Adenomatous Epithelium Arising from Conditional Biallelic Apc Inactivation. *Am. J. Pathol.* 183, 493-503 (2013).
41. H. Kim, E. L. Giovannucci, Sex differences in the association of obesity and colorectal cancer risk. *Cancer Causes Control CCC.* 28, 1-4 (2017).
42. P. Mystkowski et al., Validation of whole-body magnetic resonance spectroscopy as a tool to assess murine body composition. *Int. J. Obes. Relat. Metab. Disord. J. Int. Assoc. Study Obes.* 24, 719-724 (2000).
43. M. Yuan, S. B. Breitkopf, X. Yang, J. M. Asara, A positive/negative ion-switching, targeted mass spectrometry-based metabolomics platform for bodily fluids, cells, and fresh and fixed tissue. *Nat. Protoc.* 7, 872-881 (2012).
44. W. Lu et al., Metabolite Measurement: Pitfalls to Avoid and Practices to Follow. *Annu. Rev. Biochem.* 86, 277-304 (2017).
45. J. J. Kamphorst, J. Fan, W. Lu, E. White, J. D. Rabinowitz, Liquid chromatography-high resolution mass spectrometry analysis of fatty acid metabolism *Anal. Chem.* 83, 9114-9122 (2011).
46. L. P. S. de Carvalho et al., Activity-based metabolomic profiling of enzymatic function: identification of Rv1248c as a mycobacterial 2-hydroxy-3-oxoadipate synthase. *Chem. Biol.* 17, 323-332 (2010).
47. T. R. Sana, K. Waddell, S. M. Fischer, A sample extraction and chromatographic strategy for increasing LC/MS detection coverage of the erythrocyte metabolome. *J. Chromatogr. B Analyt. Technol. Biomed. Life, Sci,* 871, 314-321 (2008).
48. T. Hartman, K. Rhee, Y. Dai, Metabolomics Analysis of Tuberculosis Drug Activity Using an Agilent 6545 Q-TOF LC/MS (2017), (available at https://www.agilent.com/cs/library/applications/5991-7970EN.pdf).
49. O. Quehenberger et al., Lipidomics reveals a remarkable diversity of lipids in human plasma. *J. Lipid Res.* 51, 3299-3305 (2010).
50. A. Dobin et al., STAR: ultrafast universal RNA-seq aligner. *Bioinforma. Oxf Engl.* 29, 15-21 (2013).
51. C. Trapnell et al., Transcript assembly and quantification by RNA-Seq reveals unannotated transcripts and isoform switching during cell differentiation. *Nat. Biotechnol.* 28, 511-515 (2010).
52. S. Anders, P. T. Pyl, W. Huber, HTSeq-a Python framework to work with high-throughput sequencing data. *Bioinforma. Oxf. Engl.* 31, 166-169 (2015).
53. J. A. Blake et al., Mouse Genome Database (MGD)-2017: community knowledge resource for the laboratory mouse. *Nucleic Acids Res.* 45, D723-D729 (2017).
54. M. I. Love, W. Huber, S. Anders, Moderated estimation of fold change and dispersion for RNA-seq data with DESeq2. *Genome Biol.* 15, 550 (2014).
55. P. Di Tommaso et al., Nextflow enables reproducible computational workflows. *Nat. Biotechnol.* 35, 316-319 (2017).
56. S. Zur Nedden, R. Eason, A. S. Doney, B. G. Frenguelli. An ion-pair reversed-phase HPLC method for determination of fresh tissue adenine nucleotides avoiding freeze-thaw degradation of ATP. *Anal. Biochem.* 388, 108-114 (2009).

All patents and publications referenced or mentioned herein are indicative of the levels of skill of these skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A method comprising (a) reducing or eliminating sucrose, fructose, glycine, serine, or a combination thereof from a subject's diet; (b) administering a GLUT5 inhibitor; (c) administering A ketohexokinase (KUK) inhibitor; (d) administering a fatty acid synthase (FASN) inhibitor; (e) administering phosphoinositide 3 (PI3) kinase inhibitor, or (4) a combination two or more thereof to inhibit the onset of colorectal or small intestine cancer or reduce colorectal or small intestine tumor growth in the subject.
2. The method of statement 1 wherein the subject's diet is provided by one or more dieticians or medical personnel.
3. The method of statement 1 or 2, wherein the subject's diet is a sugar-free diet or a diet that involves ingestion of less than about 25 grams of sugar per day, or less than about 20 grams of sugar per day, or less than about 15 grams of sugar per day, or less than about 10 gams of sugar per day, or less than about 5 grams of sugar per day.
4. The method of statement 1, 2, or 3, wherein the subject's diet is a ketogenic diet or a low glycemic index diet.
5. The method of statement 1-3 or 4, wherein the subject's diet is a ketogenic diet comprising ingestion of a 4:1, 3.5:1, 3:1, 2.5:1, or 2:1 ratio of ketogenic-to-antiketogenic macromolecules, with approximately 85% fat, 12% protein, and 3% carbohydrates.

6. The method of statement 1-4 or 5, wherein the subject's diet is a serine-depleted, glycine-depleted, or a serine-depleted and glycine-depleted diet.
7. The method of statement 1-5 or 6, comprising administering a phosphoinositide 3 (PI3) kinase inhibitor to the subject, wherein the subject's diet is a ketogenic diet.
8. The method of statement 1-6 or 7, comprising administering a ketohexokinase (KHK) inhibitor to the subject, wherein the subject's diet is a sugar-free diet or a diet that involves ingestion of less than about 25 grains of sugar per clay, and the subject.
9. The method of statement 1-7 or 8, comprising administering a fatty acid synthase (FASN) inhibitor to the subject, wherein the subject's diet is a sugar-free diet or a diet that involves ingestion of less than about 25 grams of sugar per day, and the subject.
10. The method of statement 1-8 or 9, comprising administering a phosphoglycerate dehydrogenase (PHGDH) inhibitor, wherein the subject's diet is a serine-depleted, glycine-depleted, or a serine-depleted and glycine-depleted diet.
11. The method of statement 1-9 or 10, wherein the GLUT5 inhibitor, ketohexokinase (KHK) inhibitor, fatty acid synthase (FASN) inhibitor, or the phosphoinositide 3 (PI3) kinase inhibitor is an inhibitory nucleic acid or an antibody.
12. The method of statement 1-9 or 10, wherein the GLUT5 inhibitor, ketohexokinase (KHK) inhibitor, fatty acid synthase (FASN) inhibitor, or the phosphoinositide 3 (PI3) kinase inhibitor is a compound or small molecule.
13. The method of statement 1-1.1 or 12, wherein the subject has an APC mutation or a mutation that increases beta-catenin expression or activity.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the an that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a protein" or "a cell" includes a plurality of such nucleic acids, proteins, or cells (for example, a solution or dried preparation of nucleic acids or expression cassettes, a solution of proteins, or a population of cells), and so forth. In this document, the term "or" is used to refer to a nonexclusive or, such that "A or B" includes "A but not B," "B but not A," and "A and B." unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method comprising administering a combination of at least two of (a) a GLUT5 inhibitor;

(b) a ketohexokinase (KHK) inhibitor; or (c) a fatty acid synthase (FASN) inhibitor; and administering a pyruvate kinase M2 (PKM2) activator; to inhibit the onset of colorectal or small intestine cancer, or to reduce colorectal or small intestine tumor growth in the subject, wherein the FASN inhibitor is an inhibitory nucleic acid or an antibody, wherein the subject has an APC mutation or a mutation that increases beta-catenin expression or activity.

2. The method of claim 1, wherein the GLUT5 inhibitor, or the ketohexokinase (KHK) inhibitor, is an inhibitory nucleic acid or an antibody.

3. The method of claim 1, wherein the GLUT5 inhibitor, or the ketohexokinase (KHK) inhibitor, is a compound or small molecule.

4. The method of claim 1, further comprising administering a pyruvate kinase inhibitor to the subject.

5. The method of claim 1, further comprising administering vitamins to the subject.

6. The method of claim 1, which reduces the dose or toxicity of conventional therapies.

7. The method of claim 1, which increases the sensitivity of conventional therapies.

8. A method for maintaining a healthy intestinal system in a subject, comprising:

administering to the subject a combination of at least two of: (a) a GLUT5 inhibitor; (b) a ketohexokinase (KHK) inhibitor; or (c) a fatty acid synthase (FASN) inhibitor; and administering a pyruvate kinase M2 (PKM2) activator: wherein the FASN inhibitor is an inhibitory nucleic acid or an antibody.

9. The method of claim 1, further comprising administering a phosphoinositide 3 (PI3) Kinase inhibitor to the subject.

* * * * *

SEQUENCE LISTING

```
<160> NUMBER OF SEQ ID NOS: 19

<210> SEQ ID NO 1
<211> LENGTH: 501
<212> TYPE: PRT
<213> ORGANISM: Homo sapiens

<400> SEQUENCE: 1

Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
```

```
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190

Pro Ile Leu Leu Gly Leu Thr Gly Val Pro Ala Ala Leu Gln Leu Leu
        195                 200                 205

Leu Leu Pro Phe Phe Pro Glu Ser Pro Arg Tyr Leu Leu Ile Gln Lys
    210                 215                 220

Lys Asp Glu Ala Ala Ala Lys Lys Ala Leu Gln Thr Leu Arg Gly Trp
225                 230                 235                 240

Asp Ser Val Asp Arg Glu Val Ala Glu Ile Arg Gln Glu Asp Glu Ala
                245                 250                 255

Glu Lys Ala Ala Gly Phe Ile Ser Val Leu Lys Leu Phe Arg Met Arg
            260                 265                 270

Ser Leu Arg Trp Gln Leu Leu Ser Ile Ile Val Leu Met Gly Gly Gln
        275                 280                 285

Gln Leu Ser Gly Val Asn Ala Ile Tyr Tyr Tyr Ala Asp Gln Ile Tyr
    290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
                325                 330                 335

Glu Leu Leu Gly Arg Arg Leu Leu Leu Leu Leu Gly Phe Ser Ile Cys
            340                 345                 350

Leu Ile Ala Cys Cys Val Leu Thr Ala Ala Leu Ala Leu Gln Asp Thr
        355                 360                 365

Val Ser Trp Met Pro Tyr Ile Ser Ile Val Cys Val Ile Ser Tyr Val
    370                 375                 380

Ile Gly His Ala Leu Gly Pro Ser Pro Ile Pro Ala Leu Leu Ile Thr
385                 390                 395                 400

Glu Ile Phe Leu Gln Ser Ser Arg Pro Ser Ala Phe Met Val Gly Gly
                405                 410                 415

Ser Val His Trp Leu Ser Asn Phe Thr Val Gly Leu Ile Phe Pro Phe
            420                 425                 430

Ile Gln Glu Gly Leu Gly Pro Tyr Ser Phe Ile Val Phe Ala Val Ile
        435                 440                 445
```

```
Cys Leu Leu Thr Thr Ile Tyr Ile Phe Leu Ile Val Pro Glu Thr Lys
    450                 455                 460

Ala Lys Thr Phe Ile Glu Ile Asn Gln Ile Phe Thr Lys Met Asn Lys
465                 470                 475                 480

Val Ser Glu Val Tyr Pro Glu Lys Glu Glu Leu Lys Glu Leu Pro Pro
                485                 490                 495

Val Thr Ser Glu Gln
            500


<210> SEQ ID NO 2
<211> LENGTH: 2383
<212> TYPE: DNA
<213> ORGANISM: Homo sapiens

<400> SEQUENCE: 2

gcttctcaca gtctcccacc ccgccctgct cgcggagcct gcaggcctcg gcctcatggc     60

ggcctgaggc aggggcctgg aggctggtcc gcccgccacg aaggttgggg ggtccctggc    120

cagaagcagg acccgggcga ggctgagggg gactctggca gaagctgaag gggacccggt    180

gcacgcgtta ctttggctaa aaggaggtga gcggcactct gcccttccag agcaagcatg    240

gagcaacagg atcagagcat gaaggaaggg aggctgacgc ttgtgcttgc cctggcaacc    300

ctgatagctg cctttgggtc atccttccag tatgggtaca acgtggctgc tgtcaactcc    360

ccagcactgc tcatgcaaca attttacaat gagacttact atggtaggac cggtgaattc    420

atggaagact tcccccttgac gttgctgtgg tctgtaaccg tgtccatgtt tccatttgga    480

gggtttatcg gatccctcct ggtcggcccc ttggtgaata aatttggcag aaaaggggcc    540

ttgctgttca acaacatatt ttctatcgtg cctgcgatct taatgggatg cagcagagtc    600

gccacatcat ttgagcttat cattatttcc agacttttgg tgggaatatg tgcaggtgta    660

tcttccaacg tggtccccat gtacttaggg gagctggccc ctaaaaacct gcggggggct    720

ctcggggtgg tgccccagct cttcatcact gttggcatcc ttgtggccca gatctttggt    780

cttcggaatc tccttgcaaa cgtagatggc tggccgatcc tgctggggct gaccggggtc    840

cccgcggcgc tgcagctcct tctgctgccc ttcttccccg agagccccag gtacctgctg    900

attcagaaga aagacgaagc ggccgccaag aaagccctac agacgctgcg cggctgggac    960

tctgtggaca gggaggtggc cgagatccgg caggaggatg aggcagagaa ggccgcgggc   1020

ttcatctccg tgctgaagct gttccggatg cgctcgctgc gctggcagct gctgtccatc   1080

atcgtcctca tgggcggcca gcagctgtcg ggcgtcaacg ctatctacta ctacgcggac   1140

cagatctacc tgagcgccgg cgtgccggag gagcacgtgc agtacgtgac ggccggcacc   1200

ggggccgtga acgtggtcat gaccttctgc gccgtgttcg tggtggagct cctgggtcgg   1260

aggctgctgc tgctgctggg cttctccatc tgcctcatag cctgctgcgt gctcactgca   1320

gctctggcac tgcaggacac agtgtcctgg atgccataca tcagcatcgt ctgtgtcatc   1380

tcctacgtca taggacatgc cctcgggccc agtcccatac ccgcgctgct catcactgag   1440

atcttcctgc agtcctctcg gccatctgcc ttcatggtgg ggggcagtgt gcactggctc   1500

tccaacttca ccgtgggctt gatcttcccg ttcatccagg agggcctcgg cccgtacagc   1560

ttcattgtct tcgccgtgat ctgcctcctc accaccatct acatcttctt gattgtcccg   1620

gagaccaagg ccaagacgtt catagagatc aaccagattt tcaccaagat gaataaggtg   1680

tctgaagtgt acccggaaaa ggaggaactg aaagagcttc cacctgtcac ttcggaacag   1740
```

```
tgactctgga gaggaagcca gtggagctgg tctgccaggg gcttcccact ttggcttatt   1800

tttctgactt ctagctgtct gtgaatatcc agaaataaaa caactctgat gtggaatgca   1860

gtcctcatct ccagcctccc caccccagtg ggaactgtgc aaagggctgc cttgctgttc   1920

ttgaagctgg gctgtctctc tccatgttgg cctgtcacca gacccgagtc aattaaacag   1980

ctggtcctcc actttgctgg ttcagccttc gtgtggctcc tggtaacgtg gctccacctt   2040

gatgggtcaa cctttgtgtg gctcctggta acataacaac aacagttact atagtggtga   2100

gatggaagga atcaaatttt gccagagaaa ctaacttggt ggccccgaca ggtcttccgg   2160

ggccatgggc atttgtttag agccaaattc atcctcttac cagatccttt tccagaaata   2220

cctgtctagg aaggtgtgat gtcagaaaca atgacatcca gaaagctgag gaacaggttc   2280

ctgtggagac actgagtcag aattcttcat cctaaattat tttgttagtg gaaaatggaa   2340

ttgcttctgt gtagtcaata aaatgaacct gatcactttt caa                     2383


<210> SEQ ID NO 3
<211> LENGTH: 501
<212> TYPE: PRT
<213> ORGANISM: Homo sapiens

<400> SEQUENCE: 3

Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190

Pro Ile Leu Leu Gly Leu Thr Gly Val Pro Ala Ala Leu Gln Leu Leu
        195                 200                 205

Leu Leu Pro Phe Phe Pro Glu Ser Pro Arg Tyr Leu Leu Ile Gln Lys
    210                 215                 220

Lys Asp Glu Ala Ala Ala Lys Lys Ala Leu Gln Thr Leu Arg Gly Trp
225                 230                 235                 240

Asp Ser Val Asp Arg Glu Val Ala Glu Ile Arg Gln Glu Asp Glu Ala
                245                 250                 255

Glu Lys Ala Ala Gly Phe Ile Ser Val Leu Lys Leu Phe Arg Met Arg
```

```
            260                 265                 270

Ser Leu Arg Trp Gln Leu Leu Ser Ile Ile Val Leu Met Gly Gly Gln
        275                 280                 285

Gln Leu Ser Gly Val Asn Ala Ile Tyr Tyr Tyr Ala Asp Gln Ile Tyr
    290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
                325                 330                 335

Glu Leu Leu Gly Arg Arg Leu Leu Leu Leu Leu Gly Phe Ser Ile Cys
            340                 345                 350

Leu Ile Ala Cys Cys Val Leu Thr Ala Ala Leu Ala Leu Gln Asp Thr
        355                 360                 365

Val Ser Trp Met Pro Tyr Ile Ser Ile Val Cys Val Ile Ser Tyr Val
    370                 375                 380

Ile Gly His Ala Leu Gly Pro Ser Pro Ile Pro Ala Leu Leu Ile Thr
385                 390                 395                 400

Glu Ile Phe Leu Gln Ser Ser Arg Pro Ser Ala Phe Met Val Gly Gly
                405                 410                 415

Ser Val His Trp Leu Ser Asn Phe Thr Val Gly Leu Ile Phe Pro Phe
            420                 425                 430

Ile Gln Glu Gly Leu Gly Pro Tyr Ser Phe Ile Val Phe Ala Val Ile
        435                 440                 445

Cys Leu Leu Thr Thr Ile Tyr Ile Phe Leu Ile Val Pro Glu Thr Lys
    450                 455                 460

Ala Lys Thr Phe Ile Glu Ile Asn Gln Ile Phe Thr Lys Met Asn Lys
465                 470                 475                 480

Val Ser Glu Val Tyr Pro Glu Lys Glu Glu Leu Lys Glu Leu Pro Pro
                485                 490                 495

Val Thr Ser Glu Gln
            500
```

```
<210> SEQ ID NO 4
<211> LENGTH: 2218
<212> TYPE: DNA
<213> ORGANISM: Homo sapiens

<400> SEQUENCE: 4

cttctctctc cattcagtgc acgcgttact ttggctaaaa ggaggtgagc ggcactctgc      60

ccttccagag caagcatgga gcaacaggat cagagcatga aggaagggag gctgacgctt     120

gtgcttgccc tggcaaccct gatagctgcc tttgggtcat ccttccagta tgggtacaac     180

gtggctgctg tcaactcccc agcactgctc atgcaacaat tttacaatga gacttactat     240

ggtaggaccg gtgaattcat ggaagacttc cccttgacgt tgctgtggtc tgtaaccgtg     300

tccatgtttc catttggagg gtttatcgga tccctcctgg tcggcccctt ggtgaataaa     360

tttggcagaa aaggggcctt gctgttcaac aacatatttt ctatcgtgcc tgcgatctta     420

atgggatgca gcagagtcgc cacatcattt gagcttatca ttatttccag acttttggtg     480

ggaatatgtg caggtgtatc ttccaacgtg gtccccatgt acttagggga gctggcccct     540

aaaaacctgc ggggggctct cggggtggtg ccccagctct tcatcactgt tggcatcctt     600

gtggcccaga tctttggtct tcggaatctc cttgcaaacg tagatggctg gccgatcctg     660

ctggggctga ccggggtccc cgcggcgctg cagctccttc tgctgccctt cttccccgag     720
```

-continued

```
agccccaggt acctgctgat tcagaagaaa gacgaagcgg ccgccaagaa agccctacag    780

acgctgcgcg gctgggactc tgtggacagg gaggtggccg agatccggca ggaggatgag    840

gcagagaagg ccgcgggctt catctccgtg ctgaagctgt tccggatgcg ctcgctgcgc    900

tggcagctgc tgtccatcat cgtcctcatg ggcggccagc agctgtcggg cgtcaacgct    960

atctactact acgcggacca gatctacctg agcgccggcg tgccggagga gcacgtgcag   1020

tacgtgacgg ccggcaccgg ggccgtgaac gtggtcatga ccttctgcgc cgtgttcgtg   1080

gtggagctcc tgggtcggag gctgctgctg ctgctgggct tctccatctg cctcatagcc   1140

tgctgcgtgc tcactgcagc tctggcactg caggacacag tgtcctggat gccatacatc   1200

agcatcgtct gtgtcatctc ctacgtcata ggacatgccc tcgggcccag tcccataccc   1260

gcgctgctca tcactgagat cttcctgcag tcctctcggc catctgcctt catggtgggg   1320

ggcagtgtgc actggctctc caacttcacc gtgggcttga tcttcccgtt catccaggag   1380

ggcctcggcc cgtacagctt cattgtcttc gccgtgatct gcctcctcac caccatctac   1440

atcttcttga ttgtcccgga gaccaaggcc aagacgttca tagagatcaa ccagattttc   1500

accaagatga ataaggtgtc tgaagtgtac ccggaaaagg aggaactgaa agagcttcca   1560

cctgtcactt cggaacagtg actctggaga ggaagccagt ggagctggtc tgccaggggc   1620

ttcccacttt ggcttatttt tctgacttct agctgtctgt gaatatccag aaataaaaca   1680

actctgatgt ggaatgcagt cctcatctcc agcctcccca ccccagtggg aactgtgcaa   1740

agggctgcct tgctgttctt gaagctgggc tgtctctctc catgttggcc tgtcaccaga   1800

cccgagtcaa ttaaacagct ggtcctccac tttgctggtt cagccttcgt gtggctcctg   1860

gtaacgtggc tccaccttga tgggtcaacc tttgtgtggc tcctggtaac ataacaacaa   1920

cagttactat agtggtgaga tggaaggaat caaattttgc cagagaaact aactcggtgg   1980

ccccaacagg tcttccgggg ccatgggcat ttgtttagag ccaaattcat cctcttacca   2040

gatccttttc cagaaatacc tgtctaggaa ggtgtgatgt cagaaacaat gacatccaga   2100

aagctgagga acaggttcct gtggagacac tgagtcagaa ttcttcatcc aaattatttt   2160

gttagtggaa aatggaattg cttctgtgta gtcaataaaa tgaacctgat cacttttc     2218
```

```
<210> SEQ ID NO 5
<211> LENGTH: 298
<212> TYPE: PRT
<213> ORGANISM: Homo sapiens

<400> SEQUENCE: 5

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110
```

-continued

```
His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295
```

<210> SEQ ID NO 6
<211> LENGTH: 2397
<212> TYPE: DNA
<213> ORGANISM: Homo sapiens

<400> SEQUENCE: 6

```
aggcagggct gcagatgcga ggcccagctg tacctcgcgt gtcccgggtc gggagtcgga     60

gacgcaggtg caggagagtg cggggcaagt agcgcatttt ctctttgcat tctcgagatc    120

gcttagccgc gctttaaaaa ggtttgcatc agctgtgagt ccatctgaca agcgaggaaa    180

ctaaggctga gaagtgggag gcgttgccat ctgcaggccc aggcaacctg ctacgggaag    240

accggggacc aagacctctg ggttggcttt cctagacccg ctcgggtctt cgggtgtcgc    300

gaggaagggc cctgctcctt tcgttccctg cacccctggc cgctgcaggt ggctccctgg    360

aggaggagct cccacgcgga ggaggagcca gggcagctgg gagcggggac accatcctcc    420

tggataagag gcagaggccg ggaggaaccc cgtcagccgg gcgggcagga agctctggga    480

gtagcctcat ggaagagaag cagatcctgt gcgtggggct agtggtgctg gacgtcatca    540

gcctggtgga caagtaccct aaggaggact cggagataag gtgtttgtcc cagagatggc    600

agcgcggagg caacgcgtcc aactcctgca ccgttctctc cctgctcgga gccccctgtg    660

ccttcatggg ctcaatggct cctggccatg ttgctgactt cctggtggcc gacttcaggc    720

ggcggggcgt ggacgtgtct caggtggcct ggcagagcaa gggggacacc cccagctcct    780

gctgcatcat caacaactcc aatggcaacc gtaccattgt gctccatgac acgagcctgc    840

cagatgtgtc tgctacagac tttgagaagg ttgatctgac ccagttcaag tggatccaca    900

ttgagggccg gaacgcatcg gagcaggtga agatgctgca gcggatagac gcacacaaca    960

ccaggcagcc tccagagcag aagatccggg tgtccgtgga ggtggagaag ccacgagagg   1020

agctcttcca gctgtttggc tacggagacg tggtgtttgt cagcaaagat gtggccaagc   1080
```

```
acttggggtt ccagtcagca gaggaagcct tgaggggctt gtatggtcgt gtgaggaaag   1140

gggctgtgct tgtctgtgcc tgggctgagg agggcgccga cgccctgggc cctgatggca   1200

aattgctcca ctcggatgct ttcccgccac cccgcgtggt ggatacactg ggagctggag   1260

acaccttcaa tgcctccgtc atcttcagcc tctcccaggg gaggagcgtg caggaagcac   1320

tgagattcgg gtgccaggtg gccggcaaga agtgtggcct gcagggcttt gatggcatcg   1380

tgtgagagca ggtgccggct cctcacacac catggagact accattgcgg ctgcatcgcc   1440

ttctcccctc catccagcct ggcgtccagg ttgccctgtt caggggacag atgcaagctg   1500

tggggaggac tctgcctgtg tcctgtgttc cccacaggga gaggctctgg ggggatggct   1560

gggggatgca gagcctcaga gcaaataaat cttcctcaga gccagcttct cctctcaatg   1620

tctgaactgc tctggctggg cattcctgag gctctgactc ttcgatcctc cctctttgtg   1680

tccattcccc aaattaacct ctccgcccag gcccagagga ggggctgcct gggctagagc   1740

agcgagaagt gccctgggct tgccaccagc tctgccctgg ctggggagga cactcggtgc   1800

cccacaccca gtgaacctgc caaagaaacc gtgagagctc ttcggggccc tgcgttgtgc   1860

agactctatt cccacagctc agaagctggg agtccacacc gctgagctga actgacaggc   1920

cagtgggggg caggggtgcg cctcctctgc cctgcccacc agcctgtgat ttgatggggt   1980

cttcattgtc cagaaatacc tcctcccgct gactgcccca gagcctgaaa gtctcaccct   2040

tggagcccac cttggaatta agggcgtgcc tcagccacaa atgtgaccca ggatacagag   2100

tgttgctgtc ctcagggagg tccgatctgg aacacatatt ggaattgggg ccaactccaa   2160

tatagggtgg gtaaggcctt ataatgtaaa gagcatataa tgtaaagggc tttagagtga   2220

gacagacctg gattaaaatc tgccatttaa ttagctgcat atcaccttag ggtacagcac   2280

ttaacgcaat ctgcctcaat ttcttcatct gtcaaatgga accaattctg cttggctaca   2340

gaattattgt gaggataaaa tcatatataa aatgcccagc atgatgcctg atgtgta      2397
```

<210> SEQ ID NO 7
<211> LENGTH: 313
<212> TYPE: PRT
<213> ORGANISM: Homo sapiens

<400> SEQUENCE: 7

```
Met Gly Ser Ser His His His His His His Ser Ser Gly Leu Val Pro
1               5                   10                  15

Arg Gly Ser Gln Ile Leu Cys Val Gly Leu Val Val Leu Asp Val Ile
            20                  25                  30

Ser Leu Val Asp Lys Tyr Pro Lys Glu Asp Ser Glu Ile Arg Cys Leu
        35                  40                  45

Ser Gln Arg Trp Gln Arg Gly Gly Asn Ala Ser Asn Ser Cys Thr Val
    50                  55                  60

Leu Ser Leu Leu Gly Ala Pro Cys Ala Phe Met Gly Ser Met Ala Pro
65                  70                  75                  80

Gly His Val Ala Asp Phe Leu Val Ala Asp Phe Arg Arg Arg Gly Val
                85                  90                  95

Asp Val Ser Gln Val Ala Trp Gln Ser Lys Gly Asp Thr Pro Ser Ser
            100                 105                 110

Cys Cys Ile Ile Asn Asn Ser Asn Gly Asn Arg Thr Ile Val Leu His
        115                 120                 125

Asp Thr Ser Leu Pro Asp Val Ser Ala Thr Asp Phe Glu Lys Val Asp
    130                 135                 140
```

```
Leu Thr Gln Phe Lys Trp Ile His Ile Glu Gly Arg Asn Ala Ser Glu
145                 150                 155                 160

Gln Val Lys Met Leu Gln Arg Ile Asp Ala His Asn Thr Arg Gln Pro
                165                 170                 175

Pro Glu Gln Lys Ile Arg Val Ser Val Glu Val Glu Lys Pro Arg Glu
            180                 185                 190

Glu Leu Phe Gln Leu Phe Gly Tyr Gly Asp Val Val Phe Val Ser Lys
        195                 200                 205

Asp Val Ala Lys His Leu Gly Phe Gln Ser Ala Glu Glu Ala Leu Arg
    210                 215                 220

Gly Leu Tyr Gly Arg Val Arg Lys Gly Ala Val Leu Val Cys Ala Trp
225                 230                 235                 240

Ala Glu Glu Gly Ala Asp Ala Leu Gly Pro Asp Gly Lys Leu Leu His
                245                 250                 255

Ser Asp Ala Phe Pro Pro Pro Arg Val Val Asp Thr Leu Gly Ala Gly
            260                 265                 270

Asp Thr Phe Asn Ala Ser Val Ile Phe Ser Leu Ser Gln Gly Arg Ser
        275                 280                 285

Val Gln Glu Ala Leu Arg Phe Gly Cys Gln Val Ala Gly Lys Lys Cys
    290                 295                 300

Gly Leu Gln Gly Phe Asp Gly Ile Val
305                 310


<210> SEQ ID NO 8
<211> LENGTH: 298
<212> TYPE: PRT
<213> ORGANISM: Homo sapiens

<400> SEQUENCE: 8

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110

His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
```

```
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295


<210> SEQ ID NO 9
<211> LENGTH: 1000
<212> TYPE: DNA
<213> ORGANISM: Homo sapiens

<400> SEQUENCE: 9

gtagcctcat ggaagagaag cagatcctgt gcgtggggct agtggtgctg gacgtcatca      60

gcctggtgga caagtaccct aaggaggact cggagataag gtgtttgtcc cagagatggc     120

agcgcggagg caacgcgtcc aactcctgca ccgttctctc cctgctcgga gccccctgtg     180

ccttcatggg ctcaatggct cctggccatg ttgctgattt tgtcctggat gacctccgcc     240

gctattctgt ggacctacgc tacacagtct ttcagaccac aggctccgtc cccatcgcca     300

cggtcatcat caacgaggcc agtggtagcc gcaccatcct atactatgac aggagcctgc     360

cagatgtgtc tgctacagac tttgagaagg ttgatctgac ccagttcaag tggatccaca     420

ttgagggccg gaacgcatcg gagcaggtga agatgctgca gcggatagac gcacacaaca     480

ccaggcagcc tccagagcag aagatccggg tgtccgtgga ggtggagaag ccacgagagg     540

agctcttcca gctgtttggc tacggagacg tggtgtttgt cagcaaagat gtggccaagc     600

acttggggtt ccagtcagca gaggaagcct tgaggggctt gtatggtcgt gtgaggaaag     660

gggctgtgct tgtctgtgcc tgggctgagg agggcgccga cgccctgggc cctgatggca     720

aattgctcca ctcggatgct ttcccgccac cccgcgtggt ggatacactg ggagctggag     780

acaccttcaa tgcctccgtc atcttcagcc tctcccaggg gaggagcgtg caggaagcac     840

tgagattcgg gtgccaggtg gccggcaaga agtgtggcct gcagggcttt gatggcatcg     900

tgtgagagca ggtgccggct cctcacacac catggagact accattgcgg ctgcatcgcc     960

ttctcccctc catccagcct ggcgtccagg ttgccctgtt                          1000


<210> SEQ ID NO 10
<211> LENGTH: 298
<212> TYPE: PRT
<213> ORGANISM: Homo sapiens

<400> SEQUENCE: 10

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45
```

-continued

```
Val Leu Ser Leu Leu Gly Ala Pro Cys Ala Phe Met Gly Ser Met Ala
    50                  55                  60

Pro Gly His Val Ala Asp Phe Val Leu Asp Asp Leu Arg Arg Tyr Ser
65                  70                  75                  80

Val Asp Leu Arg Tyr Thr Val Phe Gln Thr Thr Gly Ser Val Pro Ile
                85                  90                  95

Ala Thr Val Ile Ile Asn Glu Ala Ser Gly Ser Arg Thr Ile Leu Tyr
            100                 105                 110

Tyr Asp Arg Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295


<210> SEQ ID NO 11
<211> LENGTH: 2397
<212> TYPE: DNA
<213> ORGANISM: Homo sapiens

<400> SEQUENCE: 11

aggcagggct gcagatgcga ggcccagctg tacctcgcgt gtcccgggtc gggagtcgga      60

gacgcaggtg caggagagtg cggggcaagt agcgcatttt ctctttgcat tctcgagatc     120

gcttagccgc gctttaaaaa ggtttgcatc agctgtgagt ccatctgaca agcgaggaaa     180

ctaaggctga gaagtgggag gcgttgccat ctgcaggccc aggcaacctg ctacgggaag     240

accggggacc aagacctctg ggttggcttt cctagacccg ctcgggtctt cgggtgtcgc     300

gaggaagggc cctgctcctt tcgttccctg cacccctggc cgctgcaggt ggctccctgg     360

aggaggagct cccacgcgga ggaggagcca gggcagctgg gagcggggac accatcctcc     420

tggataagag gcagaggccg ggaggaaccc cgtcagccgg gcgggcagga agctctggga     480

gtagcctcat ggaagagaag cagatcctgt gcgtggggct agtggtgctg gacgtcatca     540

gcctggtgga caagtaccct aaggaggact cggagataag gtgtttgtcc cagagatggc     600

agcgcggagg caacgcgtcc aactcctgca ccgttctctc cctgctcgga gccccctgtg     660

ccttcatggg ctcaatggct cctggccatg ttgctgattt tgtcctggat gacctccgcc     720
```

-continued gctattctgt ggacctacgc tacacagtct ttcagaccac aggctccgtc cccatcgcca 780
cggtcatcat caacgaggcc agtggtagcc gcaccatcct atactatgac aggagcctgc 840
cagatgtgtc tgctacagac tttgagaagg ttgatctgac ccagttcaag tggatccaca 900
ttgagggccg gaacgcatcg gagcaggtga agatgctgca gcggatagac gcacacaaca 960
ccaggcagcc tccagagcag aagatccggg tgtccgtgga ggtggagaag ccacgagagg 1020
agctcttcca gctgtttggc tacggagacg tggtgtttgt cagcaaagat gtggccaagc 1080
acttggggtt ccagtcagca gaggaagcct tgaggggctt gtatggtcgt gtgaggaaag 1140
gggctgtgct tgtctgtgcc tgggctgagg agggcgccga cgccctgggc cctgatggca 1200
aattgctcca ctcggatgct ttcccgccac cccgcgtggt ggatacactg ggagctggag 1260
acaccttcaa tgcctccgtc atcttcagcc tctcccaggg gaggagcgtg caggaagcac 1320
tgagattcgg gtgccaggtg gccggcaaga agtgtggcct gcagggcttt gatggcatcg 1380
tgtgagagca ggtgccggct cctcacacac catggagact accattgcgg ctgcatcgcc 1440
ttctcccctc catccagcct ggcgtccagg ttgccctgtt caggggacag atgcaagctg 1500
tggggaggac tctgcctgtg tcctgtgttc cccacaggga gaggctctgg ggggatggct 1560
gggggatgca gagcctcaga gcaaataaat cttcctcaga gccagcttct cctctcaatg 1620
tctgaactgc tctggctggg cattcctgag gctctgactc ttcgatcctc cctctttgtg 1680
tccattcccc aaattaacct ctccgcccag gcccagagga ggggctgcct gggctagagc 1740
agcgagaagt gccctgggct tgccaccagc tctgccctgg ctggggagga cactcggtgc 1800
cccacaccca gtgaacctgc caaagaaacc gtgagagctc ttcggggccc tgcgttgtgc 1860
agactctatt cccacagctc agaagctggg agtccacacc gctgagctga actgacaggc 1920
cagtgggggg caggggtgcg cctcctctgc cctgcccacc agcctgtgat ttgatggggt 1980
cttcattgtc cagaaatacc tcctcccgct gactgcccca gagcctgaaa gtctcaccct 2040
tggagcccac cttggaatta agggcgtgcc tcagccacaa atgtgaccca ggatacagag 2100
tgttgctgtc ctcagggagg tccgatctgg aacacatatt ggaattgggg ccaactccaa 2160
tatagggtgg gtaaggcctt ataatgtaaa gagcatataa tgtaaagggc tttagagtga 2220
gacagacctg gattaaaatc tgccatttaa ttagctgcat atcaccttag ggtacagcac 2280
ttaacgcaat ctgcctcaat ttcttcatct gtcaaatgga accaattctg cttggctaca 2340
gaattattgt gaggataaaa tcatatataa aatgcccagc atgatgcctg atgtgta 2397

<210> SEQ ID NO 12
<211> LENGTH: 1634
<212> TYPE: PRT
<213> ORGANISM: Homo sapiens

<400> SEQUENCE: 12

Met Ser Ser Thr Gln Asp Asn Gly Glu His Trp Lys Ser Leu Glu Ser
1 5 10 15

Val Gly Ile Ser Arg Lys Glu Leu Ala Met Ala Glu Ala Leu Gln Met
20 25 30

Glu Tyr Asp Ala Leu Ser Arg Leu Arg His Asp Lys Glu Glu Asn Arg
35 40 45

Ala Lys Gln Asn Ala Asp Pro Ser Leu Ile Ser Trp Asp Glu Pro Gly
50 55 60

Val Asp Phe Tyr Ser Lys Pro Ala Gly Arg Arg Thr Asp Leu Lys Leu
65 70 75 80

```
Leu Arg Gly Leu Ser Gly Ser Asp Pro Thr Leu Asn Tyr Asn Ser Leu
                85                  90                  95

Ser Pro Gln Glu Gly Pro Pro Asn His Ser Thr Ser Gln Gly Pro Gln
            100                 105                 110

Pro Gly Ser Asp Pro Trp Pro Lys Gly Ser Leu Ser Gly Asp Tyr Leu
        115                 120                 125

Tyr Ile Phe Asp Gly Ser Asp Gly Gly Val Ser Ser Ser Pro Gly Pro
    130                 135                 140

Gly Asp Ile Glu Gly Ser Cys Lys Lys Leu Ser Pro Pro Pro Leu Pro
145                 150                 155                 160

Pro Arg Ala Ser Ile Trp Asp Thr Pro Pro Leu Pro Pro Arg Lys Gly
                165                 170                 175

Ser Pro Ser Ser Ser Lys Ile Ser Gln Pro Ser Asp Ile Asn Thr Phe
            180                 185                 190

Ser Leu Val Glu Gln Leu Pro Gly Lys Leu Leu Glu His Arg Ile Leu
        195                 200                 205

Glu Glu Glu Glu Val Leu Gly Gly Gly Gly Gln Gly Arg Leu Leu Gly
    210                 215                 220

Ser Val Asp Tyr Asp Gly Ile Asn Asp Ala Ile Thr Arg Leu Asn Leu
225                 230                 235                 240

Lys Ser Thr Tyr Asp Val Glu Met Leu Arg Asp Ala Thr Arg Gly Trp
                245                 250                 255

Lys Glu Gly Arg Gly Pro Leu Asp Phe Ser Lys Asp Thr Ser Gly Lys
            260                 265                 270

Pro Val Ala Arg Ser Lys Thr Met Pro Pro Gln Val Pro Pro Arg Thr
        275                 280                 285

Tyr Ala Ser Arg Tyr Gly Asn Arg Lys Asn Ala Thr Pro Gly Lys Asn
    290                 295                 300

Arg Arg Ile Ser Ala Ala Pro Val Gly Ser Arg Pro His Thr Val Ala
305                 310                 315                 320

Asn Gly His Glu Leu Phe Glu Val Ser Glu Glu Arg Asp Glu Glu Val
                325                 330                 335

Ala Ala Phe Cys His Met Leu Asp Ile Leu Arg Ser Gly Ser Asp Ile
            340                 345                 350

Gln Asp Tyr Phe Leu Thr Gly Tyr Val Trp Ser Ala Val Thr Pro Ser
        355                 360                 365

Pro Glu His Leu Gly Asp Glu Val Asn Leu Lys Val Thr Val Leu Cys
    370                 375                 380

Asp Arg Leu Gln Glu Ala Leu Thr Phe Thr Cys Asn Cys Ser Ser Thr
385                 390                 395                 400

Val Asp Leu Leu Ile Tyr Gln Thr Leu Cys Tyr Thr His Asp Asp Leu
                405                 410                 415

Arg Asn Val Asp Val Gly Asp Phe Val Leu Lys Pro Cys Gly Leu Glu
            420                 425                 430

Glu Phe Leu Gln Asn Lys His Ala Leu Gly Ser His Glu Tyr Ile Gln
        435                 440                 445

Tyr Cys Arg Lys Phe Asp Ile Asp Ile Arg Leu Gln Leu Met Glu Gln
    450                 455                 460

Lys Val Val Arg Ser Asp Leu Ala Arg Thr Val Asn Asp Asp Gln Ser
465                 470                 475                 480

Pro Ser Thr Leu Asn Tyr Leu Val His Leu Gln Glu Arg Pro Val Lys
                485                 490                 495
```

-continued

```
Gln Thr Ile Ser Arg Gln Ala Leu Ser Leu Leu Phe Asp Thr Tyr His
            500                 505                 510

Asn Glu Val Asp Ala Phe Leu Leu Ala Asp Gly Asp Phe Pro Leu Lys
        515                 520                 525

Ala Asp Arg Val Val Gln Ser Val Lys Ala Ile Cys Asn Ala Leu Ala
    530                 535                 540

Ala Val Glu Thr Pro Glu Ile Thr Ser Ala Leu Asn Gln Leu Pro Pro
545                 550                 555                 560

Cys Pro Ser Arg Met Gln Pro Lys Ile Gln Lys Asp Pro Ser Val Leu
                565                 570                 575

Ala Val Arg Glu Asn Arg Glu Lys Val Val Glu Ala Leu Thr Ala Ala
            580                 585                 590

Ile Leu Asp Leu Val Glu Leu Tyr Cys Asn Thr Phe Asn Ala Asp Phe
        595                 600                 605

Gln Thr Ala Val Pro Gly Ser Arg Lys His Asp Leu Val Gln Glu Ala
    610                 615                 620

Cys His Phe Ala Arg Ser Leu Ala Phe Thr Val Tyr Ala Thr His Arg
625                 630                 635                 640

Ile Pro Ile Ile Trp Ala Thr Ser Tyr Glu Asp Phe Tyr Leu Ser Cys
                645                 650                 655

Ser Leu Ser His Gly Gly Lys Asp Met Cys Ser Pro Leu Gln Thr Arg
            660                 665                 670

Arg Ala His Phe Ser Lys Tyr Leu Phe His Leu Ile Val Trp Asp Gln
        675                 680                 685

Gln Ile Cys Phe Pro Val Gln Val Asn Arg Leu Pro Arg Glu Thr Leu
    690                 695                 700

Leu Cys Ala Thr Leu Tyr Ala Leu Pro Ile Pro Pro Pro Gly Ser Ser
705                 710                 715                 720

Ser Glu Ala Asn Lys Gln Arg Arg Val Pro Glu Ala Leu Gly Trp Val
                725                 730                 735

Thr Thr Pro Leu Phe Asn Phe Arg Gln Val Leu Thr Cys Gly Arg Lys
            740                 745                 750

Leu Leu Gly Leu Trp Pro Ala Thr Gln Glu Asn Pro Ser Ala Arg Trp
        755                 760                 765

Ser Ala Pro Asn Phe His Gln Pro Asp Ser Val Ile Leu Gln Ile Asp
    770                 775                 780

Phe Pro Thr Ser Ala Phe Asp Ile Lys Phe Thr Ser Pro Pro Gly Asp
785                 790                 795                 800

Lys Phe Ser Pro Arg Tyr Glu Phe Gly Ser Leu Arg Glu Glu Asp Gln
                805                 810                 815

Arg Lys Leu Lys Asp Ile Met Gln Lys Glu Ser Leu Tyr Trp Leu Thr
            820                 825                 830

Asp Ala Asp Lys Lys Arg Leu Trp Glu Lys Arg Tyr Tyr Cys His Ser
        835                 840                 845

Glu Val Ser Ser Leu Pro Leu Val Leu Ala Ser Ala Pro Ser Trp Glu
    850                 855                 860

Trp Ala Cys Leu Pro Asp Ile Tyr Val Leu Leu Lys Gln Trp Thr His
865                 870                 875                 880

Met Asn His Gln Asp Ala Leu Gly Leu Leu His Ala Thr Phe Pro Asp
                885                 890                 895

Gln Glu Val Arg Arg Met Ala Val Gln Trp Ile Gly Ser Leu Ser Asp
            900                 905                 910

Ala Glu Leu Leu Asp Tyr Leu Pro Gln Leu Val Gln Ala Leu Lys Tyr
```

-continued

```
        915                 920                 925

Glu Cys Tyr Leu Asp Ser Pro Leu Val Arg Phe Leu Leu Lys Arg Ala
    930                 935                 940

Val Ser Asp Leu Arg Val Thr His Tyr Phe Phe Trp Leu Leu Lys Asp
945                 950                 955                 960

Gly Leu Lys Asp Ser Gln Phe Ser Ile Arg Tyr Gln Tyr Leu Leu Ala
                965                 970                 975

Ala Leu Leu Cys Cys Cys Gly Lys Gly Leu Arg Glu Glu Phe Asn Arg
            980                 985                 990

Gln Cys Trp Leu Val Asn Ala Leu Ala Lys Leu Ala Gln Gln Val Arg
        995                 1000                1005

Glu Ala Ala Pro Ser Ala Arg Gln Gly Ile Leu Arg Thr Gly Leu Glu
    1010                1015                1020

Glu Val Lys Gln Phe Phe Ala Leu Asn Gly Ser Cys Arg Leu Pro Leu
1025                1030                1035                1040

Ser Pro Ser Leu Leu Val Lys Gly Ile Val Pro Arg Asp Cys Ser Tyr
                1045                1050                1055

Phe Asn Ser Asn Ala Val Pro Leu Lys Leu Ser Phe Gln Asn Val Asp
            1060                1065                1070

Pro Leu Gly Glu Asn Ile Arg Val Ile Phe Lys Cys Gly Asp Asp Leu
        1075                1080                1085

Arg Gln Asp Met Leu Thr Leu Gln Met Ile Arg Ile Met Ser Lys Ile
    1090                1095                1100

Trp Val Gln Glu Gly Leu Asp Met Arg Met Val Ile Phe Arg Cys Phe
1105                1110                1115                1120

Ser Thr Gly Arg Gly Arg Gly Met Val Glu Met Ile Pro Asn Ala Glu
                1125                1130                1135

Thr Leu Arg Lys Ile Gln Val Glu His Gly Val Thr Gly Ser Phe Lys
            1140                1145                1150

Asp Arg Pro Leu Ala Asp Trp Leu Gln Lys His Asn Pro Gly Glu Asp
        1155                1160                1165

Glu Tyr Glu Lys Ala Val Glu Asn Phe Ile Tyr Ser Cys Ala Gly Cys
    1170                1175                1180

Cys Val Ala Thr Tyr Val Leu Gly Ile Cys Asp Arg His Asn Asp Asn
1185                1190                1195                1200

Ile Met Leu Lys Thr Thr Gly His Met Phe His Ile Asp Phe Gly Arg
                1205                1210                1215

Phe Leu Gly His Ala Gln Met Phe Gly Asn Ile Lys Arg Asp Arg Ala
            1220                1225                1230

Pro Phe Val Phe Thr Ser Asp Met Ala Tyr Val Ile Asn Gly Gly Asp
        1235                1240                1245

Lys Pro Ser Ser Arg Phe His Asp Phe Val Asp Leu Cys Cys Gln Ala
    1250                1255                1260

Tyr Asn Leu Ile Arg Lys His Thr His Leu Phe Leu Asn Leu Leu Gly
1265                1270                1275                1280

Leu Met Leu Ser Cys Gly Ile Pro Glu Leu Ser Asp Leu Glu Asp Leu
                1285                1290                1295

Lys Tyr Val Tyr Asp Ala Leu Arg Pro Gln Asp Thr Glu Ala Asn Ala
            1300                1305                1310

Thr Thr Tyr Phe Thr Arg Leu Ile Glu Ser Ser Leu Gly Ser Val Ala
        1315                1320                1325

Thr Lys Leu Asn Phe Phe Ile His Asn Leu Ala Gln Met Lys Phe Thr
    1330                1335                1340
```

Gly Ser Asp Asp Arg Leu Thr Leu Ser Phe Ala Ser Arg Thr His Thr
1345 1350 1355 1360

Leu Lys Ser Ser Gly Arg Ile Ser Asp Val Phe Leu Cys Arg His Glu
1365 1370 1375

Lys Ile Phe His Pro Asn Lys Gly Tyr Ile Tyr Val Val Lys Val Met
1380 1385 1390

Arg Glu Asn Thr His Glu Ala Thr Tyr Ile Gln Arg Thr Phe Glu Glu
1395 1400 1405

Phe Gln Glu Leu His Asn Lys Leu Arg Leu Leu Phe Pro Ser Ser His
1410 1415 1420

Leu Pro Ser Phe Pro Ser Arg Phe Val Ile Gly Arg Ser Arg Gly Glu
1425 1430 1435 1440

Ala Val Ala Glu Arg Arg Arg Glu Glu Leu Asn Gly Tyr Ile Trp His
1445 1450 1455

Leu Ile His Ala Pro Pro Glu Val Ala Glu Cys Asp Leu Val Tyr Thr
1460 1465 1470

Phe Phe His Pro Leu Pro Arg Asp Glu Lys Ala Met Gly Thr Ser Pro
1475 1480 1485

Ala Pro Lys Ser Ser Asp Gly Thr Trp Ala Arg Pro Val Gly Lys Val
1490 1495 1500

Gly Gly Glu Val Lys Leu Ser Ile Ser Tyr Lys Asn Asn Lys Leu Phe
1505 1510 1515 1520

Ile Met Val Met His Ile Arg Gly Leu Gln Leu Leu Gln Asp Gly Asn
1525 1530 1535

Asp Pro Asp Pro Tyr Val Lys Ile Tyr Leu Leu Pro Asp Pro Gln Lys
1540 1545 1550

Thr Thr Lys Arg Lys Thr Lys Val Ala Arg Lys Thr Cys Asn Pro Thr
1555 1560 1565

Tyr Asn Glu Met Leu Val Tyr Asp Gly Ile Pro Lys Gly Asp Leu Gln
1570 1575 1580

Gln Arg Glu Leu Gln Leu Ser Val Leu Ser Glu Gln Gly Phe Trp Glu
1585 1590 1595 1600

Asn Val Leu Leu Gly Glu Val Asn Ile Arg Leu Arg Glu Leu Asp Leu
1605 1610 1615

Ala Gln Glu Lys Thr Gly Trp Phe Ala Leu Gly Ser Arg Ser His Gly
1620 1625 1630

Thr Leu

<210> SEQ ID NO 13
<211> LENGTH: 7654
<212> TYPE: DNA
<213> ORGANISM: Homo sapiens

<400> SEQUENCE: 13
actcactata gggctcgagc ggccgcccgg gcaggtaaga atcagaagac atttgtgctt 60
tggggagcag aggccctcag ggtatagaga aggaagaaga gagaggttca ctgtagtcct 120
gaagcagaaa taagacctgt ggctgaagga agccttagca attcactcct tcctcttcct 180
gagaactctc tgtaggaagt ctcacctagc agaggcttca cagtatttca gagaagccaa 240
agattgtttg cctctttgga aactgttatc cttccatcat gactgtgtca ctcctgccac 300
tgttccacca tagagatggc gtcctttgca gcaaaccgta agttataagg atgagggaag 360
aagagtagag ggccaaaagg attccatttt gaggaaaaac tacagtttgc cttgccaggt 420

-continued

```
agaagaatca ggcgcccaga caccatgtca caaccctcca gaactgacgt tggcaggaag    480
tagagacttt gttgcctgtg tcccccatcc tcaccatgtc ttcgactcag gacaatgggg    540
aacactggaa gtccctggag tctgtgggca tcagccgcaa agaactagcg atggccgaag    600
ccctgcagat ggagtatgat gccctgtccc ggctccggca tgacaaggag gagaacagag    660
ccaagcagaa cgcagacccc tctctcatca gctgggatga gcctggggta gacttttaca    720
gcaagccagc aggaaggcgg accgacctca agctgttacg cggtctctct ggctctgatc    780
ctacccttaa ctacaactca ctatccccac aggaagggcc gcccaaccac tctacctccc    840
aagggccaca gcctggctca gatccctggc ccaaaggctc cctgtctgga gactatctct    900
acatttttga tggttcagat gggggagtct cttcgtcccc aggaccaggg gacatagagg    960
gctcttgcaa gaaactatcc ccacctcctc tgcctccccg agcttctatc tgggataccc   1020
ctcccctgcc tcccagaaag ggtccccct catcctccaa gatctcccag cccagtgaca    1080
tcaacacttt ctctttggtc gaacaattgc caggcaaact gctagagcat cggatcctag   1140
aagaggaaga ggtgctggga ggtgggggtc aggggcgcct actggggtct gtggactatg   1200
atggtatcaa tgatgcaatt actaggctca acttgaaatc gacctatgat gtggagatgt   1260
tgcgggatgc caccaggggc tggaaggagg gccgagggcc gctggacttc agcaaagaca   1320
cctctggaaa acccgtggcc aggagcaaga ctatgccccc tcaggtgccc ccccgcacct   1380
atgcctcccg ctatggcaac cgaaagaatg cgacgcctgg caagaaccgc cggatttctg   1440
cagccccggt gggctcccgg ccccacactg ttgccaatgg ccatgagttg tttgaggtct   1500
cagaagagag agatgaggag gttgctgcat tttgccacat gctggatatc cttcgatctg   1560
gctctgacat ccaagactac ttcctcactg gctatgtctg gagtgctgtc acccctagcc   1620
cagagcacct cggggatgag gtcaacctga aggtgactgt gttgtgtgac aggcttcaag   1680
aggcactcac tttcacctgc aactgttcct ccactgtaga cttgcttatc taccagaccc   1740
tgtgctacac ccatgatgac ctgaggaatg tggacgtggg tgactttgtg ctaaagccct   1800
gcgggctgga ggagttcctg cagaacaagc atgccttggg cagtcatgag tacatccaat   1860
actgccgcaa gtttgacatt gacattcggc tacagctgat ggagcagaag gttgtgcgca   1920
gtgacctggc ccggacggtg aatgatgacc agagcccctc caccttgaac tacctcgtcc   1980
atctccaaga gaggcctgtc aagcagacca tcagcaggca ggccctgagt cttctgttcg   2040
acacttacca caatgaggtg gatgccttcc tgctggctga tggagacttc ccactgaagg   2100
ctgacagggt ggtccagtcc gtcaaggcca tctgcaacgc cctggccgcc gtggaaaccc   2160
ctgagatcac cagtgctctc aaccagctgc ccccctgccc ctcccgcatg cagcctaaaa   2220
ttcagaagga tcccagtgtc ttggctgtga gggaaaaccg agagaaggtc gtggaagccc   2280
tgaccgctgc catcttggac ctggtggagc tgtactgcaa cacattcaac gcagacttcc   2340
agacggcagt gcccgggagc cgcaagcatg acctggtcca ggaggcctgc catttcgcca   2400
ggtccctggc cttcactgtc tatgccaccc accgcatccc catcatctgg gctaccagct   2460
atgaagattt ctacctctcc tgctccctca gccatggcgg caaggacatg tgcagccccc   2520
tgcagacccg aagagctcac ttctccaagt acctcttcca cctcatcgtc tgggaccagc   2580
agatctgctt cccagtgcag gtgaaccggc tgcctcggga gacactgctg tgtgccactc   2640
tctatgctct gcccatcccc ccaccgggga gctcctcaga ggccaataag cagcggcggg   2700
tgcctgaagc cctgggctgg gtcactaccc cactcttcaa cttcaggcag gtcctgacct   2760
gtggccggaa gcttctgggt ttgtggccag caacacagga aaatcccagc gcccgttgga   2820
```

-continued

```
gtgcacctaa tttccaccag ccagacagtg tcatcctgca gattgacttc cccacctcgg   2880
cctttgacat caagttcacc agcccccctg gagacaagtt cagcccccgc tatgagtttg   2940
gcagcctccg ggaagaagac cagcgcaagc ttaaagacat catgcagaaa gagtccttgt   3000
actggctcac tgatgctgac aagaagcgcc tgtgggagaa gcgatattac tgccactcgg   3060
aggtgagctc gctccccctg gtgctcgcca gcgcccccag ctgggagtgg gcttgcctgc   3120
ctgacatcta tgttctcctg aagcagtgga cccacatgaa ccaccaggat gccctggggc   3180
tcctgcatgc caccttcccg gaccaggagg tgcgtcgtat ggctgtgcag tggattggct   3240
cactctcaga tgctgagctg ctagactacc tgccccagct ggtacaggcc ctgaagtatg   3300
aatgctacct ggacagcccg ttggtgcgct tcctcctgaa acgagctgtg tctgacttga   3360
gagtgactca ctacttcttc tggttactga aggacggcct caaggactct cagttcagca   3420
tccgctacca gtatctgctg gcagccttac tgtgctgctg tggcaagggg ctgagagaag   3480
agtttaaccg ccagtgctgg cttgtcaatg ccctggccaa actggcccag caggtccggg   3540
aggcagcccc atctgcaagg cagggaatcc tccgcacggg cctggaggag gtgaagcagt   3600
tctttgccct caatggctcg tgccgcttgc cactcagccc cagtctgctg gttaagggaa   3660
ttgtgcccag ggactgttcc tacttcaact ccaatgctgt ccccctcaaa ctctccttcc   3720
aaaatgtgga tcccctgggt gagaacatcc gtgtcatctt caagtgtggg gacgaccttc   3780
gccaggacat gctaacgctg cagatgattc gcatcatgag caagatctgg gtccaggagg   3840
ggctggacat gcgcatggtc atcttccgct gcttctccac cggccggggc agagggatgg   3900
tggagatgat ccctaatgct gagaccctgc gtaagatcca ggtggagcat ggggtgaccg   3960
gctcgttcaa ggaccggccc ctggcagact ggctgcagaa acacaaccct ggggaggacg   4020
agtatgagaa ggctgtggag aactttatct actcctgcgc tggctgctgc gtggccacgt   4080
acgtcttggg catctgtgac cgacataatg acaacatcat gctgaagacc actggtcaca   4140
tgttccacat tgattttggc cgcttcctgg gccatgccca gatgtttggc aacatcaagc   4200
gggaccgtgc cccctttgtc ttcacctcgg acatggcgta tgtcatcaac gggggtgaca   4260
agccttccag ccgcttccat gattttgttg acctttgctg ccaagcctac aacctcattc   4320
gcaagcacac ccacctcttc ctcaaccttc tgggcctgat gttgtcctgt gggatccctg   4380
aactctcaga cctggaggac ctcaagtatg tgtacgatgc cctgaggcct caggatacag   4440
aggccaatgc cactacctac ttcactaggt tgattgagtc cagcctgggc agtgtagcca   4500
caaagctcaa ttttttcatc cataatctgg ctcagatgaa gttcacgggc tcagatgacc   4560
ggctgaccct ctcctttgcc tcccgaacac acactctcaa gagctctggc cgaatcagtg   4620
atgttttcct ctgccgccat gagaagatct tccaccccaa caaaggctat atatatgtgg   4680
taaaggtgat gcgagagaac actcacgagg ccacctacat ccagcggacc tttgaggagt   4740
tccaggaatt acacaataag ttgcggctgc tcttcccttc ttcccacttg cccagcttcc   4800
ctagtcgctt cgtgatcggc cgctcccggg gagaggcggt ggccgagcgg cggagggagg   4860
agctaaacgg ttacatctgg cacttgatcc acgcaccccc tgaggtggcc gagtgtgatt   4920
tggtgtacac cttcttccac ccactgcccc gggatgagaa ggctatgggc accagcccag   4980
ctcctaagtc ctcagatggc acatgggccc ggcccgtcgg aaaggtggga ggggaggtga   5040
agctgtccat ctcctacaaa aacaataaac tcttcatcat ggtgatgcat attcggggct   5100
tgcaactgct ccaggatgga aatgaccctg acccctatgt gaaaatttac ctccttcctg   5160
```

```
acctcagaa aaccactaag aggaaaacca aagtggcccg gaaaacctgc aatcctacct   5220
acaatgagat gttggtatat gatgggatcc ccaagggtga cctgcagcag cgggagctcc   5280
agctgagcgt gctgagtgag cagggattct gggagaacgt cctcctcggt gaggtgaaca   5340
tccgcctgcg agagctggac ctggctcagg agaagaccgg ctggttcgcc ctgggatctc   5400
gaagtcatgg caccttgtga gcccagcaga gccaccaccc agcatcccag gctggtggca   5460
ggagctgggg gagaggactc tcccctgtga gactcctcct tgtgaagggc cagggccctg   5520
ggcaggcctc cagctcggtc caggtgattc tggcctctgt ggtaggaggc agggagagta   5580
agacatgctc tgctgtctct tcctctggag actgaacttg ggttggttgt gatgagcagc   5640
cccttggagg ctgtgaggtt gcagcaaagt tttaagttta ccttgtgtca agggagcaat   5700
gcttggtttg gggaatgtgt ggggtgggct gtatgaagta ccattttggg ggtgggtggg   5760
tggatatctt aatttttatt tttaaaaaat gaaatagtga tgttgtccta actgggacag   5820
gaagccttgc gagaagggac gtacctatgc cccacaaggc aagagaggaa cactatttgg   5880
actttttgta tgattaaggt tcttattgga cttttcccta ggtttttttt ttttgttatt   5940
gttgttgttg ttccgttttc tagctatagg aactatctgg ggaggggccc agtgggtcct   6000
cggccagagc cctctctaag gacaggttgg ggagggttgg ggagggctgc ctgtgctgga   6060
ctgaggcttg tgccactggg cctttctgat tttgcctcca aaggagagcg ctgtgatacc   6120
tacatgtgta aggaagggcc ttccgtattg gggttctgcc aaggacccgt attcagggac   6180
ccatgctctt ttggggggac ttttcctctt gtcttcccta ctttattagg acttgccctg   6240
aataccattt tctacccctt gcccctccat tctcctggcc cttctggggg tcagctggtc   6300
tctatgaata tgctgggggt gcttccccat aggtctctcc cttcatttgt ctctggtggg   6360
acaaaatact gactcagtcc ttagatgtag tttcacccaa gagcatcttg gccctgggaa   6420
gaggtcccta ggctgcagat gctactgact gcttgctagg tagcctctgg aaagcattcc   6480
ccatccatca ctccccactt ctttctgctg tgctgcttcc ctcccaaact ccatttctgt   6540
cacccttttt ataagacttt tcctcattct gtggggccat aaacctattt agtctggagc   6600
caaagggatg ccctatctga aggaaagggg catggggtgg gggattccat caaaactgtt   6660
gtttttgcc ccatgatttt tctttggtca gtaggaggct ggattggagt ggtgattatt   6720
cccctggagc taagctcagg agcccgaagg gagagactga gactgactcc cttatctctt   6780
catattcttt attccctacc agatggattt tttttttttt ttttggagac ggagtctcgc   6840
cctgtcgcca ggctggagtg tagtggcatg atctcgactc actgcaaaat ctgcctcccg   6900
ggttcaagcg attctcctac ctcagcctcc cgagtagctg ggattacagg catgtgccac   6960
cacgccaagc taatttttgt atttttagta gagacggggt ttcaccatgt tggccaggat   7020
ggtctcgatc tcttgacctc gtgatctgcc tgccttggcc tcccaaagtg ctgggattac   7080
aggcgtgagc caccatgccc cgccccagat ggattttaca tttgctcttt tgtgtttcgc   7140
tccaaagggt tgtcttcctc gccaaaagga gggagggact ttgaatttga tatgaatctt   7200
taaaaccaga attggctgga tatttcccat gattgggaaa agagtgaaat gaggacattc   7260
tgtaaactgt ccctccctaa ttccaaggat cagaaactcc ccgttttgct gactcattcc   7320
ataactggag aaagaagctc cattgaccga agccacaggg cagcatggaa gtttaaattt   7380
tctctaaaat taaaatgcca aggataaagc tggctgcttc caggaggggg aagaggagtg   7440
gggagtgggc ggtgaaactt ttccagatga acggaccata aatgtgttac tggctttgtg   7500
cctgtagctc attttattat gacctatatg ctcctgattt aaagagatct gtgtactgtt   7560
```

tacttcccac ttcccagaat cccttgtatc tcctttctcg ggaattgtat tttctaataa 7620
atgacatttg agaaaaaaaa aaaaaaaaaa aaaa 7654

<210> SEQ ID NO 14
<211> LENGTH: 2511
<212> TYPE: PRT
<213> ORGANISM: Homo sapiens

<400> SEQUENCE: 14

```
Met Glu Glu Val Val Ile Ala Gly Met Ser Gly Lys Leu Pro Glu Ser
1               5                   10                  15

Glu Asn Leu Gln Glu Phe Trp Asp Asn Leu Ile Gly Gly Val Asp Met
            20                  25                  30

Val Thr Asp Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
    50                  55                  60

Phe Gly Val His Pro Lys Gln Ala His Thr Met Asp Pro Gln Leu Arg
65                  70                  75                  80

Leu Leu Leu Glu Val Thr Tyr Glu Ala Ile Val Asp Gly Gly Ile Asn
                85                  90                  95

Pro Asp Ser Leu Arg Gly Thr His Thr Gly Val Trp Val Gly Val Ser
            100                 105                 110

Gly Ser Glu Thr Ser Glu Ala Leu Ser Arg Asp Pro Glu Thr Leu Val
        115                 120                 125

Gly Tyr Ser Met Val Gly Cys Gln Arg Ala Met Met Ala Asn Arg Leu
    130                 135                 140

Ser Phe Phe Phe Asp Phe Arg Gly Pro Ser Ile Ala Leu Asp Thr Ala
145                 150                 155                 160

Cys Ser Ser Ser Leu Met Ala Leu Gln Asn Ala Tyr Gln Ala Ile His
                165                 170                 175

Ser Gly Gln Cys Pro Ala Ala Ile Val Gly Gly Ile Asn Val Leu Leu
            180                 185                 190

Lys Pro Asn Thr Ser Val Gln Phe Leu Arg Leu Gly Met Leu Ser Pro
        195                 200                 205

Glu Gly Thr Cys Lys Ala Phe Asp Thr Ala Gly Asn Gly Tyr Cys Arg
    210                 215                 220

Ser Glu Gly Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Phe
                245                 250                 255

Lys Glu Gln Gly Val Thr Phe Pro Ser Gly Asp Ile Gln Glu Gln Leu
            260                 265                 270

Ile Arg Ser Leu Tyr Gln Ser Ala Gly Val Ala Pro Glu Ser Phe Glu
        275                 280                 285

Tyr Ile Glu Ala His Gly Thr Gly Thr Lys Val Gly Asp Pro Gln Glu
    290                 295                 300

Leu Asn Gly Ile Thr Arg Ala Leu Cys Ala Thr Arg Gln Glu Pro Leu
305                 310                 315                 320

Leu Ile Gly Ser Thr Lys Ser Asn Met Gly His Pro Glu Pro Ala Ser
                325                 330                 335

Gly Leu Ala Ala Leu Ala Lys Val Leu Leu Ser Leu Glu His Gly Leu
            340                 345                 350
```

-continued

```
Trp Ala Pro Asn Leu His Phe His Ser Pro Asn Pro Glu Ile Pro Ala
        355                 360                 365

Leu Leu Asp Gly Arg Leu Gln Val Val Asp Gln Pro Leu Pro Val Arg
    370                 375                 380

Gly Gly Asn Val Gly Ile Asn Ser Phe Gly Phe Gly Gly Ser Asn Val
385                 390                 395                 400

His Ile Ile Leu Arg Pro Asn Thr Gln Pro Pro Pro Ala Pro Ala Pro
                405                 410                 415

His Ala Thr Leu Pro Arg Leu Leu Arg Ala Ser Gly Arg Thr Pro Glu
            420                 425                 430

Ala Val Gln Lys Leu Leu Glu Gln Gly Leu Arg His Ser Gln Asp Leu
        435                 440                 445

Ala Phe Leu Ser Met Leu Asn Asp Ile Ala Ala Val Pro Ala Thr Ala
    450                 455                 460

Met Pro Phe Arg Gly Tyr Ala Val Leu Gly Gly Glu Arg Gly Gly Pro
465                 470                 475                 480

Glu Val Gln Gln Val Pro Ala Gly Glu Arg Pro Leu Trp Phe Ile Cys
                485                 490                 495

Ser Gly Met Gly Thr Gln Trp Arg Gly Met Gly Leu Ser Leu Met Arg
            500                 505                 510

Leu Asp Arg Phe Arg Asp Ser Ile Leu Arg Ser Asp Glu Ala Val Lys
        515                 520                 525

Pro Phe Gly Leu Lys Val Ser Gln Leu Leu Leu Ser Thr Asp Glu Ser
    530                 535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
                565                 570                 575

Ile Val Gly His Ser Leu Gly Glu Val Ala Cys Gly Tyr Ala Asp Gly
            580                 585                 590

Cys Leu Ser Gln Glu Glu Ala Val Leu Ala Ala Tyr Trp Arg Gly Gln
        595                 600                 605

Cys Ile Lys Glu Ala His Leu Pro Pro Gly Ala Met Ala Ala Val Gly
    610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
                645                 650                 655

Pro Val Phe Glu Phe Val Glu Gln Leu Arg Lys Glu Gly Val Phe Ala
            660                 665                 670

Lys Glu Val Arg Thr Gly Gly Met Ala Phe His Ser Tyr Phe Met Glu
        675                 680                 685

Ala Ile Ala Pro Pro Leu Leu Gln Glu Leu Lys Lys Val Ile Arg Glu
    690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
                725                 730                 735

Asn Asn Leu Val Ser Pro Val Leu Phe Gln Glu Ala Leu Trp His Val
            740                 745                 750

Pro Glu His Ala Val Val Leu Glu Ile Ala Pro His Ala Leu Leu Gln
        755                 760                 765

Ala Val Leu Lys Arg Gly Leu Lys Pro Ser Cys Thr Ile Ile Pro Leu
```

```
    770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
            820                 825                 830

Leu Ile Lys Trp Asp His Ser Leu Ala Trp Asp Val Pro Ala Ala Glu
        835                 840                 845

Asp Phe Pro Asn Gly Ser Gly Ser Pro Ser Ala Ala Ile Tyr Asn Ile
    850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
                885                 890                 895

Lys Thr Leu Ala Arg Ala Leu Gly Leu Gly Val Glu Gln Leu Pro Val
            900                 905                 910

Val Phe Glu Asp Val Val Leu His Gln Ala Thr Ile Leu Pro Lys Thr
        915                 920                 925

Gly Thr Val Ser Leu Glu Val Arg Leu Leu Glu Ala Ser Arg Ala Phe
    930                 935                 940

Glu Val Ser Glu Asn Gly Asn Leu Val Val Ser Gly Lys Val Tyr Gln
945                 950                 955                 960

Trp Asp Asp Pro Asp Pro Arg Leu Phe Asp His Pro Glu Ser Pro Thr
                965                 970                 975

Pro Asn Pro Thr Glu Pro Leu Phe Leu Ala Gln Ala Glu Val Tyr Lys
            980                 985                 990

Glu Leu Arg Leu Arg Gly Tyr Asp Tyr Gly Pro His Phe Gln Gly Ile
        995                 1000                1005

Leu Glu Ala Ser Leu Glu Gly Asp Ser Gly Arg Leu Leu Trp Lys Asp
    1010                1015                1020

Asn Trp Val Ser Phe Met Asp Thr Met Leu Gln Met Ser Ile Leu Gly
1025                1030                1035                1040

Ser Ala Lys His Gly Leu Tyr Leu Pro Thr Arg Val Thr Ala Ile His
                1045                1050                1055

Ile Asp Pro Ala Thr His Arg Gln Lys Leu Tyr Thr Leu Gln Asp Lys
            1060                1065                1070

Ala Gln Val Ala Asp Val Val Val Ser Arg Trp Leu Arg Val Thr Val
        1075                1080                1085

Ala Gly Gly Val His Ile Ser Gly Leu His Thr Glu Ser Ala Pro Arg
    1090                1095                1100

Arg Gln Gln Glu Gln Gln Val Pro Ile Leu Glu Lys Phe Cys Phe Thr
1105                1110                1115                1120

Pro His Thr Glu Glu Gly Cys Leu Ser Glu Arg Ala Ala Leu Gln Glu
                1125                1130                1135

Glu Leu Gln Leu Cys Lys Gly Leu Val Gln Ala Leu Gln Thr Lys Val
            1140                1145                1150

Thr Gln Gln Gly Leu Lys Met Val Val Pro Gly Leu Asp Gly Ala Gln
        1155                1160                1165

Ile Pro Arg Asp Pro Ser Gln Gln Glu Leu Pro Arg Leu Leu Ser Ala
    1170                1175                1180

Ala Cys Arg Leu Gln Leu Asn Gly Asn Leu Gln Leu Glu Leu Ala Gln
1185                1190                1195                1200
```

```
Val Leu Ala Gln Glu Arg Pro Lys Leu Pro Glu Asp Pro Leu Leu Ser
                1205                1210                1215

Gly Leu Leu Asp Ser Pro Ala Leu Lys Ala Cys Leu Asp Thr Ala Val
            1220                1225                1230

Glu Asn Met Pro Ser Leu Lys Met Lys Val Val Glu Val Leu Ala Gly
        1235                1240                1245

His Gly His Leu Tyr Ser Arg Ile Pro Gly Leu Leu Ser Pro His Pro
    1250                1255                1260

Leu Leu Gln Leu Ser Tyr Thr Ala Thr Asp Arg His Pro Gln Ala Leu
1265                1270                1275                1280

Glu Ala Ala Gln Ala Glu Leu Gln Gln His Asp Val Ala Gln Gly Gln
                1285                1290                1295

Trp Asp Pro Ala Asp Pro Ala Pro Ser Ala Leu Gly Ser Ala Asp Leu
            1300                1305                1310

Leu Val Cys Asn Cys Ala Val Ala Ala Leu Gly Asp Pro Ala Ser Ala
        1315                1320                1325

Leu Ser Asn Met Val Ala Ala Leu Arg Glu Gly Gly Phe Leu Leu Leu
    1330                1335                1340

His Thr Leu Leu Arg Gly His Pro Leu Gly Asp Ile Val Ala Phe Leu
1345                1350                1355                1360

Thr Ser Thr Glu Pro Gln Tyr Gly Gln Gly Ile Leu Ser Gln Asp Ala
                1365                1370                1375

Trp Glu Ser Leu Phe Ser Arg Val Ser Leu Arg Leu Val Gly Leu Lys
            1380                1385                1390

Lys Ser Phe Tyr Gly Ser Thr Leu Phe Leu Cys Arg Arg Pro Thr Pro
        1395                1400                1405

Gln Asp Ser Pro Ile Phe Leu Pro Val Asp Asp Thr Ser Phe Arg Trp
    1410                1415                1420

Val Glu Ser Leu Lys Gly Ile Leu Ala Asp Glu Asp Ser Ser Arg Pro
1425                1430                1435                1440

Val Trp Leu Lys Ala Ile Asn Cys Ala Thr Ser Gly Val Val Gly Leu
                1445                1450                1455

Val Asn Cys Leu Arg Arg Glu Pro Gly Gly Asn Arg Leu Arg Cys Val
            1460                1465                1470

Leu Leu Ser Asn Leu Ser Ser Thr Ser His Val Pro Glu Val Asp Pro
        1475                1480                1485

Gly Ser Ala Glu Leu Gln Lys Val Leu Gln Gly Asp Leu Val Met Asn
    1490                1495                1500

Val Tyr Arg Asp Gly Ala Trp Gly Ala Phe Arg His Phe Leu Leu Glu
1505                1510                1515                1520

Glu Asp Lys Pro Glu Glu Pro Thr Ala His Ala Phe Val Ser Thr Leu
                1525                1530                1535

Thr Arg Gly Asp Leu Ser Ser Ile Arg Trp Val Cys Ser Ser Leu Arg
            1540                1545                1550

His Ala Gln Pro Thr Cys Pro Gly Ala Gln Leu Cys Thr Val Tyr Tyr
        1555                1560                1565

Ala Ser Leu Asn Phe Arg Asp Ile Met Leu Ala Thr Gly Lys Leu Ser
    1570                1575                1580

Pro Asp Ala Ile Pro Gly Lys Trp Thr Ser Gln Asp Ser Leu Leu Gly
1585                1590                1595                1600

Met Glu Phe Ser Gly Arg Asp Ala Ser Gly Lys Arg Val Met Gly Leu
                1605                1610                1615
```

```
Val Pro Ala Lys Gly Leu Ala Thr Ser Val Leu Leu Ser Pro Asp Phe
            1620                1625                1630

Leu Trp Asp Val Pro Ser Asn Trp Thr Leu Glu Glu Ala Ala Ser Val
        1635                1640                1645

Pro Val Val Tyr Ser Thr Ala Tyr Tyr Ala Leu Val Val Arg Gly Arg
    1650                1655                1660

Val Arg Pro Gly Glu Thr Leu Leu Ile His Ser Gly Ser Gly Gly Val
1665                1670                1675                1680

Gly Gln Ala Ala Ile Ala Ile Ala Leu Ser Leu Gly Cys Arg Val Phe
                1685                1690                1695

Thr Thr Val Gly Ser Ala Glu Lys Arg Ala Tyr Leu Gln Ala Arg Phe
            1700                1705                1710

Pro Gln Leu Asp Ser Thr Ser Phe Ala Asn Ser Arg Asp Thr Ser Phe
        1715                1720                1725

Glu Gln His Val Leu Trp His Thr Gly Gly Lys Gly Val Asp Leu Val
    1730                1735                1740

Leu Asn Ser Leu Ala Glu Glu Lys Leu Gln Ala Ser Val Arg Cys Leu
1745                1750                1755                1760

Ala Thr His Gly Arg Phe Leu Glu Ile Gly Lys Phe Asp Leu Ser Gln
                1765                1770                1775

Asn His Pro Leu Gly Met Ala Ile Phe Leu Lys Asn Val Thr Phe His
            1780                1785                1790

Gly Val Leu Leu Asp Ala Phe Phe Asn Glu Ser Ser Ala Asp Trp Arg
        1795                1800                1805

Glu Val Trp Ala Leu Val Gln Ala Gly Ile Arg Asp Gly Val Val Arg
    1810                1815                1820

Pro Leu Lys Cys Thr Val Phe His Gly Ala Gln Val Glu Asp Ala Phe
1825                1830                1835                1840

Arg Tyr Met Ala Gln Gly Lys His Ile Gly Lys Val Val Val Gln Val
                1845                1850                1855

Leu Ala Glu Glu Pro Glu Ala Val Leu Lys Gly Ala Lys Pro Lys Leu
            1860                1865                1870

Met Ser Ala Ile Ser Lys Thr Phe Cys Pro Ala His Lys Ser Tyr Ile
        1875                1880                1885

Ile Ala Gly Gly Leu Gly Gly Phe Gly Leu Glu Leu Ala Gln Trp Leu
    1890                1895                1900

Ile Gln Arg Gly Val Gln Lys Leu Val Leu Thr Ser Arg Ser Gly Ile
1905                1910                1915                1920

Arg Thr Gly Tyr Gln Ala Lys Gln Val Arg Arg Trp Arg Arg Gln Gly
                1925                1930                1935

Val Gln Val Gln Val Ser Thr Ser Asn Ile Ser Ser Leu Glu Gly Ala
            1940                1945                1950

Arg Gly Leu Ile Ala Glu Ala Ala Gln Leu Gly Pro Val Gly Gly Val
        1955                1960                1965

Phe Asn Leu Ala Val Val Leu Arg Asp Gly Leu Leu Glu Asn Gln Thr
    1970                1975                1980

Pro Glu Phe Phe Gln Asp Val Cys Lys Pro Lys Tyr Ser Gly Thr Leu
1985                1990                1995                2000

Asn Leu Asp Arg Val Thr Arg Glu Ala Cys Pro Glu Leu Asp Tyr Phe
                2005                2010                2015

Val Val Phe Ser Ser Val Ser Cys Gly Arg Gly Asn Ala Gly Gln Ser
            2020                2025                2030

Asn Tyr Gly Phe Ala Asn Ser Ala Met Glu Arg Ile Cys Glu Lys Arg
```

-continued

```
        2035                2040                2045

Arg His Glu Gly Leu Pro Gly Leu Ala Val Gln Trp Gly Ala Ile Gly
    2050                2055                2060

Asp Val Gly Ile Leu Val Glu Thr Met Ser Thr Asn Asp Thr Ile Val
2065                2070                2075                2080

Ser Gly Thr Leu Pro Gln Arg Met Ala Ser Cys Leu Glu Val Leu Asp
                2085                2090                2095

Leu Phe Leu Asn Gln Pro His Met Val Leu Ser Ser Phe Val Leu Ala
            2100                2105                2110

Glu Lys Ala Ala Ala Tyr Arg Asp Arg Asp Ser Gln Arg Asp Leu Val
        2115                2120                2125

Glu Ala Val Ala His Ile Leu Gly Ile Arg Asp Leu Ala Ala Val Asn
    2130                2135                2140

Leu Asp Ser Ser Leu Ala Asp Leu Gly Leu Asp Ser Leu Met Ser Val
2145                2150                2155                2160

Glu Val Arg Gln Thr Leu Glu Arg Glu Leu Asn Leu Val Leu Ser Val
                2165                2170                2175

Arg Glu Val Arg Gln Leu Thr Leu Arg Lys Leu Gln Glu Leu Ser Ser
            2180                2185                2190

Lys Ala Asp Glu Ala Ser Glu Leu Ala Cys Pro Thr Pro Lys Glu Asp
        2195                2200                2205

Gly Leu Ala Gln Gln Gln Thr Gln Leu Asn Leu Arg Ser Leu Leu Val
    2210                2215                2220

Asn Pro Glu Gly Pro Thr Leu Met Arg Leu Asn Ser Val Gln Ser Ser
2225                2230                2235                2240

Glu Arg Pro Leu Phe Leu Val His Pro Ile Glu Gly Ser Thr Thr Val
                2245                2250                2255

Phe His Ser Leu Ala Ser Arg Leu Ser Ile Pro Thr Tyr Gly Leu Gln
            2260                2265                2270

Cys Thr Arg Ala Ala Pro Leu Asp Ser Ile His Ser Leu Ala Ala Tyr
        2275                2280                2285

Tyr Ile Asp Cys Ile Arg Gln Val Gln Pro Glu Gly Pro Tyr Arg Val
    2290                2295                2300

Ala Gly Tyr Ser Tyr Gly Ala Cys Val Ala Phe Glu Met Cys Ser Gln
2305                2310                2315                2320

Leu Gln Ala Gln Gln Ser Pro Ala Pro Thr His Asn Ser Leu Phe Leu
                2325                2330                2335

Phe Asp Gly Ser Pro Thr Tyr Val Leu Ala Tyr Thr Gln Ser Tyr Arg
            2340                2345                2350

Ala Lys Leu Thr Pro Gly Cys Glu Ala Glu Ala Glu Thr Glu Ala Ile
        2355                2360                2365

Cys Phe Phe Val Gln Gln Phe Thr Asp Met Glu His Asn Arg Val Leu
    2370                2375                2380

Glu Ala Leu Leu Pro Leu Lys Gly Leu Glu Glu Arg Val Ala Ala Ala
2385                2390                2395                2400

Val Asp Leu Ile Ile Lys Ser His Gln Gly Leu Asp Arg Gln Glu Leu
                2405                2410                2415

Ser Phe Ala Ala Arg Ser Phe Tyr Tyr Lys Leu Arg Ala Ala Glu Gln
            2420                2425                2430

Tyr Thr Pro Lys Ala Lys Tyr His Gly Asn Val Met Leu Leu Arg Ala
        2435                2440                2445

Lys Thr Gly Gly Ala Tyr Gly Glu Asp Leu Gly Ala Asp Tyr Asn Leu
    2450                2455                2460
```

Ser Gln Val Cys Asp Gly Lys Val Ser Val His Val Ile Glu Gly Asp
2465 2470 2475 2480

His Arg Thr Leu Leu Glu Gly Ser Gly Leu Glu Ser Ile Ile Ser Ile
2485 2490 2495

Ile His Ser Ser Leu Ala Glu Pro Arg Val Ser Val Arg Glu Gly
2500 2505 2510

<210> SEQ ID NO 15
<211> LENGTH: 8464
<212> TYPE: DNA
<213> ORGANISM: Homo sapiens

<400> SEQUENCE: 15
gagccagaga gacggcagcg gccccggcct ccctctccgc cgcgcttcag cctcccgctc 60
cgccgcgctc cagcctcgct ctccgccgcc cgcaccgccg cccgcgccct caccagagca 120
gccatggagg aggtggtgat tgccggcatg tccgggaagc tgccagagtc ggagaacttg 180
caggagttct gggacaacct catcggcggt gtggacatgg tcacggacga tgaccgtcgc 240
tggaaggcgg ggctctacgg cctgccccgg cggtccggca agctgaagga cctgtctagg 300
tttgatgcct ccttcttcgg agtccacccc aagcaggcac acacgatgga ccctcagctg 360
cggctgctgc tggaagtcac ctatgaagcc atcgtggacg gaggcatcaa cccagattca 420
ctccgaggaa cacacactgg cgtctgggtg ggcgtgagcg gctctgagac ctcggaggcc 480
ctgagccgag accccgagac actcgtgggc tacagcatgg tgggctgcca gcgagcgatg 540
atggccaacc ggctctcctt cttcttcgac ttcagagggc ccagcatcgc actggacaca 600
gcctgctcct ccagcctgat ggccctgcag aacgcctacc aggccatcca cagcgggcag 660
tgccctgccg ccatcgtggg gggcatcaat gtcctgctga agcccaacac ctccgtgcag 720
ttcttgaggc tggggatgct cagccccgag ggcacctgca aggccttcga cacagcgggg 780
aatgggtact gccgctcgga gggtgtggtg gccgtcctgc tgaccaagaa gtccctggcc 840
cggcgggtgt acgccaccat cctgaacgcc ggcaccaata cagatggctt caaggagcaa 900
ggcgtgacct tccccctcagg ggatatccag gagcagctca tccgctcgtt gtaccagtcg 960
gccggagtgg cccctgagtc atttgaatac atcgaagccc acggcacagg caccaaggtg 1020
ggcgaccccc aggagctgaa tggcatcacc cgagccctgt gcgccacccg ccaggagccg 1080
ctgctcatcg gctccaccaa gtccaacatg gggcacccgg agccagcctc ggggctggca 1140
gccctggcca aggtgctgct gtccctggag cacgggctct gggcccccaa cctgcacttc 1200
catagcccca accctgagat cccagcgctg ttggatgggc ggctgcaggt ggtggaccag 1260
cccctgcccg tccgtggcgg caacgtgggc atcaactcct ttggcttcgg gggctccaac 1320
gtgcacatca tcctgaggcc caacacgcag ccgccccccg cacccgcccc acatgccacc 1380
ctgccccgtc tgctgcgggc cagcggacgc acccctgagg ccgtgcagaa gctgctggag 1440
cagggcctcc ggcacagcca ggacctggct ttcctgagca tgctgaacga catcgcggct 1500
gtccccgcca ccgccatgcc cttccgtggc tacgctgtgc tgggtggtga gcgcggtggc 1560
ccagaggtgc agcaggtgcc cgctggcgag cgcccgctct ggttcatctg ctctgggatg 1620
ggcacacagt ggcgcgggat ggggctgagc ctcatgcgcc tggaccgctt ccgagattcc 1680
atcctacgct ccgatgaggc tgtgaagcca ttcggcctga aggtgtcaca gctgctgctg 1740
agcacagacg agagcacctt tgatgacatc gtccattcgt ttgtgagcct gactgccatc 1800
cagataggcc tcatagacct gctgagctgc atggggctga ggccagatgg catcgtcggc 1860

-continued

```
cactccctgg gggaggtggc ctgtggctac gccgacggct gcctgtccca ggaggaggcc   1920
gtcctcgctg cctactggag gggacagtgc atcaaagaag cccatctccc gccgggcgcc   1980
atggcagccg tgggcttgtc ctgggaggag tgtaaacagc gctgcccccc gggcgtggtg   2040
cccgcctgcc acaactccaa ggacacagtc accatctcgg gacctcaggc cccggtgttt   2100
gagttcgtgg agcagctgag gaaggagggt gtgtttgcca aggaggtgcg gaccggcggt   2160
atggccttcc actcctactt catggaggcc atcgcacccc cactgctgca ggagctcaag   2220
aaggtgatcc gggagccgaa gccacgttca gcccgctggc tcagcacctc tatccccgag   2280
gcccagtggc acagcagcct ggcacgcacg tcctccgccg agtacaatgt caacaacctg   2340
gtgagccctg tgctgttcca ggaggccctg tggcacgtgc ctgagcacgc ggtggtgctg   2400
gagatcgcgc cccacgccct gctgcaggct gtcctgaagc gtggcctgaa gccgagctgc   2460
accatcatcc ccctgatgaa gaaggatcac agggacaacc tggagttctt cctggccggc   2520
atcggcaggc tgcacctctc aggcatcgac gccaacccca atgccttgtt cccacctgtg   2580
gagttcccag ctccccgagg aactcccctc atctccccac tcatcaagtg ggaccacagc   2640
ctggcctggg acgtgccggc cgccgaggac ttccccaacg gttcaggttc cccctcagcc   2700
gccatctaca acatcgacac cagctccgag tctcctgacc actacctggt ggaccacacc   2760
ctcgacggtc gcgtcctctt ccccgccact ggctacctga gcatagtgtg gaagacgctg   2820
gcccgcgccc tgggcctggg cgtcgagcag ctgcctgtgg tgtttgagga tgtggtgctg   2880
caccaggcca ccatcctgcc caagactggg acagtgtccc tggaggtacg gctcctggag   2940
gcctcccgtg ccttcgaggt gtcagagaac ggcaacctgg tagtgagtgg gaaggtgtac   3000
cagtgggatg accctgaccc caggctcttc gaccacccgg aaagccccac ccccaacccc   3060
acggagcccc tcttcctggc ccaggctgaa gtttacaagg agctgcgtct gcgtggctac   3120
gactacggcc ctcatttcca gggcatcctg gaggccagcc tggaaggtga ctcggggagg   3180
ctgctgtgga aggataactg ggtgagcttc atggacacca tgctgcagat gtccatcctg   3240
ggctcggcca agcacggcct gtacctgccc acccgtgtca ccgccatcca catcgaccct   3300
gccacccaca ggcagaagct gtacacactg caggacaagg cccaagtggc tgacgtggtg   3360
gtgagcaggt ggctgagggt cacagtggcc ggaggcgtcc acatctccgg gctccacact   3420
gagtcggccc cgcggcggca gcaggagcag caggtgccca tcctggagaa gttttgcttc   3480
actccccaca cggaggaggg gtgcctgtct gagcgcgctg ccctgcagga ggagctgcaa   3540
ctgtgcaagg ggctggtgca ggcactgcag accaaggtga cccagcaggg gctgaagatg   3600
gtggtgcccg gactggatgg ggcccagatc cccccgggacc cctcacagca ggaactgccc   3660
cggctgttgt cggctgcctg caggcttcag ctcaacggga acctgcagct ggagctggcg   3720
caggtgctgg cccaggagag gcccaagctg ccagaggacc ctctgctcag cggcctcctg   3780
gactccccgg cactcaaggc ctgcctggac actgccgtgg agaacatgcc cagcctgaag   3840
atgaaggtgg tggaggtgct ggctggccac ggtcacctgt attcccgcat cccaggcctg   3900
ctcagccccc atcccctgct gcagctgagc tacacggcca ccgaccgcca cccccaggcc   3960
ctggaggctg cccaggccga gctgcagcag cacgacgttg cccagggcca gtgggatccc   4020
gcagaccctg cccccagcgc cctgggcagc gccgacctcc tggtgtgcaa ctgtgctgtg   4080
gctgccctcg ggaccccggc ctcagctctc agcaacatgg tggctgccct gagagaaggg   4140
ggctttctgc tcctgcacac actgctccgg gggcaccccc tcggggacat cgtggccttc   4200
```

-continued

```
ctcacctcca ctgagccgca gtatggccag ggcatcctga gccaggacgc gtgggagagc   4260
ctcttctcca gggtgtcgct gcgcctggtg ggcctgaaga agtccttcta cggctccacg   4320
ctcttcctgt gccgccggcc caccccgcag gacagcccca tcttcctgcc ggtggacgat   4380
accagcttcc gctgggtgga gtctctgaag ggcatcctgg ctgacgaaga ctcttcccgg   4440
cctgtgtggc tgaaggccat caactgtgcc acctcgggcg tggtgggctt ggtgaactgt   4500
ctccgccgag agcccggcgg gaaccgcctc cggtgtgtgc tgctctccaa cctcagcagc   4560
acctcccacg tcccggaggt ggacccgggc tccgcagaac tgcagaaggt gttgcaggga   4620
gacctggtga tgaacgtcta ccgcgacggg gcctgggggg ctttccgcca cttcctgctg   4680
gaggaggaca agcctgagga gccgacggca catgcctttg tgagcaccct cacccggggg   4740
gacctgtcct ccatccgctg ggtctgctcc tcgctgcgcc atgcccagcc cacctgccct   4800
ggcgcccagc tctgcacggt ctactacgcc tccctcaact tccgcgacat catgctggcc   4860
actggcaagc tgtcccctga tgccatccca gggaagtgga cctcccagga cagcctgcta   4920
ggtatggagt tctcgggccg agacgccagc ggcaagcgtg tgatgggact ggtgcctgcc   4980
aagggcctgg ccacctctgt cctgctgtca ccggacttcc tctgggatgt gccttccaac   5040
tggacgctgg aggaggcggc ctcggtgcct gtcgtctaca gcacggccta ctacgcgctg   5100
gtggtgcgtg ggcgggtgcg ccccggggag acgctgctca tccactcggg ctcgggcggc   5160
gtgggccagg ccgccatcgc catcgccctc agtctgggct gccgcgtctt caccaccgtg   5220
gggtcggctg agaagcgggc gtacctccag gccaggttcc cccagctcga cagcaccagc   5280
ttcgccaact cccgggacac atccttcgag cagcatgtgc tgtggcacac gggcgggaag   5340
ggcgttgacc tggtcttgaa ctccttggcg gaagagaagc tgcaggccag cgtgaggtgc   5400
ttggctacgc acggtcgctt cctggaaatt ggcaaattcg acctttctca gaaccacccg   5460
ctcggcatgg ctatcttcct gaagaacgtg acattccacg ggtcctact ggatgcgttc   5520
ttcaacgaga gcagtgctga ctggcgggag gtgtgggcgc ttgtgcaggc cggcatccgg   5580
gatggggtgg tacggcccct caagtgcacg gtgttccatg ggcccaggt ggaggacgcc   5640
ttccgctaca tggcccaagg gaagcacatt ggcaaagtcg tcgtgcaggt gcttgcggag   5700
gagccggagg cagtgctgaa gggggccaaa cccaagctga tgtcggccat ctccaagacc   5760
ttctgcccgg cccacaagag ctacatcatc gctggtggtc tgggtggctt cggcctggag   5820
ttggcgcagt ggctgataca gcgtggggtg cagaagctcg tgttgacttc tcgctccggg   5880
atccggacag gctaccaggc caagcaggtc cgccggtgga ggcgccaggg cgtacaggtg   5940
caggtgtcca ccagcaacat cagctcactg gaggggggccc ggggcctcat tgccgaggcg   6000
gcgcagcttg ggcccgtggg cggcgtcttc aacctggccg tggtcttgag agatggcttg   6060
ctggagaacc agaccccaga gttcttccag gacgtctgca agcccaagta cagcggcacc   6120
ctgaacctgg acagggtgac ccgagaggcg tgccctgagc tggactactt tgtggtcttc   6180
tcctctgtga gctgcgggcg tggcaatgcg ggacagagca actacggctt tgccaattcc   6240
gccatggagc gtatctgtga gaaacgccgg cacgaaggcc tcccaggcct ggccgtgcag   6300
tggggcgcca tcggcgacgt gggcattttg gtggagacga tgagcaccaa cgacacgatc   6360
gtcagtggca cgctgcccca gcgcatggcg tcctgcctgg aggtgctgga cctcttcctg   6420
aaccagcccc acatggtcct gagcagcttt gtgctggctg agaaggctgc ggcctatagg   6480
gacagggaca gccagcggga cctggtggag gccgtggcac acatcctggg catccgcgac   6540
ttggctgctg tcaacctgga cagctcactg gcggacctgg gcctggactc gctcatgagc   6600
```

gtggaggtgc gccagacgct ggagcgtgag ctcaacctgg tgctgtccgt gcgcgaggtg 6660
cggcaactca cgctccggaa actgcaggag ctgtcctcaa aggcggatga ggccagcgag 6720
ctggcatgcc ccacgcccaa ggaggatggt ctggcccagc agcagactca gctgaacctg 6780
cgctccctgc tggtgaaccc ggagggcccc accctgatgc ggctcaactc cgtgcagagc 6840
tcggagcggc ccctgttcct ggtgcaccca atcgagggct ccaccaccgt gttccacagc 6900
ctggcctccc ggctcagcat ccccacctat ggcctgcagt gcacccgagc tgcgcccctt 6960
gacagcatcc acagcctggc tgcctactac atcgactgca tcaggcaggt gcagcccgag 7020
ggcccctacc gcgtggccgg ctactcctac ggggcctgcg tggcctttga aatgtgctcc 7080
cagctgcagg cccagcagag cccagccccc acccacaaca gcctcttcct gttcgacggc 7140
tcgcccacct acgtactggc ctacacccag agctaccggg caaagctgac cccaggctgt 7200
gaggctgagg ctgagacgga ggccatatgc ttcttcgtgc agcagttcac ggacatggag 7260
cacaacaggg tgctggaggc gctgctgccg ctgaagggcc tagaggagcg tgtggcagcc 7320
gccgtggacc tgatcatcaa gagccaccag ggcctggacc gccaggagct gagctttgcg 7380
gcccggtcct tctactacaa gctgcgtgcc gctgagcagt acacacccaa ggccaagtac 7440
catggcaacg tgatgctact gcgcgccaag acgggtggcg cctacggcga ggacctgggc 7500
gcggactaca acctctccca ggtatgcgac gggaaagtat ccgtccacgt catcgagggt 7560
gaccaccgca cgctgctgga gggcagcggc ctggagtcca tcatcagcat catccacagc 7620
tccctggctg agccacgcgt gagcgtgcgg gagggctagg cccgtgcccc cgcctgccac 7680
cggaggtcac tccaccatcc ccaccccacc ccaccccacc cccgccatgc aacgggattg 7740
aagggtcctg ccggtgggac cctgtccggc ccagtgccac tgccccccga ggctgctaga 7800
tgtaggtgtt aggcatgtcc cacccacccg ccgcctccca cggcacctcg gggacaccag 7860
agctgccgac ttggagactc ctggtctgtg aagagccggt ggtgcccgtg cccgcaggaa 7920
ctgggctggg cctcgtgcgc ccgtggggtc tgcgcttggt ctttctgtgc ttggatttgc 7980
atatttattg cattgctggt agagaccccc aggcctgtcc accctgccaa gactcctcag 8040
gcagcgtgtg ggtcccgcac tctgccccca tttccccgat gtcccctgcg ggcgcgggca 8100
gccacccaag cctgctggct gcggcccccct ctcggccagg cattggctca gcccgctgag 8160
tggggggtcg tgggccagtc cccgaggagc tgggcccctg cacaggcaca cagggcccgg 8220
ccacacccag cggcccccg cacagccacc cgtggggtgc tgcccttatg cccggcgccg 8280
ggcaccaact ccatgtttgg tgtttgtctg tgtttgtttt tcaagaaatg attcaaattg 8340
ctgcttggat tttgaaattt actgtaactg tcagtgtaca cgtctggacc ccgtttcatt 8400
tttacaccaa tttggtaaaa atgctgctct cagcctccca caattaaacc gcatgtgatc 8460
tcca 8464

<210> SEQ ID NO 16
<211> LENGTH: 2683
<212> TYPE: PRT
<213> ORGANISM: Homo sapiens

<400> SEQUENCE: 16

Met Ala Ser Ser Gly Gln Ile Asp Leu Leu Glu Arg Leu Lys Glu Leu
1 5 10 15

Asn Leu Asp Ser Ser Asn Phe Pro Gly Val Lys Leu Arg Ser Lys Met
20 25 30

```
Ser Leu Arg Ser Tyr Gly Ser Arg Glu Gly Ser Val Ser Ser Arg Ser
        35                  40                  45

Gly Glu Cys Ser Pro Val Pro Met Gly Ser Phe Pro Arg Arg Gly Phe
    50                  55                  60

Val Asn Gly Ser Arg Glu Ser Thr Gly Tyr Leu Glu Glu Leu Glu Lys
65                  70                  75                  80

Glu Arg Ser Leu Leu Leu Ala Asp Leu Asp Lys Glu Glu Lys Glu Lys
                85                  90                  95

Asp Trp Tyr Tyr Ala Gln Leu Gln Asn Leu Thr Lys Arg Ile Asp Ser
            100                 105                 110

Leu Pro Leu Thr Glu Asn Phe Ser Leu Gln Thr Asp Met Thr Arg Arg
        115                 120                 125

Gln Leu Glu Tyr Glu Ala Arg Gln Ile Arg Val Ala Met Glu Glu Gln
    130                 135                 140

Leu Gly Thr Cys Gln Asp Met Glu Lys Arg Ala Gln Arg Arg Ile Ala
145                 150                 155                 160

Arg Ile Gln Gln Ile Glu Lys Asp Ile Leu Arg Ile Arg Gln Leu Leu
                165                 170                 175

Gln Ser Gln Ala Thr Glu Ala Glu Arg Ser Ser Gln Asn Lys His Glu
            180                 185                 190

Thr Gly Ser His Asp Ala Glu Arg Gln Asn Glu Gly Gln Gly Val Gly
        195                 200                 205

Glu Ile Asn Met Ala Thr Ser Gly Asn Gly Gln Gly Ser Thr Thr Arg
    210                 215                 220

Met Asp His Glu Thr Ala Ser Val Leu Ser Ser Ser Ser Thr His Ser
225                 230                 235                 240

Ala Pro Arg Arg Leu Thr Ser His Leu Gly Thr Lys Ile Arg Ala Tyr
                245                 250                 255

Cys Glu Thr Cys Trp Glu Trp Gln Glu Ala His Glu Pro Gly Met Asp
            260                 265                 270

Gln Asp Lys Asn Pro Met Pro Ala Pro Val Glu His Gln Ile Cys Pro
        275                 280                 285

Ala Val Cys Val Leu Met Lys Leu Ser Phe Asp Glu Glu His Arg His
    290                 295                 300

Ala Met Asn Glu Leu Gly Gly Leu Gln Ala Ile Ala Glu Leu Leu Gln
305                 310                 315                 320

Val Asp Cys Glu Met Tyr Gly Leu Thr Asn Asp His Tyr Ser Ile Thr
                325                 330                 335

Leu Arg Arg Tyr Ala Gly Met Ala Leu Thr Asn Leu Thr Phe Gly Asp
            340                 345                 350

Val Ala Asn Lys Ala Thr Leu Cys Ser Met Lys Gly Cys Met Arg Ala
        355                 360                 365

Leu Val Ala Gln Leu Lys Ser Glu Ser Glu Asp Leu Gln Gln Val Ile
    370                 375                 380

Ala Ser Val Leu Arg Asn Leu Ser Trp Arg Ala Asp Val Asn Ser Lys
385                 390                 395                 400

Lys Thr Leu Arg Glu Val Gly Ser Val Lys Ala Leu Met Glu Cys Ala
                405                 410                 415

Leu Glu Val Lys Lys Glu Ser Thr Leu Lys Ser Val Leu Ser Ala Leu
            420                 425                 430

Trp Asn Leu Ser Ala His Cys Thr Glu Asn Lys Ala Asp Ile Cys Ala
        435                 440                 445

Val Asp Gly Ala Leu Ala Phe Leu Val Gly Thr Leu Thr Tyr Arg Ser
```

-continued

```
    450                 455                 460

Gln Thr Asn Thr Leu Ala Ile Ile Glu Ser Gly Gly Gly Ile Leu Arg
465                 470                 475                 480

Asn Val Ser Ser Leu Ile Ala Thr Asn Glu Asp His Arg Gln Ile Leu
                485                 490                 495

Arg Glu Asn Asn Cys Leu Gln Thr Leu Leu Gln His Leu Lys Ser His
            500                 505                 510

Ser Leu Thr Ile Val Ser Asn Ala Cys Gly Thr Leu Trp Asn Leu Ser
        515                 520                 525

Ala Arg Asn Pro Lys Asp Gln Glu Ala Leu Trp Asp Met Gly Ala Val
    530                 535                 540

Ser Met Leu Lys Asn Leu Ile His Ser Lys His Lys Met Ile Ala Met
545                 550                 555                 560

Gly Ser Ala Ala Ala Leu Arg Asn Leu Met Ala Asn Arg Pro Ala Lys
                565                 570                 575

Tyr Lys Asp Ala Asn Ile Met Ser Pro Gly Ser Ser Leu Pro Ser Leu
            580                 585                 590

His Val Arg Lys Gln Lys Ala Leu Glu Ala Glu Leu Asp Ala Gln His
        595                 600                 605

Leu Ser Glu Thr Phe Asp Asn Ile Asp Asn Leu Ser Pro Lys Ala Ser
    610                 615                 620

His Arg Ser Lys Gln Arg His Lys Gln Ser Leu Tyr Gly Asp Tyr Val
625                 630                 635                 640

Phe Asp Thr Asn Arg His Asp Asp Asn Arg Ser Asp Asn Phe Asn Thr
                645                 650                 655

Gly Asn Met Thr Val Leu Ser Pro Tyr Leu Asn Thr Thr Val Leu Pro
            660                 665                 670

Ser Ser Ser Ser Ser Arg Gly Ser Leu Asp Ser Ser Arg Ser Glu Lys
        675                 680                 685

Asp Arg Ser Leu Glu Arg Glu Arg Gly Ile Gly Leu Gly Asn Tyr His
    690                 695                 700

Pro Ala Thr Glu Asn Pro Gly Thr Ser Ser Lys Arg Gly Leu Gln Ile
705                 710                 715                 720

Ser Thr Thr Ala Ala Gln Ile Ala Lys Val Met Glu Glu Val Ser Ala
                725                 730                 735

Ile His Thr Ser Gln Glu Asp Arg Ser Ser Gly Ser Thr Thr Glu Leu
            740                 745                 750

His Cys Val Thr Asp Glu Arg Asn Ala Leu Arg Arg Ser Ser Ala Ala
        755                 760                 765

His Thr His Ser Asn Thr Tyr Asn Phe Thr Lys Ser Glu Asn Ser Asn
    770                 775                 780

Arg Thr Cys Ser Met Pro Tyr Ala Lys Leu Glu Tyr Lys Arg Ser Ser
785                 790                 795                 800

Asn Asp Ser Leu Asn Ser Val Ser Ser Ser Asp Gly Tyr Gly Lys Arg
                805                 810                 815

Gly Gln Met Lys Pro Ser Ile Glu Ser Tyr Ser Glu Asp Asp Glu Ser
            820                 825                 830

Lys Phe Cys Ser Tyr Gly Gln Tyr Pro Ala Asp Leu Ala His Lys Ile
        835                 840                 845

His Ser Ala Asn His Met Asp Asp Asn Asp Gly Glu Leu Asp Thr Pro
    850                 855                 860

Ile Asn Tyr Ser Leu Lys Tyr Ser Asp Glu Gln Leu Asn Ser Gly Arg
865                 870                 875                 880
```

-continued

```
Gln Ser Pro Ser Gln Asn Glu Arg Trp Ala Arg Pro Lys His Ile Ile
                885                 890                 895

Glu Asp Glu Ile Lys Gln Ser Glu Gln Arg Gln Ser Arg Asn Gln Ser
            900                 905                 910

Thr Thr Tyr Pro Val Tyr Thr Glu Ser Thr Asp Asp Lys His Leu Lys
        915                 920                 925

Phe Gln Pro His Phe Gly Gln Gln Glu Cys Val Ser Pro Tyr Arg Ser
    930                 935                 940

Arg Gly Ala Asn Gly Ser Glu Thr Asn Arg Val Gly Ser Asn His Gly
945                 950                 955                 960

Ile Asn Gln Asn Val Ser Gln Ser Leu Cys Gln Glu Asp Asp Tyr Glu
                965                 970                 975

Asp Asp Lys Pro Thr Asn Tyr Ser Glu Arg Tyr Ser Glu Glu Glu Gln
            980                 985                 990

His Glu Glu Glu Glu Arg Pro Thr Asn Tyr Ser Ile Lys Tyr Asn Glu
        995                 1000                1005

Glu Lys Arg His Val Asp Gln Pro Ile Asp Tyr Ser Leu Lys Tyr Ala
    1010                1015                1020

Thr Asp Ile Pro Ser Ser Gln Lys Gln Ser Phe Ser Phe Ser Lys Ser
1025                1030                1035                1040

Ser Ser Gly Gln Ser Ser Lys Thr Glu His Met Ser Ser Ser Ser Glu
                1045                1050                1055

Asn Thr Ser Thr Pro Ser Ser Asn Ala Lys Arg Gln Asn Gln Leu His
            1060                1065                1070

Pro Ser Ser Ala Gln Ser Arg Ser Gly Gln Pro Gln Lys Ala Ala Thr
        1075                1080                1085

Cys Lys Val Ser Ser Ile Asn Gln Glu Thr Ile Gln Thr Tyr Cys Val
    1090                1095                1100

Glu Asp Thr Pro Ile Cys Phe Ser Arg Cys Ser Ser Leu Ser Ser Leu
1105                1110                1115                1120

Ser Ser Ala Glu Asp Glu Ile Gly Cys Asn Gln Thr Thr Gln Glu Ala
                1125                1130                1135

Asp Ser Ala Asn Thr Leu Gln Ile Ala Glu Ile Lys Glu Lys Ile Gly
            1140                1145                1150

Thr Arg Ser Ala Glu Asp Pro Val Ser Glu Val Pro Ala Val Ser Gln
        1155                1160                1165

His Pro Arg Thr Lys Ser Ser Arg Leu Gln Gly Ser Ser Leu Ser Ser
    1170                1175                1180

Glu Ser Ala Arg His Lys Ala Val Glu Phe Ser Ser Gly Ala Lys Ser
1185                1190                1195                1200

Pro Ser Lys Ser Gly Ala Gln Thr Pro Lys Ser Pro Pro Glu His Tyr
                1205                1210                1215

Val Gln Glu Thr Pro Leu Met Phe Ser Arg Cys Thr Ser Val Ser Ser
            1220                1225                1230

Leu Asp Ser Phe Glu Ser Arg Ser Ile Ala Ser Ser Val Gln Ser Glu
        1235                1240                1245

Pro Cys Ser Gly Met Val Ser Gly Ile Ile Ser Pro Ser Asp Leu Pro
    1250                1255                1260

Asp Ser Pro Gly Gln Thr Met Pro Pro Ser Arg Ser Lys Thr Pro Pro
1265                1270                1275                1280

Pro Pro Pro Gln Thr Ala Gln Thr Lys Arg Glu Val Pro Lys Asn Lys
                1285                1290                1295
```

```
Ala Pro Thr Ala Glu Lys Arg Glu Ser Gly Pro Lys Gln Ala Ala Val
            1300                1305                1310

Asn Ala Ala Val Gln Arg Val Gln Val Leu Pro Asp Ala Asp Thr Leu
        1315                1320                1325

Leu His Phe Ala Thr Glu Ser Thr Pro Asp Gly Phe Ser Cys Ser Ser
    1330                1335                1340

Ser Leu Ser Ala Leu Ser Leu Asp Glu Pro Phe Ile Gln Lys Asp Val
1345                1350                1355                1360

Glu Leu Arg Ile Met Pro Pro Val Gln Glu Asn Asp Asn Gly Asn Glu
                1365                1370                1375

Thr Glu Ser Glu Gln Pro Lys Glu Ser Asn Glu Asn Gln Glu Lys Glu
            1380                1385                1390

Ala Glu Lys Thr Ile Asp Ser Glu Lys Asp Leu Leu Asp Asp Ser Asp
        1395                1400                1405

Asp Asp Asp Ile Glu Ile Leu Glu Glu Cys Ile Ile Ser Ala Met Pro
    1410                1415                1420

Thr Lys Ser Ser Arg Lys Ala Lys Lys Pro Ala Gln Thr Ala Ser Lys
1425                1430                1435                1440

Leu Pro Pro Pro Val Ala Arg Lys Pro Ser Gln Leu Pro Val Tyr Lys
                1445                1450                1455

Leu Leu Pro Ser Gln Asn Arg Leu Gln Pro Gln Lys His Val Ser Phe
            1460                1465                1470

Thr Pro Gly Asp Asp Met Pro Arg Val Tyr Cys Val Glu Gly Thr Pro
        1475                1480                1485

Ile Asn Phe Ser Thr Ala Thr Ser Leu Ser Asp Leu Thr Ile Glu Ser
    1490                1495                1500

Pro Pro Asn Glu Leu Ala Ala Gly Glu Gly Val Arg Gly Gly Ala Gln
1505                1510                1515                1520

Ser Gly Glu Phe Glu Lys Arg Asp Thr Ile Pro Thr Glu Gly Arg Ser
                1525                1530                1535

Thr Asp Glu Ala Gln Gly Gly Lys Thr Ser Ser Val Thr Ile Pro Glu
            1540                1545                1550

Leu Asp Asp Asn Lys Ala Glu Glu Gly Asp Ile Leu Ala Glu Cys Ile
        1555                1560                1565

Asn Ser Ala Met Pro Lys Gly Lys Ser His Lys Pro Phe Arg Val Lys
    1570                1575                1580

Lys Ile Met Asp Gln Val Gln Gln Ala Ser Ala Ser Ser Ser Ala Pro
1585                1590                1595                1600

Asn Lys Asn Gln Leu Asp Gly Lys Lys Lys Lys Pro Thr Ser Pro Val
                1605                1610                1615

Lys Pro Ile Pro Gln Asn Thr Glu Tyr Arg Thr Arg Val Arg Lys Asn
            1620                1625                1630

Ala Asp Ser Lys Asn Asn Leu Asn Ala Glu Arg Val Phe Ser Asp Asn
        1635                1640                1645

Lys Asp Ser Lys Lys Gln Asn Leu Lys Asn Asn Ser Lys Val Phe Asn
    1650                1655                1660

Asp Lys Leu Pro Asn Asn Glu Asp Arg Val Arg Gly Ser Phe Ala Phe
1665                1670                1675                1680

Asp Ser Pro His His Tyr Thr Pro Ile Glu Gly Thr Pro Tyr Cys Phe
                1685                1690                1695

Ser Arg Asn Asp Ser Leu Ser Ser Leu Asp Phe Asp Asp Asp Asp Val
            1700                1705                1710

Asp Leu Ser Arg Glu Lys Ala Glu Leu Arg Lys Ala Lys Glu Asn Lys
```

-continued

```
        1715                1720                1725

Glu Ser Glu Ala Lys Val Thr Ser His Thr Glu Leu Thr Ser Asn Gln
    1730                1735                1740

Gln Ser Ala Asn Lys Thr Gln Ala Ile Ala Lys Gln Pro Ile Asn Arg
1745                1750                1755                1760

Gly Gln Pro Lys Pro Ile Leu Gln Lys Gln Ser Thr Phe Pro Gln Ser
                1765                1770                1775

Ser Lys Asp Ile Pro Asp Arg Gly Ala Ala Thr Asp Glu Lys Leu Gln
            1780                1785                1790

Asn Phe Ala Ile Glu Asn Thr Pro Val Cys Phe Ser His Asn Ser Ser
        1795                1800                1805

Leu Ser Ser Leu Ser Asp Ile Asp Gln Glu Asn Asn Asn Lys Glu Asn
    1810                1815                1820

Glu Pro Ile Lys Glu Thr Glu Pro Pro Asp Ser Gln Gly Glu Pro Ser
1825                1830                1835                1840

Lys Pro Gln Ala Ser Gly Tyr Ala Pro Lys Ser Phe His Val Glu Asp
                1845                1850                1855

Thr Pro Val Cys Phe Ser Arg Asn Ser Ser Leu Ser Ser Leu Ser Ile
            1860                1865                1870

Asp Ser Glu Asp Asp Leu Leu Gln Glu Cys Ile Ser Ser Ala Met Pro
        1875                1880                1885

Lys Lys Lys Lys Pro Ser Arg Leu Lys Gly Asp Asn Glu Lys His Ser
    1890                1895                1900

Pro Arg Asn Met Gly Gly Ile Leu Gly Glu Asp Leu Thr Leu Asp Leu
1905                1910                1915                1920

Lys Asp Ile Gln Arg Pro Asp Ser Glu His Gly Leu Ser Pro Asp Ser
                1925                1930                1935

Glu Asn Phe Asp Trp Lys Ala Ile Gln Glu Gly Ala Asn Ser Ile Val
            1940                1945                1950

Ser Ser Leu His Gln Ala Ala Ala Ala Ala Cys Leu Ser Arg Gln Ala
        1955                1960                1965

Ser Ser Asp Ser Asp Ser Ile Leu Ser Leu Lys Ser Gly Ile Ser Leu
    1970                1975                1980

Gly Ser Pro Phe His Leu Thr Pro Asp Gln Glu Glu Lys Pro Phe Thr
1985                1990                1995                2000

Ser Asn Lys Gly Pro Arg Ile Leu Lys Pro Gly Glu Lys Ser Thr Leu
                2005                2010                2015

Glu Thr Lys Lys Ile Glu Ser Glu Ser Lys Gly Ile Lys Gly Gly Lys
            2020                2025                2030

Lys Val Tyr Lys Ser Leu Ile Thr Gly Lys Val Arg Ser Asn Ser Glu
        2035                2040                2045

Ile Ser Gly Gln Met Lys Gln Pro Leu Gln Ala Asn Met Pro Ser Ile
    2050                2055                2060

Ser Arg Gly Arg Thr Met Ile His Ile Pro Gly Val Arg Asn Ser Ser
2065                2070                2075                2080

Ser Ser Thr Ser Pro Val Ser Lys Lys Gly Pro Pro Leu Lys Thr Pro
                2085                2090                2095

Ala Ser Lys Ser Pro Ser Glu Gly Gln Thr Ala Thr Thr Ser Pro Arg
            2100                2105                2110

Gly Ala Lys Pro Ser Val Lys Ser Glu Leu Ser Pro Val Ala Arg Gln
        2115                2120                2125

Thr Ser Gln Ile Gly Gly Ser Ser Lys Ala Pro Ser Arg Ser Gly Ser
    2130                2135                2140
```

-continued

Arg Asp Ser Thr Pro Ser Arg Pro Ala Gln Gln Pro Leu Ser Arg Pro
2145 2150 2155 2160

Ile Gln Ser Pro Gly Arg Asn Ser Ile Ser Pro Gly Arg Asn Gly Ile
2165 2170 2175

Ser Pro Pro Asn Lys Leu Ser Gln Leu Pro Arg Thr Ser Ser Pro Ser
2180 2185 2190

Thr Ala Ser Thr Lys Ser Ser Gly Ser Gly Lys Met Ser Tyr Thr Ser
2195 2200 2205

Pro Gly Arg Gln Met Ser Gln Gln Asn Leu Thr Lys Gln Thr Gly Leu
2210 2215 2220

Ser Lys Asn Ala Ser Ser Ile Pro Arg Ser Glu Ser Ala Ser Lys Gly
2225 2230 2235 2240

Leu Asn Gln Met Asn Asn Gly Asn Gly Ala Asn Lys Lys Val Glu Leu
2245 2250 2255

Ser Arg Met Ser Ser Thr Lys Ser Ser Gly Ser Glu Ser Asp Arg Ser
2260 2265 2270

Glu Arg Pro Val Leu Val Arg Gln Ser Thr Phe Ile Lys Glu Ala Pro
2275 2280 2285

Ser Pro Thr Leu Arg Arg Lys Leu Glu Glu Ser Ala Ser Phe Glu Ser
2290 2295 2300

Leu Ser Pro Ser Ser Arg Pro Ala Ser Pro Thr Arg Ser Gln Ala Gln
2305 2310 2315 2320

Thr Pro Val Leu Ser Pro Ser Leu Pro Asp Met Ser Leu Ser Thr His
2325 2330 2335

Ser Ser Val Gln Ala Gly Gly Trp Arg Lys Leu Pro Pro Asn Leu Ser
2340 2345 2350

Pro Thr Ile Glu Tyr Asn Asp Gly Arg Pro Ala Lys Arg His Asp Ile
2355 2360 2365

Ala Arg Ser His Ser Glu Ser Pro Ser Arg Leu Pro Ile Asn Arg Ser
2370 2375 2380

Gly Thr Trp Lys Arg Glu His Ser Lys His Ser Ser Ser Leu Pro Arg
2385 2390 2395 2400

Val Ser Thr Trp Arg Arg Thr Gly Ser Ser Ser Ser Ile Leu Ser Ala
2405 2410 2415

Ser Ser Glu Ser Ser Glu Lys Ala Lys Ser Glu Asp Glu Lys His Val
2420 2425 2430

Asn Ser Ile Ser Gly Thr Lys Gln Ser Lys Glu Asn Gln Val Ser Ala
2435 2440 2445

Lys Gly Thr Trp Arg Lys Ile Lys Glu Asn Glu Phe Ser Pro Thr Asn
2450 2455 2460

Ser Thr Ser Gln Thr Val Ser Ser Gly Ala Thr Asn Gly Ala Glu Ser
2465 2470 2475 2480

Lys Thr Leu Ile Tyr Gln Met Ala Pro Ala Val Ser Lys Thr Glu Asp
2485 2490 2495

Val Trp Val Arg Ile Glu Asp Cys Pro Ile Asn Asn Pro Arg Ser Gly
2500 2505 2510

Arg Ser Pro Thr Gly Asn Thr Pro Pro Val Ile Asp Ser Val Ser Glu
2515 2520 2525

Lys Ala Asn Pro Asn Ile Lys Asp Ser Lys Asp Asn Gln Ala Lys Gln
2530 2535 2540

Asn Val Gly Asn Gly Ser Val Pro Met Arg Thr Val Gly Leu Glu Asn
2545 2550 2555 2560

-continued

```
Arg Leu Asn Ser Phe Ile Gln Val Asp Ala Pro Asp Gln Lys Gly Thr
                2565                2570                2575

Glu Ile Lys Pro Gly Gln Asn Asn Pro Val Pro Val Ser Glu Thr Asn
            2580                2585                2590

Glu Ser Ser Ile Val Glu Arg Thr Pro Phe Ser Ser Ser Ser Ser Ser
        2595                2600                2605

Lys His Ser Ser Pro Ser Gly Thr Val Ala Ala Arg Val Thr Pro Phe
    2610                2615                2620

Asn Tyr Asn Pro Ser Pro Arg Lys Ser Ser Ala Asp Ser Thr Ser Ala
2625                2630                2635                2640

Arg Pro Ser Gln Ile Pro Thr Pro Val Asn Asn Asn Thr Lys Lys Arg
                2645                2650                2655

Asp Ser Lys Thr Asp Ser Thr Glu Ser Ser Gly Thr Gln Ser Pro Lys
            2660                2665                2670

Arg His Ser Gly Ser Tyr Leu Val Thr Ser Val
        2675                2680


<210> SEQ ID NO 17
<211> LENGTH: 10248
<212> TYPE: DNA
<213> ORGANISM: Homo sapiens

<400> SEQUENCE: 17

actggagaca gaatggaggt gctgccggac tcggaaatgg ggaagtactt aaacaactac      60

aaggaagtat tgaagatgaa gctatggctt cttctggaca gattgattta ttagagcgtc     120

ttaaagagct taacttagat agcagtaatt tccctggagt aaaactgcgg tcaaaaatgt     180

ccctccgttc ttatggaagc cgggaaggat ctgtatcaag ccgttctgga gagtgcagtc     240

ctgttcctat gggttcattt ccaagaagag ggtttgtaaa tggaagcaga gaaagtactg     300

gatatttaga agaacttgag aaagagaggt cattgcttct tgctgatctt gacaaagaag     360

aaaaggaaaa agactggtat tacgctcaac ttcagaatct cactaaaaga atagatagtc     420

ttcctttaac tgaaaatttt tccttacaaa cagatatgac cagaaggcaa ttggaatatg     480

aagcaaggca aatcagagtt gcgatggaag aacaactagg tacctgccag gatatggaaa     540

aacgagcaca gcgaagaata gccagaattc agcaaatcga aaaggacata cttcgtatac     600

gacagctttt acagtcccaa gcaacagaag cagagaggtc atctcagaac aagcatgaaa     660

ccggctcaca tgatgctgag cggcagaatg aaggtcaagg agtgggagaa atcaacatgg     720

caacttctgg taatggtcag ggttcaacta cacgaatgga ccatgaaaca gccagtgttt     780

tgagttctag tagcacacac tctgcacctc gaaggctgac aagtcatctg ggaaccaaga     840

tacgcgctta ctgtgaaacc tgttgggagt ggcaggaagc tcatgaacca ggcatggacc     900

aggacaaaaa tccaatgcca gctcctgttg aacatcagat ctgtcctgct gtgtgtgttc     960

taatgaaact ttcatttgat gaagagcata gacatgcaat gaatgaacta gggggactac    1020

aggccattgc agaattattg caagtggact gtgaaatgta tgggcttact aatgaccact    1080

acagtattac actaagacga tatgctggaa tggctttgac aaacttgact tttggagatg    1140

tagccaacaa ggctacgcta tgctctatga aaggctgcat gagagcactt gtggcccaac    1200

taaaatctga aagtgaagac ttacagcagg ttattgcgag tgttttgagg aatttgtctt    1260

ggcgagcaga tgtaaatagt aaaaagacgt tgcgagaagt tggaagtgtg aaagcattga    1320

tggaatgtgc tttagaagtt aaaaaggaat caaccctcaa aagcgtattg agtgccttat    1380

ggaatttgtc agcacattgc actgagaata aagctgatat atgtgctgta gatggtgcac    1440
```

-continued

```
ttgcattttt ggttggcact cttacttacc ggagccagac aaacacttta gccattattg   1500
aaagtggagg tgggatatta cggaatgtgt ccagcttgat agctacaaat gaggaccaca   1560
ggcaaatcct aagagagaac aactgtctac aaactttatt acaacactta aaatctcata   1620
gtttgacaat agtcagtaat gcatgtggaa ctttgtggaa tctctcagca agaaatccta   1680
aagaccagga agcattatgg gacatggggg cagttagcat gctcaagaac ctcattcatt   1740
caaagcacaa aatgattgct atgggaagtg ctgcagcttt aaggaatctc atggcaaata   1800
ggcctgcgaa gtacaaggat gccaatatta tgtctcctgg ctcaagcttg ccatctcttc   1860
atgttaggaa acaaaaagcc ctagaagcag aattagatgc tcagcactta tcagaaactt   1920
ttgacaatat agacaattta agtcccaagg catctcatcg tagtaagcag agacacaagc   1980
aaagtctcta tggtgattat gtttttgaca ccaatcgaca tgatgataat aggtcagaca   2040
attttaatac tggcaacatg actgtccttt caccatattt gaatactaca gtgttaccca   2100
gctcctcttc atcaagagga agcttagata gttctcgttc tgaaaaagat agaagtttgg   2160
agagagaacg cggaattggt ctaggcaact accatccagc aacagaaaat ccaggaactt   2220
cttcaaagcg aggtttgcag atctccacca ctgcagccca gattgccaaa gtcatggaag   2280
aagtgtcagc cattcatacc tctcaggaag acagaagttc tgggtctacc actgaattac   2340
attgtgtgac agatgagaga aatgcactta gaagaagctc tgctgcccat acacattcaa   2400
acacttacaa tttcactaag tcggaaaatt caaataggac atgttctatg ccttatgcca   2460
aattagaata caagagatct tcaaatgata gtttaaatag tgtcagtagt agtgatggtt   2520
atggtaaaag aggtcaaatg aaaccctcga ttgaatccta ttctgaagat gatgaaagta   2580
agttttgcag ttatggtcaa tacccagccg acctagccca taaaatacat agtgcaaatc   2640
atatggatga taatgatgga gaactagata caccaataaa ttatagtctt aaatattcag   2700
atgagcagtt gaactctgga aggcaaagtc cttcacagaa tgaaagatgg gcaagaccca   2760
aacacataat agaagatgaa ataaaacaaa gtgagcaaag acaatcaagg aatcaaagta   2820
caacttatcc tgtttatact gagagcactg atgataaaca cctcaagttc caaccacatt   2880
ttggacagca ggaatgtgtt tctccataca ggtcacgggg agccaatggt tcagaaacaa   2940
atcgagtggg ttctaatcat ggaattaatc aaaatgtaag ccagtctttg tgtcaagaag   3000
atgactatga agatgataag cctaccaatt atagtgaacg ttactctgaa gaagaacagc   3060
atgaagaaga agagagacca acaaattata gcataaaata taatgaagag aaacgtcatg   3120
tggatcagcc tattgattat agtttaaaat atgccacaga tattccttca tcacagaaac   3180
agtcattttc attctcaaag agttcatctg gacaaagcag taaaaccgaa catatgtctt   3240
caagcagtga gaatacgtcc acaccttcat ctaatgccaa gaggcagaat cagctccatc   3300
caagttctgc acagagtaga agtggtcagc ctcaaaaggc tgccacttgc aaagtttctt   3360
ctattaacca agaaacaata cagacttatt gtgtagaaga tactccaata tgtttttcaa   3420
gatgtagttc attatcatct ttgtcatcag ctgaagatga aataggatgt aatcagacga   3480
cacaggaagc agattctgct aataccctgc aaatagcaga aataaaagaa aagattggaa   3540
ctaggtcagc tgaagatcct gtgagcgaag ttccagcagt gtcacagcac cctagaacca   3600
aatccagcag actgcagggt tctagtttat cttcagaatc agccaggcac aaagctgttg   3660
aattttcttc aggagcgaaa tctccctcca aaagtggtgc tcagacaccc aaaagtccac   3720
ctgaacacta tgttcaggag accccactca tgtttagcag atgtacttct gtcagttcac   3780
```

ttgatagttt tgagagtcgt tcgattgcca gctccgttca gagtgaacca tgcagtggaa 3840
tggtaagtgg cattataagc cccagtgatc ttccagatag ccctggacaa accatgccac 3900
caagcagaag taaaacacct ccaccacctc ctcaaacagc tcaaaccaag cgagaagtac 3960
ctaaaaataa agcacctact gctgaaaaga gagagagtgg acctaagcaa gctgcagtaa 4020
atgctgcagt tcagagggtc caggttcttc cagatgctga tactttatta cattttgcca 4080
cggaaagtac tccagatgga ttttcttgtt catccagcct gagtgctctg agcctcgatg 4140
agccatttat acagaaagat gtggaattaa gaataatgcc tccagttcag gaaaatgaca 4200
atgggaatga aacagaatca gagcagccta aagaatcaaa tgaaaaccaa gagaaagagg 4260
cagaaaaaac tattgattct gaaaaggacc tattagatga ttcagatgat gatgatattg 4320
aaatactaga agaatgtatt atttctgcca tgccaacaaa gtcatcacgt aaagcaaaaa 4380
agccagccca gactgcttca aaattacctc cacctgtggc aaggaaacca agtcagctgc 4440
ctgtgtacaa acttctacca tcacaaaaca ggttgcaacc ccaaaagcat gttagtttta 4500
caccggggga tgatatgcca cgggtgtatt gtgttgaagg gacacctata aacttttcca 4560
cagctacatc tctaagtgat ctaacaatcg aatcccctcc aaatgagtta gctgctggag 4620
aaggagttag aggaggggca cagtcaggtg aatttgaaaa acgagatacc attcctacag 4680
aaggcagaag tacagatgag gctcaaggag gaaaaacctc atctgtaacc atacctgaat 4740
tggatgacaa taaagcagag gaaggtgata ttcttgcaga atgcattaat tctgctatgc 4800
ccaaagggaa aagtcacaag cctttccgtg tgaaaaagat aatggaccag gtccagcaag 4860
catctgcgtc ttcttctgca cccaacaaaa atcagttaga tggtaagaaa aagaaaccaa 4920
cttcaccagt aaaacctata ccacaaaata ctgaatatag gacacgtgta agaaaaaatg 4980
cagactcaaa aaataattta aatgctgaga gagttttctc agacaacaaa gattcaaaga 5040
aacagaattt gaaaaataat tccaaggtct tcaatgataa gctcccaaat aatgaagata 5100
gagtcagagg aagttttgct tttgattcac ctcatcatta cacgcctatt gaaggaactc 5160
cttactgttt ttcacgaaat gattctttga gttctctaga ttttgatgat gatgatgttg 5220
acctttccag ggaaaaggct gaattaagaa aggcaaaaga aaataaggaa tcagaggcta 5280
aagttaccag ccacacagaa ctaacctcca accaacaatc agctaataag acacaagcta 5340
ttgcaaagca gccaataaat cgaggtcagc ctaaacccat acttcagaaa caatccactt 5400
ttccccagtc atccaaagac ataccagaca gaggggcagc aactgatgaa aagttacaga 5460
attttgctat tgaaaatact ccggtttgct tttctcataa ttcctctctg agttctctca 5520
gtgacattga ccaagaaaac aacaataaag aaaatgaacc tatcaaagag actgagcccc 5580
ctgactcaca gggagaacca agtaaacctc aagcatcagg ctatgctcct aaatcatttc 5640
atgttgaaga taccccagtt tgtttctcaa gaaacagttc tctcagttct cttagtattg 5700
actctgaaga tgacctgttg caggaatgta taagctccgc aatgccaaaa aagaaaaagc 5760
cttcaagact caagggtgat aatgaaaaac atagtcccag aaatatgggt ggcatattag 5820
gtgaagatct gacacttgat ttgaaagata tacagagacc agattcagaa catggtctat 5880
cccctgattc agaaaatttt gattggaaag ctattcagga aggtgcaaat tccatagtaa 5940
gtagtttaca tcaagctgct gctgctgcat gtttatctag acaagcttcg tctgattcag 6000
attccatcct ttccctgaaa tcaggaatct ctctgggatc accatttcat cttacacctg 6060
atcaagaaga aaaacccttt acaagtaata aaggcccacg aattctaaaa ccaggggaga 6120
aaagtacatt ggaaactaaa aagatagaat ctgaaagtaa aggaatcaaa ggaggaaaaa 6180

-continued

```
aagtttataa aagtttgatt actggaaaag ttcgatctaa ttcagaaatt tcaggccaaa   6240
tgaaacagcc ccttcaagca aacatgcctt caatctctcg aggcaggaca atgattcata   6300
ttccaggagt tcgaaatagc tcctcaagta caagtcctgt ttctaaaaaa ggcccacccc   6360
ttaagactcc agcctccaaa agccctagtg aaggtcaaac agccaccact tctcctagag   6420
gagccaagcc atctgtgaaa tcagaattaa gccctgttgc caggcagaca tcccaaatag   6480
gtgggtcaag taaagcacct tctagatcag gatctagaga ttcgacccct tcaagacctg   6540
cccagcaacc attaagtaga cctatacagt ctcctggccg aaactcaatt tcccctggta   6600
gaaatggaat aagtcctcct aacaaattat ctcaacttcc aaggacatca tcccctagta   6660
ctgcttcaac taagtcctca ggttctggaa aaatgtcata tacatctcca ggtagacaga   6720
tgagccaaca gaaccttacc aaacaaacag gtttatccaa gaatgccagt agtattccaa   6780
gaagtgagtc tgcctccaaa ggactaaatc agatgaataa tggtaatgga gccaataaaa   6840
aggtagaact ttctagaatg tcttcaacta aatcaagtgg aagtgaatct gatagatcag   6900
aaagacctgt attagtacgc cagtcaactt tcatcaaaga agctccaagc ccaaccttaa   6960
gaagaaaatt ggaggaatct gcttcatttg aatctctttc tccatcatct agaccagctt   7020
ctcccactag gtcccaggca caaactccag ttttaagtcc ttcccttcct gatatgtctc   7080
tatccacaca ttcgtctgtt caggctggtg gatggcgaaa actcccacct aatctcagtc   7140
ccactataga gtataatgat ggaagaccag caaagcgcca tgatattgca cggtctcatt   7200
ctgaaagtcc ttctagactt ccaatcaata ggtcaggaac ctggaaacgt gagcacagca   7260
aacattcatc atcccttcct cgagtaagca cttggagaag aactggaagt tcatcttcaa   7320
ttctttctgc ttcatcagaa tccagtgaaa aagcaaaaag tgaggatgaa aaacatgtga   7380
actctatttc aggaaccaaa caaagtaaag aaaaccaagt atccgcaaaa ggaacatgga   7440
gaaaaataaa agaaaatgaa ttttctccca caaatagtac ttctcagacc gtttcctcag   7500
gtgctacaaa tggtgctgaa tcaaagactc taatttatca aatggcacct gctgtttcta   7560
aaacagagga tgtttgggtg agaattgagg actgtcccat taacaatcct agatctggaa   7620
gatctcccac aggtaatact cccccggtga ttgacagtgt ttcagaaaag gcaaatccaa   7680
acattaaaga ttcaaaagat aatcaggcaa aacaaaatgt gggtaatggc agtgttccca   7740
tgcgtaccgt gggtttggaa aatcgcctga actcctttat tcaggtggat gcccctgacc   7800
aaaaaggaac tgagataaaa ccaggacaaa ataatcctgt ccctgtatca gagactaatg   7860
aaagttctat agtggaacgt accccattca gttctagcag ctcaagcaaa cacagttcac   7920
ctagtgggac tgttgctgcc agagtgactc cttttaatta caacccaagc cctaggaaaa   7980
gcagcgcaga tagcacttca gctcggccat ctcagatccc aactccagtg aataacaaca   8040
caaagaagcg agattccaaa actgacagca cagaatccag tggaacccaa agtcctaagc   8100
gccattctgg gtcttacctt gtgacatctg tttaaaagag aggaagaatg aaactaagaa   8160
aattctatgt taattacaac tgctatatag acattttgtt tcaaatgaaa ctttaaaaga   8220
ctgaaaaatt ttgtaaatag gtttgattct tgttagaggg tttttgttct ggaagccata   8280
tttgatagta tactttgtct tcactggtct tattttggga ggcactcttg atggttagga   8340
aaaaaatagt aaagccaagt atgtttgtac agtatgtttt acatgtattt aaagtagcat   8400
cccatcccaa cttcctttaa ttattgcttg tcttaaaata atgaacacta cagatagaaa   8460
atatgatata ttgctgttat caatcatttc tagattataa actgactaaa cttacatcag   8520
```

-continued

```
ggaaaaattg gtatttatgc aaaaaaaaat gtttttgtcc ttgtgagtcc atctaacatc   8580
ataattaatc atgtggctgt gaaattcaca gtaatatggt tcccgatgaa caagtttacc   8640
cagcctgctt tgctttactg catgaatgaa actgatggtt caatttcaga agtaatgatt   8700
aacagttatg tggtcacatg atgtgcatag agatagctac agtgtaataa tttacactat   8760
tttgtgctcc aaacaaaaca aaaatctgtg taactgtaaa acattgaatg aaactatttt   8820
acctgaacta gattttatct gaaagtaggt agaatttttg ctatgctgta atttgttgta   8880
tattctggta tttgaggtga gatggctgct cttttattaa tgagacatga attgtgtctc   8940
aacagaaact aaatgaacat ttcagaataa attattgctg tatgtaaact gttactgaaa   9000
ttggtatttg tttgaagggt cttgtttcac atttgtatta ataattgttt aaaatgcctc   9060
ttttaaaagc ttatataaat ttttttcttc agcttctatg cattaagagt aaaattcctc   9120
ttactgtaat aaaaacaatt gaagaagact gttgccactt aaccattcca tgcgttggca   9180
cttatctatt cctgaaattt cttttatgtg attagctcat cttgattttt aatatttttc   9240
cacttaaact ttttttcttt actccactgg agctcagtaa aagtaaattc atgtaatagc   9300
aatgcaagca gcctagcaca gactaagcat tgagcataat aggcccacat aatttcctct   9360
ttcttaatat tatagaattc tgtacttgaa attgattctt agacattgca gtctcttcga   9420
ggctttacag tgtaaactgt cttgcccctt catcttcttg ttgcaactgg gtctgacatg   9480
aacacttttt atcaccctgt atgttagggc aagatctcag cagtgaagta taatcagcac   9540
tttgccatgc tcagaaaatt caaatcacat ggaactttag aggtagattt aatacgatta   9600
agatattcag aagtatattt tagaatccct gcctgttaag gaaactttat ttgtggtagg   9660
tacagttctg ggtacatgt taagtgtccc cttatacagt ggagggaagt cttccttcct    9720
gaaggaaaat aaactgacac ttattaacta agataattta cttaatatat cttccctgat   9780
ttgttttaaa agatcagagg gtgactgatg atacatgcat acatatttgt tgaataaatg   9840
aaaatttatt tttagtgata agattcatac actctgtatt tggggaggga aaaccttttt   9900
aagcatggtg gggcactcag ataggagtga atacacctac ctggtgcctt gaaaatcaca   9960
tcaagtagtt aattatctac cccttacctg tgtttataac ttccaggtaa tgagaatgat  10020
ttttttaaa gctaaaatgc cagtaaataa aagtgctatg acttgagcta agatatttga   10080
ctccaatgcc tgtactgtgt ctactgcacc actttgtaaa cacttcaatt tactatcttt  10140
gaaatgattg acctttaaat ttttgccaaa tgttatctga aattgtctat gaataccatc  10200
tacttctgtt gttttcccag gcttccataa acaatggaga tacatgca               10248
```

<210> SEQ ID NO 18
<211> LENGTH: 774
<212> TYPE: PRT
<213> ORGANISM: Homo sapiens

<400> SEQUENCE: 18

```
Met Glu Leu Asp Met Ala Met Glu Pro Asp Arg Lys Ala Ala Val Ser
1               5                   10                  15

His Trp Gln Gln Gln Ser Tyr Leu Asp Ser Gly Ile His Ser Gly Ala
            20                  25                  30

Thr Thr Thr Ala Pro Ser Leu Ser Gly Lys Gly Asn Pro Glu Glu Glu
        35                  40                  45

Asp Val Asp Thr Ser Gln Val Leu Tyr Glu Trp Glu Gln Gly Phe Ser
    50                  55                  60

Gln Ser Phe Thr Gln Glu Gln Val Ala Asp Ile Asp Gly Gln Tyr Ala
```

-continued

```
65                  70                  75                  80

Met Thr Arg Ala Gln Arg Val Arg Ala Ala Met Phe Pro Glu Thr Leu
                85                  90                  95

Asp Glu Gly Met Gln Ile Pro Ser Thr Gln Phe Asp Ala Ala His Pro
            100                 105                 110

Thr Asn Val Gln Arg Leu Ala Glu Pro Ser Gln Met Leu Lys His Ala
        115                 120                 125

Val Val Asn Leu Ile Asn Tyr Gln Asp Asp Ala Glu Leu Ala Thr Arg
    130                 135                 140

Ala Ile Pro Glu Leu Thr Lys Leu Leu Asn Asp Glu Asp Gln Val Val
145                 150                 155                 160

Val Asn Lys Ala Ala Val Met Val His Gln Leu Ser Lys Lys Glu Ala
                165                 170                 175

Ser Arg His Ala Ile Met Arg Ser Pro Gln Met Val Ser Ala Ile Val
            180                 185                 190

Arg Thr Met Gln Asn Thr Asn Asp Val Glu Thr Ala Arg Cys Thr Ala
        195                 200                 205

Gly Thr Leu His Asn Leu Ser His His Arg Glu Gly Leu Leu Ala Ile
    210                 215                 220

Phe Lys Ser Gly Gly Ile Pro Ala Leu Val Lys Met Leu Gly Ser Pro
225                 230                 235                 240

Val Asp Ser Val Leu Phe Tyr Ala Ile Thr Thr Leu His Asn Leu Leu
                245                 250                 255

Leu His Gln Glu Gly Ala Lys Met Ala Val Arg Leu Ala Gly Gly Leu
            260                 265                 270

Gln Lys Met Val Ala Leu Leu Asn Lys Thr Asn Val Lys Phe Leu Ala
        275                 280                 285

Ile Thr Thr Asp Cys Leu Gln Ile Leu Ala Tyr Gly Asn Gln Glu Ser
    290                 295                 300

Lys Leu Ile Ile Leu Ala Ser Gly Gly Pro Gln Ala Leu Val Asn Ile
305                 310                 315                 320

Met Arg Thr Tyr Thr Tyr Glu Lys Leu Leu Trp Thr Thr Ser Arg Val
                325                 330                 335

Leu Lys Val Leu Ser Val Cys Ser Ser Asn Lys Pro Ala Ile Val Glu
            340                 345                 350

Ala Gly Gly Met Gln Ala Leu Gly Leu His Leu Thr Asp Pro Ser Gln
        355                 360                 365

Arg Leu Val Gln Asn Cys Leu Trp Thr Leu Arg Asn Leu Ser Asp Ala
    370                 375                 380

Ala Thr Lys Gln Glu Gly Met Glu Gly Leu Leu Gly Thr Leu Val Gln
385                 390                 395                 400

Leu Leu Gly Ser Asp Asp Ile Asn Val Val Thr Cys Ala Ala Gly Ile
                405                 410                 415

Leu Ser Asn Leu Thr Cys Asn Asn Tyr Lys Asn Lys Met Met Val Cys
            420                 425                 430

Gln Val Gly Gly Ile Glu Ala Leu Val Arg Thr Val Leu Arg Ala Gly
        435                 440                 445

Asp Arg Glu Asp Ile Thr Glu Pro Ala Ile Cys Ala Leu Arg His Leu
    450                 455                 460

Thr Ser Arg His Gln Glu Ala Glu Met Ala Gln Asn Ala Val Arg Leu
465                 470                 475                 480

His Tyr Gly Leu Pro Val Val Val Lys Leu Leu His Pro Pro Ser His
                485                 490                 495
```

```
Trp Pro Leu Ile Lys Ala Thr Val Gly Leu Ile Arg Asn Leu Ala Leu
            500                 505                 510

Cys Pro Ala Asn His Ala Pro Leu Arg Glu Gln Gly Ala Ile Pro Arg
        515                 520                 525

Leu Val Gln Leu Leu Val Arg Ala His Gln Asp Thr Gln Arg Arg Thr
    530                 535                 540

Ser Met Gly Gly Thr Gln Gln Gln Phe Val Glu Gly Val Arg Met Glu
545                 550                 555                 560

Glu Ile Val Glu Gly Cys Thr Gly Ala Leu His Ile Leu Ala Arg Asp
                565                 570                 575

Val His Asn Arg Ile Val Ile Arg Gly Leu Asn Thr Ile Pro Leu Phe
            580                 585                 590

Val Gln Leu Leu Tyr Ser Pro Ile Glu Asn Ile Gln Arg Val Ala Ala
        595                 600                 605

Gly Val Leu Cys Glu Leu Ala Gln Asp Lys Glu Ala Ala Glu Ala Ile
    610                 615                 620

Glu Ala Glu Gly Ala Thr Ala Pro Leu Thr Glu Leu Leu His Ser Arg
625                 630                 635                 640

Asn Glu Gly Val Ala Thr Tyr Ala Ala Ala Val Leu Phe Arg Met Ser
                645                 650                 655

Glu Asp Lys Pro Gln Asp Tyr Lys Lys Arg Leu Ser Val Glu Leu Thr
            660                 665                 670

Ser Ser Leu Phe Arg Thr Glu Pro Met Ala Trp Asn Glu Thr Ala Asp
        675                 680                 685

Leu Gly Leu Asp Ile Gly Ala Gln Gly Glu Pro Leu Gly Tyr Arg Gln
    690                 695                 700

Asp Asp Pro Ser Tyr Arg Ser Phe His Ser Gly Gly Tyr Gly Gln Asp
705                 710                 715                 720

Ala Leu Gly Met Asp Pro Met Met Glu His Glu Met Gly Gly His His
                725                 730                 735

Pro Gly Ala Asp Tyr Pro Val Asp Gly Leu Pro Asp Leu Gly His Ala
            740                 745                 750

Gln Asp Leu Met Asp Gly Leu Pro Pro Gly Asp Ser Asn Gln Leu Ala
        755                 760                 765

Trp Phe Asp Thr Asp Leu
    770
```

<210> SEQ ID NO 19
<211> LENGTH: 3488
<212> TYPE: DNA
<213> ORGANISM: Homo sapiens

<400> SEQUENCE: 19

```
aagcctctcg gtctgtggca gcagcgttgg cccggccccg ggagcggaga gcgaggggag      60

gcggagacgg aggaaggtct gaggagcagc ttcagtcccc gccgagccgc caccgcaggt     120

cgaggacggt cggactcccg cggcgggagg agcctgttcc cctgagggta tttgaagtat     180

accatacaac tgttttgaaa atccagcgtg gacaatggct actcaaggct accttttgct     240

ccattttctg ctcactcctc ctaatggctt ggtgaaatag caaacaagcc accagcagga     300

atctagtctg gatgactgct tctggagcct ggatgcagta ccattcttcc actgattcac     360

tgatttgatg gagttggaca tggccatgga accagacaga aaagcggctg ttagtcactg     420

gcagcaacag tcttacctgg actctggaat ccattctggt gccactacca cagctccttc     480
```

-continued

```
tctgagtggt aaaggcaatc ctgaggaaga ggatgtggat acctcccaag tcctgtatga    540
gtgggaacag ggattttctc agtccttcac tcaagaacaa gtagctgata ttgatggaca    600
gtatgcaatg actcgagctc agagggtacg agctgctatg ttccctgaga cattagatga    660
gggcatgcag atcccatcta cacagtttga tgctgctcat cccactaatg tccagcgttt    720
ggctgaacca tcacagatgc tgaaacatgc agttgtaaac ttgattaact atcaagatga    780
tgcagaactt gccacacgtg caatccctga actgacaaaa ctgctaaatg acgaggacca    840
ggtggtggtt aataaggctg cagttatggt ccatcagctt tctaaaaagg aagcttccag    900
acacgctatc atgcgttctc ctcagatggt gtctgctatt gtacgtacca tgcagaatac    960
aaatgatgta gaaacagctc gttgtaccgc tgggaccttg cataaccttt cccatcatcg   1020
tgagggctta ctggccatct ttaagtctgg aggcattcct gccctggtga aaatgcttgg   1080
ttcaccagtg gattctgtgt tgttttatgc cattacaact ctccacaacc ttttattaca   1140
tcaagaagga gctaaaatgg cagtgcgttt agctggtggg ctgcagaaaa tggttgcctt   1200
gctcaacaaa acaaatgtta aattcttggc tattacgaca gactgccttc aaattttagc   1260
ttatggcaac caagaaagca agctcatcat actggctagt ggtggacccc aagctttagt   1320
aaatataatg aggacctata cttacgaaaa actactgtgg accacaagca gagtgctgaa   1380
ggtgctatct gtctgctcta gtaataagcc ggctattgta gaagctggtg gaatgcaagc   1440
tttaggactt cacctgacag atccaagtca acgtcttgtt cagaactgtc tttggactct   1500
caggaatctt tcagatgctg caactaaaca ggaagggatg gaaggtctcc ttgggactct   1560
tgttcagctt ctgggttcag atgatataaa tgtggtcacc tgtgcagctg gaattctttc   1620
taacctcact tgcaataatt ataagaacaa gatgatggtc tgccaagtgg gtggtataga   1680
ggctcttgtg cgtactgtcc ttcgggctgg tgacagggaa gacatcactg agcctgccat   1740
ctgtgctctt cgtcatctga ccagccgaca ccaagaagca gagatggccc agaatgcagt   1800
tcgccttcac tatggactac cagttgtggt taagctctta cacccaccat cccactggcc   1860
tctgataaag gctactgttg gattgattcg aaatcttgcc ctttgtcccg caaatcatgc   1920
acctttgcgt gagcagggtg ccattccacg actagttcag ttgcttgttc gtgcacatca   1980
ggatacccag cgccgtacgt ccatgggtgg gacacagcag caatttgtgg agggggtccg   2040
catggaagaa atagttgaag gttgtaccgg agcccttcac atcctagctc gggatgttca   2100
caaccgaatt gttatcagag gactaaatac cattccattg tttgtgcagc tgctttattc   2160
tcccattgaa aacatccaaa gagtagctgc aggggtcctc tgtgaacttg ctcaggacaa   2220
ggaagctgca gaagctattg aagctgaggg agccacagct cctctgacag agttacttca   2280
ctctaggaat gaaggtgtgg cgacatatgc agctgctgtt ttgttccgaa tgtctgagga   2340
caagccacaa gattacaaga aacggctttc agttgagctg accagctctc tcttcagaac   2400
agagccaatg gcttggaatg agactgctga tcttggactt gatattggtg cccagggaga   2460
acccccttgga tatcgccagg atgatcctag ctatcgttct tttcactctg gtggatatgg   2520
ccaggatgcc ttgggtatgg accccatgat ggaacatgag atgggtggcc accaccctgg   2580
tgctgactat ccagttgatg ggctgccaga tctggggcat gcccaggacc tcatggatgg   2640
gctgcctcca ggtgacagca atcagctggc ctggtttgat actgacctgt aaatcatcct   2700
ttagctgtat tgtctgaact tgcattgtga ttggcctgta gagttgctga gagggctcga   2760
ggggtgggct ggtatctcag aaagtgcctg acacactaac caagctgagt ttcctatggg   2820
aacaattgaa gtaaactttt tgttctggtc ctttttggtc gaggagtaac aatacaaatg   2880
```

-continued

```
gattttggga gtgactcaag aagtgaagaa tgcacaagaa tggatcacaa gatggaattt   2940
atcaaaccct agccttgctt gttaaatttt tttttttttt tttttaagaa tatctgtaat   3000
ggtactgact ttgcttgctt tgaagtagct cttttttttt tttttttttt ttttttgcag   3060
taactgtttt ttaagtctct cgtagtgtta agttatagtg aatactgcta cagcaatttc   3120
taatttttaa gaattgagta atggtgtaga acactaattc ataatcactc taattaattg   3180
taatctgaat aaagtgtaac aattgtgtag cctttttgta taaaatagac aaatagaaaa   3240
tggtccaatt agtttccttt ttaatatgct taaaataagc aggtggatct atttcatgtt   3300
tttgatcaaa aactatttgg gatatgtatg ggtagggtaa atcagtaaga ggtgttattt   3360
ggaaccttgt tttggacagt ttaccagttg ccttttatcc caaagttgtt gtaacctgct   3420
gtgatacgat gcttcaagag aaaatgcggt tataaaaaat ggttcagaat taaactttta   3480
attcattc                                                            3488
```